United States Patent
Holyoke, Jr. et al.

(10) Patent No.: US 9,018,220 B2
(45) Date of Patent: *Apr. 28, 2015

(54) MESOIONIC PESTICIDES

(71) Applicant: E I du Pont de Nemours and Company, Wilmington, DE (US)

(72) Inventors: Caleb William Holyoke, Jr., Newark, DE (US); Wenming Zhang, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 32 days.

This patent is subject to a terminal disclaimer.

(21) Appl. No.: 13/967,629

(22) Filed: Aug. 15, 2013

(65) Prior Publication Data

US 2013/0338002 A1 Dec. 19, 2013

Related U.S. Application Data

(62) Division of application No. 12/866,462, filed as application No. PCT/US2009/032584 on Jan. 30, 2009, now Pat. No. 8,552,007.

(60) Provisional application No. 61/063,789, filed on Feb. 6, 2008, provisional application No. 61/043,428, filed on Apr. 9, 2008.

(51) Int. Cl.
| | | |
|---|---|---|
| *A01N 41/12* | (2006.01) |
| *A01N 63/00* | (2006.01) |
| *C07D 239/70* | (2006.01) |
| *A01N 43/90* | (2006.01) |
| *A01N 43/54* | (2006.01) |
| *A01N 43/56* | (2006.01) |
| *A01N 43/647* | (2006.01) |
| *A01N 43/78* | (2006.01) |
| *C07D 239/54* | (2006.01) |
| *C07D 401/06* | (2006.01) |
| *C07D 417/06* | (2006.01) |
| *C07D 471/04* | (2006.01) |
| *C07D 487/04* | (2006.01) |
| *C07D 498/04* | (2006.01) |
| *C07D 513/04* | (2006.01) |

(52) U.S. Cl.
CPC .............. *A01N 43/90* (2013.01); *A01N 43/54* (2013.01); *A01N 43/56* (2013.01); *A01N 43/647* (2013.01); *A01N 43/78* (2013.01); *C07D 239/54* (2013.01); *C07D 401/06* (2013.01); *C07D 417/06* (2013.01); *C07D 471/04* (2013.01); *C07D 487/04* (2013.01); *C07D 498/04* (2013.01); *C07D 513/04* (2013.01)

(58) Field of Classification Search
CPC ....................................................... A01N 43/54
See application file for complete search history.

(56) References Cited

U.S. PATENT DOCUMENTS

| | | | |
|---|---|---|---|
| 5,089,501 | A | 2/1992 | Molleyres |
| 5,151,427 | A | 9/1992 | Molleyres |
| 2010/0323887 | A1 | 12/2010 | Holyoke, Jr. et al. |
| 2012/0115722 | A1 | 5/2012 | Holyoke, Jr. et al. |
| 2012/0122679 | A1 | 5/2012 | Zhang et al. |
| 2012/0122680 | A1 | 5/2012 | Holyoke, Jr. et al. |
| 2012/0277100 | A1 | 11/2012 | Zhang et al. |
| 2013/0190171 | A1 | 7/2013 | Pahutski, Jr. |

FOREIGN PATENT DOCUMENTS

| | | |
|---|---|---|
| AU | 633661 B2 | 6/1991 |
| EP | 415889 A2 | 3/1991 |
| EP | 430883 A2 | 6/1991 |
| EP | 430885 A2 | 6/1991 |
| WO | 2012106495 A1 | 8/2012 |

OTHER PUBLICATIONS

Giandinoto, S., et al. "A Facile Preparation of some Novel Class II Mesoionic Xanthine Acyclonucleosides." J. Hetero. Chem. (1996), vol. 33, Issue 6, pp. 1839-1845.*

U.S. Food and Drug Administration. "Guidance for Industry: Nonclinical Studies for the Safety Evaluation of Pharmaceutical Excipients." (C) May 2005. Available from: < http://www.fda.gov/ohrms/dockets/98fr/2002d-0389-gdl0002.pdf >.*

(Continued)

*Primary Examiner* — Noble Jarrell
*Assistant Examiner* — John S Kenyon
(74) *Attorney, Agent, or Firm* — Roman Kucharczyk

(57) ABSTRACT

Disclosed are compounds of Formula 1,

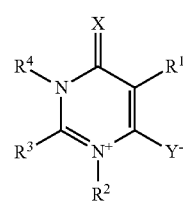

wherein
 X is O or S;
 Y is O or S;
 and $R^1$, $R^2$, $R^3$ and $R^4$ are as defined in the disclosure.

Also disclosed are compositions containing the compounds of Formula 1 and methods for controlling an invertebrate pest comprising contacting the invertebrate pest or its environment with a biologically effective amount of a compound or a composition of the invention.

12 Claims, No Drawings

(56) References Cited

OTHER PUBLICATIONS

Urban, R., et al. Alkylation des "malonyl-αaminopyridines." Helvetica Chimica Acta. (1970), vol. 53, Issue 5, pp. 905-922.*
Bottcher, A. et al., Journal of Organic Chemistry, vol. 50, No. 25, 1985, pp. 5050-5055.
Urban, R. et al., Helvetica Chimica Acta, vol. 53, No. 5, 1970, pp. 905-922.
Rogers, M. E. et al., Journal of Medicinal Chemistry, vol. 24, No. 11, 1981, pp. 1284-1287.
Glennon, R. A. et al., Journal of Pharmaceutical Sciences, vol. 67, No. 12, 1978, pp. 1762-1765.
Giandinoto, S. et al., Journal of Heterocyclic Chemistry, vol. 33, No. 6, 1996, pp. 1839-1845.
Hellberg, M. et al., Bioorganic and Medicinal Chemistry, vol. 8, No. 8, 2000, pp. 1917-1923.
Glennon, R. A. et al., Journal of Heterocyclic Chemistry, vol. 17, No. 2, 1980, pp. 337-340.
Coburn, R. A. et al., Journal of Heterocyclic Chemistry, vol. 10, No. 4, 1973, pp. 487-494.
Schubert, E. M. et al., Journal of Heterocyclic Chemistry, vol. 22, No. 3, 1985, pp. 889-905.
Kappe, T., Encyclopedia of Reagents for Organic Synthesis, 2001, no page number available (carbon suboxide entry), John Wiley & Sons, Ltd.
Cesar, V. et al., Journal of the American Chemical Society, vol. 130, No. 34, 2008, pp. 11286-11287.
Jonas, U. et al., Tetrahedron, vol. 60, No. 44, 2004, pp. 10011-10018.
Ritter, H. et al., Macromolecules, vol. 36, No. 20, 2003, pp. 7520-7526.
Ritter, H. et al., Macromolecules, vol. 36, No. 20, 2003, pp. 7552-7559.
Ritter, H. et al., Macromolecular Chemistry and Physics, vol. 204, No. 10, 2003, pp. 1297-1304.
Ritter, H. et al., Macromolecular Chemistry and Physics, vol. 204, No. 8, 2003, pp. 1079-1084.
Ritter, H. et al., Designed Monomers and Polymers, vol. 4, No. 2, 2001, pp. 177-194.
Wentrup, C. et al., Journal of the Chemical Society, Perkin Trans. 2, No. 10, 2000, pp. 2096-2108.
Ritter, H. et al., Macromolecular Chemistry and Physics, vol. 201, No. 11, 2000, pp. 1200-1205.
Issac, Y., Bulletin of the Chemical Society of Japan, vol. 72, No. 3, 1999, pp. 503-509.
Ritter, H. et al., Macromolecular Rapid Communications, vol. 17, No. 10, 1996, pp. 723-730.
Ritter, H. et al., Macromolecular Rapid Communications, vol. 16, No. 6, 1995, pp. 407-415.
Kappe, T. et al., Heterocycles, vol. 40, No. 2, 1995, pp. 681-689.
Ritter, H. et al., Macromolecular Chemistry and Physics, vol. 195, No. 12, 1994, pp. 3823-3824.
Kappe, T. et al., Archiv der Pharmazie (Weinheim), vol. 324, No. 11, 1991, pp. 863-866.
Gotthardt, H. et al., Chemische Berichte, vol. 121, No. 6, 1988, pp. 1143-1146.
Gotthardt, H. et al., Chemische Berichte, vol. 119, No. 4, 1986, pp. 1315-1330.
Gotthardt, H. et al., Chemische Berichte, vol. 118, No. 11, 1985, pp. 4567-4577.
Gotthardt, H. et al., Chemische Berichte, vol. 118, No. 11, 1985, pp. 4578-4587.
Friedrichsen, W. et al., Zeitschrift fuer Naturforschung, vol. 37b2, 1982, pp. 222-233.
Friedrichsen, W. et al., Liebigs Annalen der Chemie, No. 3, 1981, pp. 521-531.
Moore, H. et al., Journal of the American Chemical Society, vol. 103, No. 7, 1981, pp. 1769-1777.
Kappe, T. et al., Chemische Berichte, vol. 112, No. 5, 1979, pp. 1584-1594.
Moore, H. et al., Heterocycles, vol. 12, No. 1, 1979, pp. 45-49.
Friedrichsen, W. et al., Liebigs Annalen der Chemie, No. 10, 1978, pp. 1655-1665.
Ziegler, E. et al., Zeitschrift fuer Naturforschung, vol. 32b, No. 10, 1977, pp. 1204-1208.
Huhn, M. et al., Tetrahedron, vol. 32, No. 17, 1976, pp. 2117-2120.
Kappe, T. et al., Chemische Berichte, vol. 109, No. 11, 1985, pp. 3668-3674.
Kappe, T. et al., Synthesis, No. 4, 1975, pp. 247-249.
Maki, Y. et al., Journal of the Chemical Society, Chemical Communications, No. 17, 1972, pp. 999-1000.
Kotarska, A. et al., Societatis Scientiarum Lodziensis, Acta Chimica, vol. 16, 1971, pp. 89-93.
Potts, K. et al., Journal of Organic Chemistry, vol. 37, No. 9, 1972, pp. 1422-1425.
Kappe, T. et al., Monatshefte fur Chemie, vol. 102, No. 3, 1971, pp. 781-787.
Kappe, T. et al., Monatshefte fur Chemie, vol. 102, No. 2, 1971, pp. 412-424.
Potts, K. et al., Journal of Organic Chemistry, vol. 36, No. 1, 1971, pp. 8-10.
Berre, A. et al., Bulletin de la Societe Chimique de France, vol. 9, 1969, pp. 3133-3138.
Ingalls, E. et al., Journal of Heterocyclic Chemistry, vol. 4, No. 4, 1967, pp. 5223-5526.
Prystas, M., Collection of Czechoslovak Chemical Communications, vol. 32, No. 12, 1967, pp. 4241-4259.
Prystas, M.et al., Collection of Czechoslovak Chemical Communications, vol. 32, No. 3, 1967, pp. 1298-1304.
Kheifets, G. et al., Doklady Akademii Nauk SSSR, vol. 166, No. 3, 1966, pp. 635-638.
Katritzky, A. et al., Journal of the Chemical Society, 1962, pp. 1544-1548.
Kheifets, G. et al., Zhurnal Organicheskoi Khimii, vol. 2, No. 8, 1966, pp. 1497-1502.
Glennon, R. et al., Journal of Medicinal Chemistry, vol. 27, 1984, pp. 1364-1367.
Glennon, R. et al., Journal of Medicinal Chemistry, vol. 24, 1981, pp. 658-661.
Bass, R. et al., Journal of Heterocyclic Chemistry, vol. 22, 1985, pp. 465-474.
Bass, R. et al., Organic Magnetic Resonance, vol. 21, No. 9, 1983, pp. 527-531.
Friedrichsen, W. et al., Heterocycles, vol. 19, No. 6, 1982, pp. 1083-1113.
XP002628604 (Gotthardt, H. et al., Chemische Berichte, vol. 120, No. 1, 1987, pp. 109-114).
XP002628606 (Katritzky, A. et al., Journal of the Chemical Society, 1962, pp. 1540-1544).
XP002628608 (Stoelting, D. et al., Journal of Heterocyclic Chemistry, vol. 39, No. 4, 2002, pp. 719-725).
XP002628612 (Prabhakar, Y. et al., Journal of Pharmacobio-Dynamics, vol. 7, No. 6, 1984, pp. 366-371).
XP002628614 (Coburn, R. et al., Journal of Heterocyclic Chemistry, vol. 10, No. 4, 1973, pp. 479-485).
XP002628617 (Siddiqi, S. et al., Nucleosides & Nucleotides, vol. 15, Nos. 1-3, 1996, pp. 693-717).
XP002628619 (Schindler, G. et al., Zeitschrift fuer Naturforschung, Teil B, vol. 31B, No. 4, 1976, pp. 500-504).
XP002628622 (Szargan, R. et al., Recent Adv. Anal. Spectrosc., Proc. Int. Conf. At. Spectroscs., 9th, 1982 (Meeting date 1981), pp. 175-184).
XP002628623 (Gotthardt, H. et al., Chemische Berichte, vol. 118, No. 5, 1985, pp. 2079-2094).
XP002628625 (Rickborn, B., Organic Reactions, vol. 53, 1998, no pages given).
XP002628626 (Kappe, T. et al., Heterocycles, vol. 40, No. 2, pp. 681-689), (c) 2001.
U.S. Appl. No. 12/866,462 Office Action dated Jan. 18, 2013.
U.S. Appl. No. 12/866,462 Office Action dated Apr. 25, 2013.
U.S. Appl. No. 13/386,160 Office Action dated Apr. 10, 2013.

* cited by examiner

MESOIONIC PESTICIDES

This application is a division of application Ser. No. 12/866,462, filed Aug. 6, 2010, which is a national stage entry of PCT/US2009/032584, filed Jan. 30, 2009. PCT/US2009/032584 claims priority benefit from Provisional Application 61/063,789, filed Feb. 6, 2008, and from Provisional Application 61/043,428, filed Apr. 9, 2008.

FIELD OF THE INVENTION

This invention relates to certain pyrimidinium compounds and their compositions suitable for agronomic, nonagronomic and animal health uses, methods of their use for controlling invertebrate pests such as arthropods in both agronomic and nonagronomic environments, and for treatment of parasite infections in animals or infestations in the general environment.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public health is also important. Many products are commercially available for these purposes, but the need continues for new compounds that are more effective, less costly, less toxic, environmentally safer or have different sites of action.

The control of animal parasites in animal health is essential, especially in the areas of food production and companion animals. Existing methods of treatment and parasite control are being compromised due to growing resistance to many current commercial parasiticides. The discovery of more effective ways to control animal parasites is therefore imperative.

U.S. Pat. No. 5,151,427 discloses mesoionic pyrimidinium compounds of Formula i as anthelmintics

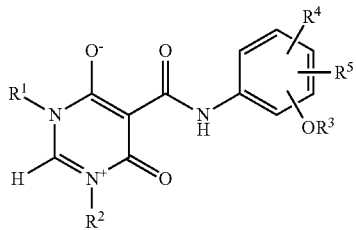

wherein, inter alia, $R^1$ and $R^2$ are independently $C_1$-$C_6$ alkyl, $R^3$ is a heteroaromatic 6-membered ring, and $R^4$ and $R^5$ are independently hydrogen or $C_1$-$C_4$ alkyl.

The pyrimidinium compounds of the present invention are not disclosed in this publication.

SUMMARY OF THE INVENTION

This invention is directed to compounds of Formula 1 (including all geometric and stereoisomers) and compositions containing them and their use for controlling invertebrate pests:

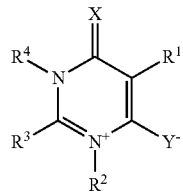

wherein
X is O or S;
Y is O or S;
$R^1$ is H, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $CR^{24}$=$C(R^{24})R^{10}$ or C≡$CR^{10}$; or
$R^1$ is $C_3$-$C_7$ cycloalkyl, $C_4$-$C_8$ cycloalkylalkyl or $C_5$-$C_7$ cycloalkenyl, each optionally substituted with 1 to 4 substituents independently selected from the group consisting of halogen, $C_1$-$C_2$ alkyl, $C_1$-$C_2$ alkoxy, 1 cyclopropyl, 1$CF_3$ and 1$OCF_3$; or
$R^1$ is phenyl, naphthalenyl or a 5- or 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N(—$CH_2Z^2CH_2$—), $C_1$-$C_4$ alkoxy, $C_1$-$C_4$ haloalkoxy, $C_2$-$C_6$ alkoxyalkyl, $S(O)_nR^{12}$, $S(O)_2R^{13}$, $C_1$-$C_4$ alkylamino, $C_2$-$C_6$ dialkylamino, $SF_5$, $Si(CH_3)_3$, CHO, hydroxy, $OC(O)R^{19}$ and $N(R^{20})C(O)R^{19}$; or
$R^1$ is

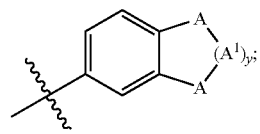

or
$R^1$ is $C(X^1)R^{18}$, C(=$NOR^{23}$)$R^{18}$, C(O)$NR^{16}R^{18a}$, C(=$NNR^{20a}R^{23}$)$R^{18}$, C(=$NNR^{20a}$C(O)$R^{23}$)$R^{18}$, C(=$NNR^{20a}$C(O)$OR^{23a}$)$R^{18}$ or C(=$NNR^{20a}$C(O)$NR^{20a}R^{23}$)$R^{18}$; or
$R^1$ is an 8- to 10-membered heteroaromatic bicyclic ring system optionally substituted on carbon ring members with up to 3 substituents independently selected from the group consisting of halogen, cyano, nitro, $SF_5$, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N(—$CH_2Z^2CH_2$—), $C_1$-$C_4$ alkoxy, $C_1$-$C_4$ haloalkoxy, $C_2$-$C_6$ alkoxyalkyl, $S(O)_nR^{12}$, $S(O)_2R^{13}$, $C_1$-$C_4$ alkylamino, $C_2$-$C_6$ dialkylamino, $Si(CH_3)_3$, CHO, hydroxy, $OC(O)R^{19}$ and $N(R^{20})C(O)R^{19}$, and optionally substituted on nitrogen ring members with methyl; or $R^1$ is phenyl or a 5- or 6-membered heteroaromatic ring, each substituted with $GQ^1$, each optionally substituted with $1Q^2$ and each optionally substituted with 1 or 2 substituents independently selected from the group consisting of halogen, cyano, nitro, $SF_5$, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, Si(CH$_3$)$_3$, CHO, hydroxy, OC(O)R$^{19}$ and N(R$^{20}$)C(O)R$^{19}$; or $R^1$ is phenyl or a 5- or 6-membered heteroaromatic ring, each substituted with $LQ^1$ and optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino and $C_2$-$C_6$ dialkylamino;

each A is independently C(R$^{16}$)$_2$, O, S(O)$_n$ or NR$^{15}$;

each A$^1$ is independently C(R$^{17}$)$_2$;

$X^1$ is O or S;

G is a direct bond, O, S(O)$_n$, NH, N(CH$_3$), CH$_2$, CH$_2$O, OCH$_2$, C(O), C(O)O, OC(O), C(O)NH or NHC(O);

L is a phenyl or 5- or 6-membered heteroaromatic ring optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino and $C_2$-$C_6$ dialkylamino;

$Q^1$ is phenyl or a 5- or 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, $SF_5$, Si(CH$_3$)$_3$, CHO, hydroxy, OC(O)R$^{19}$ and N(R$^{20}$)C(O)R$^{19}$;

$Q^2$ is phenyl or a 5- or 6-membered heteroaromatic ring, each optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino and $C_2$-$C_6$ dialkylamino;

$R^2$ is $C_2$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl, CH$_2$CO$_2$R$^{21}$, CR$^5$R$^6$CH$_2$OR$^{21}$, CR$^5$R$^6$CH$_2$CH$_2$OR$^{21}$, CR$^5$R$^6$CH$_2$S(O)$_n$R$^{21}$ or CR$^5$R$^6$CH$_2$CH$_2$S(O)$_n$R$^{21}$; or $R^2$ is $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and 1CF$_3$; or $R^2$ is CR$^5$R$^6$Q; or $R^2$ is

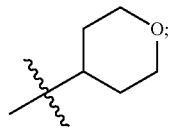 [SMILES: *C1CCOCC1]

$R^3$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or C≡CR$^{10}$; or $R^3$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and 1CF$_3$; or $R^3$ is phenyl, naphthalenyl or a 5- or 6-membered heteroaromatic ring, each optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino and $C_2$-$C_6$ dialkylamino;

$R^4$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or C≡CR$^{10}$; or $R^4$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and 1CF$_3$; or $R^4$ is phenyl, naphthalenyl or a 5- or 6-membered heteroaromatic ring, each optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino and $C_2$-$C_6$ dialkylamino; or $R^3$ and $R^4$ are taken together with the contiguous linking nitrogen and carbon atoms to form an optionally substituted ring R-1

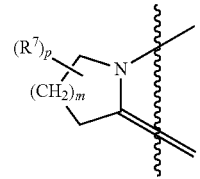

or ring R-2

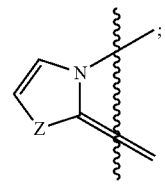

Z is C(R$^{8a}$)=C(R$^{8b}$), S, O or NCH$_3$, provided that the C(R$^{8a}$)=C(R$^{8b}$) moiety is oriented so the carbon atom bonded to R$^{8b}$ is connected as R$^3$ in Formula 1;

each $R^5$ is independently H, F, Cl, cyano or $C_1$-$C_4$ alkyl;
each $R^6$ is independently H, F, $C_1$ or $CH_3$;
Q is

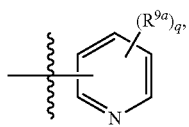
Q-1

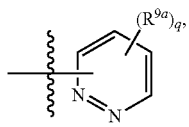
Q-2

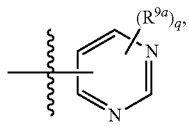
Q-3

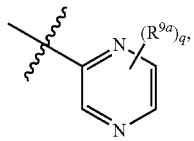
Q-4

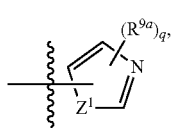
Q-5

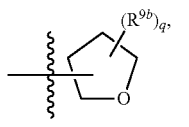
Q-6

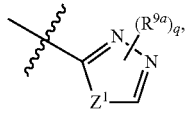
Q-8

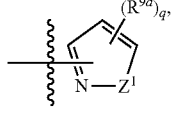
Q-9

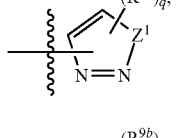
Q-10

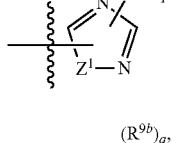
Q-11

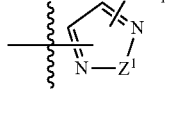
Q-12

-continued

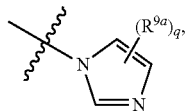
Q-13

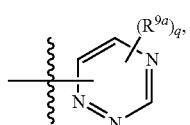
Q-14

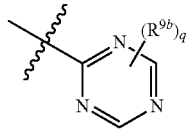
Q-15

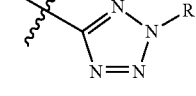
Q-15 or

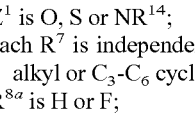
Q-16

$Z^1$ is O, S or $NR^{14}$;
each $R^7$ is independently H, halogen, cyano, $CF_3$, $C_1$-$C_3$ alkyl or $C_3$-$C_6$ cycloalkyl;
$R^{8a}$ is H or F;
$R^{8b}$ is H, F, $CF_2H$ or $CF_3$;
each $R^{9a}$ is independently H, halogen, cyano, nitro, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy, $C_1$-$C_4$ haloalkoxy, $C_2$-$C_4$ alkylcarbonyl, $C_2$-$C_4$ haloalkylcarbonyl, $C_2$-$C_4$ alkoxycarbonyl, $C_2$-$C_4$ haloalkoxycarbonyl, $C(O)NH_2$, $C_2$-$C_4$ alkylaminocarbonyl, $C_3$-$C_7$ dialkylaminocarbonyl, $C(O)N$—($CH_2Z^2CH_2$)—, $C_2$-$C_4$ haloalkylaminocarbonyl, $C_3$-$C_7$ halodialkylaminocarbonyl, $SF_5$, $S(O)_nR^{12}$ or $S(O)_2R^{13}$; or $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and 1$CF_3$; or phenyl or a 5- or 6-membered heteroaromatic ring, each optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C(O)N$—($CH_2Z^2CH_2$)—, $C_1$-$C_4$ alkoxy, $C_1$-$C_4$ haloalkoxy, $C_2$-$C_6$ alkoxyalkyl, $S(O)_nR^{12}$, $S(O)_2R^{13}$, $C_1$-$C_4$ alkylamino and $C_2$-$C_6$ dialkylamino;
each $R^{9b}$ is independently H, halogen, cyano, $C_1$-$C_4$ alkyl, $C_1$-$C_4$ haloalkyl, $C_1$-$C_4$ alkoxy or $C_1$-$C_4$ haloalkoxy; or phenyl or pyridinyl, each optionally substituted with 1 or 2 substituents independently selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $S(O)_nR^{12}$ and $S(O)_2R^{13}$;
each $R^{10}$ is independently $Si(R^{11})_3$; or phenyl or pyridinyl, each optionally substituted with 1 to 3 substituents independently selected from the group consisting of halogen, cyano, nitro, $SF_5$, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C(O)N$—($CH_2Z^2CH_2$)—, $C_2$-$C_6$ alkoxyalkyl, $C_1$-$C_4$ alkoxy, $C_1$-$C_4$ haloalkoxy, $S(O)_nR^{12}$, $S(O)_2R^{13}$, $C_1$-$C_4$ alkylamino and $C_2$-$C_6$ dialkylamino;

each $R^{11}$ is independently $C_1$-$C_4$ alkyl;

each $R^{12}$ is independently $C_1$-$C_4$ alkyl or $C_1$-$C_4$ haloalkyl;

each $R^{13}$ is independently $C_1$-$C_4$ alkylamino, $C_2$-$C_6$ dialkylamino or —N($-CH_2Z^2CH_2-$);

$R^{14}$ is H, $C_1$-$C_4$ alkyl, $C_1$-$C_4$ haloalkyl, $C_2$-$C_5$ alkoxycarbonyl, $C_2$-$C_5$ alkylaminocarbonyl, $C_3$-$C_7$ dialkylaminocarbonyl, $C(O)N(-CH_2Z^2CH_2-)$, $S(O)_nR^{12}$ or $S(O)_2R^{13}$; or phenyl or pyridinyl, each optionally substituted with 1 to 3 substituents independently selected from the group consisting of halogen, cyano, $C_1$-$C_4$ alkyl, $C_1$-$C_4$ alkoxy, $C_1$-$C_4$ haloalkoxy, $S(O)_nR^{12}$ and $S(O)_2R^{13}$;

each $R^{15}$ is independently $C_1$-$C_4$ alkyl;

each $R^{16}$ is independently H or $C_1$-$C_4$ alkyl;

each $R^{17}$ is independently H, F or $CH_3$;

$R^{18}$ is H, $C_1$-$C_6$ alkyl, $C_1$-$C_6$ haloalkyl, $C_3$-$C_6$ cycloalkyl, $C_1$-$C_6$ alkoxy, $C_1$-$C_6$ alkylamino or $C_2$-$C_7$ dialkylamino; or phenyl or a 5- or 6-membered heteroaromatic ring, each optionally substituted with 1 to 3 substituents independently selected from the group consisting of halogen, $C_1$-$C_4$ alkyl, $C_1$-$C_4$ alkoxy, $C_1$-$C_4$ haloalkoxy, $S(O)_nR^{12}$ and $S(O)_2R^{13}$;

$R^{18a}$ is phenyl or a 5- or 6-membered heteroaromatic ring, each optionally substituted with 1 to 3 substituents independently selected from the group consisting of halogen, $C_1$-$C_4$ alkyl, $C_1$-$C_4$ alkoxy, $C_1$-$C_4$ haloalkoxy, $S(O)_nR^{12}$ and $S(O)_2R^{13}$;

each $R^{19}$ is independently $C_1$-$C_4$ alkyl;

each $R^{20}$ is independently H or $C_1$-$C_4$ alkyl;

each $R^{20a}$ is independently $C_1$-$C_4$ alkyl;

each $R^{21}$ is independently H or $C_1$-$C_4$ alkyl;

$R^{23}$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl or $CH_2CO_2R^{21}$; or $R^{23}$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and 1$CF_3$; or $R^{23}$ is phenyl or a 5- or 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C(O)N(-CH_2Z^2CH_2-)$, $C_1$-$C_4$ alkoxy, $C_1$-$C_4$ haloalkoxy, $C_2$-$C_6$ alkoxyalkyl, $S(O)_nR^{12}$, $S(O)_2R^{13}$, $C_1$-$C_4$ alkylamino and $C_2$-$C_6$ dialkylamino;

$R^{23a}$ is $C_1$-$C_6$ alkyl, $C_2$-$C_6$ haloalkyl, $C_3$-$C_6$ alkenyl or $C_3$-$C_6$ cycloalkyl;

each $R^{24}$ is independently H, F or $CH_3$;

m is 0, 1, 2 or 3;

each n is independently 0, 1 or 2;

p is 0, 1, 2, 3 or 4;

each q is independently 0, 1 or 2;

y is 1 or 2; and each $Z^2$ is independently $CH_2CH_2$, $CH_2CH_2CH_2$ or $CH_2OCH_2$.

This invention is also directed to such compounds of Formula 1 (including all geometric and stereoisomers) and compositions containing them and their use for controlling invertebrate pests as described above, and further herein, provided that (a) when $R^2$ is $CH_2CH=CH_2$, $R^3$ and $R^4$ are taken together to form ring R-2, Z is CH=CH, X is O and Y is O, then $R^1$ is other than H, $CH(CH_3)_2$, $CH_2CH_2CH_2CH_3$, $CH_2CH=CH_2$ or unsubstituted phenyl; (b) when $R^1$ is H, $R^3$ and $R^4$ are taken together to form ring R-2, Z is CH=CH, X is O and Y is O, then $R^2$ is other than $CH_2CH=CH_2$ or $CH_2C\equiv CH$; (c) when $R^1$ is $CH_2CH_3$, $R^3$ and $R^4$ are taken together to form ring R-2, Z is CH=CH, X is O and Y is O, then $R^2$ is other than $CH_2(CH_2)_3CH_3$; (d) when $R^3$ is H, $R^2$ and $R^4$ are both cyclohexyl, X is O and Y is O, then $R^1$ is other than $CH_3$; (e) when $R^1$ is H or $C_1$-$C_3$ n-alkyl, $R^3$ and $R^4$ are taken together to form ring R-2, Z is S, X is O and Y is O, then $R^2$ is other than $C_1$-$C_6$ alkyl or $C_3$-$C_4$ alkoxyalkyl; (f) when $R^2$ is cyclopropylmethyl, $R^3$ and $R^4$ are taken together to form ring R-2, Z is S, X is O and Y is O, then $R^1$ is other than $CH_3$, $CH_2CH_3$ or $CH_2CH_2CH_3$; (g) when $R^1$ is unsubstituted phenyl, $R^3$ and $R^4$ are taken together to form ring R-2, Z is S, X is O and Y is O, then $R^2$ is other than $C_3$-$C_4$ alkoxyalkyl; and (h) when $R^1$ is Br, $R^3$ and $R^4$ are taken together to form ring R-2, Z is S, X is O and Y is O, then $R^2$ is other than $CH_2CH_3$.

This invention also provides a composition comprising a compound of Formula 1 and at least one additional component selected from the group consisting of surfactants, solid diluents and liquid diluents. In one embodiment, this invention also provides a composition for controlling an invertebrate pest comprising a compound of Formula 1 (i.e. in a biologically effective amount) and at least one additional component selected from the group consisting of surfactants, solid diluents and liquid diluents, said composition optionally further comprising at least one additional biologically active compound or agent (i.e. in a biologically effective amount).

This invention further provides a composition for protecting an animal from an invertebrate parasitic pest comprising a parasiticidally effective amount of a compound of Formula 1 (i.e. in a parasiticidally effective amount) and at least one carrier.

This invention further provides a spray composition for controlling an invertebrate pest comprising a compound of Formula 1 or the compositions described above (i.e. in a biologically effective amount), and a propellant. This invention also provides a bait composition for controlling an invertebrate pest comprising a compound of Formula 1 or the compositions described in the embodiments above (i.e. in a biologically effective amount), one or more food materials, optionally an attractant, and optionally a humectant.

This invention further provides a trap device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

This invention provides a method for controlling an invertebrate pest comprising contacting the invertebrate pest or its environment with a biologically effective amount of a compound of Formula 1 (e.g., as a composition described herein). This invention also relates to such method wherein the invertebrate pest or its environment is contacted with a composition comprising a biologically effective amount of a compound of Formula 1 and at least one additional component selected from the group consisting of surfactants, solid diluents and liquid diluents, said composition optionally further comprising a biologically effective amount of at least one additional biologically active compound or agent.

This invention also provides a method for protecting a seed from an invertebrate pest comprising contacting the seed with a biologically effective amount of a compound of Formula 1 (e.g., as a composition described herein). This invention also relates to the treated seed.

This invention further provides a method for treating, preventing, inhibiting and/or killing ecto and/or endoparasites comprising administering to and/or on the animal a parasiticidally effective amount of a compound of Formula 1 (e.g., as a composition described herein). This invention also relates to such method wherein a parasiticidally effective amount of a compound of Formula 1 (e.g., as a composition described herein) is administered to the environment (e.g., a stall or blanket) in which an animal resides.

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the invention, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_2OCH_3$, $CH_2CH_2OCH_3$, $CH_2OCH_2CH_3$, $CH_2OCH_2CH_2CH_3$ and $CH_2CH_2OCH_2CH_3$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $CF_3$, $CH_2Cl$, $CH_2CF_3$ and $CCl_2CF_3$. The terms "haloalkoxy", "haloalkenyl", "haloalkynyl", and the like, are defined analogously to the term "haloalkyl". Examples of "haloalkoxy" include $OCF_3$, $OCH_2CCl_3$, $OCH_2CH_2CHF_2$ and $OCH_2CF_3$. Examples of "haloalkenyl" include $CH_2CH=C(Cl)_2$ and $CH_2CH=CHCH_2CF_3$. Examples of "haloalkynyl" include $CHClC\equiv CH$, $C\equiv CCF_3$, $C\equiv CCl_3$ and $CH_2C\equiv CCH_2F$.

"Alkylamino" denotes an NH radical substituted with straight-chain or branched alkyl. Examples of "alkylamino" include $NHCH_2CH_3$, $NHCH_2CH_2CH_3$, and $NHCH_2CH(CH_3)_2$. "Dialkylamino" denotes an N radical substituted independently with two straight-chain or branched alkyl groups. Examples of "dialkylamino" include $N(CH_3)_2$, $N(CH_3CH_2CH_2)_2$ and $N(CH_3)CH_2CH_3$. "Halodialkylamino" denotes one straight-chain or branched alkyl moiety and one straight-chain or branched haloalkyl moiety bonded to an N radical, or two independent straight-chain or branched haloalkyl moieties bonded to an N radical, wherein "haloalkyl" is as defined above. Examples of "halodialkylamino" include N(CH$_2$CH$_3$)(CH$_2$CH$_2$Cl) and N(CF$_2$CF$_3$)$_2$.

"Alkoxycarbonyl" denotes a straight-chain or branched alkyl moiety bonded to a CO$_2$ moiety. The chemical abbreviations CO$_2$ and C(O)O as used herein represent an ester moiety. Examples of "alkoxycarbonyl" include C(O)OCH$_3$, C(O)OCH$_2$CH$_3$, C(O)OCH$_2$CH$_2$CH$_3$ and C(O)OCH(CH$_3$)$_2$.

"Alkoxycarbonyl" denotes a straight-chain or branched alkyl moiety bonded to a CO$_2$ moiety. The chemical abbreviations CO$_2$ and C(O)O as used herein represent an ester moiety. Examples of "alkoxycarbonyl" include C(O)OCH$_3$, C(O)OCH$_2$CH$_3$, C(O)OCH$_2$CH$_2$CH$_3$ and C(O)OCH(CH$_3$)$_2$.

"Alkylaminocarbonyl" denotes a straight-chain or branched alkyl moiety bonded to a C(O)NH moiety. The chemical abbreviations C(O)NH, and C(O)N as used herein represent an amide moiety (i.e. an aminocarbonyl group). Examples of "alkylaminocarbonyl" include C(O)NHCH$_3$, C(O)NHCH$_2$CH$_3$ and C(O)NHCH(CH$_3$)$_2$. "Dialkylaminocarbonyl" denotes two independent straight-chain or branched alkyl moieties bonded to a C(O)N moiety. Examples of "dialkylaminocarbonyl" include C(O)N(CH$_3$)$_2$ and C(O)N(CH$_3$)(CH$_2$CH$_3$).

The chemical abbreviation C(O)N—(CH$_2$Z$^2$CH$_2$—) as used herein represents a dialkylaminocarbonyl moiety wherein the two alkyl groups are connected to form a ring as shown below.

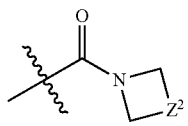

The chemical abbreviation N—(CH$_2$Z$^2$CH$_2$—) is defined analogously.

The chemical abbreviation C(=NOR$^{23}$)R$^{18}$ as used herein represents both geometric isomers of the oxime moiety as shown below.

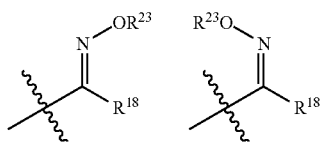

When R$^3$ and R$^4$ are taken together with the contiguous linking nitrogen and carbon atoms to form an optionally substituted ring R-2 and Z is C(R$^{8a}$)=C(R$^{8b}$), the C(R$^{8a}$)=C(R$^{8b}$) moiety is oriented so the carbon atom bonded to R$^{8b}$ is connected as R$^3$ in Formula 1 as shown below.

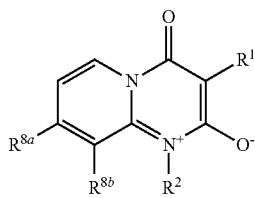

The wavy line in the above structures and elsewhere in the disclosure (e.g., X-24 through X-128 and Y-30 through Y-71 preceding Table 1) indicates the attachment position of the molecular fragment to the remainder of the molecule.

The total number of carbon atoms in a substituent group is indicated by the "C$_i$-C$_j$" prefix where i and j are numbers from 1 to 7. For example, C$_1$-C$_4$ alkyl designates methyl through butyl; C$_2$ alkoxyalkyl designates CH$_2$OCH$_3$; C$_3$ alkoxyalkyl designates, for example, CH$_3$CH(OCH$_3$), CH$_2$CH$_2$OCH$_3$ or CH$_2$OCH$_2$CH$_3$; and C$_4$ alkoxyalkyl designates the various isomers of an alkyl group substituted with an alkoxy group containing a total of four carbon atoms, examples including CH$_2$OCH$_2$CH$_2$CH$_3$ and CH$_2$CH$_2$OCH$_2$CH$_3$.

When a compound is substituted with a substituent bearing a subscript that indicates the number of said substituents can exceed 1, said substituents (when they exceed 1) are independently selected from the group of defined substituents, e.g., (R$^7$)$_p$, p is 0, 1, 2, 3 or 4. When a group contains a substituent which can be hydrogen, for example R$^1$ or R$^3$, then when this substituent is taken as hydrogen, it is recognized that this is equivalent to said group being unsubstituted. When a variable group is shown to be optionally attached to a position, for example (R$^v$)$_r$ in U-36 of Exhibit 1 wherein r may be 0, then hydrogen can be at the position even if not recited in the variable group definition. When one or more positions on a group are said to be "not substituted" or "unsubstituted", then hydrogen atoms are attached to take up any free valency.

The term "heteroaromatic ring" denotes an aromatic ring in which at least one atom forming the ring backbone is not carbon, e.g., nitrogen, oxygen or sulfur. Typically a heteroaromatic ring contains no more than 4 nitrogens, no more than 1 oxygen and no more than 1 sulfur. Unless otherwise indicated, heteroaromatic rings can be attached through any available carbon or nitrogen by replacement of a hydrogen on said carbon or nitrogen. "Aromatic" indicates that each of the ring atoms is essentially in the same plane and has a p-orbital perpendicular to the ring plane, and in which (4n+2)π electrons, where n is a positive integer, are associated with the ring to comply with Hückel's rule. The term "heteroaromatic bicyclic ring system" denotes a ring system consisting of two fused rings, in which at least one of the two rings is a heteroaromatic ring as defined above.

When a radical (e.g., cycloalkyl in the definition of R$^1$) is optionally substituted with listed substituents with the number of substituents stated (e.g., "1 to 4"), then the radical may be unsubstituted or substituted with a number of substituents ranging up to the high number stated (e.g., "4"), and the attached substituents are independently selected from the substituents listed. When the substituent list includes a lower limit for a particular substituent (e.g., "1 cyclopropyl"), this accordingly restricts number of instances of that particular substituent among the substituents attached to the radical. Thus in regards to R$^1$, while up to four substituents may be attached to the cycloalkyl radical, only one of the substituents may be cyclopropyl.

When a substituent (e.g., R$^1$) is a 5- or 6-membered nitrogen-containing heteroaromatic ring, it can be attached to the remainder of Formula 1 though any available carbon or nitrogen ring atom, unless otherwise described. As noted above, substituents such as R$^1$ can be (among others) phenyl optionally substituted with one to three substituents selected from a group of substituents as defined in the Summary of the Invention. An example of phenyl optionally substituted with one to three substituents is the ring illustrated as U-1 in Exhibit 1, wherein R$^v$ is as defined in the Summary of the Invention (e.g., for R$^1$) and r is an integer from 0 to 3.

As noted above, substituents such as R$^1$ can be (among others) a 5- or 6-membered heteroaromatic ring, optionally substituted with one or more substituents selected from a group of substituents as defined in the Summary of Invention. Examples of a 5- or 6-membered heteroaromatic ring optionally substituted with one or more substituents include the rings U-2 through U-61 illustrated in Exhibit 1 wherein $R^v$ is any substituent as defined in the Summary of the Invention (e.g., for $R^1$) and r is an integer from 0 to 2, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

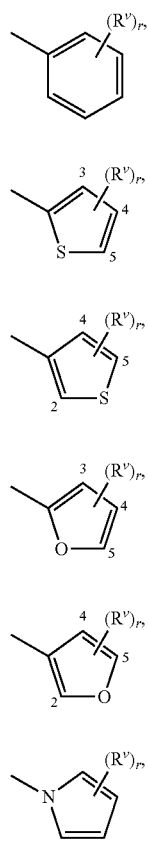

U-1
U-2
U-3
U-4
U-5
U-6
U-7
U-8
U-9

-continued

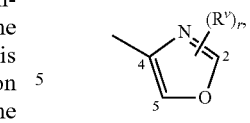

U-10

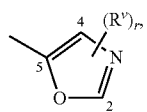

U-11

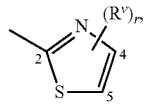

U-12

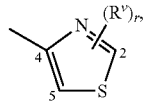

U-13

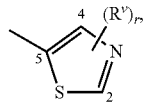

U-14

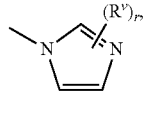

U-15

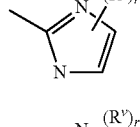

U-16

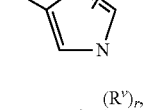

U-17

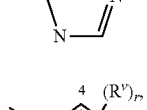

U-18

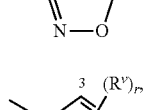

U-19

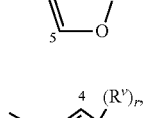

U-20

U-21

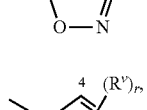

U-22

U-23 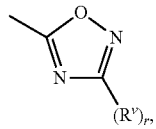
U-24 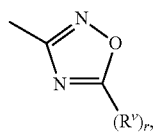
U-25 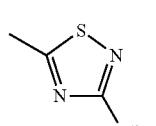
U-26 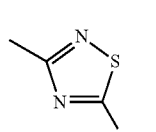
U-27 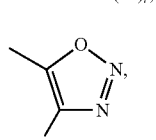
U-28 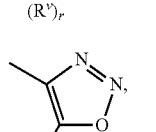
U-29 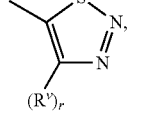
U-30 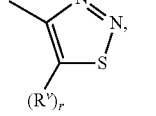
U-31 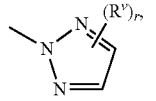
U-32 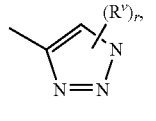
U-33 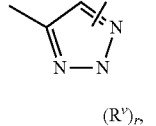
U-34 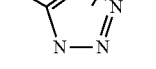
U-11 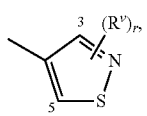
U-12 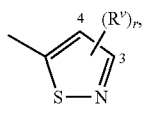
U-13 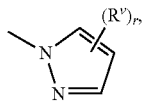
U-14 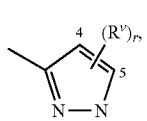
U-15 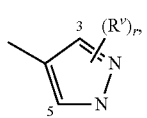
U-16 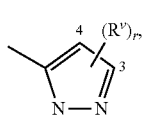
U-17 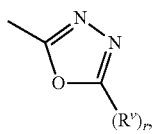
U-18 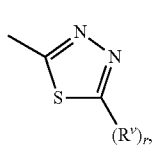
U-19 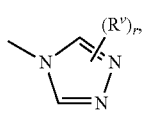
U-20 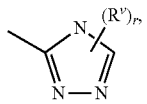
U-21 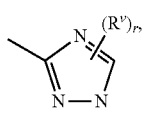
U-22 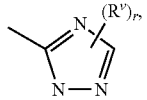
U-35 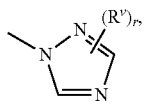

-continued

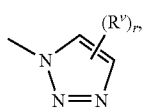
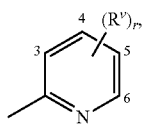
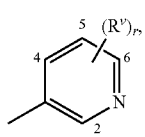
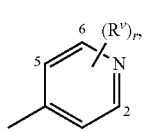
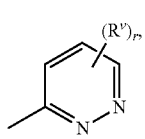
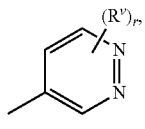
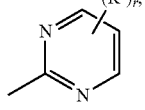
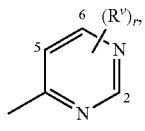
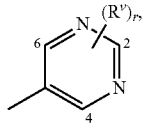
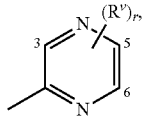
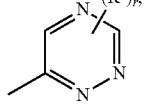

U-48
U-49
U-50
U-51
U-52
U-53
U-54
U-55
U-56
U-57
U-58

-continued

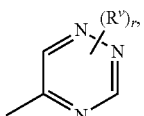  U-59

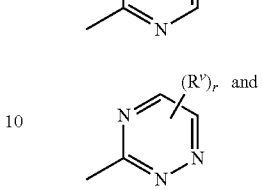  U-60

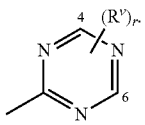  U-61

As noted above, substituents such as $R^1$ can be (among others) an 8-, 9- or 10-membered heteroaromatic bicyclic ring system optionally substituted with up to 3 substituents selected from a group of substituents as defined in the Summary of Invention. Examples of a 8-, 9- or 10-membered heteroaromatic bicyclic ring system optionally substituted with up to 3 substituents include the ring systems H-1 through H-23 illustrated in Exhibit 2 wherein $R^v$ is any substituent as defined in the Summary of the Invention (e.g., halogen, cyano, nitro, $SF_5$, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino on carbon ring members and methyl on nitrogen ring members) and r is an integer from 0 to 3, limited by the number of available positions on each H group.

Exhibit 2

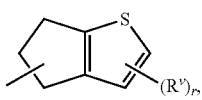  H-1

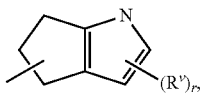  H-2

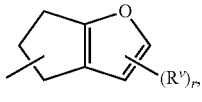  H-3

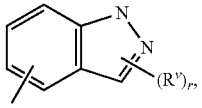  H-4

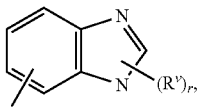  H-5

-continued

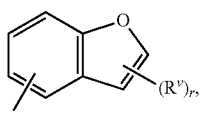
H-6

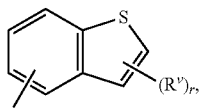
H-7

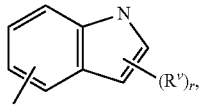
H-8

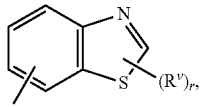
H-9

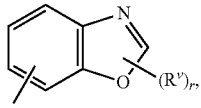
H-10

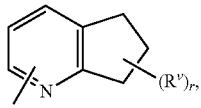
H-11

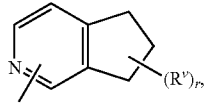
H-12

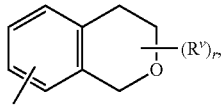
H-13

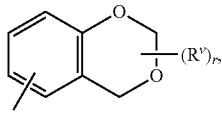
H-14

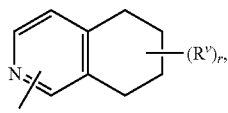
H-15

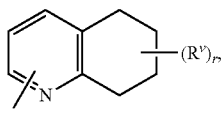
H-16

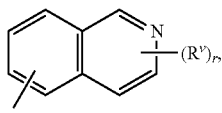
H-17

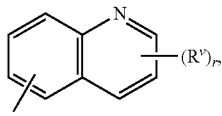
H-18

-continued

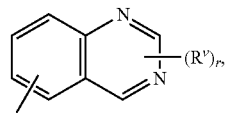
H-19

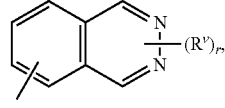
H-20

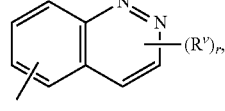
H-21

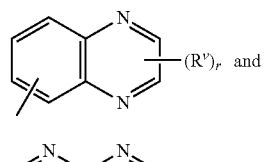
H-22

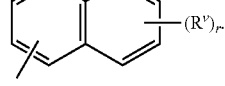
H-23

Although $R^v$ groups are shown in the structures U-1 through U-61 and H-1 through H-23, it is noted that they do not need to be present since they are optional substituents. The nitrogen atoms that require substitution to fill their valence are substituted with H or $R^v$. Note that when the attachment point between $(R^v)_r$ and the U or H group is illustrated as floating, $(R^v)_r$ can be attached to any available carbon atom or nitrogen atom of the U or H group. Note that when the attachment point on the U or H group is illustrated as floating, the U or H group can be attached to the remainder of Formula 1 through any available carbon or nitrogen of the U or H group by replacement of a hydrogen atom. Note that some U groups can only be substituted with less than 2 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

The compounds of Formula 1 are mesoionic inner salts. "Inner salts", also known in the art as "zwitterions", are electrically neutral molecules but carry formal positive and negative charges on different atoms in each valence bond structure according to valence bond theory. Furthermore the molecular structure of the compounds of Formula 1 can be represented by the six valence bond structures shown below, each placing the formal positive and negative charges on different atoms. Because of this resonance, the compounds of Formula 1 are also described as "mesoionic". Although for sake of simplicity, the molecular structure of Formula 1 is depicted as a single valence bond structure in the present disclosure and claims, this particular valence bond structure is to be understood as representative of all six valence bond structures relevant to bonding in molecules of compounds of Formula 1. Therefore reference to Formula 1 in the present disclosure and claims relates to all six applicable valence bond structures and other (e.g., molecular orbital theory) structures unless otherwise specified.

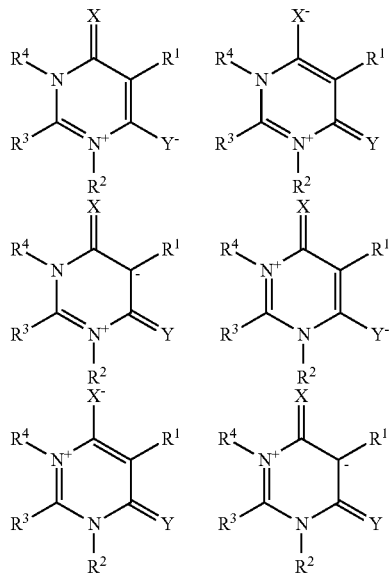

Compounds of this invention can exist as one or more stereoisomers. The various stereoisomers include enantiomers, diastereomers, atropisomers and geometric isomers. For example, substituents and other molecular constituents such as $R^1$ may contain chiral centers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. This invention comprises racemic mixtures as well as enriched and essentially pure stereoconfigurations at these chiral centers.

Compounds of this invention can exist as one or more conformational isomers due to restricted bond rotation caused by steric hinderance. For example, a compound of Formula 1 wherein $R^1$ is phenyl substituted in the ortho-position with a sterically demanding alkyl group (e.g., isopropyl) may exist as two rotamers due to restricted rotation about the $R^1$-pyrimidinium ring bond. This invention comprises mixtures of conformational isomers. In addition, this invention includes compounds that are enriched in one conformer relative to others.

Compounds of Formula 1 can exist in the solid phase as polymorphs (i.e. different crystalline forms). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. This invention comprises both individual polymorphs and mixtures of polymorphs, including mixtures enriched in one polymorph relative to others.

Embodiments of the present invention as described in the Summary of the Invention include those described below. In the following Embodiments reference to "a compound of Formula 1" includes the definitions of substituents specified in the Summary of the Invention unless further defined in the Embodiments. The compounds of Formulae 1r and 1s are various subsets of Formula 1.

Embodiment 1. A compound of Formula 1 wherein X is O.

Embodiment 2. A compound of Formula 1 wherein X is S.

Embodiment 3. A compound of Formula 1 or Embodiments 1 or 2 wherein Y is O.

Embodiment 4. A compound of Formula 1 or Embodiments 1 or 2 wherein Y is S.

Embodiment 5. A compound of Formula 1 or any of Embodiments 1-4 wherein $R^1$ is H or halogen.

Embodiment 6. A compound of Formula 1 or any of Embodiments 1-4 wherein $R^1$ is phenyl or a 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, SF$_5$, Si(CH$_3$)$_3$, CHO, hydroxy, OC(O)R$^{19}$ and N(R$^{20}$)C(O)R$^{19}$.

Embodiment 7. A compound of Embodiment 6 wherein $R^1$ is phenyl or pyridinyl, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, SF$_5$, Si(CH$_3$)$_3$, CHO, hydroxy, OC(O)R$^{19}$ and N(R$^{20}$)C(O)R$^{19}$.

Embodiment 8. A compound of Embodiment 7 wherein $R^1$ is phenyl or pyridinyl, each optionally substituted with 1 to 3 substituents independently selected from the group consisting of halogen, cyano, $C_1$-$C_4$ alkyl, $C_1$-$C_4$ haloalkyl, $C_2$-$C_4$ alkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$ and S(O)$_2$R$^{13}$.

Embodiment 9. A compound of Formula 1 or any of Embodiments 1-4 wherein $R^1$ is

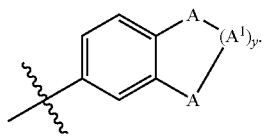

Embodiment 10. A compound of Formula 1 or any of Embodiments 1-4 wherein $R^1$ is $C(X^1)R^{18}$ or $C(=NOR^{23})R^{18}$.

Embodiment 11. A compound of Embodiment 10 wherein $R^1$ is $C(X^1)R^{18}$.

Embodiment 12. A compound of Formula 1 or any of Embodiments 1-11 wherein $X^1$ is O.

Embodiment 13. A compound of Formula 1 or any of Embodiments 1-11 wherein $X^1$ is S.

Embodiment 14. A compound of Embodiment 10 wherein $R^1$ is $C(=NOR^{23})R^{18}$.

Embodiment 15. A compound of Formula 1 or any of Embodiments 1-4 wherein $R^1$ is an 8- to 10-membered heteroaromatic bicyclic ring system optionally substituted on carbon ring members with up to 3 substituents independently selected from the group consisting of halogen, cyano, nitro, $SF_5$, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C(O)N(CH_2Z^2CH_2)$, $C_1$-$C_4$ alkoxy, $C_1$-$C_4$ haloalkoxy, $C_2$-$C_6$ alkoxyalkyl, $S(O)_nR^{12}$, $S(O)_2R^{13}$, $C_1$-$C_4$ alkylamino, $C_2$-$C_6$ dialkylamino, $Si(CH_3)_3$, CHO, hydroxy, $OC(O)R^{19}$ and $N(R^{20})C(O)R^{19}$, and optionally substituted on nitrogen ring members with methyl.

Embodiment 16. A compound of Formula 1 or any of Embodiments 1-4 wherein $R^1$ is phenyl or a 5- or 6-membered heteroaromatic ring, each substituted with $GQ^1$ and further optionally substituted with 1 or 2 substituents independently selected from the group consisting of halogen, cyano, nitro, $SF_5$, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C(O)N(CH_2Z^2CH_2)$, $C_1$-$C_4$ alkoxy, $C_1$-$C_4$ haloalkoxy, $C_2$-$C_6$ alkoxyalkyl, $S(O)_nR^{12}$, $S(O)_2R^{13}$, $C_1$-$C_4$ alkylamino, $C_2$-$C_6$ dialkylamino, $Si(CH_3)_3$, CHO, hydroxy, $OC(O)R^{19}$ and $N(R^{20})C(O)R^{19}$.

Embodiment 17. A compound of Embodiment 16 wherein $R^1$ is phenyl or pyridinyl, each substituted with $GQ^1$ and further optionally substituted with 1 or 2 substituents independently selected from the group consisting of halogen, cyano, $SF_5$, $C_1$-$C_4$ alkyl, $C_1$-$C_4$ haloalkyl, $C_2$-$C_4$ alkylcarbonyl, $C_2$-$C_4$ alkoxycarbonyl, $C_2$-$C_4$ alkylaminocarbonyl, $C_3$-$C_7$ dialkylaminocarbonyl, $C(O)N(CH_2Z^2CH_2)$, $C_1$-$C_4$ alkoxy, $C_1$-$C_4$ haloalkoxy, $C_2$-$C_6$ alkoxyalkyl, $S(O)_nR^{12}$ and $S(O)_2R^{13}$.

Embodiment 18. A compound of Formula 1 or any of Embodiments 1-17 wherein $Q^1$ is phenyl or pyridinyl, each optionally substituted with 1 to 3 substituents independently selected from the group consisting of halogen, cyano, $C_1$-$C_4$ alkyl, $C_1$-$C_4$ haloalkyl, $C_2$-$C_4$ alkylcarbonyl, $C_2$-$C_4$ alkoxycarbonyl, $C_2$-$C_4$ alkylaminocarbonyl, $C_3$-$C_7$ dialkylaminocarbonyl, $C(O)N(CH_2Z^2CH_2)$, $C_1$-$C_4$ alkoxy, $C_1$-$C_4$ haloalkoxy, $C_2$-$C_6$ alkoxyalkyl, $S(O)_nR^{12}$ and $S(O)_2R^{13}$.

Embodiment 19. A compound of Formula 1 or any of Embodiments 1-4 wherein $R^1$ is selected from Embodiments 5, 6, 9, 10, 15 and 16.

Embodiment 20. A compound of Formula 1 or any of Embodiments 1-19 wherein $R^2$ is $C_2$-$C_6$ alkyl, $C_1$-$C_6$ haloalkyl, $CH_2CO_2R^{21}$, $CR^5R^6CH_2OR^{21}$, $CR^5R^6CH_2CH_2OR^{21}$, $CR^5R^6CH_2S(O)_nR^{21}$ or $CR^5R^6CH_2CH_2S(O)_nR^{21}$.

Embodiment 21. A compound of Formula 1 or any of Embodiments 1-19 wherein $R^2$ is $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and $1CF_3$.

Embodiment 22. A compound of Formula 1 or any of Embodiments 1-19 wherein $R^2$ is $CR^5R^6Q$.

Embodiment 22a. A compound of Formula 1 or any of Embodiments 1-19 wherein $R^2$ is selected from Embodiments 20, 21 and 22.

Embodiment 23. A compound of Embodiment 20 wherein $R^2$ is $C_2$-$C_6$ alkyl, $C_1$-$C_6$ haloalkyl or $CR^5R^6CH_2OR^{21}$.

Embodiment 24. A compound of Embodiment 21 wherein $R^2$ is $C_4$-$C_7$ cycloalkylalkyl optionally substituted with 1 to 4 substituents selected from the group consisting of halogen, $C_1$-$C_2$ alkyl, 1 cyclopropyl and $1CF_3$.

Embodiment 24a. A compound of Formula 1 or any of Embodiments 1-19 wherein $R^2$ is selected from Embodiments 23 and 24.

Embodiment 25. A compound of Formula 1 or any of Embodiments 1-24 wherein G is a direct bond.

Embodiment 26. A compound of Formula 1 or any of Embodiments 1-25 wherein $R^3$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or $C\equiv CR^{10}$.

Embodiment 27. A compound of Formula 1 or any of Embodiments 1-25 wherein $R^3$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and $1CF_3$.

Embodiment 28. A compound of Embodiment 26 wherein $R^3$ is $C_1$-$C_6$ alkyl or $C_1$-$C_6$ haloalkyl.

Embodiment 29. A compound of Embodiment 28 wherein $R^3$ is $CH_3$.

Embodiment 29a. A compound of Formula 1 or any of Embodiments 1-29 wherein $R^4$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or $C\equiv CR^{10}$.

Embodiment 29b. A compound of Formula 1 or any of Embodiments 1-29 wherein $R^4$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and $1CF_3$.

Embodiment 29c. A compound of Embodiment 29a wherein $R^4$ is $C_1$-$C_6$ alkyl or $C_1$-$C_6$ haloalkyl.

Embodiment 29d. A compound of Embodiment 29c wherein $R^4$ is $CH_3$.

Embodiment 30. A compound of Formula 1 or any of Embodiments 1-25 wherein $R^3$ and $R^4$ are taken together with the contiguous linking nitrogen and carbon atoms to form an optionally substituted ring R-1

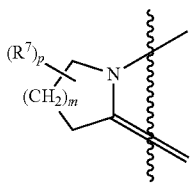

R-1 or ring R-2

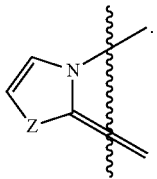

R-2

Embodiment 31. A compound of Embodiment 30 wherein $R^3$ and $R^4$ are taken together with the contiguous linking nitrogen and carbon atoms to form an optionally substituted ring R-1.

Embodiment 32. A compound of Embodiment 30 wherein $R^3$ and $R^4$ are taken together with the contiguous linking nitrogen and carbon atoms to form an optionally substituted ring R-2.

Embodiment 32a. A compound of Formula 1 or any of Embodiments 1-25 wherein $R^3$ is selected from Embodiments 26 and 27, and $R^4$ is selected from Embodiments 29a and 29b; or $R^3$ and $R^4$ are taken together with the contiguous linking nitrogen and carbon atoms to form an optionally substituted ring as described in Embodiment 30.

Embodiment 32b. A compound of Formula 1 or any of Embodiments 1-32a wherein m is 2 or 3.

Embodiment 32c. A compound of Formula 1 or any of Embodiments 1-32b wherein p is 0.

Embodiment 32d. A compound of Formula 1 or any of Embodiments 1-32c wherein Z is $C(R^{8a})$=$C(R^{8b})$ or S, provided that the $C(R^{8a})$=$C(R^{8b})$ moiety is oriented so the carbon atom bonded to $R^{8b}$ is connected as $R^3$ in Formula 1.

Embodiment 33. A compound of Embodiment 32d wherein Z is CH=CH or CH=CF, provided that the CH=CF moiety is oriented so the carbon atom bonded to F is connected as $R^3$ in Formula 1.

Embodiment 34. A compound of Embodiment 32d wherein Z is S.

Embodiment 35. A compound of Formula 1 or any of Embodiments 1-34 wherein each $R^5$ is independently H or $C_1$-$C_4$ alkyl.

Embodiment 36. A compound of Embodiment 35 wherein each $R^5$ is independently H or methyl.

Embodiment 37. A compound of Formula 1 or any of Embodiments 1-36 wherein $R^6$ is H.

Embodiment 38. A compound of Formula 1 or any of Embodiments 1-37 wherein Q is Q-1, Q-5, Q-6 or Q-9.

Embodiment 39. A compound of Embodiment 38 wherein Q is Q-1, Q-5 or Q-9.

Embodiment 40. A compound of Embodiment 38 wherein Q is Q-1.

Embodiment 41. A compound of Embodiment 38 wherein Q is Q-5.

Embodiment 42. A compound of Embodiment 38 wherein Q is Q-6.

Embodiment 43. A compound of Embodiment 38 wherein Q is Q-9.

Embodiment 44. A compound of any of Embodiments 38, 39, 41 or 43 wherein $Z^1$ is O.

Embodiment 45. A compound of any of Embodiments 38, 39, 41 or 43 wherein $Z^1$ is S.

Embodiment 46. A compound of any of Embodiments 38, 39, 41 or 43 wherein $Z^1$ is $NR^{14}$.

Embodiment 47. A compound of Formula 1 or any of Embodiments 1-46 wherein each $R^{9a}$ is independently H, halogen, cyano, $C_1$-$C_4$ alkyl, $C_1$-$C_4$ haloalkyl, $C_1$-$C_4$ alkoxy, $C_1$-$C_4$ haloalkoxy, $SF_5$ or $S(O)_nR^{12}$; or $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and 1$CF_3$.

Embodiment 48. A compound of Embodiment 47 wherein each $R^{9a}$ is independently H, halogen, cyano, $C_1$-$C_4$ alkyl, $C_1$-$C_4$ haloalkyl, $C_1$-$C_4$ alkoxy, $C_1$-$C_4$ haloalkoxy, $SF_5$ or $S(O)_nR^{12}$.

Embodiment 49. A compound of Embodiment 47 wherein each $R^{9a}$ is independently $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and 1$CF_3$.

Embodiment 50. A compound of Formula 1 or any of Embodiments 1-49 wherein each $R^{9b}$ is independently H, halogen, cyano, $C_1$-$C_4$ alkyl, $C_1$-$C_4$ haloalkyl, $C_1$-$C_4$ alkoxy or $C_1$-$C_4$ haloalkoxy.

Embodiment 51. A compound of Formula 1r

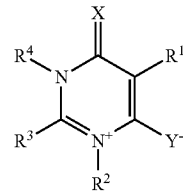

1r wherein
X is O or S;
Y is O or S;
$R^1$ is H, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or C≡$CR^{10}$; or
$R^1$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and 1$CF_3$; or
$R^1$ is phenyl, naphthalenyl or a 5- or 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino; or $R^1$ is

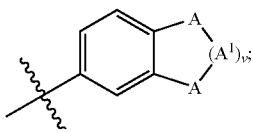

or ring R-2

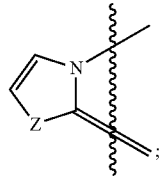

R-2 each A is independently $C(R^{16})_2$, O, S or $NR^{15}$;
each $A^1$ is independently $C(R^{17})_2$;
$R^2$ is $C_2$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl or $C_2$-$C_6$ alkoxyalkyl; or
$R^2$ is $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and $1CF_3$; or
$R^2$ is $CR^5R^6Q$;
$R^3$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or $C\equiv CR^{10}$; or
$R^3$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and $1CF_3$; or
$R^3$ is phenyl, naphthalenyl or a 5- or 6-membered heteroaromatic ring, each optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino;
$R^4$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or $C\equiv CR^{10}$; or
$R^4$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and $1CF_3$; or
$R^4$ is phenyl, naphthalenyl or a 5- or 6-membered heteroaromatic ring, each optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino; or
$R^3$ and $R^4$ are taken together with the contiguous linking nitrogen and carbon atoms to form an optionally substituted ring R-1

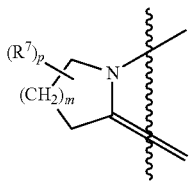

R-1

Z is $C(R^8)=C(R^8)$ or S;
$R^5$ is H, F, Cl, cyano or $C_1$-$C_4$ alkyl;
$R^6$ is H, F, $C_1$ or $CH_3$;
Q is

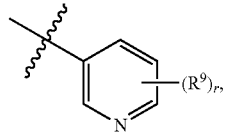

Q-1a

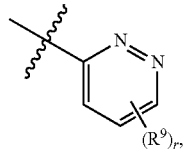

Q-2a

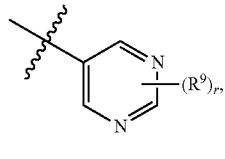

Q-3a

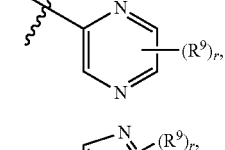

Q-4a

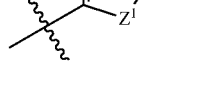

Q-5a

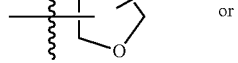

Q-6a or

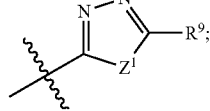

Q-8a $Z^1$ is O, S or $NR^{14}$;
$R^7$ is H, halogen, cyano, $CF_3$, $C_1$-$C_3$ alkyl or $C_3$-$C_6$ cycloalkyl;
each $R^8$ is independently H or F;
each $R^9$ is independently H, halogen, cyano, nitro, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy, $C_1$-$C_4$ haloalkoxy, $C_2$-$C_4$ alkylcarbonyl, $C_2$-$C_4$ haloalkylcarbonyl, $C_2$-$C_4$ alkoxycarbonyl, C$_2$-C$_4$ haloalkoxycarbonyl, C(O)NH$_2$, C$_2$-C$_4$ alkylaminocarbonyl, C$_3$-C$_7$ dialkylaminocarbonyl, C$_2$-C$_4$ haloalkylaminocarbonyl, C$_3$-C$_7$ halodialkylaminocarbonyl or S(O)$_n$R$^{12}$; or each R$^9$ is independently C$_3$-C$_6$ cycloalkyl or C$_4$-C$_7$ cycloalkylalkyl, each optionally substituted with 1 to 4 substituents selected from the group consisting of halogen, C$_1$-C$_2$ alkyl, 1 cyclopropyl and 1CF$_3$; or each R$^9$ is independently phenyl or a 5- or 6-membered heteroaromatic ring, each optionally substituted with 1 or 2 substituents independently selected from the group consisting of halogen, cyano, nitro, C$_1$-C$_4$ alkyl, C$_2$-C$_4$ alkenyl, C$_2$-C$_4$ alkynyl, C$_1$-C$_4$ haloalkyl, C$_2$-C$_4$ alkylcarbonyl, C$_2$-C$_4$ haloalkylcarbonyl, C$_2$-C$_4$ alkoxycarbonyl, C$_2$-C$_4$ alkylaminocarbonyl, C$_3$-C$_7$ dialkylaminocarbonyl, C$_1$-C$_4$ alkoxy, C$_1$-C$_4$ haloalkoxy, C$_2$-C$_6$ alkoxyalkyl, S(O)$_n$R$^{12}$, C$_1$-C$_4$ alkylamino and C$_2$-C$_6$ dialkylamino;

each R$^{10}$ is independently Si(R$^{11}$)$_3$; or phenyl optionally substituted with halogen, cyano, nitro, C$_1$-C$_4$ alkyl, C$_2$-C$_4$ alkenyl, C$_2$-C$_4$ alkynyl, C$_1$-C$_4$ haloalkyl, C$_2$-C$_4$ alkylcarbonyl, C$_2$-C$_4$ haloalkylcarbonyl, C$_2$-C$_4$ alkoxycarbonyl, C$_2$-C$_4$ alkylaminocarbonyl, C$_3$-C$_7$ dialkylaminocarbonyl, C$_2$-C$_6$ alkoxyalkyl, C$_1$-C$_4$ alkoxy, C$_1$-C$_4$ haloalkoxy, S(O)$_n$R$^{12}$, C$_1$-C$_4$ alkylamino or C$_2$-C$_6$ dialkylamino;

each R$^{11}$ is independently C$_1$-C$_4$ alkyl;

each R$^{12}$ is independently C$_1$-C$_4$ alkyl or C$_1$-C$_4$ haloalkyl;

R$^{14}$ is C$_1$-C$_4$ alkyl;

each R$^{15}$ is independently C$_1$-C$_4$ alkyl;

each R$^{16}$ is independently H or C$_1$-C$_4$ alkyl;

each R$^{17}$ is independently H or F;

m is 1, 2 or 3;

each n is independently 0, 1 or 2;

p is 0, 1, 2, 3 or 4;

each r is independently 0, 1 or 2; and v is 1 or 2;

provided that (a) when R$^2$ is CH$_2$CH=CH$_2$, R$^3$ and R$^4$ are taken together to form ring R-2, Z is CH=CH, X is O and Y is O, then R$^1$ is other than H, CH(CH$_3$)$_2$, CH$_2$CH$_2$CH$_2$CH$_3$, CH$_2$CH=CH$_2$ or unsubstituted phenyl; (b) when R$^1$ is H, R$^3$ and R$^4$ are taken together to form ring R-2, Z is CH=CH, X is O and Y is O, then R$^2$ is other than CH$_2$CH=CH$_2$ or CH$_2$C≡CH; (c) when R$^1$ is CH$_2$CH$_3$, R$^3$ and R$^4$ are taken together to form ring R-2, Z is CH=CH, X is O and Y is O, then R$^2$ is other than CH$_2$(CH$_2$)$_3$CH$_3$; (d) when R$^3$ is H, R$^2$ and R$^4$ are both cyclohexyl, X is O and Y is O, then R$^1$ is other than CH$_3$; (e) when R$^1$ is H or C$_1$-C$_3$ n-alkyl, R$^3$ and R$^4$ are taken together to form ring R-2, Z is S, X is O and Y is O, then R$^2$ is other than C$_1$-C$_6$ alkyl or C$_3$-C$_4$ alkoxyalkyl; (f) when R$^2$ is cyclopropylmethyl, R$^3$ and R$^4$ are taken together to form ring R-2, Z is S, X is O and Y is O, then R$^1$ is other than CH$_3$, CH$_2$CH$_3$ or CH$_2$CH$_2$CH$_3$; (g) when R$^1$ is unsubstituted phenyl, R$^3$ and R$^4$ are taken together to form ring R-2, Z is S, X is O and Y is O, then R$^2$ is other than C$_3$-C$_4$ alkoxyalkyl; and (h) when R$^1$ is Br, R$^3$ and R$^4$ are taken together to form ring R-2, Z is S, X is O and Y is O, then R$^2$ is other than CH$_2$CH$_3$.

Embodiment 52. A compound of Embodiment 51 wherein X is O.

Embodiment 53. A compound of Embodiment 51 wherein Y is O.

Embodiment 54. A compound of Embodiment 51 wherein R$^1$ is phenyl, naphthalenyl or a 5- or 6-membered heteroaromatic ring, each optionally substituted with 1 to 3 substituents independently selected from the group consisting of halogen, cyano, nitro, C$_1$-C$_4$ alkyl, C$_2$-C$_4$ alkenyl, C$_2$-C$_4$ alkynyl, C$_1$-C$_4$ haloalkyl, C$_2$-C$_4$ alkylcarbonyl, C$_2$-C$_4$ haloalkylcarbonyl, C$_2$-C$_4$ alkoxycarbonyl, C$_2$-C$_4$ alkylaminocarbonyl, C$_3$-C$_7$ dialkylaminocarbonyl, C$_1$-C$_4$ alkoxy, C$_1$-C$_4$ haloalkoxy, C$_2$-C$_6$ alkoxyalkyl, S(O)$_n$R$^{12}$, C$_1$-C$_4$ alkylamino and C$_2$-C$_6$ dialkylamino.

Embodiment 55. A compound of Embodiment 54 wherein R$^1$ is phenyl optionally substituted with 1 or 2 substituents independently selected from the group consisting of halogen, cyano, C$_1$-C$_2$ haloalkyl, C$_1$-C$_2$ alkoxy and C$_1$-C$_2$ haloalkoxy.

Embodiment 56. A compound of Embodiment 54 wherein R$^1$ is 2-, 3- or 4-pyridinyl optionally substituted with halogen, cyano, C$_1$-C$_2$ haloalkyl, C$_1$-C$_2$ alkoxy or C$_1$-C$_2$ haloalkoxy.

Embodiment 57. A compound of Formula 1r wherein R$^1$ is

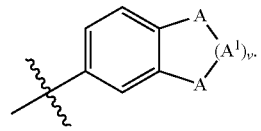

Embodiment 58. A compound of Embodiment 51 wherein R$^2$ is C$_2$-C$_6$ alkyl, C$_1$-C$_6$ haloalkyl, C$_3$-C$_6$ alkenyl or C$_3$-C$_6$ haloalkenyl.

Embodiment 59. A compound of Embodiment 51 wherein R$^2$ is CH$_2$CF$_3$ or CR$^5$R$^6$Q.

Embodiment 60. A compound of Embodiment 59 wherein R$^2$ is CR$^5$R$^6$Q.

Embodiment 61. A compound of Embodiment 59 wherein R$^2$ is CH$_2$CF$_3$.

Embodiment 62. A compound of Embodiment 51 or Embodiment 60 wherein R$^5$ is H or CH$_3$.

Embodiment 63. A compound of Embodiment 51 or Embodiment 60 wherein R$^6$ is H.

Embodiment 64. A compound of Embodiment 51 wherein Q is Q-1a, Q-2a, Q-3a, Q-4-a or Q-5a.

Embodiment 65. A compound of Embodiment 64 wherein Q is Q-1a or Q-5a.

Embodiment 66. A compound of Embodiment 51 wherein R$^9$ is F or Cl.

Embodiment 67. A compound of Embodiment 51 wherein R$^3$ and R$^4$ are taken together with the contiguous linking nitrogen and carbon atoms to form ring R-2

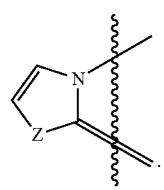

R-2

Embodiment 68. A compound of Embodiment 51 or Embodiment 67 wherein Z is CH=CH.

Embodiment 69. A compound of Embodiment 51 or Embodiment 67 wherein Z is S.

Embodiment 70. A compound of Formula 1s

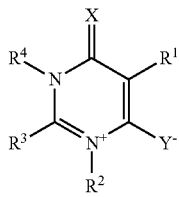

wherein
X is O or S;
Y is O or S;
$R^1$ is H, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or C≡$CR^{10}$; or
$R^1$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and $1CF_3$; or
$R^1$ is phenyl, naphthalenyl or a 5- or 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino; or
$R^1$ is

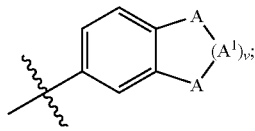

each A is independently $C(R^{16})_2$, O, S or $NR^{15}$;
each $A^1$ is independently $C(R^{17})_2$;
$R^2$ is $C_2$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl or $C_2$-$C_6$ alkoxyalkyl; or
$R^2$ is $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and $1CF_3$; or
$R^2$ is $CR^5R^6Q$;
$R^3$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or C≡$CR^{10}$; or
$R^3$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and $1CF_3$; or
$R^3$ is phenyl, naphthalenyl or a 5- or 6-membered heteroaromatic ring, each optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino;
$R^4$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or C≡$CR^{10}$; or
$R^4$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and $1CF_3$; or
$R^4$ is phenyl, naphthalenyl or a 5- or 6-membered heteroaromatic ring, each optionally substituted with 1 or 2 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino; or
$R^3$ and $R^4$ are taken together with the contiguous linking nitrogen and carbon atoms to form an optionally substituted ring R-1

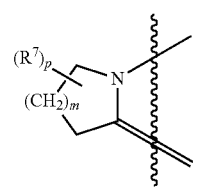

or an optionally substituted aromatic ring R-2

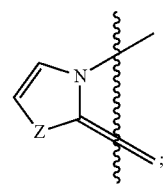

Z is $C(R^8)=C(R^8)$;
$R^5$ is H, F, Cl, cyano or $C_1$-$C_4$ alkyl;
$R^6$ is H, F, $C_1$ and $CH_3$;
Q is

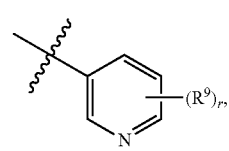

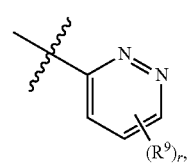

-continued

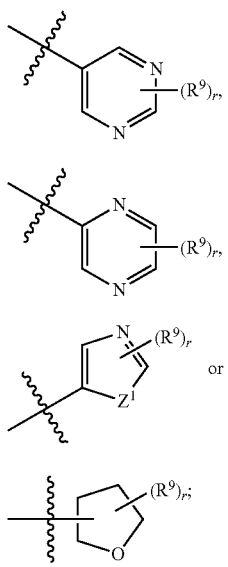

$Z^1$ is O, S or $NR^{14}$;

$R^7$ is H, halogen, cyano, $CF_3$, $C_1$-$C_3$ alkyl or $C_3$-$C_6$ cycloalkyl;

each $R^8$ is independently H or F;

each $R^9$ is independently H, halogen, cyano, nitro, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy, $C_1$-$C_4$ haloalkoxy, $C_2$-$C_4$ alkylcarbonyl, $C_2$-$C_4$ haloalkylcarbonyl, $C_2$-$C_4$ alkoxycarbonyl, $C_2$-$C_4$ haloalkoxycarbonyl, $C(O)NH_2$, $C_2$-$C_4$ alkylaminocarbonyl, $C_3$-$C_7$ dialkylaminocarbonyl, $C_2$-$C_4$ haloalkylaminocarbonyl, $C_3$-$C_7$ halodialkylaminocarbonyl or $S(O)_nR^{12}$; or each $R^9$ is independently $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and 1$CF_3$;

each $R^{10}$ is independently $Si(R^{11})_3$; or phenyl optionally substituted with halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_2$-$C_6$ alkoxyalkyl, $C_1$-$C_4$ alkoxy, $C_1$-$C_4$ haloalkoxy, $S(O)_nR^{12}$, $C_1$-$C_4$ alkylamino and $C_2$-$C_6$ dialkylamino;

each $R^{11}$ is independently $C_1$-$C_4$ alkyl;

each $R^{12}$ is independently $C_1$-$C_4$ alkyl or $C_1$-$C_4$ haloalkyl;

$R^{14}$ is $C_1$-$C_4$ alkyl;

each $R^{15}$ is independently $C_1$-$C_4$ alkyl;

each $R^{16}$ is independently H or $C_1$-$C_4$ alkyl;

each $R^{17}$ is independently H or F;

m is 1, 2 or 3;

each n is independently 0, 1 or 2;

p is 0, 1, 2, 3 or 4;

each r is independently 0, 1 or 2; and v is 1 or 2;

provided that (a) when $R^2$ is $CH_2CH{=}CH_2$, $R^3$ and $R^4$ are taken together to form carbocyclic ring R-2, Z is CH=CH, X is O and Y is O, then $R^1$ is other than H, $CH(CH_3)_2$, $CH_2CH_2CH_2CH_3$, $CH_2CH{=}CH_2$ or unsubstituted phenyl; (b) when $R^1$ is H, $R^3$ and $R^4$ are taken together to form carbocyclic ring R-2, Z is CH=CH, X is O and Y is O, then $R^2$ is other than $CH_2CH{=}CH_2$ or $CH_2C{\equiv}CH$; (c) when $R^1$ is $CH_2CH_3$, $R^3$ and $R^4$ are taken together to form carbocyclic ring R-2, Z is CH=CH, X is O and Y is O, then $R^2$ is other than $CH_2(CH_2)_3CH_3$; and (d) when $R^3$ is H, $R^2$ and $R^4$ are both cyclohexyl, X is O and Y is O, then $R^1$ is other than $CH_3$.

Embodiment 71. A compound of Embodiment 70 wherein X is O.

Embodiment 72. A compound of Embodiment 70 wherein Y is O.

Embodiment 73. A compound of Embodiment 70 wherein $R^1$ is phenyl, naphthalenyl or a 5- or 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino.

Embodiment 74. A compound of Embodiment 73 wherein $R^1$ is phenyl optionally substituted with 1 or 2 substituents independently selected from the group consisting of halogen, cyano, $C_1$-$C_2$ haloalkyl, $C_1$-$C_2$ alkoxy and $C_1$-$C_2$ haloalkoxy.

Embodiment 75. A compound of Embodiment 73 wherein $R^1$ is 2-, 3- or 4-pyridinyl optionally substituted with halogen, cyano, $C_1$-$C_2$ haloalkyl, $C_1$-$C_2$ alkoxy and $C_1$-$C_2$ haloalkoxy.

Embodiment 76. A compound of Embodiment 70 wherein $R^1$ is

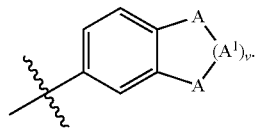

Embodiment 77. A compound of Formula 1s wherein $R^2$ is $C_2$-$C_6$ alkyl, $C_1$-$C_6$ haloalkyl, $C_3$-$C_6$ alkenyl or $C_3$-$C_6$ haloalkenyl.

Embodiment 78. A compound of Embodiment 70 wherein $R^2$ is $CH_2CF_3$ or $CR^5R^6Q$.

Embodiment 79. A compound of Embodiment 78 wherein $R^2$ is $CR^5R^6Q$.

Embodiment 80. A compound of Embodiment 78 wherein $R^2$ is $CH_2CF_3$.

Embodiment 81. A compound of Embodiment 70 or Embodiment 79 wherein $R^5$ is H or $CH_3$.

Embodiment 82. A compound of Embodiment 70 or Embodiment 79 wherein $R^6$ is H.

Embodiment 83. A compound of Embodiment 70 wherein Q is Q-1a, Q-2a, Q-3a, Q-4-a or Q-5a.

Embodiment 84. A compound of Embodiment 83 wherein Q is Q-1a or Q-5a.

Embodiment 85. A compound of Embodiment 70 wherein $R^9$ is F or Cl.

Embodiment 86. A compound of Embodiment 70 wherein $R^3$ and $R^4$ are taken together with the contiguous linking nitrogen and carbon atoms to form an optionally substituted aromatic ring R-2

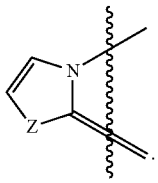

R-2

Embodiment 87. A compound of Embodiment 70 or Embodiment 86 wherein Z is CH=CH.

Of note are compounds of Formulae 1, 1r and 1s or any one of Embodiments 1-87 wherein X and Y are O, a composition comprising said compound, and its use for controlling an invertebrate pest.

Embodiments of this invention, including Embodiments 1-87 above as well as any other embodiments described herein, can be combined in any manner, and the descriptions of variables in the embodiments pertain not only to the compounds of Formulae 1, 1r and 1s but also to the starting compounds and intermediate compounds useful for preparing the compounds of Formulae 1, 1r and 1s. In addition, embodiments of this invention, including Embodiments 1-87 above as well as any other embodiments described herein, and any combination thereof, pertain to the compositions and methods of the present invention.

Combinations of Embodiments 1-50 are illustrated by:

Embodiment A. A compound of Formula 1 wherein
X is O;
Y is O;
$R^1$ is H or halogen; or
$R^1$ is phenyl or a 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, SF$_5$, Si(CH$_3$)$_3$, CHO, hydroxy, OC(O)R$^{19}$ and N(R$^{20}$)C(O)R$^{19}$; or
$R^1$ is

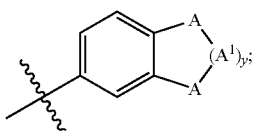

or
$R^1$ is C(X$^1$)R$^{18}$ or C(=NOR$^{23}$)R$^{18}$; or
$R^1$ is an 8- to 10-membered heteroaromatic bicyclic ring system optionally substituted on carbon ring members with up to 3 substituents independently selected from the group consisting of halogen, cyano, nitro, SF$_5$, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, Si(CH$_3$)$_3$, CHO, hydroxy, OC(O)R$^{19}$ and N(R$^{20}$)C(O)R$^{19}$, and optionally substituted on nitrogen ring members with methyl; or
$R^1$ is phenyl or a 5- or 6-membered heteroaromatic ring, each substituted with GQ$^1$, each optionally substituted with 1Q$^2$ and each optionally substituted with 1 or 2 substituents independently selected from the group consisting of halogen, cyano, nitro, SF$_5$, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, Si(CH$_3$)$_3$, CHO, hydroxy, OC(O)R$^{19}$ and N(R$^{20}$)C(O)R$^{19}$;

G is a direct bond;

Q$^1$ is phenyl or a 5- or 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, SF$_5$, Si(CH$_3$)$_3$, CHO, hydroxy, OC(O)R$^{19}$ and N(R$^{20}$)C(O)R$^{19}$;

$R^2$ is $C_2$-$C_6$ alkyl, $C_1$-$C_6$ haloalkyl, CH$_2$CO$_2$R$^{21}$, CR$^5$R$^6$CH$_2$OR$^{21}$, CR$^5$R$^6$CH$_2$CH$_2$OR$^{21}$, CR$^5$R$^6$CH$_2$S(O)$_n$R$^{21}$ or CR$^5$R$^6$CH$_2$CH$_2$S(O)$_n$R$^{21}$; or
$R^2$ is $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and 1CF$_3$; or
$R^2$ is CR$^5$R$^6$Q;

$R^3$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or C≡CR$^{10}$; or
$R^3$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and 1CF$_3$;

$R^4$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or C≡CR$^{10}$; or
$R^4$ is $C_3$-$C_6$ cycloalkyl or $C_4$-$C_7$ cycloalkylalkyl, each optionally substituted with 1 to 4 substituents independently selected from the group consisting of halogen, $C_1$-$C_2$ alkyl, 1 cyclopropyl and 1CF$_3$; or $R^3$ and $R^4$ are taken together with the contiguous linking nitrogen and carbon atoms to form an optionally substituted ring R-1

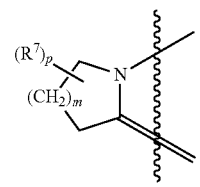

R-1 or ring R-2

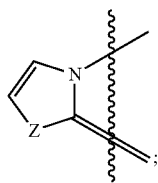

Z is C(R$^{8a}$)=C(R$^{8b}$) or S, provided that the C(R$^{8a}$)=C(R$^{8b}$) moiety is oriented so the carbon atom bonded to R$^{8b}$ is connected as R$^3$ in Formula 1;
each R$^5$ is independently H, F, Cl, cyano or C$_1$-C$_4$ alkyl;
each R$^6$ is independently H, F, C$_1$ or CH$_3$; and
Q is

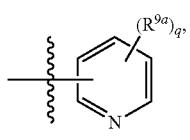

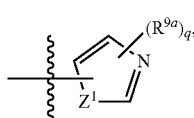

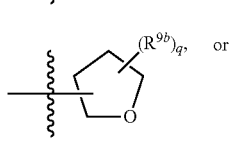

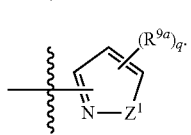

Embodiment B. A compound of Embodiment A wherein
X is O; and
Y is O.

Embodiment C. A compound of Embodiment B wherein
R$^3$ is C$_1$-C$_6$ alkyl or C$_1$-C$_6$ haloalkyl; and
R$^4$ is C$_1$-C$_6$ alkyl or C$_1$-C$_6$ haloalkyl.

Embodiment D. A compound of Embodiment C wherein
R$^3$ is CH$_3$; and
R$^4$ is CH$_3$.

Embodiment E. A compound of Embodiment B wherein
R$^3$ and R$^4$ are taken together with the contiguous linking nitrogen and carbon atoms to form an optionally substituted ring R-1;
m is 2 or 3; and
p is 0.

Embodiment F. A compound of Embodiment B wherein
R$^3$ and R$^4$ are taken together with the contiguous linking nitrogen and carbon atoms to form an optionally substituted ring R-2; and
Z is CH=CH or CH=CF, provided that the CH=CF moiety is oriented so the carbon atom bonded to F is connected as R$^3$ in Formula 1.

Embodiment G. A compound of Embodiment B wherein
R$^3$ and R$^4$ are taken together with the contiguous linking nitrogen and carbon atoms to form an optionally substituted ring R-2; and
Z is S.

Embodiment H. A compound of any one of Embodiments C-G wherein
R$^1$ is H or halogen.

Embodiment I. A compound of any one of Embodiments C-G wherein
R$^1$ is phenyl or pyridinyl, each optionally substituted with 1 to 3 substituents independently selected from the group consisting of halogen, cyano, nitro, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ alkylcarbonyl, C$_2$-C$_4$ haloalkylcarbonyl, C$_2$-C$_4$ alkoxycarbonyl, C$_2$-C$_4$ alkylaminocarbonyl, C$_3$-C$_7$ dialkylaminocarbonyl, C(O)N(CH$_2$Z$^2$CH$_2$), C$_1$-C$_4$ alkoxy, C$_1$-C$_4$ haloalkoxy, C$_2$-C$_6$ alkoxyalkyl, S(O)$_n$R$^{12}$, S(O)$_2$R$^{13}$, C$_1$-C$_4$ alkylamino, C$_2$-C$_6$ dialkylamino, SF$_5$, Si(CH$_3$)$_3$, CHO, hydroxy, OC(O)R$^{19}$ and N(R$^{20}$)C(O)R$^{19}$.

Embodiment J. A compound of Embodiment I wherein
R$^1$ is phenyl or pyridinyl, each optionally substituted with 1 to 3 substituents independently selected from the group consisting of halogen, cyano, C$_1$-C$_4$ alkyl, C$_1$-C$_4$ haloalkyl, C$_2$-C$_4$ alkylcarbonyl, C$_2$-C$_4$ alkoxycarbonyl, C$_2$-C$_4$ alkylaminocarbonyl, C$_3$-C$_7$ dialkylaminocarbonyl, C(O)N(CH$_2$Z$^2$CH$_2$), C$_1$-C$_4$ alkoxy, C$_1$-C$_4$ haloalkoxy, C$_2$-C$_6$ alkoxyalkyl, S(O)$_n$R$^{12}$ and S(O)$_2$R$^{13}$.

Embodiment K. A compound of any one of Embodiments C-G wherein
R$^1$ is C(X$^1$)R$^{18}$ or C(=NOR$^{23}$)R$^{18}$; and
X$^1$ is O.

Embodiment L. A compound of any one of Embodiments C-G wherein
R$^1$ is phenyl or pyridinyl, each substituted with GQ$^1$ and further optionally substituted with 1 or 2 substituents independently selected from the group consisting of halogen, cyano, nitro, SF$_5$, C$_1$-C$_4$ alkyl, C$_2$-C$_4$ alkenyl, C$_2$-C$_4$ alkynyl, C$_1$-C$_4$ haloalkyl, C$_2$-C$_4$ alkylcarbonyl, C$_2$-C$_4$ haloalkylcarbonyl, C$_2$-C$_4$ alkoxycarbonyl, C$_2$-C$_4$ alkylaminocarbonyl, C$_3$-C$_7$ dialkylaminocarbonyl, C(O)N(CH$_2$Z$^2$CH$_2$), C$_1$-C$_4$ alkoxy, C$_1$-C$_4$ haloalkoxy, C$_2$-C$_6$ alkoxyalkyl, S(O)$_n$R$^{12}$, S(O)$_2$R$^{13}$, C$_1$-C$_4$ alkylamino, C$_2$-C$_6$ dialkylamino, Si(CH$_3$)$_3$, CHO, hydroxy, OC(O)R$^{19}$ and N(R$^{20}$)C(O)R$^{19}$.

Embodiment M. A compound of Embodiment L wherein
R$^1$ is phenyl or pyridinyl, each substituted with GQ$^1$ and further optionally substituted with 1 or 2 substituents independently selected from the group consisting of halogen, cyano, SF$_5$, C$_1$-C$_4$ alkyl, C$_1$-C$_4$ haloalkyl, C$_2$-C$_4$ alkylcarbonyl, C$_2$-C$_4$ alkoxycarbonyl, C$_2$-C$_4$ alkylaminocarbonyl, C$_3$-C$_7$ dialkylaminocarbonyl, C(O)N(CH$_2$Z$^2$CH$_2$), C$_1$-C$_4$ alkoxy, C$_1$-C$_4$ haloalkoxy, C$_2$-C$_6$ alkoxyalkyl, S(O)$_n$R$^{12}$ and S(O)$_2$R$^{13}$; and Q$^1$ is phenyl or pyridinyl, each optionally substituted with 1 to 3 substituents independently selected from the group consisting of halogen, cyano, C$_1$-C$_4$ alkyl, C$_1$-C$_4$ haloalkyl, C$_2$-C$_4$ alkylcarbonyl, C$_2$-C$_4$ alkoxycarbonyl, C$_2$-C$_4$ alkylaminocarbonyl, C$_3$-C$_7$ dialkylaminocarbonyl, C(O)N(CH$_2$Z$^2$CH$_2$), C$_1$-C$_4$ alkoxy, C$_1$-C$_4$ haloalkoxy, C$_2$-C$_6$ alkoxyalkyl, S(O)$_n$R$^{12}$ and S(O)$_2$R$^{13}$.

Embodiment N. A compound of any one of Embodiments C-G wherein
R$^2$ is C$_2$-C$_6$ alkyl, C$_1$-C$_6$ haloalkyl or CR$^5$R$^6$CH$_2$OR$^{21}$; or $R^2$ is $C_4$-$C_7$ cycloalkylalkyl optionally substituted with 1 to 4 substituents selected from the group consisting of halogen, $C_1$-$C_2$ alkyl, 1 cyclopropyl and 1$CF_3$.

Embodiment O. A compound of any one of Embodiments C-G wherein $R^2$ is $CR^5R^6Q$.

Embodiment P. A compound of Embodiment O wherein

Q is Q-1, Q-5, Q-6 or Q-9;

$R^5$ is H or methyl;

$R^6$ is H;

each $R^{9a}$ is independently H, halogen, cyano, $C_1$-$C_4$ alkyl, $C_1$-$C_4$ haloalkyl, $C_1$-$C_4$ alkoxy, $C_1$-$C_4$ haloalkoxy, $SF_5$ or $S(O)_nR^{12}$; or $C_3$-$C_6$ cycloalkyl or $C_4$-$C_7$ cycloalkylalkyl, each optionally substituted with 1 to 4 substituents selected from the group consisting of halogen, $C_1$-$C_2$ alkyl, 1 cyclopropyl and 1$CF_3$; and each $R^{9b}$ is independently H, halogen, cyano, $C_1$-$C_4$ alkyl, $C_1$-$C_4$ haloalkyl, $C_1$-$C_4$ alkoxy or $C_1$-$C_4$ haloalkoxy.

Combinations of Embodiments 51-69 are illustrated by:

Embodiment A1. A compound of Formula 1r

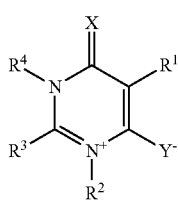

1r wherein

X is O;

Y is O; and $R^3$ and $R^4$ are taken together with the contiguous linking nitrogen and carbon atoms to form ring R-2

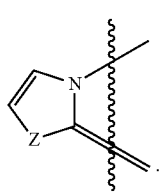

R-2

Embodiment B1. A compound of Embodiment A1 wherein $R^1$ is phenyl, naphthalenyl or a 5- or 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, $C_1$-$C_4$ alkoxy, $C_1$-$C_4$ haloalkoxy, $C_2$-$C_6$ alkoxyalkyl, $S(O)_nR^{12}$, $C_1$-$C_4$ alkylamino and $C_2$-$C_6$ dialkylamino; or $R^1$ is

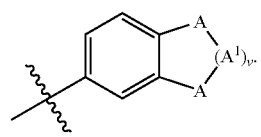

Embodiment C1. A compound of Embodiment B1 wherein $R^2$ is $C_2$-$C_6$ alkyl, $C_1$-$C_6$ haloalkyl, $C_3$-$C_6$ alkenyl or $C_3$-$C_6$ haloalkenyl; or $R^2$ is $CR^5R^6Q$; and Q is Q-1a, Q-2a, Q-3a, Q-4-a or Q-5a.

Embodiment D1. A compound of Embodiment C1 wherein

Z is CH=CH;

$R^1$ is phenyl optionally substituted with 1 or 2 substituents independently selected from the group consisting of halogen, cyano, $C_1$-$C_2$ haloalkyl, $C_1$-$C_2$ alkoxy and $C_1$-$C_2$ haloalkoxy;

$R^2$ is $CH_2CF_3$ or $CR^5R^6Q$;

$R^5$ is H or $CH_3$;

Q is Q-1a or Q-5a;

$R^6$ is H;

$R^9$ is F or Cl; and r is 1.

Embodiment E1. A compound of Embodiment C1 wherein

Z is S;

$R^1$ is phenyl optionally substituted with 1 or 2 substituents independently selected from the group consisting of halogen, cyano, $C_1$-$C_2$ haloalkyl, $C_1$-$C_2$ alkoxy and $C_1$-$C_2$ haloalkoxy;

$R^2$ is $CH_2CF_3$ or $CR^5R^6Q$;

$R^5$ is H or $CH_3$;

Q is Q-1a or Q-5a;

$R^6$ is H;

$R^9$ is F or Cl; and r is 1.

Combinations of Embodiments 70-87 are illustrated by:

Embodiment A2. A compound of Formula 1s

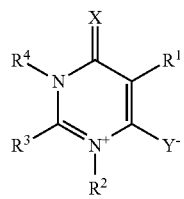

1s wherein

X is O;

Y is O; and $R^3$ and $R^4$ are taken together with the contiguous linking nitrogen and carbon atoms to form an optionally substituted aromatic ring R-2

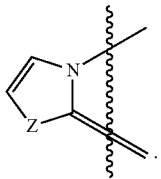

Embodiment B2. A compound of Embodiment A2 wherein R$^1$ is phenyl, naphthalenyl or a 5- or 6-membered heteroaromatic ring, each optionally substituted with 1 to 3 substituents independently selected from the group consisting of halogen, cyano, nitro, C$_1$-C$_4$ alkyl, C$_2$-C$_4$ alkenyl, C$_2$-C$_4$ alkynyl, C$_1$-C$_4$ haloalkyl, C$_2$-C$_4$ alkylcarbonyl, C$_2$-C$_4$ haloalkylcarbonyl, C$_2$-C$_4$ alkoxycarbonyl, C$_2$-C$_4$ alkylaminocarbonyl, C$_3$-C$_7$ dialkylaminocarbonyl, C$_1$-C$_4$ alkoxy, C$_1$-C$_4$ haloalkoxy, C$_2$-C$_6$ alkoxyalkyl, S(O)$_n$R$^{12}$, C$_1$-C$_4$ alkylamino and C$_2$-C$_6$ dialkylamino; or R$^1$ is

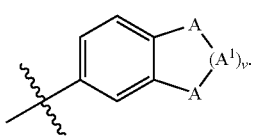

Embodiment C2. A compound of Embodiment B2 wherein R$^2$ is C$_2$-C$_6$ alkyl, C$_1$-C$_6$ haloalkyl, C$_3$-C$_6$ alkenyl or C$_3$-C$_6$ haloalkenyl; or R$^2$ is CR$^5$R$^6$Q; and Q is Q-1a, Q-2a, Q-3a, Q-4-a or Q-5a.

Embodiment D2. A compound of Embodiment C2 wherein Z is CH=CH;

R$^1$ is phenyl optionally substituted with 1 or 2 substituents independently selected from the group consisting of halogen, cyano, C$_1$-C$_2$ haloalkyl, C$_1$-C$_2$ alkoxy and C$_1$-C$_2$ haloalkoxy;

R$^2$ is CH$_2$CF$_3$ or CR$^5$R$^6$Q;

R$^5$ is H or CH$_3$;

Q is Q-1a or Q-5a;

R$^6$ is H;

R$^9$ is F or Cl; and r is 1.

Specific embodiments include compounds of Formula 1 selected from the group consisting of:

3-(2,4-difluorophenyl)-2-hydroxy-4-oxo-1-(2,2,2-trifluoroethyl)-4H-pyrido[1,2-a]pyrimidinium inner salt;
3-(4-fluorophenyl)-2-hydroxy-4-oxo-1-(2,2,2-trifluoroethyl)-4H-pyrido[1,2-a]pyrimidinium inner salt;
1-[(6-chloro-3-pyridinyl)methyl]-3-(2,4-difluorophenyl)-2-hydroxy-4-oxo-4H-pyrido[1,2-a]pyrimidinium inner salt;
1-[(6-chloro-3-pyridinyl)methyl]-3-(4-fluorophenyl)-2-hydroxy-4-oxo-4H-pyrido[1,2-a]pyrimidinium inner salt;
3-(3-chlorophenyl)-1-[(2-chloro-5-thiazolyl)methyl]-2-hydroxy-4-oxo-4H-pyrido[1,2-a]pyrimidinium inner salt;
1-[(2-chloro-5-thiazolyl)methyl]-2-hydroxy-4-oxo-3-[3-(trifluoromethyl)phenyl]-4H-pyrido[1,2-a]pyrimidinium inner salt;
1-[(2-chloro-5-thiazolyl)methyl]-2-hydroxy-4-oxo-3-[3-(trifluoromethoxy)phenyl]-4H-pyrido[1,2-a]pyrimidinium inner salt;
1-[(2-chloro-5-thiazolyl)methyl]-3-(4-fluorophenyl)-2-hydroxy-4-oxo-4H-pyrido[1,2-a]pyrimidinium inner salt;
1-[(2-chloro-5-thiazolyl)methyl]-2-hydroxy-4-oxo-3-phenyl-4H-pyrido[1,2-a]pyrimidinium inner salt;
1-[(2-chloro-5-thiazolyl)methyl]-3-(2,4-difluorophenyl)-2-hydroxy-4-oxo-4H-pyrido[1,2-a]pyrimidinium inner salt;
1-[(2-chloro-5-thiazolyl)methyl]-2-hydroxy-3-(4-methoxyphenyl)-4-oxo-4H-pyrido[1,2-a]pyrimidinium inner salt;
1-[(2-chloro-5-thiazolyl)methyl]-2-hydroxy-3-(3-methoxyphenyl)-4-oxo-4H-pyrido[1,2-a]pyrimidinium inner salt;
1-[(6-fluoro-3-pyridinyl)methyl]-3-(4-fluorophenyl)-2-hydroxy-4-oxo-4H-pyrido[1,2-a]pyrimidinium inner salt;
3-(3-bromophenyl)-1-[(2-chloro-5-thiazolyl)methyl]-2-hydroxy-4-oxo-4H-pyrido[1,2-a]pyrimidinium inner salt;
3-(3-bromophenyl)-1-[(6-chloro-3-pyridinyl)methyl]-2-hydroxy-4-oxo-4H-pyrido[1,2-a]pyrimidinium inner salt;
1-[(6-chloro-3-pyridinyl)methyl]-2-hydroxy-4-oxo-3-[3-(trifluoromethoxy)phenyl]-4H-pyrido[1,2-a]pyrimidinium inner salt;
1-[(2-chloro-5-thiazolyl)methyl]-2-hydroxy-4-oxo-3-[4-(trifluoromethyl)-2-pyridinyl]-4H-pyrido[1,2-a]pyrimidinium inner salt;
1-[(2-chloro-5-thiazolyl)methyl]-3-(2-cyanophenyl)-2-hydroxy-4-oxo-4H-pyrido[1,2-a]pyrimidinium inner salt;
8-[(6-chloro-3-pyridinyl)methyl]-7-hydroxy-5-oxo-6-phenyl-5H-thiazolo[3,2-a]pyrimidinium inner salt;
8-[(6-chloro-3-pyridinyl)methyl]-6-(4-fluorophenyl)-7-hydroxy-5-oxo-5H-thiazolo[3,2-a]pyrimidinium inner salt;
8-[(6-chloro-3-pyridinyl)methyl]-7-hydroxy-5-oxo-6-[3-(trifluoromethoxy)phenyl]-5H-thiazolo[3,2-a]pyrimidinium inner salt;
8-[(2-chloro-5-thiazolyl)methyl]-7-hydroxy-5-oxo-6-phenyl-5H-thiazolo[3,2-a]pyrimidinium inner salt;
8-[(2-chloro-5-thiazolyl)methyl]-6-(4-fluorophenyl)-7-hydroxy-5-oxo-5H-thiazolo[3,2-a]pyrimidinium inner salt;
8-[(2-chloro-5-thiazolyl)methyl]-7-hydroxy-5-oxo-6-[3-(trifluoromethoxy)phenyl]-5H-thiazolo[3,2-a]pyrimidinium inner salt;
3-[3-(6-chloro-3-pyridinyl)phenyl]-1-[(2-chloro-5-thiazolyl)methyl]-2-hydroxy-4-oxo-4H-pyrido[1,2-a]pyrimidinium inner salt;
1-[(6-fluoro-3-pyridinyl)methyl]-2-hydroxy-4-oxo-3-[3-(trifluoromethoxy)phenyl]-4H-pyrido[1,2-a]pyrimidinium inner salt;
3-(5-chloro-2-fluorophenyl)-1-[(2-chloro-5-thiazolyl)methyl]-2-hydroxy-4-oxo-4H-pyrido[1,2-a]pyrimidinium inner salt;
1-[(2-chloro-5-thiazolyl)methyl]-3-[2-chloro-5-(trifluoromethoxy)phenyl]-2-hydroxy-4-oxo-4H-pyrido[1,2-a]pyrimidinium inner salt;
3-(4-fluorophenyl)-2-hydroxy-1-[(1-methyl-1H-pyrazol-4-yl)methyl]-4-oxo-4H-pyrido[1,2-a]pyrimidinium inner salt;
2-hydroxy-1-[(1-methyl-1H-pyrazol-4-yl)methyl]-4-oxo-3-phenyl-4H-pyrido[1,2-a]pyrimidinium inner salt;
1-[(2-chloro-5-thiazolyl)methyl]-3-(3,5-dimethoxyphenyl)-2-hydroxy-4-oxo-4H-pyrido[1,2-a]pyrimidinium inner salt;
1-[(2-chloro-5-thiazolyl)methyl]-3-[2-fluoro-5-(trifluoromethoxy)phenyl]-2-hydroxy-4-oxo-4H-pyrido[1,2-a]pyrimidinium inner salt;
3-(2-chloro-4-pyridinyl)-1-[(2-chloro-5-thiazolyl)methyl]-2-hydroxy-4-oxo-4H-pyrido[1,2-a]pyrimidinium inner salt;
1-[(2-chloro-5-thiazolyl)methyl]-3-(2-fluoro-5-bromophenyl)-2-hydroxy-4-oxo-4H-pyrido[1,2-a]pyrimidinium inner salt;

1-[(2-chloro-5-thiazolyl)methyl]-2-hydroxy-4-oxo-3-(2,4,5-trifluorophenyl)-4H-pyrido[1,2-a]pyrimidinium inner salt;
3-[3-bromo-5-(trifluoromethoxy)phenyl]-1-[(2-chloro-5-thiazolyl)methyl]-2-hydroxy-4-oxo-4H-pyrido[1,2-a]pyrimidinium inner salt;
3-[3-bromo-5-(trifluoromethyl)phenyl]-1-[(2-chloro-5-thiazolyl)methyl]-2-hydroxy-4-oxo-4H-pyrido[1,2-a]pyrimidinium inner salt;
1-[(2-chloro-5-thiazolyl)methyl]-3-[2-fluoro-5-(trifluoromethyl)phenyl]-2-hydroxy-4-oxo-4H-pyrido[1,2-a]pyrimidinium inner salt;
1-[(2-chloro-5-thiazolyl)methyl]-2-hydroxy-3-(2-methoxyphenyl)-4-oxo-4H-pyrido[1,2-a]pyrimidinium inner salt;
1-[(2-chloro-5-thiazolyl)methyl]-3-(2-fluorophenyl)-2-hydroxy-4-oxo-4H-pyrido[1,2-a]pyrimidinium inner salt;
1-[(6-chloro-3-pyridinyl)methyl]-3-(2-fluorophenyl)-2-hydroxy-4-oxo-5H-thiazolo[3,2-a]pyrimidinium inner salt;
2-hydroxy-4-oxo-3-phenyl-1-(2,2,2-trifluoroethyl)-4H-pyrido[1,2-a]pyrimidinium inner salt;
3-[(6-chloro-3-pyridinyl)methyl]-5-(4-fluorophenyl)-3,6-dihydro-4-hydroxy-1,2-dimethyl-6-oxopyrimidinium inner salt;
1-[(2-chloro-5-thiazolyl)methyl]-3-[3-(6-fluoro-3-pyridinyl)-5-(trifluoromethyl)phenyl]-2-hydroxy-4-oxo-4H-pyrido[1,2-a]pyrimidinium inner salt;
1-[1-(6-chloro-3-pyridinyl)ethyl]-3-(4-fluorophenyl)-2-hydroxy-4-oxo-4H-pyrido[1,2-a]pyrimidinium inner salt;
1-[(2-chloro-5-thiazolyl)methyl]-3-(ethoxycarbonyl)-2-hydroxy-4-oxo-4H-pyrido[1,2-a]pyrimidinium inner salt;
3-benzoyl-1-[(2-chloro-5-thiazolyl)methyl]-2-hydroxy-4-oxo-4H-pyrido[1,2-a]pyrimidinium inner salt;
3-(2,4-difluorophenyl)-1-[(6-fluoro-3-pyridinyl)methyl]-2-hydroxy-4-oxo-4H-pyrido[1,2-a]pyrimidinium inner salt;
1-[(6-chloro-3-pyridinyl)methyl]-2-hydroxy-3-(3-methoxyphenyl)-4-oxo-4H-pyrido[1,2-a]pyrimidinium inner salt;
1-[(6-chloro-3-pyridinyl)methyl]-3-(2,3-difluorophenyl)-2-hydroxy-4-oxo-4H-pyrido[1,2-a]pyrimidinium inner salt;
1-[(6-chloro-3-pyridinyl)methyl]-3-(2-fluoro-3-methoxyphenyl)-2-hydroxy-4-oxo-4H-pyrido[1,2-a]pyrimidinium inner salt;
3-(3,5-dimethoxyphenyl)-1-[(6-fluoro-3-pyridinyl)methyl]-2-hydroxy-4-oxo-4H-pyrido[1,2-a]pyrimidinium inner salt;
1-[(6-fluoro-3-pyridinyl)methyl]-2-hydroxy-4-oxo-3-[3-(trifluoromethyl)phenyl]-4H-pyrido[1,2-a]pyrimidinium inner salt;
3-(4-fluorophenyl)-2-hydroxy-1-[(2-methyl-5-thiazolyl)methyl]-4-oxo-4H-pyrido[1,2-a]pyrimidinium inner salt;
2-hydroxy-4-oxo-3-phenyl-1-[(5-thiazolyl)methyl]-4H-pyrido[1,2-a]pyrimidinium inner salt;
3-(4-fluorophenyl)-2-hydroxy-4-oxo-1-[(5-thiazolyl)methyl]-4H-pyrido[1,2-a]pyrimidinium inner salt;
3-(2-fluorophenyl)-1-[(6-fluoro-3-pyridinyl)methyl]-2-hydroxy-4-oxo-4H-pyrido[1,2-a]pyrimidinium inner salt;
1-[(6-chloro-3-pyridinyl)methyl]-3-[2-chloro-5-(trifluoromethyl)phenyl]-2-hydroxy-4-oxo-4H-pyrido[1,2-a]pyrimidinium inner salt;
3-(2-fluoro-4-cyanophenyl)-1-[(6-fluoro-3-pyridinyl)methyl]-2-hydroxy-4-oxo-4H-pyrido[1,2-a]pyrimidinium inner salt;
1-[(6-fluoro-3-pyridinyl)methyl]-3-[2-fluoro-5-(trifluoromethyl)phenyl]-2-hydroxy-4-oxo-4H-pyrido[1,2-a]pyrimidinium inner salt; and
1-[(2-chloro-5-thiazolyl)methyl]-2-hydroxy-4-oxo-3-[3-(6-trifluoromethyl-3-pyridinyl)phenyl]-4H-pyrido[1,2-a]pyrimidinium inner salt.

Of note is that compounds of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling an invertebrate pest comprising a biologically effective amount of a compound of any of the preceding Embodiments, as well as any other embodiments described herein, and any combinations thereof, and at least one additional component selected from the group consisting of a surfactant, a solid diluent and a liquid diluent, said compositions optionally further comprising a biologically effective amount of at least one additional biologically active compound or agent.

Embodiments of the invention also include a composition for protecting an animal comprising a compound (i.e. in a parasiticidally effective amount) of any of the preceding Embodiments and a carrier.

Embodiments of the invention further include methods for controlling an invertebrate pest comprising contacting the invertebrate pest or its environment with a biologically effective amount of a compound of any of the preceding Embodiments (e.g., as a composition described herein). Of particular note is a method for protecting an animal comprising administering to the animal a parasiticidally effective amount of a compound of any of the preceding Embodiments (e.g., as a composition described herein).

Embodiments of the invention also include a composition comprising a compound of any of the preceding Embodiments, in the form of a soil drench liquid formulation. Embodiments of the invention further include methods for controlling an invertebrate pest comprising contacting the soil with a liquid composition as a soil drench comprising a biologically effective amount of a compound of any of the preceding Embodiments.

Embodiments of the invention also include a spray composition for controlling an invertebrate pest comprising a biologically effective amount of a compound of any of the preceding Embodiments and a propellant. Embodiments of the invention further include a bait composition for controlling an invertebrate pest comprising a biologically effective amount of a compound of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the invention also include a method for protecting a seed from an invertebrate pest comprising contacting the seed with a biologically effective amount of a compound of any of the preceding Embodiments (e.g., as a composition described herein).

Embodiments of the invention also include methods for protecting an animal from an invertebrate parasitic pest comprising administering to the animal a parasiticidally effective amount of a compound of any of the preceding Embodiments.

Embodiments of the invention also include methods for controlling an invertebrate pest comprising contacting the invertebrate pest or its environment with a biologically effective amount of a compound of Formula 1, an N-oxide or a salt thereof, (e.g., as a composition described herein), provided that the methods are not methods of medical treatment of a human or animal body by therapy.

This invention also relates to such methods wherein the invertebrate pest or its environment is contacted with a composition comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

One or more of the following methods and variations as described in Schemes 1-19 can be used to prepare the compounds of Formula 1. The definitions of $R^1$, $R^2$, $R^3$, $R^4$, $R^9$, $R^{10}$, $R^{18}$, $R^{23}$, X and Y in the compounds of Formulae 1-22 below are as defined above in the Summary of the Invention unless otherwise noted. Formulae 1a-1l are various subsets of Formula 1, and all substituents for Formulae 1a-1l are as defined above for Formula 1 unless otherwise indicated. Ambient or room temperature is defined as about 20-25° C.

Compounds of Formula 1a (i.e. Formula 1 wherein X and Y are O) can be prepared by condensation of appropriately substituted compounds of Formula 2 with optionally substituted malonic acids (3a) in the presence of condensing agents as shown in Scheme 1. Condensing agents can be carbodiimides such as dicyclohexyl carbodiimide (see, for example, Koch, A. et al. *Tetrahedron* 2004, 60, 10011-10018) or other agents well known in the art to form amide bonds with or without activating agents such as N-hydroxybenzotriazole as described in *Science of Synthesis* 2005, 21, 17-25 and *Tetrahedron* 2005, 61, 10827-10852. This reaction is typically carried out in an inert organic solvent, such as dichloromethane or 1,2-dichloroethane, at temperatures from about 0 to about 80° C. for a period of 10 min to several days.

Scheme 1

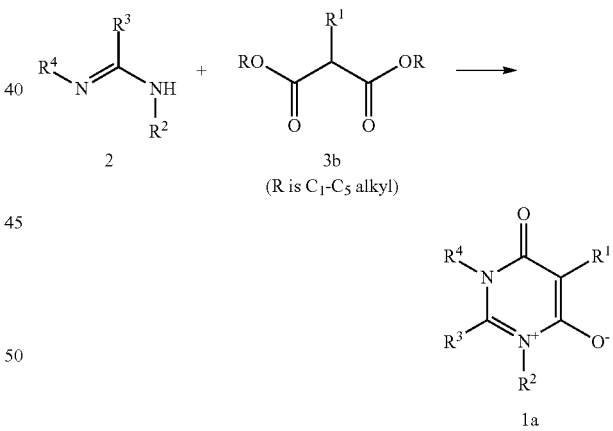

-continued

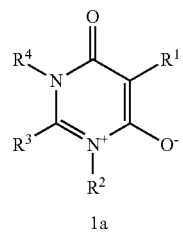

1a

Compounds of Formula 1a can also be prepared by the condensation of compounds of Formula 2 with malonic acid esters (3b) wherein R is a $C_1$-$C_5$ alkyl group, preferably a $C_1$-$C_4$ alkyl group, as shown in Scheme 2. These reactions can be performed neat or in the presence of inert solvents as described in *Bulletin of the Chemical Society of Japan* 1999, 72(3), 503-509. Inert solvents include, but are not limited to, high boiling hydrocarbons such as mesitylene, tetralin or cymene, or high boiling ethers such as diphenyl ether. Typical temperatures range from 50 to 250° C. Of note are temperatures from 150 to 200° C., which typically provide rapid reaction times and high yields. These reactions can also be performed in microwave reactors within the same temperature ranges. Typical reaction times range from 5 min to several hours.

Compounds of the Formula 3a can be prepared by a variety of methods known in the art, for example by base hydrolysis of compounds of Formula 3b. Compounds of Formula 3b can be prepared by arylation of malonate esters catalyzed by palladium (*J. Org. Chem* 2002, 67, 541-555) or copper (*Org. Lett.* 2002, 4, 269-272 and *Org. Lett.* 2005, 7, 4693-4695).

Scheme 2

Compounds of Formula 1a can also be prepared by treatment of compounds of Formula 2 with activated esters of Formula 3c wherein LvO is an activated leaving group as shown in Scheme 3. Examples of Lv preferred for ease of synthesis or reactivity are 2,4,6-trichlorophenyl, pentachlorophenyl or pentafluorophenyl as described in *Archiv der Pharmazie* (Weinheim, Germany) 1991, 324, 863-6. Other activated esters are well known in the art and include, but are not limited to, N-hydroxysuccinimide esters (see, for example, *J. Am. Chem. Soc.* 2002, 124, 6872-6878). Typical temperatures range from 50 to 200° C. Of note are temperatures from 50 to 150° C., which typically provide rapid reaction times and high yields. These reactions can be performed with or without solvent, such as toluene, and in microwave reactors within the same temperature ranges. Typical reaction times range from 5 min to 2 h.

Scheme 3

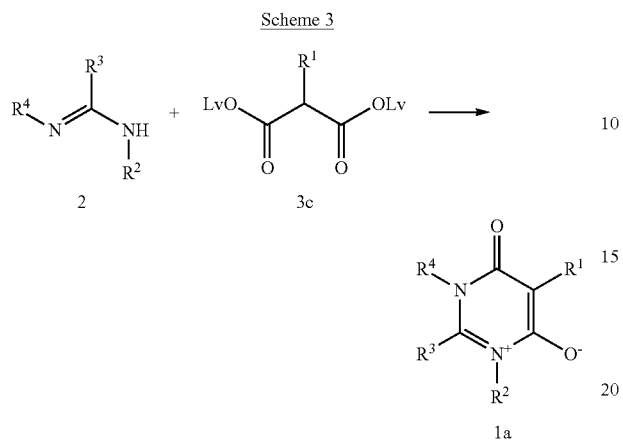

Compounds of the Formula 3c can be prepared, for example, from compounds of Formula 3a (see, for example, *J. Het. Chem.* 1980, 17, 337).

Compounds of Formula 1a can also be prepared by condensation of compounds of Formula 2 with compounds of Formulas 3d or 3e, or by condensation of compounds of Formula 2 with mixtures of compounds of Formulae 3d and 3e as shown in Scheme 4. These reactions are typically performed in an inert solvent, such as dichloromethane, and optionally in the presence of two or more equivalents of an acid acceptor (see, for example, *Zeitschrift für Naturforschung, Teil B: Anorganische Chemie, Organische Chemie* 1982, 37B(2), 222-33). Typical acid acceptors include, but are not limited to, triethylamine, N,N-diisopropylethylamine, pyridine and substituted pyridines.

Scheme 4

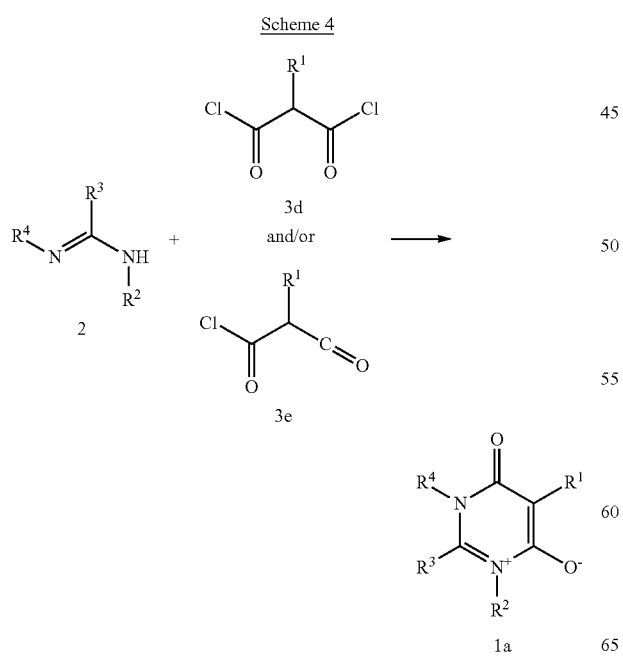

Compounds of Formula 1b (i.e. Formula 1a wherein $R^1$ is H) can be prepared by condensation of compounds of Formula 2 with carbon suboxide (3f) (see, for example, *J. Org. Chem.* 1972, 37(9), 1422-5) as shown in Scheme 5. The reactions are typically performed in an inert solvent such as ether and can include the use of a catalyst such as $AlCl_3$.

Scheme 5

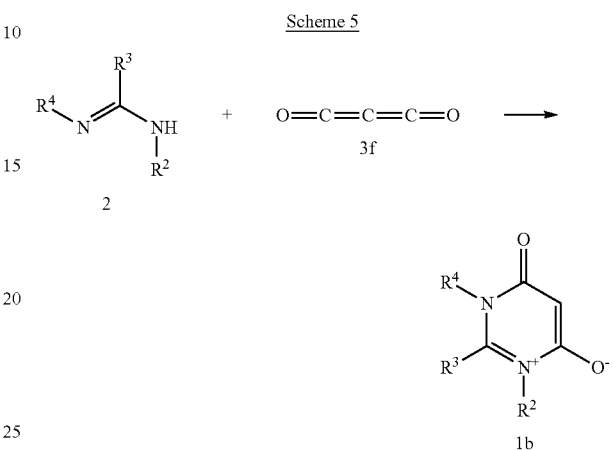

Compounds of Formula 2 can be prepared in a variety of ways known in the art; see, for example, Patai, S. *The Chemistry of Functional Groups: The Chemistry of Amidines and Imidates*; Wiley: Chichester, UK, 1975; *The Chemistry of Amidines and Imidates*; Patai, S.; Rappoport, Z., Eds.; Wiley: Chichester, UK, 1991; Vol. 2; Mega, T. et al. *Bulletin of the Chemical Society of Japan* 1988, 61(12), 4315-21; Ife, R. et al. *European Journal of Medicinal Chemistry* 1989, 24(3), 249-57; Wagaw, S.; Buchwald, S. *Journal of Organic Chemistry* 1996, 61(21), 7240-7241; Shen, Q. et al. *Angewandte Chemie, International Edition* 2005, 44(9), 1371-1375; and Okano, K. et al. *Organic Letters* 2003, 5(26), 4987-4990.

Compounds of Formula 1a wherein $R^1$ is $CR^{24}=C(R^{24})R^{10}$, optionally substituted phenyl, naphthalenyl, a 5- or 6-membered heteroaromatic ring or an 8- to 10-membered heteroaromatic bicyclic ring system can be prepared from compounds of Formula 1d (i.e. Formula 1 wherein $R^1$ is Cl, Br or I, preferably wherein $R^1$ is Br or I) and compounds of Formula 4 wherein M with $R^1$ forms a boronic acid, boronic acid ester or trifluoroborate salt, or M is trialkylstannyl or zinc and $R^1$ is $CR^{24}=C(R^{24})R^{10}$, optionally substituted phenyl, naphthalenyl, a 5- or 6-membered heteroaromatic ring or an 8- to 10-membered heteroaromatic bicyclic ring system as shown in Scheme 6.

Scheme 6

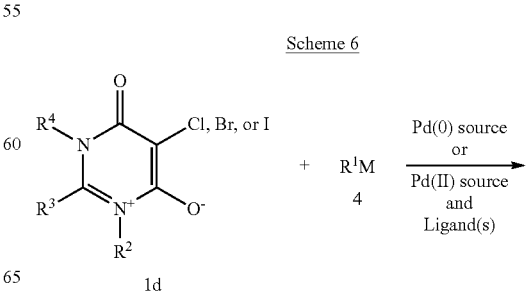

-continued

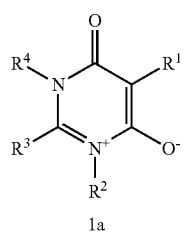

1a

Compounds of Formula 1e (i.e. Formula 1a wherein $R^2$ is $CR^5R^6Q$, and Q is a heterocycle substituted with a phenyl or a 5- or 6-membered heteroaromatic ring) can be prepared from compounds of Formula 1f and compounds of Formula 4a wherein M with $R^{9c}$ forms a boronic acid, boronic acid ester or trifluoroborate salt, or M is trialkylstannyl or zinc and $R^{9c}$ is a phenyl or a 5- or 6-membered heteroaromatic ring as shown in Scheme 7.

Scheme 7

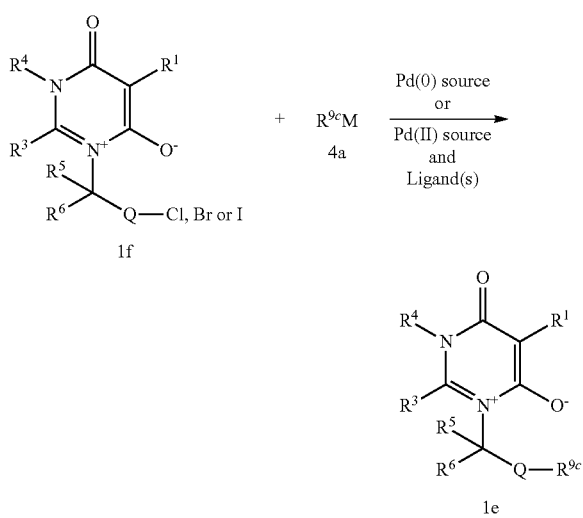

1e

Compounds of Formula 1g (i.e. Formula 1a wherein $R^1$ is phenyl or pyridyl substituted with $GQ^1$ and G is a direct bond) can be prepared from compounds of Formula 1h (i.e. Formula 1a wherein $R^1$ is phenyl substituted with Br or I) and compounds of Formula 4b wherein M with $Q^1$ forms a boronic acid, boronic acid ester or trifluoroborate salt, or M is trialkylstannyl or zinc, and $Q^1$ is a phenyl or 5- or 6-membered heteroaromatic ring) as shown in Scheme 8.

Scheme 8

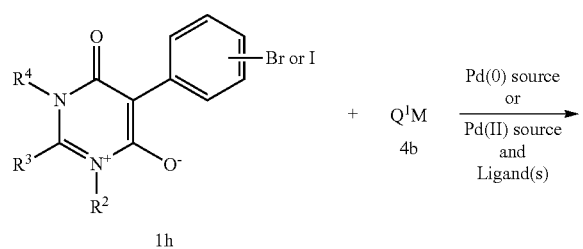

1h

-continued

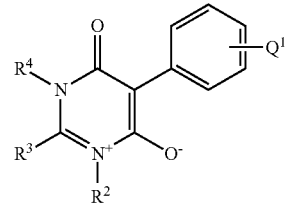

1g

The reactions of Schemes 6, 7 and 8 are typically carried out in the presence of a palladium catalyst and a base optionally under an inert atmosphere. The palladium catalysts used for the reactions of Schemes 6, 7 and 8 typically comprises palladium in a formal oxidation state of either 0 (i.e. Pd(0)) or 2 (i.e. Pd(II)). A wide variety of such palladium-containing compounds and complexes are useful as catalysts for these reactions. Examples of palladium-containing compounds and complexes useful as catalysts in the methods of Schemes 6, 7 and 8 include $PdCl_2(PPh_3)_2$ (bis(triphenylphosphine)palladium (II) dichloride), $Pd(PPh_3)_4$ (tetrakis(triphenylphosphine)palladium(0)), $Pd(C_5H_7O_2)_2$ (palladium(II) acetylacetonate), $Pd_2(dba)_3$ (tris(dibenzylideneacetone)dipalladium (0)), and [1,1'-bis(diphenylphosphino)ferrocene]dichloropalladium(II). The methods of Schemes 6, 7 and 8 are generally conducted in a liquid phase, and therefore to be most effective the palladium catalyst preferably has good solubility in the liquid phase. Useful solvents include, for example, water, ethers such as 1,2-dimethoxyethane, amides such as N,N-dimethyl-acetamide, and non-halogenated aromatic hydrocarbons such as toluene.

The methods of Schemes 6, 7 and 8 can be conducted over a wide range of temperatures, ranging from about 25 to about 200° C. Of note are temperatures from about 60 to about 150° C., which typically provide fast reaction times and high product yields. The general methods and procedures for Stille, Negishi and Suzuki couplings with aryl iodides, bromides or chlorides and an aryl tin, aryl zinc or aryl boronic acid respectively are well known in the literature; see, for example, E. Negishi, *Handbook of Organopalladium Chemistry for Organic Synthesis*, Wiley-Interscience, 2002, New York, N.Y.

Compounds of Formula 1a wherein $R^1$ is optionally substituted phenyl, naphthalenyl, a 5- or 6-membered heteroaromatic ring or an 8- to 10-membered heteroaromatic bicyclic ring system can be prepared from compounds of Formula 1b (i.e. Formula 1a wherein $R^1$ is H) and compounds of Formula 5 wherein $X^1$ is Cl, Br or I (preferably wherein $X^1$ is Br or I) as shown in Scheme 9.

Scheme 9

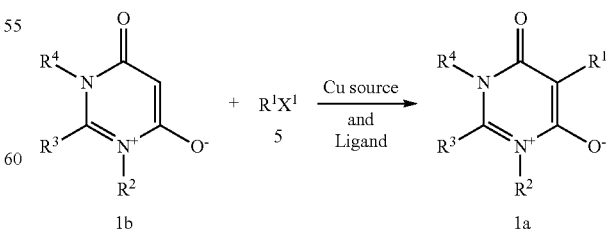

These reactions are typically carried out in the presence of a copper catalyst optionally under an inert atmosphere. The copper catalysts used for the present method typically comprise copper in metallic form (e.g., as a powder) or copper in a formal oxidation state of 1 (i.e. Cu(I)). Examples of copper-containing compounds useful as catalysts in the method of Scheme 9 include, but are not limited to, Cu, CuI, CuBr, CuCl. Useful solvents for the method of Scheme 9 include, for example, ethers such as 1,4-dioxane, amides such as N,N-dimethylacetamide and dimethyl sulfoxide.

The method of Scheme 9 can be conducted over a wide range of temperatures from 25 to 200° C. Of note are temperatures from 40 to 150° C. The method of Scheme 9 can be conducted in the presence of a ligand. A wide variety of such copper-binding compounds are useful as ligands for the present method. Examples of useful ligands include, but are not limited to, 1,10-phenanthroline, N,N-dimethylethylene-diamine, L-proline and 2-picolinic acid. The general methods and procedures for copper-catalyzed Ullmann-type coupling reactions are well known in the literature; see, for example, Xie, Ma, et al. *Org. Lett.* 2005, 7, 4693-4695.

Compounds of Formula 1i can be prepared from compounds of Formula 1b by carbonylation with compounds of Formula 6 as shown in Scheme 10. Examples of carbonylation agents of Formula 6 useful in the method of Scheme 10 include, but are not limited to, aliphatic or aromatic carboxylic acids, acid anhydrides, acid halides, isocyanates and isothiocyanates. Typically the reaction is performed in an inert solvent, more typically a polar solvent such as N,N-dimethylacetamide or 1-methyl-2-pyrrolidinone. The reaction is typically performed at temperatures from 0 to 180° C., more typically at ambient temperature to 150° C. Microwave irradiation can be advantageous in heating the reaction mixture.

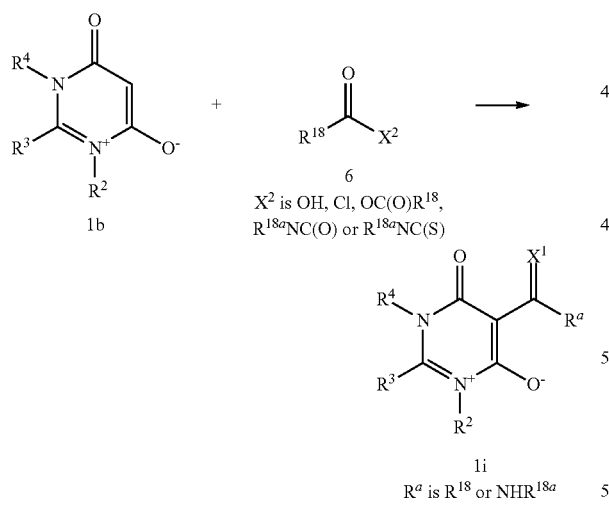

Compounds of the Formula 1j can be prepared by reacting compounds of Formula 1i with an alkoxyamine salt of the Formula 7, where $X^3$ is a counterion such as halide or oxalate, as shown in Scheme 11. The reaction can be run in an alcoholic solvent such as ethanol or propanol at temperatures ranging from 80° C. to the reflux temperature of the solvent in 3 to 24 hours.

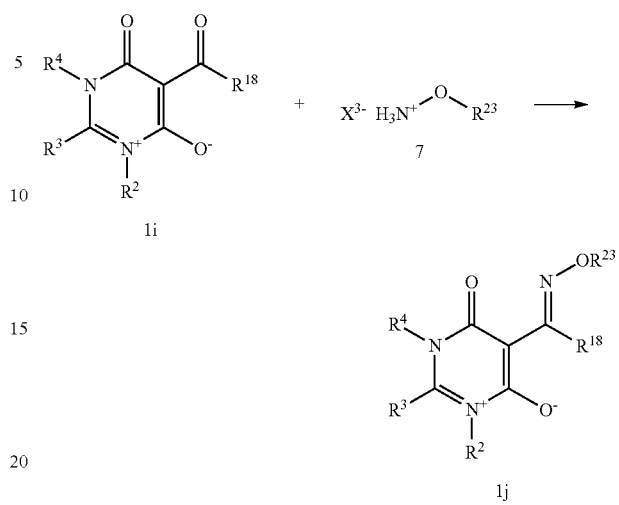

Compounds of Formula 1a wherein $R^1$ is $C(=NNR^{20}R^{23})R^{18}$, $C(=NNR^{20}C(O)R^{23})R^{18}$, $C(=NNR^{20}C(O)OR^{23a})R^{18}$ or $C(=NNR^{20}C(O)NR^{20}R^{23})R^{18}$ can be prepared from compounds of Formula 1i and the appropriately substituted hydrazine by the method shown in Scheme 11.

Compounds of Formula 1a wherein $R^1$ is $C_2$-$C_6$ alkynyl, $C_2$-$C_6$ haloalkynyl or $C≡CR^{10}$ can be prepared from compounds of Formula 1d (i.e. Formula 1a wherein $R^1$ is Cl, Br or I) and substituted alkynes of Formula 8 by a Sonigashira coupling reaction as shown in Scheme 12. Sonigashira couplings are well known in the literature. See, for example, K. Sonogashira, *Sonogashira Alkyne Synthesis* Vol 2, p. 493 in E. Negishi, *Handbook of Organopalladium Chemistry for Organic Synthesis*, Wiley-Interscience, 2002, New York, N.Y.

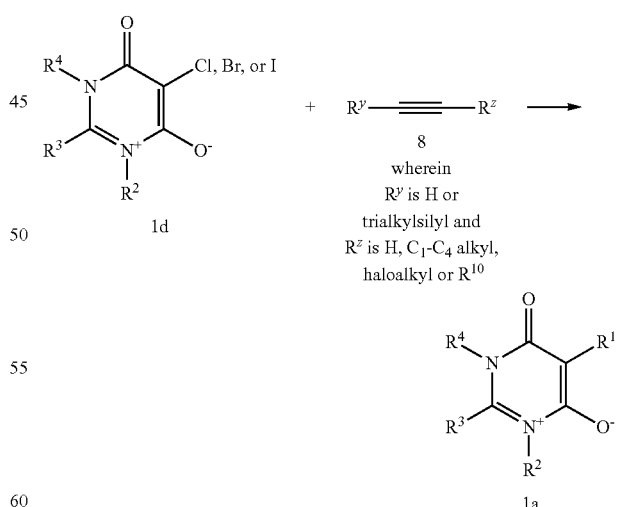

Compounds of Formula 1d can be prepared from compounds of Formula 1b by halogenation using, for example, liquid bromine or N-halosuccinimides (9) as shown in Scheme 13. Typically the reaction is performed in an inert solvent, more typically a halogenated solvent such as methylene chloride or 1,2-dichloroethane. The reaction is typically performed at temperatures from 0 to 80° C., more typically at ambient temperature.

Scheme 13

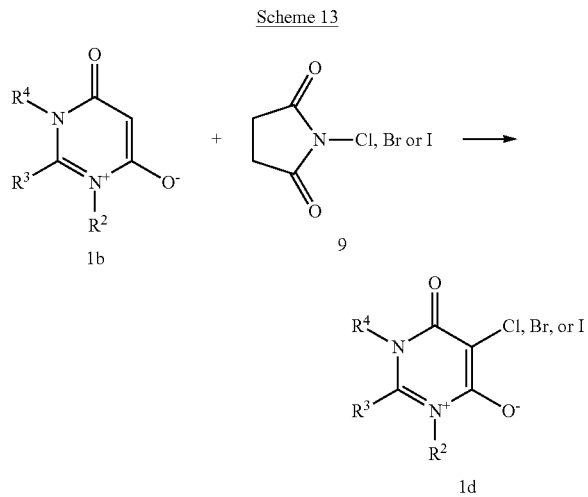

Compounds of Formula 1k (i.e. Formula 1a wherein $R^3$ and $R^4$ are taken together to form an optionally substituted carbocyclic ring R-1 wherein m is 2) can be prepared from compounds of Formula 11 (i.e. Formula 1 wherein $R^3$ and $R^4$ are taken together to form an optionally substituted aromatic ring R-2 wherein Z is CH=CH) by reduction using hydrogen in the presence of a platinum group metal or metal oxide catalyst as shown in Scheme 14. Typically the platinum group metal is platinum or palladium or their oxides and the reduction is performed in an inert solvent (see, for example, Kappe, Thomas, et al. *Heterocycles* 1995, 40, 681-9). Suitable solvents include, but are not limited to, methanol, ethanol, tetrahydrofuran and methyl t-butyl ether. The reaction is typically performed at ambient temperature and at approximately 100 kPa of pressure.

Scheme 14

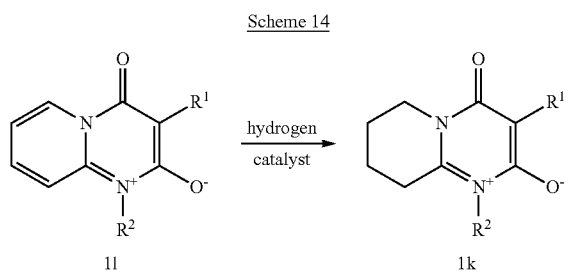

Compounds of Formula 11 can be prepared from compounds of Formula 2 (wherein $R^3$ and $R^4$ are taken together with the contiguous linking nitrogen and carbon atoms to form ring R-1 and Z is CH=CH) by the methods shown in Schemes 1 through 5.

Compounds of Formula 1a can also be prepared by alkylation of compounds of Formula 10 using appropriately substituted alkylating agents and bases such as potassium carbonate as shown in Scheme 15 (see, for example, Kappe, T. et al. *Monatschefte fur Chemie* 1971, 102, 412-424 and Urban, M. G.; Arnold, W. *Helvetica Chimica Acta* 1970, 53, 905-922). Alkylating agents include, but are not limited to, alkyl chlorides, bromides, iodides and sulfonate esters. A wide variety of bases and solvents can be employed in the method of Scheme 15, and these bases and solvents are well known in the art.

Scheme 15

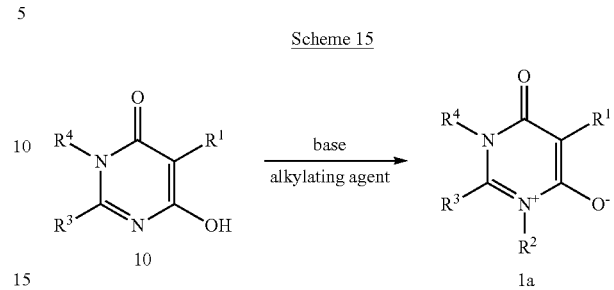

Compounds of Formula 10 can be prepared from compounds of Formula 2a by methods analogous to those shown in Schemes 1 through 5. Compounds of Formula 2a are commercially available or can be prepared by general methods well known in the art.

One skilled in the art will appreciate that compounds of Formula 2 wherein $R^3$ and $R^4$ are taken together to form ring R-2 and wherein $R^a$ is the subset of $R^2$ substituents containing a terminal $CH_2$ group can be prepared by general methods well known in the art. For example, Scheme 16 illustrates a method wherein a compound of Formula 12 is acylated with a compound of Formula 13 in the presence of an appropriate base. The resulting intermediate of Formula 14 is reduced with an appropriate reagent such as diborane to provide the compound of Formula 11.

Scheme 16

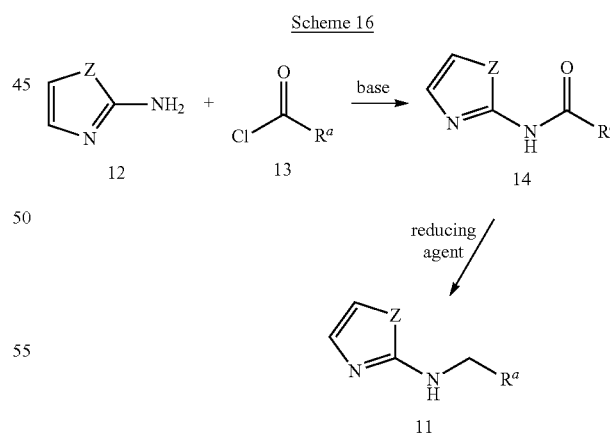

Z is $C(R^8)$=$C(R^8)$, S, O or $NCH_3$

Compounds of Formula 11a (compounds of Formula 11 where Z is CH=CH) can be prepared by direct displacement reaction of alpha-halopyridine compounds of Formula 15 by suitable amines of Formula 16 as shown in Scheme 17. Examples of alpha-halopyridine compounds useful in the method of Scheme 17 include, but are not limited to, 2-fluoropyridine and 2-chloropyridine. Examples of suitable amines include, but are not limited to, 2,2,2-trifluoroethylamine and 5-aminomethyl-2-chloropyridine. Typically the reaction is performed in an inert solvent, more typically a polar solvent such as N,N-dimethylacetamide or 1-methyl-2-pyrrolidinone. The reaction is typically performed at temperatures from 0 to 250° C., more typically at ambient temperature to 150° C. Alternatively, the reaction can be performed in a sealed tube in a laboratory microwave reactor; typical reaction temperatures are from 200 to 240° C. The hydrochloride salts of the compounds of Formula 15 are suitable starting materials for this method.

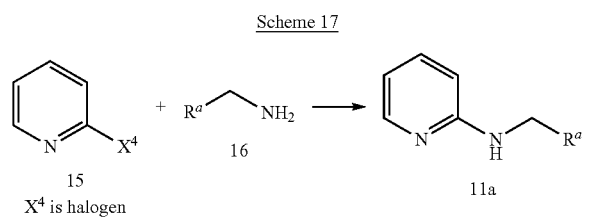

Scheme 17

15 $X^4$ is halogen

11a

Compounds of Formula 11 can be prepared by reductive amination reaction between amines of Formula 12 and suitable aldehydes of Formula 17. These reactions are either performed in one-pot or by stepwise reaction via the imine intermediate of Formula 18 as shown in Scheme 18. Examples of amine compounds useful in the method of Scheme 18 include, but are not limited to, 2-aminopyridine and 2-aminothiazole. Examples of suitable aldehydes in the method of Scheme 18 include, but are not limited to, 6-chloronicotinaldehyde. Examples of suitable reducing agents in the method of Scheme 18 include, but are limited to, sodium borohydride, zinc borohydride and sodium cyanoborohydride. General methods and procedures for reductive amination reactions are well known in the literature; see, for example, Abdel-Magid, et al. *J. Org. Chem.* 1996, 61(11), 3849-3862.

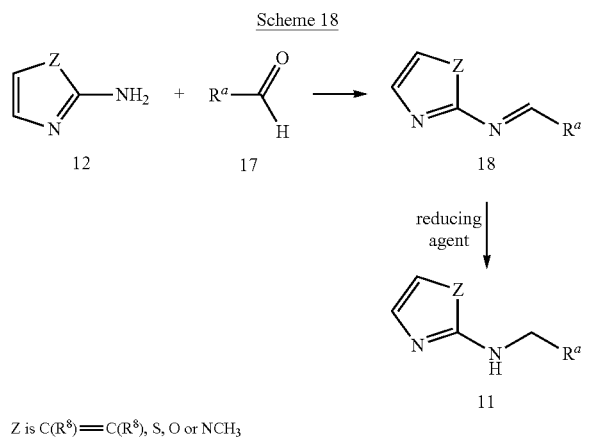

Scheme 18

Z is $C(R^8)=C(R^8)$, S, O or $NCH_3$

An alternative method for the preparation of compounds of Formula 11 is shown in Scheme 19. In the method of Scheme 19, compounds of Formula 12 are protected with suitable protecting groups such as, but not limited to, tert-butoxycarbonyl, acetyl or formyl to form the intermediate of Formula 20 wherein PG is a protecting group. The compound of Formula 20 is then alkylated with an appropriate reagent of Formula 21 (wherein $R^a$ is the subset of $R^2$ substituents containing a terminal $CH_2$ group and $X^5$ is a leaving group such as a halogen) to give an intermediate of Formula 22. The protecting group is removed to provide a compound of Formula 11. Conditions for the formation and removal of protecting groups on an amine function are known in the literature (see, for example, Greene, T. W.; Wuts, P. G. M. *Protective Groups in Organic Synthesis,* 2nd ed.; Wiley: New York, 1991).

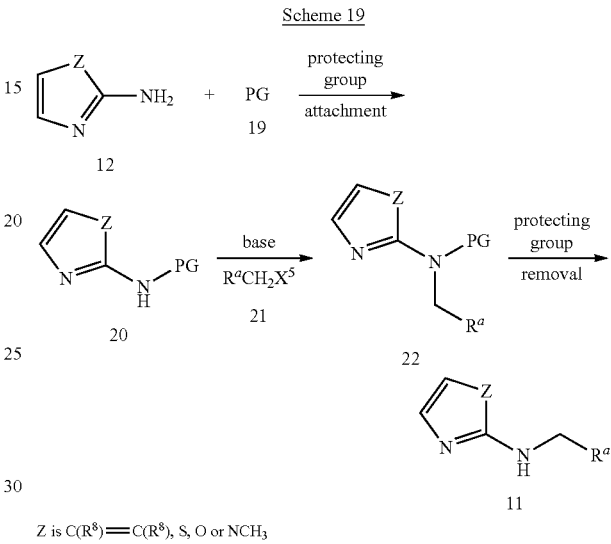

Scheme 19

Z is $C(R^8)=C(R^8)$, S, O or $NCH_3$

Compounds of Formula 1 wherein X and/or Y are S can be prepared from corresponding compounds of Formula 1a by general methods known in the art involving treatment with thionating reagents such as $P_4S_{10}$ or Lawessen's Reagent (2,4-bis-(4-methoxyphenyl)-1,3-dithia-2,4-diphosphetane 2,4-disulfide). Alternatively, malonic acids of Formula 3a can be treated with $P_2S_6(CH_3)_2$ as described in *J. Am. Chem. Soc.* 1988, 110 (4), 1316-1318. The resulting malonic acid sulfur derivatives can then be used to prepare the compounds of Formula 1 wherein X and/or Y are S by the method of Scheme 1.

Schemes 1 through 19 illustrate methods to prepare compounds of Formula 1 having a variety of substituents noted for $R^1$, $R^2$, $R^3$ and $R^4$. Compounds of Formula 1 having $R^1$, $R^2$, $R^3$ and $R^4$ substituents other than those particularly noted for Schemes 1 through 19 can be prepared by general methods known in the art of synthetic organic chemistry, including methods analogous to those described for Schemes 1 to 19.

Examples of intermediates useful in the preparation of compounds of this invention are shown in Tables I-1 through I-19. The following abbreviations are used in the Tables which follow: Me means methyl, Et means ethyl and C(O)O (2,4,6-trichlorophenyl) means

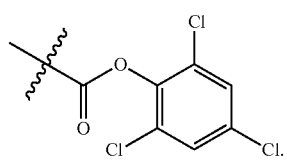 [SMILES: *C(=O)Oc1c(Cl)cc(Cl)cc1Cl]

TABLE I-1

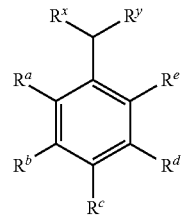

$R^x$ is C(O)OH and $R^y$ is H

| $R^a$ | $R^b$ | $R^c$ | $R^d$ | $R^e$ |
|---|---|---|---|---|
| H | H | H | H | H |
| F | H | H | H | H |
| H | F | H | H | H |
| H | H | F | H | H |
| OMe | H | H | H | H |
| H | OMe | H | H | H |
| H | H | OMe | H | H |
| F | F | H | H | H |
| F | H | F | H | H |
| F | H | H | F | H |
| F | H | H | H | F |
| Cl | H | H | H | H |
| H | Cl | H | H | H |
| H | H | Cl | H | H |
| H | Br | H | H | H |
| H | I | H | H | H |
| H | Cl | H | Cl | H |
| H | Cl | H | Br | H |
| H | Cl | H | OCF$_3$ | H |
| H | Cl | H | CF$_3$ | H |
| H | Br | H | Br | H |
| H | Br | H | OCF$_3$ | H |
| H | Br | H | CF$_3$ | H |
| H | H | cyano | H | H |
| F | H | cyano | H | H |
| H | OCF$_3$ | H | H | H |
| H | CF$_3$ | H | H | H |
| H | SCF$_3$ | H | H | H |
| F | H | H | Cl | H |
| F | H | H | Br | H |
| F | H | H | OCF$_3$ | H |
| F | H | H | CF$_3$ | H |
| F | H | H | OMe | H |
| F | H | H | SCF$_3$ | H |
| Cl | H | H | OCF$_3$ | H |
| Cl | H | H | CF$_3$ | H |
| H | H | H | SF$_5$ | H |
| Cl | H | H | SF$_5$ | H |
| H | OCF$_2$H | H | H | H |
| H | H | OCF$_2$H | H | H |
| F | F | H | F | H |
| F | H | F | H | F |
| F | H | F | F | H |
| F | F | F | H | H |
| H | OMe | H | OMe | H |
| F | OMe | H | H | H |
| OMe | H | H | Cl | H |
| OMe | H | H | Br | H |
| OMe | H | H | OCF$_3$ | H |
| OMe | H | H | CF$_3$ | H |
| H | CF$_3$ | H | CF$_3$ | H |
| Me | H | H | H | H |
| H | Me | H | H | H |
| H | H | Me | H | H |
| H | 6-fluoro-3-pyridinyl | H | H | H |
| H | 6-chloro-3-pyridinyl | H | H | H |
| H | 6-bromo-3-pyridinyl | H | H | H |
| H | 6-trifluoromethyl-3-pyridinyl | H | H | H |
| H | 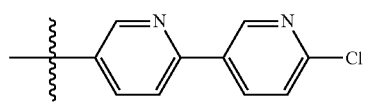 | H | H | H |

TABLE I-1-continued

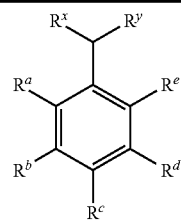

$R^x$ is C(O)OH and $R^y$ is H

| $R^a$ | $R^b$ | $R^c$ | $R^d$ | $R^e$ |
|---|---|---|---|---|
| H | 6-fluoro-3-pyridinyl | H | OMe | H |
| H | 6-chloro-3-pyridinyl | H | OMe | H |
| H | 6-bromo-3-pyridinyl | H | OMe | H |
| H | 6-trifluoromethyl-3-pyridinyl | H | OMe | H |
| H | 6-fluoro-3-pyridinyl | H | $CF_3$ | H |
| H | 6-chloro-3-pyridinyl | H | $CF_3$ | H |
| H | 6-bromo-3-pyridinyl | H | $CF_3$ | H |
| H | 6-trifluoromethyl-3-pyridinyl | H | $CF_3$ | H |
| H | 6-fluoro-3-pyridinyl | H | Br | H |
| H | 6-chloro-3-pyridinyl | H | Br | H |
| H | 6-bromo-3-pyridinyl | H | Br | H |
| H | 6-trifluoromethyl-3-pyridinyl | H | Br | H |
| H | 6-fluoro-3-pyridinyl | H | Cl | H |
| H | 6-chloro-3-pyridinyl | H | Cl | H |
| H | 6-bromo-3-pyridinyl | H | Cl | H |
| H | 6-trifluoromethyl-3-pyridinyl | H | Cl | H |
| H | 6-fluoro-3-pyridinyl | OMe | H | H |
| H | 6-chloro-3-pyridinyl | OMe | H | H |
| H | 6-bromo-3-pyridinyl | OMe | H | H |
| H | 6-trifluoromethyl-3-pyridinyl | OMe | H | H |
| H | 6-fluoro-3-pyridinyl | F | H | H |
| H | 6-chloro-3-pyridinyl | F | H | H |
| H | 6-bromo-3-pyridinyl | F | H | H |
| H | 6-trifluoromethyl-3-pyridinyl | F | H | H |
| $SCF_3$ | H | H | Cl | H |
| $SCF_3$ | H | H | Br | H |
| $SCF_3$ | H | H | $OCF_3$ | H |
| $SCF_3$ | H | H | $CF_3$ | H |
| $SCF_3$ | H | H | $SCF_3$ | H |
| $SCF_3$ | H | H | 6-trifluoromethyl-3-pyridinyl | H |
| $SCF_3$ | H | H | 6-fluoro-3-pyridinyl | H |
| $SCF_3$ | H | H | 6-chloro-3-pyridinyl | H |
| $SCF_3$ | H | H | 6-bromo-3-pyridinyl | H |

TABLE I-2

Table I-2 is constructed the same as Table I-1, except that $R^x$ is C(O)OMe and $R^y$ is H.

TABLE I-3

Table I-3 is constructed the same as Table I-1, except that $R^x$ is C(O)OEt and $R^y$ is H.

TABLE I-4

Table I-4 is constructed the same as Table I-1, except that $R^x$ is C(O)OH and $R^y$ is C(O)OH.

TABLE I-5

Table I-5 is constructed the same as Table I-1, except that $R^x$ is C(O)OH and $R^y$ is C(O)OMe.

TABLE I-6

Table I-6 is constructed the same as Table I-1, except that $R^x$ is C(O)OH and $R^y$ is C(O)OEt.

TABLE I-7

Table I-7 is constructed the same as Table I-1, except that $R^x$ is C(O)OH and $R^y$ is $C(O)OC(CH_3)_3$.

TABLE I-8

Table I-8 is constructed the same as Table I-1, except that $R^x$ is C(O)Cl and $R^y$ is C(O)Cl.

TABLE I-9

Table I-9 is constructed the same as Table I-1, except that $R^x$ is C(O)OMe and $R^y$ is C(O)OMe.

TABLE I-10

Table I-10 is constructed the same as Table I-1, except that $R^x$ is C(O)OEt and $R^y$ is C(O)OEt.

TABLE I-11

Table I-11 is constructed the same as Table I-1, except that $R^x$ is $C(O)OC(CH_3)_3$ and $R^y$ is $C(O)OC(CH_3)_3$.

TABLE I-12

Table I-12 is constructed the same as Table I-1, except that $R^x$ is C(O)O(2,4,6-trichlorophenyl) and $R^y$ is C(O)O(2,4,6-trichlorophenyl).

TABLE I-12a

Table I-12a is constructed the same as Table I-1, except that $R^x$ is H and $R^y$ is $C(O)OC(CH_3)_3$.

TABLE I-13

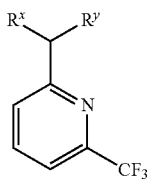

| $R^x$ | $R^y$ |
|---|---|
| H | C(O)OH |
| H | C(O)OMe |
| H | C(O)OEt |
| C(O)OH | C(O)OH |
| C(O)Cl | C(O)Cl |
| C(O)O(2,4,6-trichlorophenyl) | C(O)O(2,4,6-trichlorophenyl) |
| H | $C(O)OC(CH_3)_3$ |
| C(O)OMe | C(O)OMe |
| C(O)OEt | C(O)OEt |
| $C(O)OC(CH_3)_3$ | $C(O)OC(CH_3)_3$ |
| C(O)OH | C(O)OMe |
| C(O)OH | C(O)OEt |
| C(O)OH | $C(O)OC(CH_3)_3$ |

TABLE I-14

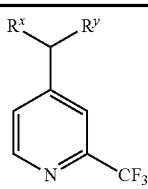

| $R^x$ | $R^y$ |
|---|---|
| H | C(O)OH |
| H | C(O)OMe |
| H | C(O)OEt |
| C(O)OH | C(O)OH |
| C(O)Cl | C(O)Cl |
| C(O)O(2,4,6-trichlorophenyl) | C(O)O(2,4,6-trichlorophenyl) |
| H | $C(O)OC(CH_3)_3$ |
| C(O)OMe | C(O)OMe |
| C(O)OEt | C(O)OEt |
| $C(O)OC(CH_3)_3$ | $C(O)OC(CH_3)_3$ |
| C(O)OH | C(O)OMe |
| C(O)OH | C(O)OEt |
| C(O)OH | $C(O)OC(CH_3)_3$ |

TABLE I-15

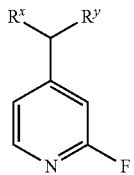

| $R^x$ | $R^y$ |
|---|---|
| H | C(O)OH |
| H | C(O)OMe |
| H | C(O)OEt |
| C(O)OH | C(O)OH |
| C(O)Cl | C(O)Cl |
| C(O)O(2,4,6-trichlorophenyl) | C(O)O(2,4,6-trichlorophenyl) |
| H | $C(O)OC(CH_3)_3$ |
| C(O)OMe | C(O)OMe |
| C(O)OEt | C(O)OEt |
| $C(O)OC(CH_3)_3$ | $C(O)OC(CH_3)_3$ |
| C(O)OH | C(O)OMe |
| C(O)OH | C(O)OEt |
| C(O)OH | $C(O)OC(CH_3)_3$ |

TABLE I-16

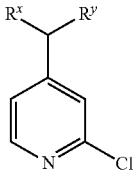

| $R^x$ | $R^y$ |
|---|---|
| H | C(O)OH |
| H | C(O)OMe |
| H | C(O)OEt |
| C(O)OH | C(O)OH |
| C(O)Cl | C(O)Cl |
| C(O)O(2,4,6-trichlorophenyl) | C(O)O(2,4,6-trichlorophenyl) |
| H | $C(O)OC(CH_3)_3$ |
| C(O)OMe | C(O)OMe |
| C(O)OEt | C(O)OEt |
| $C(O)OC(CH_3)_3$ | $C(O)OC(CH_3)_3$ |
| C(O)OH | C(O)OMe |
| C(O)OH | C(O)OEt |
| C(O)OH | $C(O)OC(CH_3)_3$ |

TABLE I-17

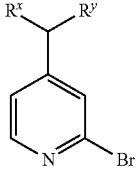

| $R^x$ | $R^y$ |
|---|---|
| H | C(O)OH |
| H | C(O)OMe |
| H | C(O)OEt |
| C(O)OH | C(O)OH |
| C(O)Cl | C(O)Cl |
| C(O)O(2,4,6-trichlorophenyl) | C(O)O(2,4,6-trichlorophenyl) |
| H | $C(O)OC(CH_3)_3$ |
| C(O)OMe | C(O)OMe |
| C(O)OEt | C(O)OEt |
| $C(O)OC(CH_3)_3$ | $C(O)OC(CH_3)_3$ |

TABLE I-17-continued

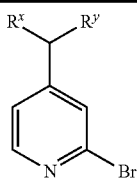

| $R^x$ | $R^y$ |
|---|---|
| C(O)OH | C(O)OMe |
| C(O)OH | C(O)OEt |
| C(O)OH | C(O)OC(CH$_3$)$_3$ |

TABLE I-18

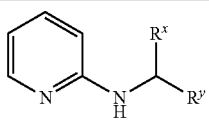

| $R^x$ | $R^y$ |
|---|---|
| H | CF$_3$ |
| Me | CF$_3$ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | CH$_2$CHFCF$_2$Cl |
| Me | CH$_2$CHFCF$_2$Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-bromo-5-thiazolyl |
| Me | 2-bromo-5-thiazolyl |
| H | 3-methyl-5-isoxazolyl |
| Me | 3-methyl-5-isoxazolyl |

TABLE I-19

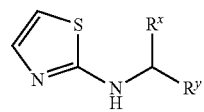

| $R^x$ | $R^y$ |
|---|---|
| H | CF$_3$ |
| Me | CF$_3$ |
| H | Et |
| Me | Et |
| H | 3-pyridinyl |
| Me | 3-pyridinyl |
| H | 6-fluoro-3-pyridinyl |

TABLE I-19-continued

| $R^x$ | $R^y$ |
|---|---|
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | CH$_2$CHFCF$_2$Cl |
| Me | CH$_2$CHFCF$_2$Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-bromo-5-thiazolyl |
| Me | 2-bromo-5-thiazolyl |
| H | 3-methyl-5-isoxazolyl |
| Me | 3-methyl-5-isoxazolyl |

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Ambient or room temperature is defined as about 20-25° C. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "dd" means doublet of doublets, "ddd" means doublet of doublet of doublets, "t" means triplet, "m" means multiplet, and "br s" means broad singlet. For mass spectral data, the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$).

Synthesis Example 1

Preparation of 2-hydroxy-4-oxo-3-phenyl-1-(2,2,2-trifluoroethyl)-4H-pyrido[1,2-a]-pyrimidinium inner salt A mixture of diethyl phenylmalonate (0.62 g, 2.7 mmol) and N-(2,2,2-trifluoroethyl)-2-pyridinamine (0.87 g, 2.7 mmol, prepared by the method of Bissell, E. R.; Swanslger, R. W. *J. Chem. Eng. Data*. 1981, 26, 234-235) was heated to 180° C. for 2 h. After cooling, the reaction mixture was purified by chromatography on silica gel by elution with ethyl acetate to provide the title compound (compound number 7), a compound of this invention, as a yellow solid (45 mg).

$^1$H NMR (CDCl$_3$) δ 9.61 (dd, 1H), 8.17 (ddd, 1H), 7.74 (d, 2H), 7.55 (d, 1H), 7.45 (t, 1H), 7.39 (m, 2H), 7.21-7.25 (m, 1H), 5.10 (br s, 2H).

Synthesis Example 2

Preparation of 1-[(2-chloro-5-thiazolyl)methyl]-2-hydroxy-4-oxo-4H-pyrido[1,2-a]-pyrimidinium inner salt and 1-[(2-chloro-5-thiazolyl)methyl]-2-hydroxy-4-oxo-3-(2,2,2-trifluoroacetyl)-4H-pyrido[1,2-a]pyrimidinium inner salt Step A: Preparation of 1,1-dimethylethyl N-[(2-chloro-5-thiazolyl)methyl]-N-2-pyridinylcarbamate (alternatively named 2-chlorothiazol-5-ylmethyl)pyridin-2-yl-carbamic acid t-butyl ester)

Sodium hydride in mineral oil (60%, 2.22 g, 55.6 mmol) was added portionwise to a solution of 1,1-dimethylethyl N-2-pyridinylcarbamate (9.0 g, 46.3 mmol, prepared by the method of Krein, D. M.; Lowary, T. L. *J. Org. Chem*. 2002, 67, 4965-4967) in N,N-dimethylformamide (40 mL) in a round bottom flask cooled to 0° C. in an ice/water bath. The suspension was stirred vigorously for an additional 30 min, followed by the addition of 2-chloro-5-(chloromethyl)thiazole (7.4 g, 55.6 mmol). The reaction mixture was gradually warmed to room temperature and stirred for 16-24 h. Water (200 mL) was then added, and the reaction mixture was extracted three times with 50 mL of ethyl acetate. The combined organic extracts were washed four times with 20 mL of water, dried over Na$_2$SO$_4$, and concentrated under reduced pressure. The resulting residue was purified by chromatography on silica gel by elution with ethyl acetate/hexane to provide the title compound as an amber oil (9.3 g).

$^1$H NMR (CDCl$_3$) δ 8.40 (d, 1H), 7.78 (d, 1H), 7.64 (t, 1H), 7.49 (s, 1H), 7.03 (t, 1H), 5.18 (s, 2H), 1.54 (s, 9H).

Step B: Preparation of N-[(chloro-5-thiazolyl)methyl]-2-pyridinamine (alternatively named (2-chlorothiazol-5-ylmethyl)-pyridin-2-yl-amine)

Trifluoroacetic acid (13.2 mL, 171 mmol) was added to a solution of 1,1-dimethylethyl N-[(2-chloro-5-thiazolyl)methyl]-N-2-pyridinylcarbamate (i.e. the product of Step A) (9.3 g, 28.5 mmol) in dichloromethane:water (60 mL:8 mL) in a round bottom flask, and the mixture was stirred for 66 h. The reaction mixture was then cooled to 0° C. and neutralized with 3 M NaOH to approximately pH 12 before being extracted twice with 100 mL of ethyl acetate. The organic layers were combined, dried over Na$_2$SO$_4$, and concentrated under reduced pressure to provide the title compound as a tan solid (5.0 g).

$^1$H NMR (CDCl$_3$) δ 8.19 (d, 1H), 7.43 (m, 2H), 7.65 (t, 1H), 6.42 (d, 1H), 4.80 (s, NH), 4.67 (d, 2H).

Step C: Preparation of 1-[(2-chloro-5-thiazolyl)methyl]-2-hydroxy-4-oxo-4H-pyrido[1,2-a]pyrimidinium inner salt A solution of dicyclohexylcarbodiimide (1.0 M in dichloromethane, 26.6 mL, 26.6 mmol) was added to a solution of N-[(chloro-5-thiazolyl)methyl]-2-pyridinamine (i.e. the product of Step B) (3.0 g, 13.3 mmol) and malonic acid (1.38 g, 13.3 mmol) in dichloromethane (30 mL) in a round bottom flask. The reaction mixture was stirred at room temperature for 16-24 h. The reaction mixture was then filtered through a pad of Celite® diatomaceaus filter aid, and the filtration cake was washed with dichloromethane. The combined organic phases were concentrated under reduced pressure, and the resulting residue was purified by chromatography on silica gel by elution with ethyl acetate/hexane to provide the title compound (compound number 125), a compound of this invention, as a pale yellow solid (2.90 g).

$^1$H NMR (CD$_3$S(O)CD$_3$) δ 9.20 (d, 1H), 8.36 (t, 1H), 8.11 (d, 1H), 7.95 (s, 1H), 7.52 (t, 1H), 5.56 (s, 2H), 4.98 (s, 1H).

Step D: Preparation of 1-[(2-chloro-5-thiazolyl)methyl]-2-hydroxy-4-oxo-3-(2,2,2-trifluoroacetyl)-4H-pyrido[1,2-a]pyrimidinium inner salt 1-[(2-Chloro-5-thiazolyl)methyl]-2-hydroxy-4-oxo-4H-pyrido[1,2-a]pyrimidinium inner salt (i.e. the product of Step C) (300 mg, 1.02 mmol), 1,4-diazabicyclo[2.2.2]octane (11.5 mg, 0.102 mmol), and trifluoroacetic anhydride (0.14 mL, 1.02 mmol) were dissolved in N-methyl-2-pyrrolidinone (3 mL), and the reaction mixture was stirred at room temperature for 1 h. The mixture was diluted with dichloromethane (30 mL), washed with water (10 mL), saturated aqueous sodium bicarbonate (10 mL) and water (10 mL×4 times), concentrated and triturated with diethyl ether to yield the title compound (compound number 702), a compound of this invention, as a solid (98 mg).

$^1$H NMR (CD$_3$COCD$_3$) δ 9.38 (d, 1H), 8.58 (t, 1H), 8.22 (d, 1H), 7.94 (s, 1H), 7.70 (t, 1H), 5.71 (br s, 2H).

Synthesis Example 3

Preparation of 1-[(6-chloro-3-pyridinyl)methyl]-3-[2-fluoro-5-(trifluoromethoxy)phenyl]-2-hydroxy-4-oxo-4H-pyrido[1,2-a]pyrimidinium inner salt, 1-[(6-chloro-3-pyridinyl)methyl]-2-hydroxy-4-oxo-4H-pyrido[1,2-a]pyrimidinium inner salt and 1-[(6-chloro-3-pyridinyl)methyl]-2-hydroxy-3-iodo-4-oxo-4H-pyrido[1,2-a]pyrimidinium inner salt Step A: Preparation of 6-chloro-N-2-pyridinyl-3-pyridinemethanamine A mixture of 2-fluoropyridine (1.4 g, 15 mmol) and 6-chloro-3-pyridinemethanamine (alternatively named 5-aminomethyl-2-chloropyridine) (2.55 g, 18 mmol) in N-methylpyrrolidinone (5 mL) was heated at 230° C. in a microwave reactor for 30 min. This reaction was repeated four times using the same amounts of starting materials for each repetition. All five of the reaction mixtures were then poured into saturated aqueous sodium bicarbonate solution and extracted into ethyl acetate. The organic layer was washed with saturated aqueous sodium bicarbonate solution, dried over $Na_2SO_4$, and concentrated under reduced pressure. The crude product was then purified by chromatography on silica gel using 10% ethyl acetate in hexanes as the eluent to provide the title compound as an oil (5.1 g).

$^1$H NMR (CDCl$_3$) δ 8.38 (s, 1H), 8.1 (m, 1H), 7.67 (d, 1H), 7.42 (dd, 1H), 7.28 (d, 1H), 6.63 (m, 1H), 6.38 (d, 1H), 4.88 (s, 1H), 4.56 (d, 2H).

Step B: Preparation of 1-[(6-chloro-3-pyridinyl)methyl]-2-hydroxy-4-oxo-4H-pyrido[1,2-a]pyrimidinium inner salt A solution of dicyclohexylcarbodiimide (4.12 g, 20 mmol in 10 mL of dichloromethane) was added to a solution of 6-chloro-N-2-pyridinyl-3-pyridinemethanamine (i.e. the product of Step A) (2.19 g, 10 mmol) and malonic acid (1.04 g, 10 mmol) in dichloromethane (10 mL) in a round bottom flask. The reaction mixture was stirred at room temperature for 16-24 h. The reaction mixture was then filtered, and the filtration cake was washed with diethyl ether. The filtrate was concentrated under reduced pressure, and the resulting residue was washed with methanol to provide the title compound (compound number 611), a compound of this invention, as a pale yellow solid (2.54 g).

$^1$H NMR (acetone-d$_6$) δ 9.32 (d, 1H), 8.52 (s, 1H), 8.29 (dd, 1H), 7.79 (m, 2H), 7.52 (t, 1H), 7.42 (d, 1H), 5.63 (s, 2H), 5.03 (s, 1H).

Step C: Preparation of 1-[(6-chloro-3-pyridinyl)methyl]-2-hydroxy-3-iodo-4-oxo-4H-pyrido[1,2-a]pyrimidinium inner salt N-iodosuccinimide (1.12 g, 5 mmol) was added to a solution of 1-[(6-chloro-3-pyridinyl)methyl]-2-hydroxy-4-oxo-4H-pyrido[1,2-a]pyrimidinium inner salt (i.e. the product of Step B) (1.4 g, 5 mmol) in N,N-dimethylformamide (10 mL) and stirred for 5 min. Water was added, and the mixture was extracted with dichloromethane. The combined organic phases were washed repeatedly with water, dried over $Na_2SO_4$, and concentrated under reduced pressure. The resulting crude product (compound number 118), a compound of this invention, (1.8 g) was used in the next step without further purification.

$^1$H NMR (CDCl$_3$) δ 9.49 (d, 1H), 8.45 (d, 1H), 8.12 (dd, 1H), 7.40 (m, 2H), 7.32 (d, 1H), 5.50 (s, 2H).

Step D: Preparation of 1-[(6-chloro-3-pyridinyl)methyl]-3-[2-fluoro-5-(trifluoromethoxy)phenyl]-2-hydroxy-4-oxo-4H-pyrido[1,2-a]pyrimidinium inner salt 1-[(6-Chloro-3-pyridinyl)methyl]-2-hydroxy-3-iodo-4-oxo-4H-pyrido[1,2-a]pyrimidinium inner salt (i.e. the product of Step C) (206 mg, 0.5 mmol), 2-fluoro-5-(trifluoromethoxy)benzeneboronic acid (224 mg, 1 mmol) and bis(triphenylphosphino)-palladium dichloride (35 mg, 0.005 mmol) were dissolved in dioxane (2 mL). Aqueous sodium carbonate solution (2 N, 1 mL) was added, and the reaction mixture was heated in a microwave reactor for 10 min at 160° C. The cooled reaction mixture was poured directly onto a silica gel column and eluted successively with hexanes, 30% ethyl acetate in hexanes, 50% ethyl acetate in hexanes, and finally ethyl acetate to yield the title compound (compound number 58), a compound of this invention, as a solid (20 mg).

$^1$H NMR (CDCl$_3$) δ 9.53 (d, 1H), 8.49 (s, 1H), 8.11 (dd, 1H), 7.69 (d, 1H), 7.50 (d, 1H), 7.41 (m, 2H), 7.34 (d, 1H), 7.16 (d, 2H), 7.58 (br s, 2H).

Synthesis Example 4

Preparation of 2-hydroxy-4-oxo-3-phenyl-1-(2-propen-1-yl)-4H-pyrido[1,2-a]pyrimidinium inner salt N-2-propen-1-yl-2-pyridinamine (670 mg, 5 mmol) and 1,3-bis(2,4,6-trichlorophenyl) 2-phenylpropanedioate (3.0 g, 6 mmol) were dissolved in dioxane (3 mL) and heated at 60° C. for 15 min. The reaction mixture was then poured onto a silica gel column, which was eluted with 50% ethyl acetate in hexanes to provide the title compound (compound number 122), a compound of this invention, as a solid (14 mg).

$^1$H NMR (CDCl$_3$) δ 9.52 (d, 1H), 8.04 (dd, 1H), 7.76 (d, 1H), 7.2-7.45 (m, 6H), 5.95 (m, 1H), 5.34 (d, 1H), 5.30 (d, 1H), 5.01 (d, 2H).

Synthesis Example 5

Preparation of 2-hydroxy-4-oxo-3-phenyl-1-(2,2,2-trifluoroethyl)-4H-pyrido[1,2-a]-pyrimidinium inner salt Step A: Preparation of N-(2,2,2-trifluoroethyl)-2-pyridinamine A mixture of 2-fluoropyridine (2.00 g, 20.6 mmol) and 2,2,2-trifluoroethylamine hydrogen chloride (5.00 g, 36.9 mmol) was heated to 220° C. for 30 min in a microwave reactor. The same reaction was repeated 5 times. The reaction mixtures from all 6 reactions were cooled, combined and diluted with ethyl acetate (150 mL). The organic mixture was neutralized by washing with saturated aqueous sodium bicarbonate, water (30 mL) and brine (30 mL). The organic phase was dried over $Na_2SO_4$ and concentrated, and the resulting residue was purified by chromatography on silica gel using 80% ethyl acetate/hexane as eluant to give the title compound as a white solid (17.0 g).

$^1$H NMR (CDCl$_3$) δ 8.15 (d, 1H), 7.45 (dd, 1H), 6.69 (dd, 1H), 6.49 (d, 1H), 4.58 (br s, 1H), 4.11 (q, 2H).

Step B: Preparation of 1,3-bis(2,4,6-trichlorophenyl) 2-phenylpropanedioate

To a slurry of phenylmalonic acid (5.00 g, 27.8 mmol) in dichloromethane (7 mL) at room temperature was added a drop of N,N-dimethylformamide, followed by the dropwise addition of oxalyl chloride (9.09 g, 71.6 mmol) at such a rate to keep gas evolution under control. The reaction mixture was stirred for an additional hour at room temperature, during which time the reaction mixture clarified. 2,4,6-Trichlorophenol (15 g, 76 mmol) was added, and the reaction mixture was stirred at room temperature for 18 h. The reaction mixture was concentrated under vacuum, and methanol (100 mL) was added to the residue, which resulted in precipitation of a large amount of solid. The solid was collected by filtration, rinsed with methanol (80 mL) and air dried to give the title product as a white solid (13 g).

$^1$H NMR (CDCl$_3$) δ 7.64-7.62 (m, 2H), 7.46-7.43 (m, 3H), 7.36 (s, 4H), 5.32 (s, 1H).

Step C: Preparation of 2-hydroxy-4-oxo-3-phenyl-1-(2,2,2-trifluoroethyl)-4H-pyrido[1,2-a]-pyrimidinium inner salt A solution of N-(2,2,2-trifluoroethyl)-2-pyridinamine (i.e. the product of Step A) (2.00 g, 11.4 mmol) and 1,3-bis(2,4,6-trichlorophenyl) 2-phenylpropanedioate (i.e. the product of Step B) (6.40 g, 11.9 mmol) in toluene (40 mL) was refluxed for 1 h. The reaction mixture was cooled in an ice-water bath with stirring for 2 h. The solid that precipitated was collected by filtration, rinsed with diethyl ether and air dried to give the title compound (compound number 7), a compound of this invention, as a yellow solid (3.44 g).

$^1$H NMR (CD$_3$S(O)CD$_3$) δ 9.37 (d, 1H), 8.42 (m, 1H), 8.11 (d, 1H), 7.66 (d, 2H), 7.61 (m, 1H), 7.32 (t, 2H), 7.18 (t, 1H), 5.35 (q, 2H).

Synthesis Example 6

Preparation of 8-[(6-chloro-3-pyridinyl)methyl]-7-hydroxy-5-oxo-6-[3-(trifluoromethoxy)phenyl]-5H-thiazolo[3,2-a]pyrimidinium inner salt Step A: Preparation of N-[(6-chloro-3-pyridinyl)methylene]-2-thiazolamine 2-Aminothiazole (0.75 g, 7.5 mmol) was added to 2-chloropyridine-5-carboxaldehyde (1.0 g, 7.1 mmol) in dichloromethane (25 mL) at room temperature. The suspension was stirred an additional 10 min and then concentrated to dryness under vacuum. The resulting residue was heated to 90 °C. on a rotory evaporator with a non-returning bump trap to facilitate water removal. After 30 min the resultant yellow solid was checked by NMR to verify reaction completion (by disappearance of the characteristic aldehyde peak at 10.10 ppm (s, 1H)). The title compound was obtained as a yellow solid (1.55 g) and used in the next step without further purification.

$^1$H NMR (CDCl$_3$) δ 9.10 (s, 1H), 8.84 (d, 1H), 8.35-8.32 (dd, 1H), 7.72-7.70 (d, 1H), 7.48-7.46 (d, 1H), 7.32-7.31 (d, 1H).

Step B: Preparation of 6-chloro-N-2-thiazolyl-3-pyridinemethanamine

N-[(6-chloro-3-pyridinyl)methylene]-2-thiazolamine (i.e. the product of Step A) (0.55 g, 2.46 mmol) was added portionwise to a stirred excess of sodium borohydride (0.45 g, 11.8 mmol) in methanol (30 mL). Additional portions of sodium borohydride (2×1 equivalent) were added during the addition of the imine to maintain an exothermic reaction. After addition was complete, the reaction mixture was allowed to stir for 5 min at ambient temperature. The excess reducing agent was quenched by adding glacial acetic acid until gas evolution ceased. The clear reaction mixture was concentrated, and the resulting residue was partitioned between saturated aqueous sodium carbonate and ethyl acetate. The aqueous phase was extracted with ethyl acetate (3×30 mL), and the combined organic phases were washed with brine, dried (MgSO$_4$) and concentrated to give the title compound as a tan powder (0.55 g).

$^1$H NMR (CDCl$_3$) δ 8.39 (d, 1H), 7.71-7.68 (dd, 1H), 7.30-7.28 (d, 1H), 6.98 (d, 1H), 6.48 (d, 1H), 4.48 (s, 2H).

Step C: Preparation of 2-[3-(trifluoromethoxy)phenyl]propanedioic acid

Diethyl 3-trifluoromethoxyphenylmalonate (3.00 g, 9.38 mmol) was stirred in an aqueous sodium hydroxide solution (15 g, 20% by weight) at 65° C. for 10 min. The reaction mixture was then cooled in an ice bath, and ice (7 g) was added to the reaction mixture, followed by 6 N hydrochloric acid to adjust the pH to about 2. The aqueous mixture was saturated with sodium chloride and extracted with ethyl acetate three times. The combined organic phases were dried (MgSO$_4$) and concentrated to give a solid, which was triturated with a mixture of 33% diethyl ether/hexane to give the title compound as a white solid (2.24 g).

$^1$H NMR (CD$_3$C(O)CD$_3$) δ 11.51 (br s, 2H), 7.54-7.51 (m, 3H), 7.35-7.30 (m, 1H), 4.91 (s, 1H).

Step D: Preparation of 8-[(6-chloro-3-pyridinyl)methyl]-7-hydroxy-5-oxo-6-[3-(trifluoromethoxy)phenyl]-5H-thiazolo[3,2-a]pyrimidinium inner salt Oxalyl chloride (1.0 mL, 11 mmol) was added dropwise at ambient temperature to a slurry of 2-[3-(trifluoromethoxy)phenyl]propanedioic acid (i.e. the product of Step C) (0.17 g, 0.66 mmol) in dichloromethane (0.2 mL) containing a catalytic amount of N,N-dimethylformamide. The reaction mixture was stirred for an additional 10 min during which time gas evolution ceased. The reaction mixture was briefly concentrated under vacuum at ambient temperature. The resultant oil was taken up in dichloromethane (2 mL) and added to a solution of 6-chloro-N-2-thiazolyl-3-pyridinemethanamine (i.e. the product of Step B) (0.23 g, 1.02 mmol) and triethylamine (0.40 g, 3.37 mmol) in dichloromethane (4 mL) at 0° C. After stirring for 15 min, the reaction mixture was concentrated, and the resultant residue was purified by chromatography on silica gel using 50-100% ethyl acetate/hexane as eluant to give the title compound (compound number 138), a compound of this invention, as a solid (0.19 g).

$^1$H NMR (CDCl$_3$) δ 8.50 (s, 1H), 8.25 (d, 1H), 7.87 (d, 1H), 7.75 (d, 1H), 7.70 (s, 1H), 7.41-7.35 (m, 2H), 7.08 (d, 1H), 7.03 (d, 1H), 5.29 (s, 2H).

Synthesis Example 7

Preparation of 2-hydroxy-4-oxo-1-propyl-3-[2-(trifluoromethyl)phenyl]-4H-pyrido[1,2-a]-pyrimidinium inner salt and 2-hydroxy-4-oxo-1-propyl-4H-pyrido[1,2-a]-pyrimidinium inner salt Step A: Preparation of 2-hydroxy-4-oxo-1-propyl-4H-pyrido[1,2-a]-pyrimidinium inner salt A solution of dicyclohexylcarbodiimide (15.63 g in 45 mL of dichloromethane, 75.76 mmol) was added to a solution of N-propyl-2-aminopyridine (5.16 g, 37.8 mmol) and malonic acid (3.94 g, 37.8 mmol) in dichloromethane (90 mL). The reaction mixture was stirred at room temperature for 24 h. The reaction mixture was then filtered through a pad of Celite®, and the filtration cake was washed with dichloromethane. The combined organic phases were concentrated, and the resulting residue was purified by chromatography on silica gel using 50-100% ethyl acetate/hexane as eluant to give the title compound (compound number 609), a compound of this invention, as a pale yellow solid (5.60 g).

$^1$H NMR (CDCl$_3$) δ 9.40 (d, 1H), 8.15 (t, 1H), 7.42 (d, 1H), 7.30 (t, 1H), 5.38 (s, 1H), 4.24 (t, 2H), 1.88 (m, 2H), 1.06 (t, 3H).

Step B: Preparation of 2-hydroxy-4-oxo-1-propyl-3-[2-(trifluoromethyl)phenyl]-4H-pyrido[1,2-a]-pyrimidinium inner salt 2-Hydroxy-4-oxo-1-propyl-4H-pyrido[1,2-a]pyrimidinium inner salt (i.e. the product of Step A) (500 mg, 2.45 mmol), 1-iodo-2-(trifluoromethyl)benzene (0.34 mL, 2.45 mmol), copper iodide (46.6 mg, 0.245 mmol), 1,10-phenanthroline (44.1 mg, 0.245 mmol) and cesium carbonate (798 mg, 2.45 mmol) were combined in N,N-dimethylformamide (3 mL). The reaction mixture was heated at 118° C. under nitrogen for 24 h. The reaction mixture was cooled and concentrated, and the resulting residue was purified by reverse phase liquid chromatography on a XTerra® C18 OBD column (5 micron particle, 30×100 mm, manufactured by Waters) using a gradient of 30-90% (1:1 acetonitrile/methanol)/water to provide the title compound (compound number 308), a compound of this invention, as a solid (20 mg).

$^1$H NMR (CDCl$_3$) δ 9.44 (d, 1H), 8.13 (t, 1H), 7.75 (d, 1H), 7.58 (t, 1H), 7.42-7.52 (m, 3H), 7.35 (t, 1H), 4.42-4.35 (m, 1H), 4.24-4.18 (m, 1H), 1.80 (q, 2H), 1.05 (t, 3H).

Synthesis Example 8

Preparation of 2-hydroxy-3-iodo-1-[[2-(3-methoxyphenyl)-5-thiazolyl]methyl]-4-oxo-4H-pyrido[1,2-a]-pyrimidinium inner salt Step A: Preparation of 1-[(2-chloro-5-thiazolyl)methyl]-2-hydroxy-3-iodo-4-oxo-4H-pyrido[1,2-a]-pyrimidinium inner salt N-iodosuccinimide (2.19 g, 9.76 mmol) was added to a solution of 1-[(2-chloro-5-thiazolyl)methyl]-2-hydroxy-4-oxo-4H-pyrido[1,2-a]pyrimidinium inner salt (i.e. the product of Example 2, Step C) (2.9 g, 9.76 mmol) in N,N-dimethylformamide (30 mL), and the mixture was stirred for 5 min. Water was added, and the mixture was extracted with ethyl acetate. The combined organic phases were washed several times with water, dried over Na$_2$SO$_4$ and concentrated under reduced pressure. The resulting crude product (compound number 608) (1.2 g), a compound of this invention, was used in the next step without further purification.

$^1$H NMR (CD$_3$COCD$_3$) δ 9.36 (d, 1H), 8.45 (t, 1H), 8.20 (d, 1H), 7.94 (s, 1H), 7.58 (t, 1H), 5.77 (s, 2H).

Step B: Preparation of 2-hydroxy-3-iodo-1-[[2-(3-methoxyphenyl)-5-thiazolyl]methyl]-4-oxo-4H-pyrido[1,2-a]-pyrimidinium inner salt 1-[(2-chloro-5-thiazolyl)methyl]-2-hydroxy-3-iodo-4-oxo-4H-pyrido[1,2-a]-pyrimidinium inner salt (i.e. the product of Step A) (250 mg, 0.59 mmol), 3-methoxybenzeneboronic acid (89 mg, 0.59 mmol) and bis(triphenylphosphine)-palladium(II) dichloride (20 mg, 0.029 mmol) were dissolved in dioxane (3 mL). Aqueous sodium carbonate solution (2 N, 1 mL) was added, and the reaction mixture was heated in a microwave reactor for 15 min at 150° C. The cooled reaction mixture was poured directly onto a silica gel column and eluted successively with hexanes, 30% ethyl acetate in hexanes, 50% ethyl acetate in hexanes, and finally ethyl acetate to yield the title compound (compound number 613), a compound of this invention, as a solid (35 mg).

$^1$H NMR (CD$_3$COCD$_3$) δ 9.38 (d, 1H), 8.43 (t, 1H), 8.20 (d, 1H), 8.13 (s, 1H), 7.58 (t, 1H), 7.50 (m, 2H), 7.39 (t, 1H), 7.02 (d, 1H), 5.88 (br s, 2H), 3.86 (s, 3H).

Synthesis Example 9

Preparation of 2-hydroxy-4-oxo-1-(2,2,2-trifluoroethyl)-3-[2,2,2-trifluoro-1-(methoxyimino)ethyl]-4H-pyrido[1,2-a]-pyrimidinium inner salt, 2-hydroxy-4-oxo-1-(2,2,2-trifluoroethyl)-4H-pyrido[1,2-a]-pyrimidinium inner salt and 2-hydroxy-4-oxo-3-(2,2,2-trifluoroacetyl)-1-(2,2,2-trifluoroethyl)-4H-pyrido[1,2-a]-pyrimidinium inner salt Step A: Preparation of 2-hydroxy-4-oxo-1-(2,2,2-trifluoroethyl)-4H-pyrido[1,2-a]-pyrimidinium inner salt A solution of dicyclohexylcarbodiimide (1.0 M in dichloromethane, 108 mL, 108 mmol) was added to a solution of N-(2,2,2-trifluoroethyl)-2-pyridinamine (i.e. the product of Example 5, Step A) (9.51 g, 54.0 mmol) and malonic acid (5.62 g, 54.0 mmol) in dichloromethane (190 mL). The reaction mixture was stirred at room temperature for 24 h. The reaction mixture was then filtered through a pad of Celite®, and the filtration cake washed with dichloromethane. The combined organic phases were concentrated under reduced pressure, and the resulting residue was purified by chromatography on silica gel using 50-100% ethyl acetate/hexane as eluant to give the title compound (compound number 610), a compound of this invention, as a pale yellow solid (7.0 g).

$^1$H NMR (CD$_3$S(O)CD$_3$) δ 9.22 (d, 1H), 8.42 (t, 1H), 8.11 (d, 1H), 7.59 (t, 1H), 5.25 (q, 2H), 4.96 (s, 1H).

Step B: Preparation of 2-hydroxy-4-oxo-3-(2,2,2-trifluoroacetyl)-1-(2,2,2-trifluoroethyl)-4H-pyrido[1,2-a]-pyrimidinium inner salt 2-Hydroxy-4-oxo-1-(2,2,2-trifluoroethyl)-4H-pyrido[1,2-a]-pyrimidinium inner salt (i.e. the product of Step A) (1.12 g, 4.57 mmol), 1,4-diazabicyclo[2.2.2]octane (132.0 mg, 1.12 mmol) and trifluoroacetic anhydride (1.50 mL, 10.92 mmol) were dissolved in 1-methyl-2-pyrrolidinone (10 mL), and the reaction mixture was stirred at room temperature for 18 h. The mixture was diluted with ethyl acetate (250 mL), washed with saturated aqueous sodium bicarbonate (150 mL) water (3×100 mL), and concentrated. The residue was triturated with diethyl ether to yield the title compound (compound number 711), a compound of this invention, as a solid (1.10 g).

$^1$H NMR (CD$_3$S(O)CD$_3$) δ 9.25 (d, 1H), 8.58 (t, 1H), 8.10 (d, 1H), 7.65 (t, 1H), 5.25 (q, 2H).

Step C: Preparation of 2-hydroxy-4-oxo-1-(2,2,2-trifluoroethyl)-3-[2,2,2-trifluoro-1-(methoxyimino)ethyl]-4H-pyrido[1,2-a]-pyrimidinium inner salt A solution of 2-hydroxy-4-oxo-3-(2,2,2-trifluoroacetyl)-1-(2,2,2-trifluoroethyl)-4H-pyrido[1,2-a]-pyrimidinium inner salt (i.e. the product of Step B) (75 mg, 0.22 mmol) and methoxyamine hydrochloride (62 mg, 0.74 mmol) in ethanol (7 mL) was refluxed for 3 h. The solvent was concentrated under vacuum, and ethyl acetate (60 mL) was added. The organic phase was washed successively with a solution of dilute sodium hydroxide (3 mL of 1 N NaOH and 30 mL water) and water (20 mL). The organic phase was then filtered through a Chem Elut™ cartridge (manufactured by Varian) prepacked with Celite® and concentrated to a crude oil. The resultant residue was purified by preparative thin layer chromatography on an Analtech Uniplate™ (20×20 cm, 2000 microns layer of silica gel) eluted with ethyl acetate to provide the title compound (compound number 637), a compound of this invention, as a thick oil (53 mg, 1:1 mixture of E and Z isomers).

$^1$H NMR (CDCl$_3$) δ 9.49 (d, 0.5H), 9.47 (d, 0.5H), 8.23 (t, 1H), 7.61 (d, 1H), 7.50 (m, 1H), 5.00 (m, 2H), 4.10 (s, 1.5H), 4.04 (s, 1.5H)

Synthesis Example 10

Preparation of 1-[(6-chloro-3-pyridinyl)methyl]-4-hydroxy-2-imino-3-(2-methoxyphenyl)-2H-pyrido[1,2-a]pyrimidinium inner salt

Step A: Preparation of phenyl α-cyano-2-methoxybenzeneacetate

To a slurry of sodium hydride (3.39 g of 60% in mineral oil, 84.9 mmol) in tetrahydrofuran (200 mL) at room temperature was added 2-(2-methoxyphenyl)acetonitrile (10.0 g, 67.9 mmol) dropwise. The reaction mixture was then heated to reflux and the gray suspension turned dark red over 30 min. Diphenyl carbonate (18.2 g, 84.9 mmol) was added portionwise, and the reaction suspension was heated at reflux for an additional 18 h. The reaction mixture was cooled, poured into 1 N HCl (200 mL) and extracted with ethyl acetate (3×200 mL). The organic phases were combined, dried over magnesium sulfate, filtered and concentrated onto Celite® under reduced pressure. The resultant residue was purified by chromatography on silica gel using 10-90% ethyl acetate/hexane as eluant to give the title compound as a light yellow solid (14.3 g).

$^1$H NMR (CD$_3$S(O)CD$_3$) δ 7.48-7.44 (m, 3H), 7.31 (t, 1H), 7.19-7.03 (m, 4H), 6.75 (d, 1H), 5.97 (s, 1H), 3.93 (s, 3H).

Step B: Preparation of 1-[(6-chloro-3-pyridinyl)methyl]-4-hydroxy-2-imino-3-(2-methoxyphenyl)-2H-pyrido[1,2-a]pyrimidinium inner salt To a solution containing 6-chloro-N-2-pyridinyl-3-pyridinemethanamine (0.82 g, 3.74 mmol) in xylene (100 mL) under nitrogen was added phenyl α-cyano-2-methoxybenzeneacetate (i.e. the product of Step A) (1.00 g, 3.74 mmol). The reaction mixture was heated to reflux for 24 h. The mixture was cooled, Celite® was added, and the xylene was evaporated under reduced pressure. The resultant residue was purified by chromatography on silica gel using a gradient of 100% ethyl acetate to 1% triethylamine/40% methanol/59% ethyl acetate as eluant to give the title compound (compound number 662), a compound of this invention, as a cream solid (4.7 mg). MS (AP+)=393.

$^1$H NMR (CD$_3$COCD$_3$) δ 8.47 (d, 1H), 8.28 (s, 1H), 7.83 (t, 1H), 7.76 (d, 1H), 7.38-7.27 (m, 5H), 6.94-6.88 (m, 2H), 5.71 (s, NH), 5.62 (s, 2H), 3.64 (s, 3H).

Synthesis Example 11

Preparation of 1-[(6-chloro-3-pyridinyl)methyl]-2-hydroxy-4-oxo-3-phenyl-4H-pyrido[1,2-a]pyrimidinium inner salt

Step A: Preparation of N-[(6-chloro-3-pyridinyl)methyl]-2-phenyl-N-(2-pyridinyl)malonamic acid ethyl ester 2-Phenylmalonic acid monoethyl ester was prepared following the procedure in *Journal of Organic Chemistry* 2000, 65, 5834-5836. 2-Phenylmalonic acid monoethyl ester (1.02 g, 5.0 mmol) was dissolved in anhydrous dichloromethane (10 mL), and oxalyl chloride (0.52 mL, 6.0 mmol) was added, followed by one drop of N,N-dimethylformamide. The reaction mixture was stirred for 30 min, then concentrated, redissolved in anhydrous dichloromethane (5 mL) and added to a solution of 6-chloro-N-2-pyridinyl-3-pyridinemethanamine (i.e. the product of Example 3, Step A) (1.1 g, 5.0 mmol) and triethyl amine (0.83 mL, 6.0 mmol) in anhydrous dichloromethane (5 mL) at 0° C. The stirred reaction mixture was allowed to warm to room temperature over 30 min. The reaction mixture was poured onto a silica gel cartridge (Bond Elute manufactured by Varian) and purified using a gradient of 0-50% ethyl acetate/hexanes. A mixture of desired product and starting amine was isolated (1.3 g of 33 mol % recovered amine/67 mol % desired product). 2-Phenylmalonic acid monoethyl ester (0.54 g, 2.6 mmol) was dissolved in anhydrous dichloromethane (3 mL), and oxalyl chloride (0.26 mL, 3.0 mmol) was added, followed by one drop of N,N-dimethylformamide. The reaction mixture was stirred until gas evolution ceased and then concentrated, redissolved in anhydrous dichloromethane (3 mL) and added to the mixture of recovered amine and desired product isolated previously. The reaction mixture was stirred for 30 min and then concentrated, and the crude residue was chromatographed as already described to give the title compound as a solid (0.9 g).

$^1$H NMR (CDCl$_3$) δ 8.50 (m, 1H), 8.18 (s, 1H), 7.60-7.75 (m, 2H), 7.2-7.3 (m, 5H), 7.13 (m, 2H), 6.87 (s, 1H), 5.13-4.88 (dd, 2H), 4.86 (s, 1H), 4.16 (m, 2H), 1.22 (t, 3H).

Step B: Preparation of 1-[(6-chloro-3-pyridinyl)methyl]-2-hydroxy-4-oxo-3-phenyl-4H-pyrido[1,2-a]pyrimidinium inner salt N-[(6-chloro-3-pyridinyl)methyl]-2-phenyl-N-(2-pyridinyl)malonamic acid ethyl ester (i.e. the product of Step A) (200 mg, 0.49 mmol) was added to tetralin (0.5 mL) and heated at 200° C. for 30 min. The reaction mixture was cooled and concentrated, and the resulting residue was purified by chromatography on silica gel using 50-100% ethyl acetate/hexane as eluant to give the title compound (compound number 59), a compound of this invention, as a solid (15 mg).

$^1$H NMR (CDCl$_3$) δ 9.55 (dd, 1H), 8.47 (d, 1H), 8.04 (m, 1H), 7.98 (d, 2H), 7.70 (dd, 1H), 7.2-7.4 (m, 6H), 5.58 (s, 2H).

By the procedures described herein together with methods known in the art, the following compounds of Tables 1 to 8 can be prepared. Abbreviations used in Tables 1 to 8 are shown below as X-1 through X-128 and Y-1 through Y-71.

| | |
|---|---|
| isopropyl | X-1 |
| isobutyl | X-2 |
| | X-3 |
| cyclopropyl | |
| | X-4 |
| cyclobutyl | |
| | X-5 |
| cyclopentyl | |
| | X-6 |
| cyclohexyl | |
| | X-7 |
| $CF_3$ | |
| | X-8 |
| $CH_2CF_3$ | |
| | X-9 |
| $C_2F_5$ | |

C(CF₃)₂F
1-naphthalenyl
2-naphthalenyl
4-fluoro-1-naphthalenyl
C(O)Me
C(O)CF₃
C(O)Ph
C(O)OMe
C(O)OEt
C(O)NHMe
C(O)NHPh
C(S)NHPh
C(O)NH(3-methoxyphenyl)
C(=NOEt)CF₃
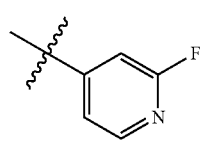
X-10
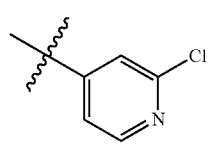
X-11
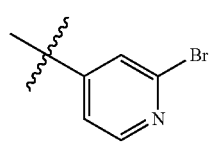
X-12
X-13
X-14
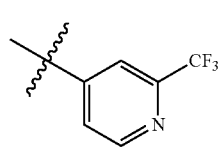
X-15
X-16
X-17
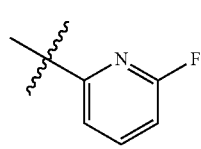
X-18
X-19
X-20
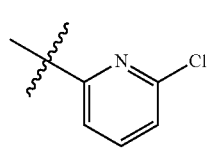
X-21
X-22
X-23
X-24
X-25
X-26
X-27
X-28
X-29
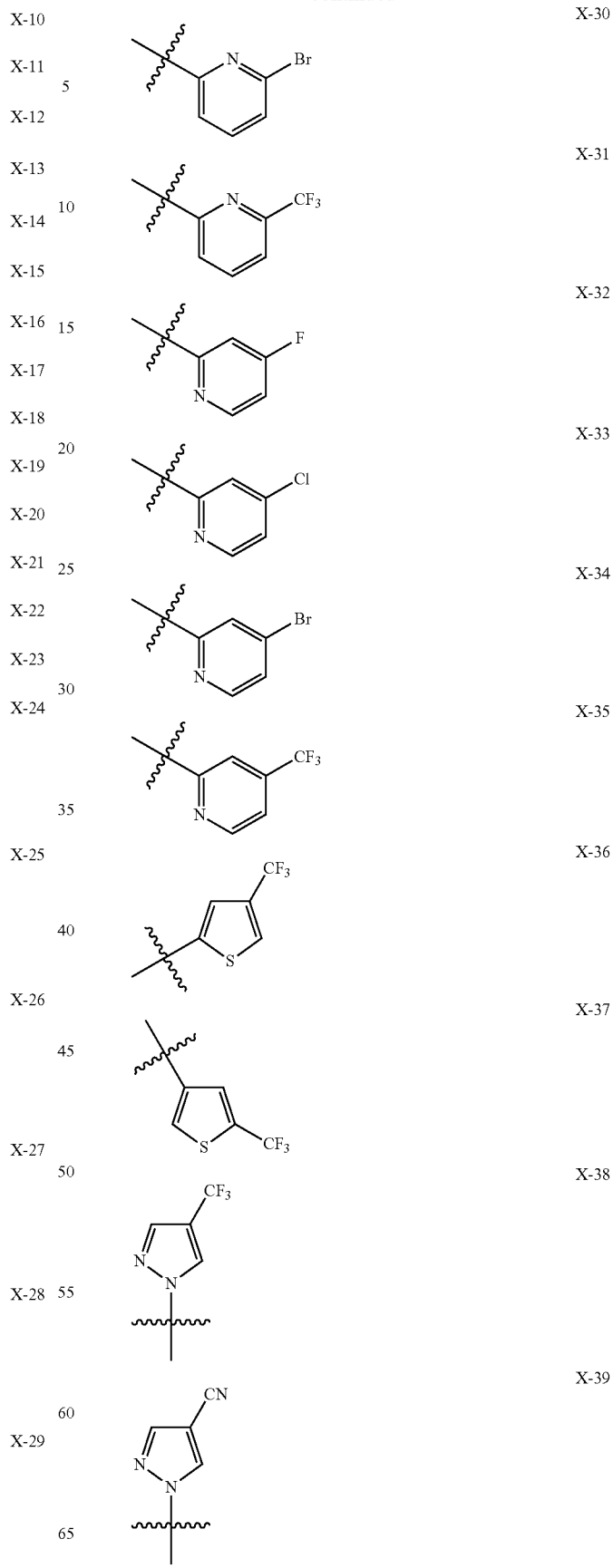
X-30
X-31
X-32
X-33
X-34
X-35
X-36
X-37
X-38
X-39

-continued

X-40 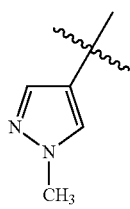

X-41 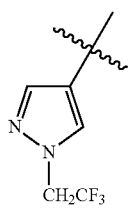

X-42 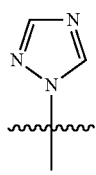

Abbreviations X-50 to X-128 pertain to the substituted phenyl ring as shown below. Blank entries in the table denote a hydrogen atom.

|  | $R^a$ | $R^b$ | $R^c$ | $R^d$ | $R^e$ |
|---|---|---|---|---|---|
| X-50 | F | | | | |
| X-51 | OMe | | | | |
| X-52 | Cl | | | | |
| X-53 | | F | | | |
| X-54 | | OMe | | | |
| X-55 | | Cl | | | |
| X-56 | | | F | | |
| X-57 | | | OMe | | |
| X-58 | | | Cl | | |
| X-59 | | | CF$_3$ | | |
| X-60 | | | OCF$_3$ | | |
| X-61 | | | SCF$_3$ | | |
| X-62 | | | SF$_5$ | | |
| X-63 | | | Br | | |
| X-64 | | | cyano | | |
| X-65 | F | | CF$_3$ | | |
| X-66 | F | | OCF$_3$ | | |
| X-67 | F | | SCF$_3$ | | |
| X-68 | F | | Br | | |
| X-69 | S(O)CF$_3$ | | | | |
| X-70 | | S(O)CF$_3$ | | | |
| X-71 | | | S(O)CF$_3$ | | |
| X-72 | Cl | | cyano | | |
| X-73 | Cl | | CF$_3$ | | |
| X-74 | Cl | | OCF$_3$ | | |
| X-75 | Cl | | SCF$_3$ | | |
| X-76 | Cl | | Br | | |
| X-77 | | Cl | | CF$_3$ | |
| X-78 | | Cl | | OCF$_3$ | |
| X-79 | | Cl | | SCF$_3$ | |
| X-80 | | Cl | | Br | |

-continued

|  | $R^a$ | $R^b$ | $R^c$ | $R^d$ | $R^e$ |
|---|---|---|---|---|---|
| X-81 | | Br | | CF$_3$ | |
| X-82 | | Br | | OCF$_3$ | |
| X-83 | | Br | | SCF$_3$ | |
| X-84 | | Br | | Br | |
| X-85 | F | | | CF$_3$ | |
| X-86 | F | | | OCF$_3$ | |
| X-87 | F | | | SCF$_3$ | |
| X-88 | F | | | Br | |
| X-89 | F | | | F | F |
| X-90 | F | | | F | F |
| X-91 | | F | | CF$_3$ | |
| X-92 | | F | | OCF$_3$ | |
| X-93 | F | CF$_3$ | | | |
| X-94 | F | OCF$_3$ | | | |
| X-95 | | F | | F | |
| X-96 | OCHF$_2$ | | | | |
| X-97 | | OCHF$_2$ | | | |
| X-98 | | | OCHF$_2$ | | |
| X-99 | SCHF$_2$ | | | | |
| X-100 | | SCHF$_2$ | | | |
| X-101 | | | SCHF$_2$ | | |
| X-102 | F | | F | | |
| X-103 | F | F | | | |
| X-104 | F | | | | F |
| X-105 | | CF$_3$ | | CF$_3$ | |
| X-106 | F | | | OMe | |
| X-107 | | OMe | | OMe | |
| X-108 | F | OMe | | | |
| X-109 | F | | | | OMe |
| X-110 | | OMe | | CF$_3$ | |
| X-111 | | OMe | | OCF$_3$ | |
| X-112 | | OMe | | Cl | |
| X-113 | | OMe | | Br | |
| X-114 | OMe | | | CF$_3$ | |
| X-115 | OMe | | | OCF$_3$ | |
| X-116 | OMe | | | Cl | |
| X-117 | OMe | | | Br | |
| X-118 | OMe | F | | | |
| X-119 | OMe | OMe | | | |
| X-120 | OMe | | | | F |

X-121 
[pyridine with F at 2-position, attached at 5-position]

X-122 
[pyridine with Cl at 2-position, attached at 5-position]

X-123 
[pyridine with Br at 2-position, attached at 5-position]

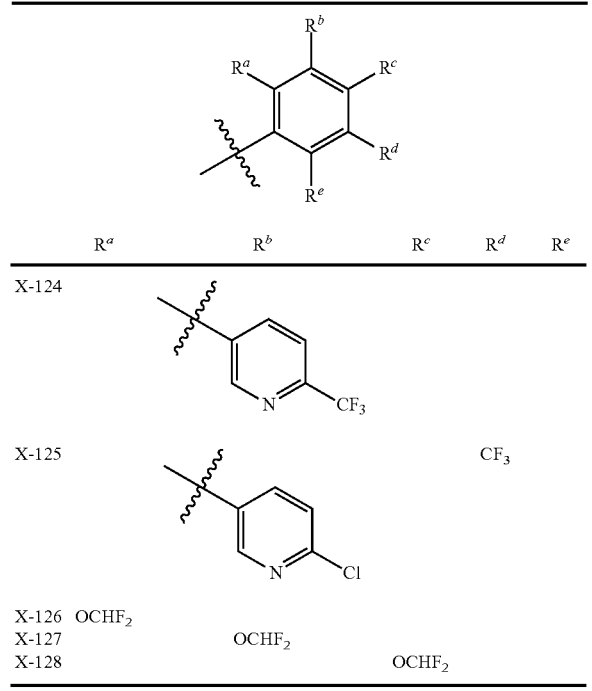
| | $R^a$ | $R^b$ | $R^c$ | $R^d$ | $R^e$ |
|---|---|---|---|---|---|
| X-124 | | 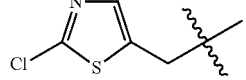 | | | |
| X-125 | | 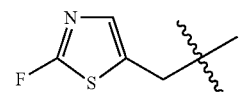 | CF₃ | | |
| X-126 | OCHF₂ | | | | |
| X-127 | | OCHF₂ | | | |
| X-128 | | | OCHF₂ | | |
| | | |
|---|---|---|
| methyl | Y-1 | |
| ethyl | Y-2 | |
| n-propyl | Y-3 | |
| n-butyl | Y-4 | |
| CHF₂ | Y-5 | |
| CH₂CH₂CF₃ | Y-6 | |
| CH₂CH₂CF₂Cl | Y-7 | |
| isopropyl | Y-8 | |
| s-butyl | Y-9 | |
| i-butyl | Y-10 | |
| CH₂CH₂OCH₃ | Y-11 | |
| CH₂C(O)OCH₃ | Y-12 | |
| CH₂CH₂SCH₃ | Y-13 | |
| CH₂CH₂S(O)CH₃ | Y-14 | |
| CH₂CH=CH₂ | Y-15 | |
| CH₂C≡CH | Y-16 | |
| cyclopropyl | Y-17 | |
| cyclobutyl | Y-18 | |
| CH₂CF₃ | Y-19 | |
| CH(CH₃)CF₃ | Y-20 | |
| CH₂CF₂CF₃ | Y-21 | |
| CH₂CH₂CHFCF₂Cl | Y-22 | |
| 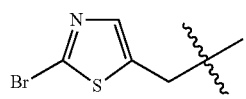 [SMILES: *Cc1cnc(Br)s1] | Y-30 | |
| 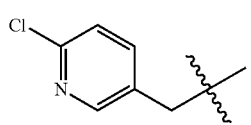 [SMILES: *Cc1ccc(Br)nc1] | Y-31 | |
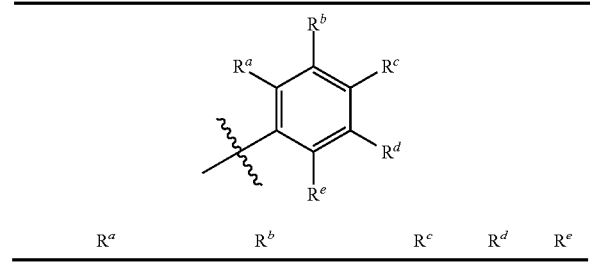
| | $R^a$ | $R^b$ | $R^c$ | $R^d$ | $R^e$ |
|---|---|---|---|---|---|
| Y-34 | | | | | 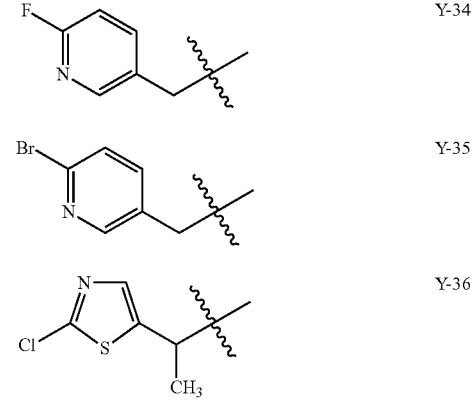 |
Y-32
Y-33
Y-35
Y-36
Y-37
Y-38
Y-39
Y-40
Y-41
Y-42
Y-43
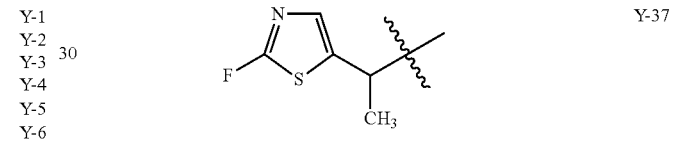
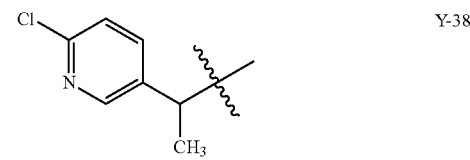
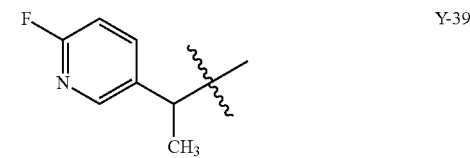
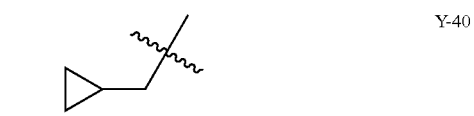
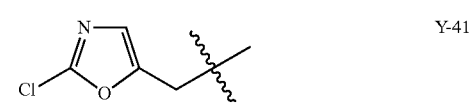
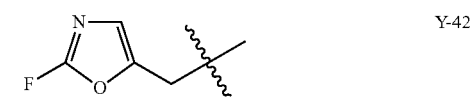
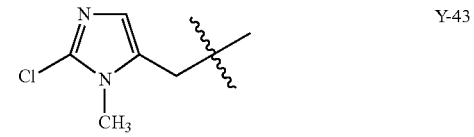

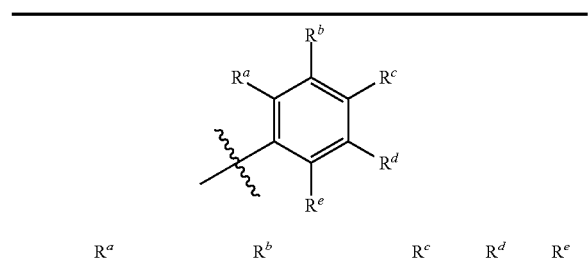
| $R^a$ | $R^b$ | $R^c$ | $R^d$ | $R^e$ | |
|---|---|---|---|---|---|
| | 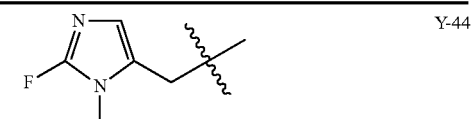 | | | | Y-44 |
| | 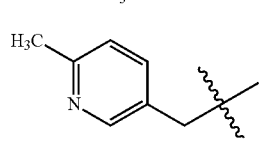 | | | | Y-45 |
| | 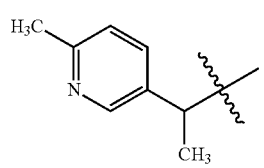 | | | | Y-46 |
| | 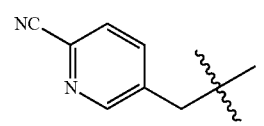 [SMILES: *Cc1ccc(C#N)nc1] | | | | Y-47 |
| | 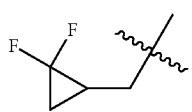 [SMILES: *CC1CC1(F)F] | | | | Y-48 |
| | 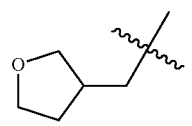 [SMILES: *CC1CCOC1] | | | | Y-49 |
| | 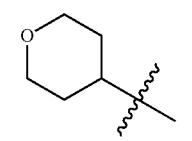 | | | | Y-50 |
| | 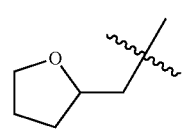 [SMILES: *CC1CCCO1] | | | | Y-51 |
| | 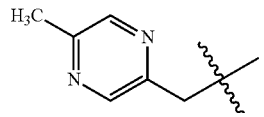 [SMILES: *Cc1cnc(C)cn1] | | | | Y-52 |
| | 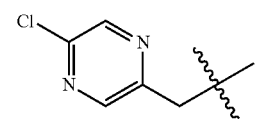 [SMILES: *Cc1cnc(Cl)cn1] | | | | Y-53 |
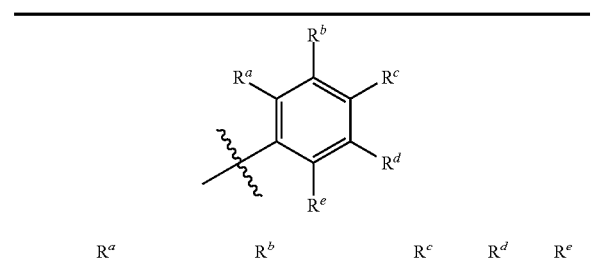
| $R^a$ | $R^b$ | $R^c$ | $R^d$ | $R^e$ | |
|---|---|---|---|---|---|
| | 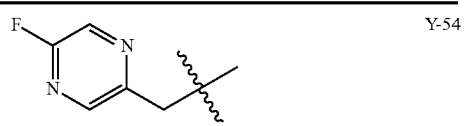 | | | | Y-54 |
| | 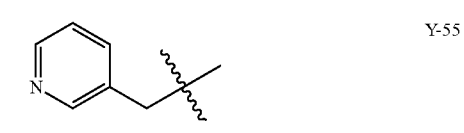 | | | | Y-55 |
| | 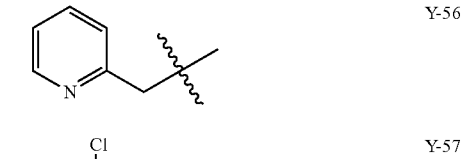 | | | | Y-56 |
| | 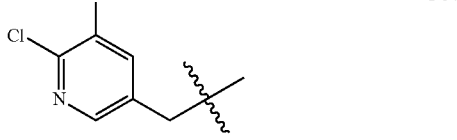 | | | | Y-57 |
| |  | | | | Y-58 |
| |  | | | | Y-59 |
| | 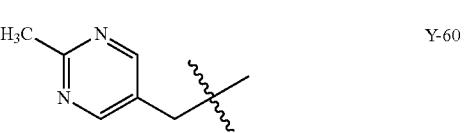 | | | | Y-60 |
| | 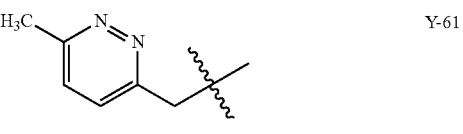 | | | | Y-61 |
| | 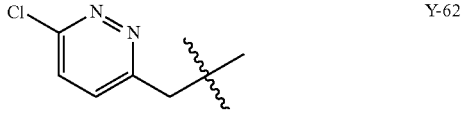 | | | | Y-62 |
| | 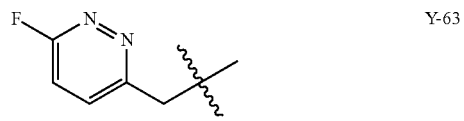 | | | | Y-63 |

83

-continued

| Rᵃ | Rᵇ | Rᶜ | Rᵈ | Rᵉ |
|---|---|---|---|---|
| | 4-(1-methylpyrazolyl)-CH₂-C(CH₃)- | | | Y-64 |
| | 4-(1-methylpyrazolyl)-CH(CH₃)- | | | Y-65 |
| | 5-thiazolyl-CH₂- | | | Y-66 |
| | 5-thiazolyl-CH(CH₃)- | | | Y-67 |
| | 2-methyl-5-thiazolyl-CH₂- | | | Y-68 |
| | 2-methyl-5-thiazolyl-CH(CH₃)- | | | Y-69 |
| | 5-oxazolyl-CH₂- | | | Y-70 |
| | 5-oxazolyl-CH(CH₃)- | | | Y-71 |

84

TABLE 1

[Structure: pyrido-pyrimidine N-oxide core with $R^1$ and $R^2$ substituents]

$R^1$ $R^2$ is Y-1

X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68
X-69
X-70
X-71
X-72
X-73

TABLE 1-continued

[Structure: pyrido-pyrimidine with O, R¹, N+, O-, R²]

R¹

X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128

R² is Y-2

X-1
X-2
X-3
X-4
X-5
X-6
X-7
X-8
X-9
X-10
X-11

TABLE 1-continued

[Structure: pyrido-pyrimidine with O, R¹, N+, O-, R²]

R¹

X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68
X-69
X-70
X-71
X-72
X-73
X-74
X-75
X-76
X-77
X-78
X-79
X-80
X-81
X-82
X-83
X-84
X-85
X-86

TABLE 1-continued

[Structure: pyrido-pyrimidine with R¹ and R² (N⁺—O⁻)]

R¹

| X-87 |
|---|
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |

R² is Y-3

| X-1 |
|---|
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |

TABLE 1-continued

[Structure: pyrido-pyrimidine with R¹ and R² (N⁺—O⁻)]

R¹

| X-25 |
|---|
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |

TABLE 1-continued
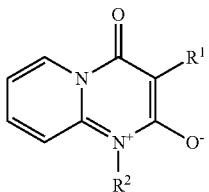
R¹
| | |
|---|---|
| X-100 | |
| X-101 | |
| X-102 | |
| X-103 | |
| X-104 | |
| X-105 | |
| X-106 | |
| X-107 | |
| X-108 | |
| X-109 | |
| X-110 | |
| X-111 | |
| X-112 | |
| X-113 | |
| X-114 | |
| X-115 | |
| X-116 | |
| X-117 | |
| X-118 | |
| X-119 | |
| X-120 | |
| X-121 | |
| X-122 | |
| X-123 | |
| X-124 | |
| X-125 | |
| X-126 | |
| X-127 | |
| X-128 | |
| R² is Y-4 | |
| X-1 | |
| X-2 | |
| X-3 | |
| X-4 | |
| X-5 | |
| X-6 | |
| X-7 | |
| X-8 | |
| X-9 | |
| X-10 | |
| X-11 | |
| X-12 | |
| X-13 | |
| X-14 | |
| X-15 | |
| X-16 | |
| X-17 | |
| X-18 | |
| X-19 | |
| X-20 | |
| X-21 | |
| X-22 | |
| X-23 | |
| X-24 | |
| X-25 | |
| X-26 | |
| X-27 | |
| X-28 | |
| X-29 | |
| X-30 | |
| X-31 | |
| X-32 | |
| X-33 | |
| X-34 | |
| X-35 | |
| X-36 | |
| X-37 | |
TABLE 1-continued
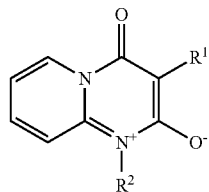
R¹
| | |
|---|---|
| X-38 | |
| X-39 | |
| X-40 | |
| X-41 | |
| X-42 | |
| X-50 | |
| X-51 | |
| X-52 | |
| X-53 | |
| X-54 | |
| X-55 | |
| X-56 | |
| X-57 | |
| X-58 | |
| X-59 | |
| X-60 | |
| X-61 | |
| X-62 | |
| X-63 | |
| X-64 | |
| X-65 | |
| X-66 | |
| X-67 | |
| X-68 | |
| X-69 | |
| X-70 | |
| X-71 | |
| X-72 | |
| X-73 | |
| X-74 | |
| X-75 | |
| X-76 | |
| X-77 | |
| X-78 | |
| X-79 | |
| X-80 | |
| X-81 | |
| X-82 | |
| X-83 | |
| X-84 | |
| X-85 | |
| X-86 | |
| X-87 | |
| X-88 | |
| X-89 | |
| X-90 | |
| X-91 | |
| X-92 | |
| X-93 | |
| X-94 | |
| X-95 | |
| X-96 | |
| X-97 | |
| X-98 | |
| X-99 | |
| X-100 | |
| X-101 | |
| X-102 | |
| X-103 | |
| X-104 | |
| X-105 | |
| X-106 | |
| X-107 | |
| X-108 | |
| X-109 | |
| X-110 | |
| X-111 | |
| X-112 | |

TABLE 1-continued

[Structure: pyrido-pyrimidine with R¹ and R² substituents]

R¹

X-113
X-114
X-115
X-116
X-117
X-118
X-119
X-120
X-121
X-122
X-123
X-124
X-125
X-126
X-127
X-128

R² is Y-5

X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57

TABLE 1-continued

[Structure: pyrido-pyrimidine with R¹ and R² substituents]

R¹

X-58
X-59
X-60
X-61
X-62
X-63
X-64
X-65
X-66
X-67
X-68
X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125

TABLE 1-continued

[Structure: pyrido-pyrimidine with O, R¹, N+, O-, R²]

R¹

| |
|---|
| X-126 |
| X-127 |
| X-128 |
| R² is Y-6 |
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |

TABLE 1-continued

[Structure: pyrido-pyrimidine with O, R¹, N+, O-, R²]

R¹

| |
|---|
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
| R² is Y-7 |
| X-1 |
| X-2 |
| X-3 |
| X-4 |
| X-5 |
| X-6 |
| X-7 |
| X-8 |

TABLE 1-continued
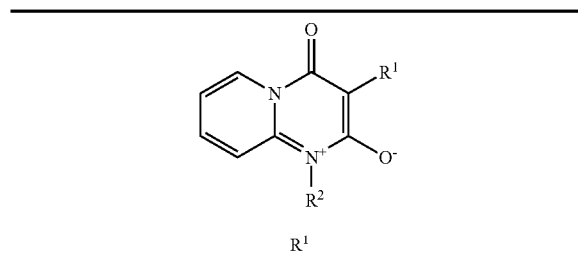
R$^1$
| |
|---|
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
TABLE 1-continued
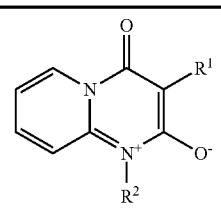
R$^1$
| |
|---|
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R$^2$ is Y-8
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |

TABLE 1-continued
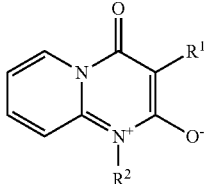
R[1]
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68
X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
TABLE 1-continued
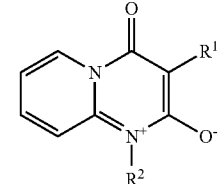
R[1]
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128
R[2] is Y-9
X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34

TABLE 1-continued
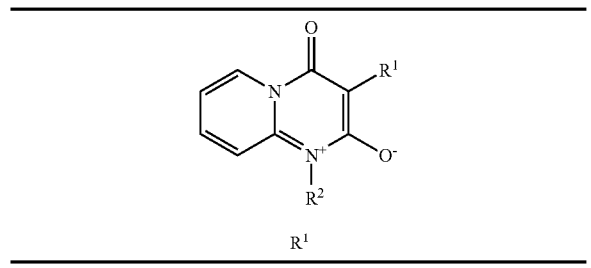
R$^1$
| | |
|---|---|
| X-35 | |
| X-36 | |
| X-37 | |
| X-38 | |
| X-39 | |
| X-40 | |
| X-41 | |
| X-42 | |
| X-50 | |
| X-51 | |
| X-52 | |
| X-53 | |
| X-54 | |
| X-55 | |
| X-56 | |
| X-57 | |
| X-58 | |
| X-59 | |
| X-60 | |
| X-61 | |
| X-62 | |
| X-63 | |
| X-64 | |
| X-65 | |
| X-66 | |
| X-67 | |
| X-68 | |
| X-69 | |
| X-70 | |
| X-71 | |
| X-72 | |
| X-73 | |
| X-74 | |
| X-75 | |
| X-76 | |
| X-77 | |
| X-78 | |
| X-79 | |
| X-80 | |
| X-81 | |
| X-82 | |
| X-83 | |
| X-84 | |
| X-85 | |
| X-86 | |
| X-87 | |
| X-88 | |
| X-89 | |
| X-90 | |
| X-91 | |
| X-92 | |
| X-93 | |
| X-94 | |
| X-95 | |
| X-96 | |
| X-97 | |
| X-98 | |
| X-99 | |
| X-100 | |
| X-101 | |
| X-102 | |
| X-103 | |
| X-104 | |
| X-105 | |
| X-106 | |
| X-107 | |
| X-108 | |
| X-109 | |
TABLE 1-continued
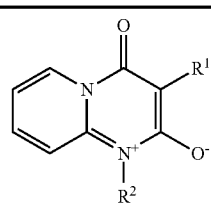
R$^1$
| |
|---|
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R$^2$ is Y-10
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |

TABLE 1-continued

|  |
|---|
| (structure: pyrido-pyrimidinone with R¹ and R²-N⁺-O⁻) |

| R¹ |
|---|
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |

TABLE 1-continued

|  |
|---|
| (structure: pyrido-pyrimidinone with R¹ and R²-N⁺-O⁻) |

| R¹ |
|---|
| X-123 |
| X-124 |
| X-125 |
| X-126 |
| X-127 |
| X-128 |

| R² is Y-11 |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |

TABLE 1-continued
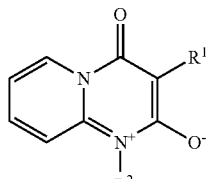
R¹
| |
|---|
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R² is Y-12
| |
|---|
| X-1 |
| X-2 |
| X-3 |
| X-4 |
| X-5 |
TABLE 1-continued
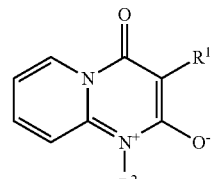
R¹
| |
|---|
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |

TABLE 1-continued
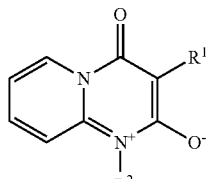
R$^1$
| | |
|---|---|
| X-81 | |
| X-82 | |
| X-83 | |
| X-84 | |
| X-85 | |
| X-86 | |
| X-87 | |
| X-88 | |
| X-89 | |
| X-90 | |
| X-91 | |
| X-92 | |
| X-93 | |
| X-94 | |
| X-95 | |
| X-96 | |
| X-97 | |
| X-98 | |
| X-99 | |
| X-100 | |
| X-101 | |
| X-102 | |
| X-103 | |
| X-104 | |
| X-105 | |
| X-106 | |
| X-107 | |
| X-108 | |
| X-109 | |
| X-110 | |
| X-111 | |
| X-112 | |
| X-113 | |
| X-114 | |
| X-115 | |
| X-116 | |
| X-117 | |
| X-118 | |
| X-119 | |
| X-120 | |
| X-121 | |
| X-122 | |
| X-123 | |
| X-124 | |
| X-125 | |
| X-126 | |
| X-127 | |
| X-128 | |
R$^2$ is Y-13
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
TABLE 1-continued
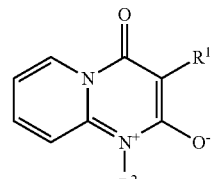
R$^1$
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |

TABLE 1-continued
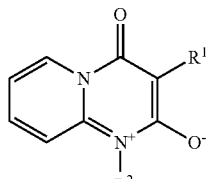
R¹
| | |
|---|---|
| X-94 | |
| X-95 | |
| X-96 | |
| X-97 | |
| X-98 | |
| X-99 | |
| X-100 | |
| X-101 | |
| X-102 | |
| X-103 | |
| X-104 | |
| X-105 | |
| X-106 | |
| X-107 | |
| X-108 | |
| X-109 | |
| X-110 | |
| X-111 | |
| X-112 | |
| X-113 | |
| X-114 | |
| X-115 | |
| X-116 | |
| X-117 | |
| X-118 | |
| X-119 | |
| X-120 | |
| X-121 | |
| X-122 | |
| X-123 | |
| X-124 | |
| X-125 | |
| X-126 | |
| X-127 | |
| X-128 | |
R² is Y-14
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
TABLE 1-continued
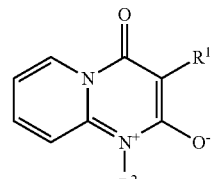
R¹
| |
|---|
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |

TABLE 1-continued
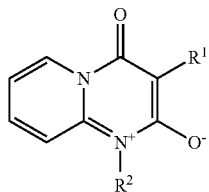
R$^1$
X-107
X-108
X-109
X-110
X-111
X-112
X-113
X-114
X-115
X-116
X-117
X-118
X-119
X-120
X-121
X-122
X-123
X-124
X-125
X-126
X-127
X-128
R$^2$ is Y-15
X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
TABLE 1-continued
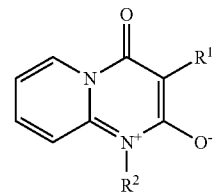
R$^1$
X-52
X-53
X-54
X-55
X-56
X-57
X-58
X-59
X-60
X-61
X-62
X-63
X-64
X-65
X-66
X-67
X-68
X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119

TABLE 1-continued
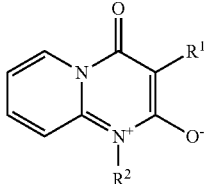
R¹
| |
|---|
| X-120 |
| X-121 |
| X-122 |
| X-123 |
| X-124 |
| X-125 |
| X-126 |
| X-127 |
| X-128 |
R² is Y-16
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
TABLE 1-continued
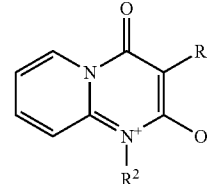
R¹
| |
|---|
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R² is Y-17
| |
|---|
| X-1 |
| X-2 |

TABLE 1-continued
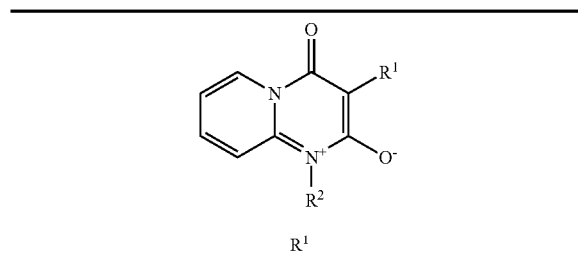
| R$^1$ |
|---|
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
TABLE 1-continued
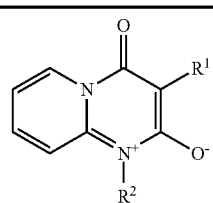
| R$^1$ |
|---|
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R$^2$ is Y-18
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |

TABLE 1-continued
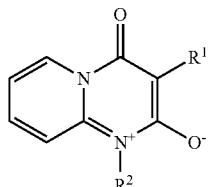
| R¹ |
|---|
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
TABLE 1-continued
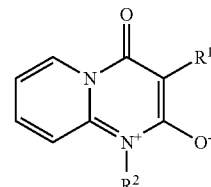
| R¹ |
|---|
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R² is Y-19
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |

TABLE 1-continued

[Structure: pyrido-pyrimidine with R¹ at 3-position, O⁻ at 2-position on N⁺, R² on N⁺]

R¹

| |
|---|
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |

TABLE 1-continued

[Structure: pyrido-pyrimidine with R¹ at 3-position, O⁻ at 2-position on N⁺, R² on N⁺]

R¹

| |
|---|
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |

R² is Y-20

| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |

TABLE 1-continued
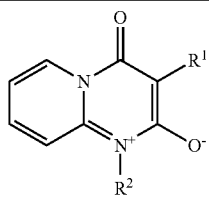
R$^1$
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
TABLE 1-continued
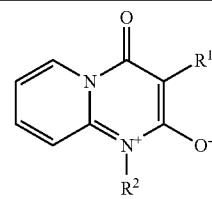
R$^1$
| X-117 |
| X-118 |
| X-119 |
| X-120 |
| X-121 |
| X-122 |
| X-123 |
| X-124 |
| X-125 |
| X-126 |
| X-127 |
| X-128 |
R$^2$ is Y-21
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |

TABLE 1-continued (structure: pyrido-pyrimidinone with R¹ and R² substituents, N⁺–O⁻)

R¹

| |
|---|
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |

TABLE 1-continued (structure: pyrido-pyrimidinone with R¹ and R² substituents, N⁺–O⁻)

R¹

| |
|---|
| X-127 |
| X-128 |

R² is Y-22

| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |

TABLE 1-continued

![structure with R¹ and R²]

R¹

X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128
R² is Y-30

X-1
X-2
X-3
X-4
X-5
X-6
X-7
X-8
X-9

TABLE 1-continued

![structure with R¹ and R²]

R¹

X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68
X-69
X-70
X-71
X-72
X-73
X-74
X-75
X-76
X-77
X-78
X-79
X-80
X-81
X-82
X-83
X-84

TABLE 1-continued

[Structure: pyrido-pyrimidinone with R¹ and R² (N⁺-O⁻)]

R¹

| |
|---|
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |

R² is Y-31

| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |

TABLE 1-continued

[Structure: pyrido-pyrimidinone with R¹ and R² (N⁺-O⁻)]

R¹

| |
|---|
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |

TABLE 1-continued
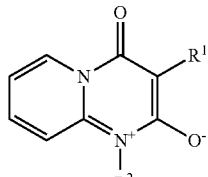
R¹
- X-98
- X-99
- X-100
- X-101
- X-102
- X-103
- X-104
- X-105
- X-106
- X-107
- X-108
- X-109
- X-110
- X-111
- X-112
- X-113
- X-114
- X-115
- X-116
- X-117
- X-118
- X-119
- X-120
- X-121
- X-122
- X-123
- X-124
- X-125
- X-126
- X-127
- X-128
R² is Y-32
- X-1
- X-2
- X-3
- X-4
- X-5
- X-6
- X-7
- X-8
- X-9
- X-10
- X-11
- X-12
- X-13
- X-14
- X-15
- X-16
- X-17
- X-18
- X-19
- X-20
- X-21
- X-22
- X-23
- X-24
- X-25
- X-26
- X-27
- X-28
- X-29
- X-30
- X-31
- X-32
- X-33
- X-34
- X-35
TABLE 1-continued
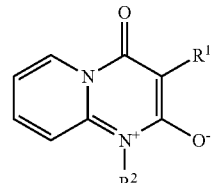
R¹
- X-36
- X-37
- X-38
- X-39
- X-40
- X-41
- X-42
- X-50
- X-51
- X-52
- X-53
- X-54
- X-55
- X-56
- X-57
- X-58
- X-59
- X-60
- X-61
- X-62
- X-63
- X-64
- X-65
- X-66
- X-67
- X-68
- X-69
- X-70
- X-71
- X-72
- X-73
- X-74
- X-75
- X-76
- X-77
- X-78
- X-79
- X-80
- X-81
- X-82
- X-83
- X-84
- X-85
- X-86
- X-87
- X-88
- X-89
- X-90
- X-91
- X-92
- X-93
- X-94
- X-95
- X-96
- X-97
- X-98
- X-99
- X-100
- X-101
- X-102
- X-103
- X-104
- X-105
- X-106
- X-107
- X-108
- X-109
- X-110

TABLE 1-continued
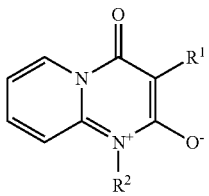
R¹
| | |
|---|---|
| X-111 | X-56 |
| X-112 | X-57 |
| X-113 | X-58 |
| X-114 | X-59 |
| X-115 | X-60 |
| X-116 | X-61 |
| X-117 | X-62 |
| X-118 | X-63 |
| X-119 | X-64 |
| X-120 | X-65 |
| X-121 | X-66 |
| X-122 | X-67 |
| X-123 | X-68 |
| X-124 | X-69 |
| X-125 | X-70 |
| X-126 | X-71 |
| X-127 | X-72 |
| X-128 | X-73 |
R² is Y-33
| | |
|---|---|
| | X-74 |
| | X-75 |
| X-1 | X-76 |
| X-2 | X-77 |
| X-3 | X-78 |
| X-4 | X-79 |
| X-5 | X-80 |
| X-6 | X-81 |
| X-7 | X-82 |
| X-8 | X-83 |
| X-9 | X-84 |
| X-10 | X-85 |
| X-11 | X-86 |
| X-12 | X-87 |
| X-13 | X-88 |
| X-14 | X-89 |
| X-15 | X-90 |
| X-16 | X-91 |
| X-17 | X-92 |
| X-18 | X-93 |
| X-19 | X-94 |
| X-20 | X-95 |
| X-21 | X-96 |
| X-22 | X-97 |
| X-23 | X-98 |
| X-24 | X-99 |
| X-25 | X-100 |
| X-26 | X-101 |
| X-27 | X-102 |
| X-28 | X-103 |
| X-29 | X-104 |
| X-30 | X-105 |
| X-31 | X-106 |
| X-32 | X-107 |
| X-33 | X-108 |
| X-34 | X-109 |
| X-35 | X-110 |
| X-36 | X-111 |
| X-37 | X-112 |
| X-38 | X-113 |
| X-39 | X-114 |
| X-40 | X-115 |
| X-41 | X-116 |
| X-42 | X-117 |
| X-50 | X-118 |
| X-51 | X-119 |
| X-52 | X-120 |
| X-53 | X-121 |
| X-54 | X-122 |
| X-55 | X-123 |

TABLE 1-continued

[Structure: pyrido-pyrimidine with R¹ and R²=Y-34]

R¹

X-124
X-125
X-126
X-127
X-128

R² is Y-34

X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68

TABLE 1-continued

[Structure: pyrido-pyrimidine with R¹ and R²]

R¹

X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128

R² is Y-35

X-1
X-2
X-3
X-4
X-5
X-6

TABLE 1-continued
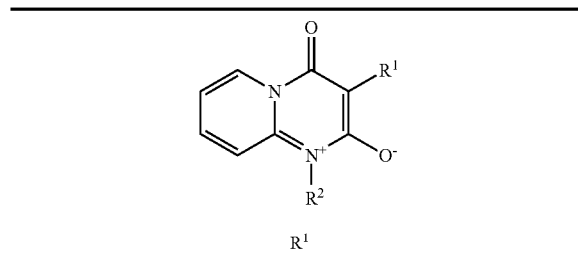
R$^1$
| X-7 | X-82 |
| X-8 | X-83 |
| X-9 | X-84 |
| X-10 | X-85 |
| X-11 | X-86 |
| X-12 | X-87 |
| X-13 | X-88 |
| X-14 | X-89 |
| X-15 | X-90 |
| X-16 | X-91 |
| X-17 | X-92 |
| X-18 | X-93 |
| X-19 | X-94 |
| X-20 | X-95 |
| X-21 | X-96 |
| X-22 | X-97 |
| X-23 | X-98 |
| X-24 | X-99 |
| X-25 | X-100 |
| X-26 | X-101 |
| X-27 | X-102 |
| X-28 | X-103 |
| X-29 | X-104 |
| X-30 | X-105 |
| X-31 | X-106 |
| X-32 | X-107 |
| X-33 | X-108 |
| X-34 | X-109 |
| X-35 | X-110 |
| X-36 | X-111 |
| X-37 | X-112 |
| X-38 | X-113 |
| X-39 | X-114 |
| X-40 | X-115 |
| X-41 | X-116 |
| X-42 | X-117 |
| X-50 | X-118 |
| X-51 | X-119 |
| X-52 | X-120 |
| X-53 | X-121 |
| X-54 | X-122 |
| X-55 | X-123 |
| X-56 | X-124 |
| X-57 | X-125 |
| X-58 | X-126 |
| X-59 | X-127 |
| X-60 | X-128 |
R$^2$ is Y-36
| X-61 | |
| X-62 | |
| X-63 | X-1 |
| X-64 | X-2 |
| X-65 | X-3 |
| X-66 | X-4 |
| X-67 | X-5 |
| X-68 | X-6 |
| X-69 | X-7 |
| X-70 | X-8 |
| X-71 | X-9 |
| X-72 | X-10 |
| X-73 | X-11 |
| X-74 | X-12 |
| X-75 | X-13 |
| X-76 | X-14 |
| X-77 | X-15 |
| X-78 | X-16 |
| X-79 | X-17 |
| X-80 | X-18 |
| X-81 | X-19 |

TABLE 1-continued
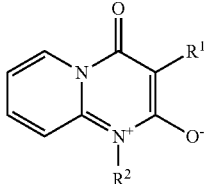
R¹
- X-20
- X-21
- X-22
- X-23
- X-24
- X-25
- X-26
- X-27
- X-28
- X-29
- X-30
- X-31
- X-32
- X-33
- X-34
- X-35
- X-36
- X-37
- X-38
- X-39
- X-40
- X-41
- X-42
- X-50
- X-51
- X-52
- X-53
- X-54
- X-55
- X-56
- X-57
- X-58
- X-59
- X-60
- X-61
- X-62
- X-63
- X-64
- X-65
- X-66
- X-67
- X-68
- X-69
- X-70
- X-71
- X-72
- X-73
- X-74
- X-75
- X-76
- X-77
- X-78
- X-79
- X-80
- X-81
- X-82
- X-83
- X-84
- X-85
- X-86
- X-87
- X-88
- X-89
- X-90
- X-91
- X-92
- X-93
- X-94
TABLE 1-continued
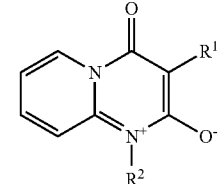
R¹
- X-95
- X-96
- X-97
- X-98
- X-99
- X-100
- X-101
- X-102
- X-103
- X-104
- X-105
- X-106
- X-107
- X-108
- X-109
- X-110
- X-111
- X-112
- X-113
- X-114
- X-115
- X-116
- X-117
- X-118
- X-119
- X-120
- X-121
- X-122
- X-123
- X-124
- X-125
- X-126
- X-127
- X-128
R² is Y-37
- X-1
- X-2
- X-3
- X-4
- X-5
- X-6
- X-7
- X-8
- X-9
- X-10
- X-11
- X-12
- X-13
- X-14
- X-15
- X-16
- X-17
- X-18
- X-19
- X-20
- X-21
- X-22
- X-23
- X-24
- X-25
- X-26
- X-27
- X-28
- X-29
- X-30
- X-31
- X-32

TABLE 1-continued
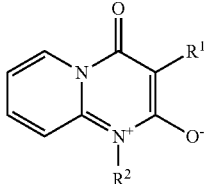
R¹
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
TABLE 1-continued
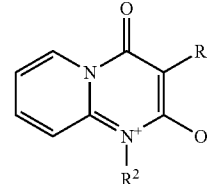
R¹
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R² is Y-38
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |

TABLE 1-continued

[Structure: pyrido-pyrimidine with O, R¹, N⁺, O⁻, R²]

| R¹ |
|---|
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |

TABLE 1-continued

[Structure: pyrido-pyrimidine with O, R¹, N⁺, O⁻, R²]

| R¹ |
|---|
| X-121 |
| X-122 |
| X-123 |
| X-124 |
| X-125 |
| X-126 |
| X-127 |
| X-128 |

| R² is Y-39 |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |

TABLE 1-continued

[Structure: pyrido-pyrimidine with R¹ and R² substituents, N⁺-O⁻]

R¹

| |
|---|
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
| R² is Y-40 |
| X-1 |
| X-2 |
| X-3 |

TABLE 1-continued

[Structure: pyrido-pyrimidine with R¹ and R² substituents, N⁺-O⁻]

R¹

| |
|---|
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |

TABLE 1-continued

[Structure: pyrido-pyrimidinone with R¹ and R² substituents, N⁺–O⁻]

R¹

| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |

R² is Y-41

| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |

TABLE 1-continued

[Structure: pyrido-pyrimidinone with R¹ and R² substituents, N⁺–O⁻]

R¹

| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |

TABLE 1-continued

[Structure: pyrido-pyrimidine with R¹ and R² substituents, N⁺-O⁻]

R¹

| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |

R² is Y-42

| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |

TABLE 1-continued

[Structure: pyrido-pyrimidine with R¹ and R² substituents, N⁺-O⁻]

R¹

| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |

TABLE 1-continued
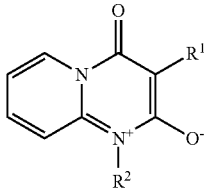
R¹
| | |
|---|---|
| X-105 | |
| X-106 | |
| X-107 | |
| X-108 | |
| X-109 | |
| X-110 | |
| X-111 | |
| X-112 | |
| X-113 | |
| X-114 | |
| X-115 | |
| X-116 | |
| X-117 | |
| X-118 | |
| X-119 | |
| X-120 | |
| X-121 | |
| X-122 | |
| X-123 | |
| X-124 | |
| X-125 | |
| X-126 | |
| X-127 | |
| X-128 | |
R² is Y-43
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
TABLE 1-continued
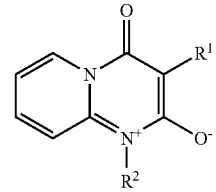
R¹
| |
|---|
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |

TABLE 1-continued

[Structure: pyrido-pyrimidine with O, R¹, N⁺, O⁻, R²]

R¹

X-118
X-119
X-120
X-121
X-122
X-123
X-124
X-125
X-126
X-127
X-128

R² is Y-44

X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60

TABLE 1-continued

[Structure: pyrido-pyrimidine with O, R¹, N⁺, O⁻, R²]

R¹

X-61
X-62
X-63
X-64
X-65
X-66
X-67
X-68
X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126

TABLE 1-continued
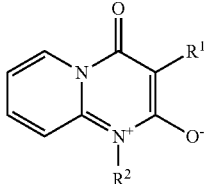
R¹
X-127
X-128
R² is Y-45
X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68
X-69
X-70
X-71
TABLE 1-continued
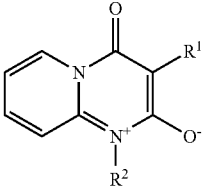
R¹
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128
R² is Y-46
X-1
X-2
X-3
X-4
X-5
X-6
X-7
X-8
X-9

TABLE 1-continued
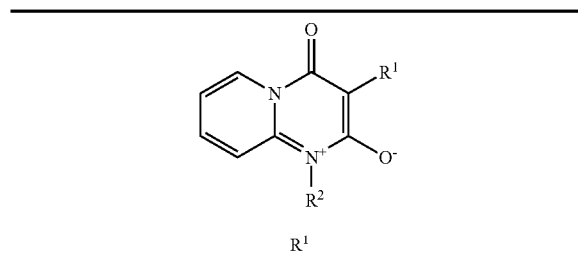
R¹
| | |
|---|---|
| X-10 | |
| X-11 | |
| X-12 | |
| X-13 | |
| X-14 | |
| X-15 | |
| X-16 | |
| X-17 | |
| X-18 | |
| X-19 | |
| X-20 | |
| X-21 | |
| X-22 | |
| X-23 | |
| X-24 | |
| X-25 | |
| X-26 | |
| X-27 | |
| X-28 | |
| X-29 | |
| X-30 | |
| X-31 | |
| X-32 | |
| X-33 | |
| X-34 | |
| X-35 | |
| X-36 | |
| X-37 | |
| X-38 | |
| X-39 | |
| X-40 | |
| X-41 | |
| X-42 | |
| X-50 | |
| X-51 | |
| X-52 | |
| X-53 | |
| X-54 | |
| X-55 | |
| X-56 | |
| X-57 | |
| X-58 | |
| X-59 | |
| X-60 | |
| X-61 | |
| X-62 | |
| X-63 | |
| X-64 | |
| X-65 | |
| X-66 | |
| X-67 | |
| X-68 | |
| X-69 | |
| X-70 | |
| X-71 | |
| X-72 | |
| X-73 | |
| X-74 | |
| X-75 | |
| X-76 | |
| X-77 | |
| X-78 | |
| X-79 | |
| X-80 | |
| X-81 | |
| X-82 | |
| X-83 | |
| X-84 | |
TABLE 1-continued
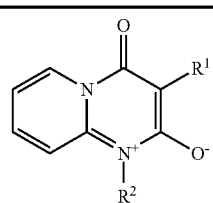
R¹
| | |
|---|---|
| X-85 | |
| X-86 | |
| X-87 | |
| X-88 | |
| X-89 | |
| X-90 | |
| X-91 | |
| X-92 | |
| X-93 | |
| X-94 | |
| X-95 | |
| X-96 | |
| X-97 | |
| X-98 | |
| X-99 | |
| X-100 | |
| X-101 | |
| X-102 | |
| X-103 | |
| X-104 | |
| X-105 | |
| X-106 | |
| X-107 | |
| X-108 | |
| X-109 | |
| X-110 | |
| X-111 | |
| X-112 | |
| X-113 | |
| X-114 | |
| X-115 | |
| X-116 | |
| X-117 | |
| X-118 | |
| X-119 | |
| X-120 | |
| X-121 | |
| X-122 | |
| X-123 | |
| X-124 | |
| X-125 | |
| X-126 | |
| X-127 | |
| X-128 | |
| R² is Y-47 | |
| X-1 | |
| X-2 | |
| X-3 | |
| X-4 | |
| X-5 | |
| X-6 | |
| X-7 | |
| X-8 | |
| X-9 | |
| X-10 | |
| X-11 | |
| X-12 | |
| X-13 | |
| X-14 | |
| X-15 | |
| X-16 | |
| X-17 | |
| X-18 | |
| X-19 | |
| X-20 | |
| X-21 | |
| X-22 | |

TABLE 1-continued

[Structure: pyrido-pyrimidine with O, R¹, N⁺, O⁻, R²]

| R¹ |
|---|
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |

TABLE 1-continued

[Structure: pyrido-pyrimidine with O, R¹, N⁺, O⁻, R²]

| R¹ |
|---|
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |

| R² is Y-48 |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |

TABLE 1-continued
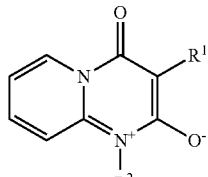
R¹
| | |
|---|---|
| X-36 | |
| X-37 | |
| X-38 | |
| X-39 | |
| X-40 | |
| X-41 | |
| X-42 | |
| X-50 | |
| X-51 | |
| X-52 | |
| X-53 | |
| X-54 | |
| X-55 | |
| X-56 | |
| X-57 | |
| X-58 | |
| X-59 | |
| X-60 | |
| X-61 | |
| X-62 | |
| X-63 | |
| X-64 | |
| X-65 | |
| X-66 | |
| X-67 | |
| X-68 | |
| X-69 | |
| X-70 | |
| X-71 | |
| X-72 | |
| X-73 | |
| X-74 | |
| X-75 | |
| X-76 | |
| X-77 | |
| X-78 | |
| X-79 | |
| X-80 | |
| X-81 | |
| X-82 | |
| X-83 | |
| X-84 | |
| X-85 | |
| X-86 | |
| X-87 | |
| X-88 | |
| X-89 | |
| X-90 | |
| X-91 | |
| X-92 | |
| X-93 | |
| X-94 | |
| X-95 | |
| X-96 | |
| X-97 | |
| X-98 | |
| X-99 | |
| X-100 | |
| X-101 | |
| X-102 | |
| X-103 | |
| X-104 | |
| X-105 | |
| X-106 | |
| X-107 | |
| X-108 | |
| X-109 | |
| X-110 | |
TABLE 1-continued
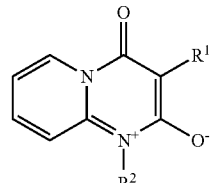
R¹
| |
|---|
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R² is Y-49
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |

TABLE 1-continued
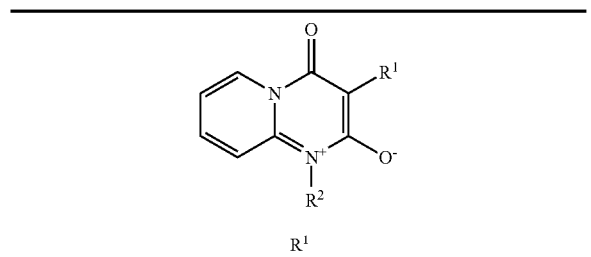
R$^1$
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
TABLE 1-continued
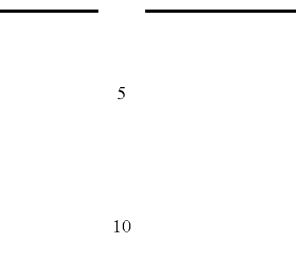
R$^1$
| X-124 |
| X-125 |
| X-126 |
| X-127 |
| X-128 |
R$^2$ is Y-50
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |

TABLE 1-continued
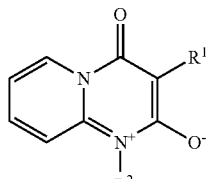
R$^1$
X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128
R$^2$ is Y-51
X-1
X-2
X-3
X-4
X-5
X-6
TABLE 1-continued
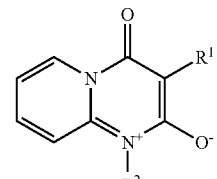
R$^1$
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68
X-69
X-70
X-71
X-72
X-73
X-74
X-75
X-76
X-77
X-78
X-79
X-80
X-81

TABLE 1-continued
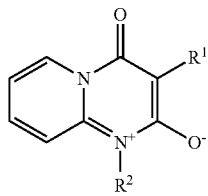
R¹
| |
|---|
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R² is Y-52
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
TABLE 1-continued
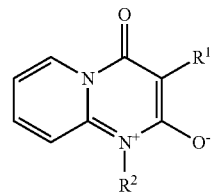
R¹
| |
|---|
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |

TABLE 1-continued

| | |
|---|---|
| R¹ | |
| X-95 | X-33 |
| X-96 | X-34 |
| X-97 | X-35 |
| X-98 | X-36 |
| X-99 | X-37 |
| X-100 | X-38 |
| X-101 | X-39 |
| X-102 | X-40 |
| X-103 | X-41 |
| X-104 | X-42 |
| X-105 | X-50 |
| X-106 | X-51 |
| X-107 | X-52 |
| X-108 | X-53 |
| X-109 | X-54 |
| X-110 | X-55 |
| X-111 | X-56 |
| X-112 | X-57 |
| X-113 | X-58 |
| X-114 | X-59 |
| X-115 | X-60 |
| X-116 | X-61 |
| X-117 | X-62 |
| X-118 | X-63 |
| X-119 | X-64 |
| X-120 | X-65 |
| X-121 | X-66 |
| X-122 | X-67 |
| X-123 | X-68 |
| X-124 | X-69 |
| X-125 | X-70 |
| X-126 | X-71 |
| X-127 | X-72 |
| X-128 | X-73 |
| R² is Y-53 | X-74 |
| X-1 | X-75 |
| X-2 | X-76 |
| X-3 | X-77 |
| X-4 | X-78 |
| X-5 | X-79 |
| X-6 | X-80 |
| X-7 | X-81 |
| X-8 | X-82 |
| X-9 | X-83 |
| X-10 | X-84 |
| X-11 | X-85 |
| X-12 | X-86 |
| X-13 | X-87 |
| X-14 | X-88 |
| X-15 | X-89 |
| X-16 | X-90 |
| X-17 | X-91 |
| X-18 | X-92 |
| X-19 | X-93 |
| X-20 | X-94 |
| X-21 | X-95 |
| X-22 | X-96 |
| X-23 | X-97 |
| X-24 | X-98 |
| X-25 | X-99 |
| X-26 | X-100 |
| X-27 | X-101 |
| X-28 | X-102 |
| X-29 | X-103 |
| X-30 | X-104 |
| X-31 | X-105 |
| X-32 | X-106 |
| | X-107 |

TABLE 1-continued
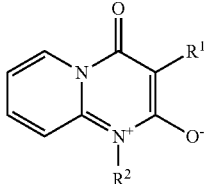
R¹
| |
|---|
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R² is Y-54
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
TABLE 1-continued
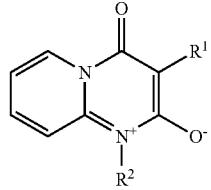
R¹
| |
|---|
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |

TABLE 1-continued

[Structure: pyrido-pyrimidine with R¹ and R² substituents, N⁺-O⁻]

R¹

| | |
|---|---|
| X-121 | X-66 |
| X-122 | X-67 |
| X-123 | X-68 |
| X-124 | X-69 |
| X-125 | X-70 |
| X-126 | X-71 |
| X-127 | X-72 |
| X-128 | X-73 |
| R² is Y-55 | X-74 |
| | X-75 |
| X-1 | X-76 |
| X-2 | X-77 |
| X-3 | X-78 |
| X-4 | X-79 |
| X-5 | X-80 |
| X-6 | X-81 |
| X-7 | X-82 |
| X-8 | X-83 |
| X-9 | X-84 |
| X-10 | X-85 |
| X-11 | X-86 |
| X-12 | X-87 |
| X-13 | X-88 |
| X-14 | X-89 |
| X-15 | X-90 |
| X-16 | X-91 |
| X-17 | X-92 |
| X-18 | X-93 |
| X-19 | X-94 |
| X-20 | X-95 |
| X-21 | X-96 |
| X-22 | X-97 |
| X-23 | X-98 |
| X-24 | X-99 |
| X-25 | X-100 |
| X-26 | X-101 |
| X-27 | X-102 |
| X-28 | X-103 |
| X-29 | X-104 |
| X-30 | X-105 |
| X-31 | X-106 |
| X-32 | X-107 |
| X-33 | X-108 |
| X-34 | X-109 |
| X-35 | X-110 |
| X-36 | X-111 |
| X-37 | X-112 |
| X-38 | X-113 |
| X-39 | X-114 |
| X-40 | X-115 |
| X-41 | X-116 |
| X-42 | X-117 |
| X-50 | X-118 |
| X-51 | X-119 |
| X-52 | X-120 |
| X-53 | X-121 |
| X-54 | X-122 |
| X-55 | X-123 |
| X-56 | X-124 |
| X-57 | X-125 |
| X-58 | X-126 |
| X-59 | X-127 |
| X-60 | X-128 |
| X-61 | R² is Y-56 |
| X-62 | |
| X-63 | X-1 |
| X-64 | X-2 |
| X-65 | X-3 |

TABLE 1-continued
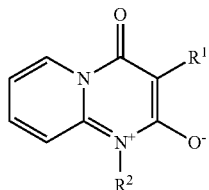
R$^1$
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
TABLE 1-continued
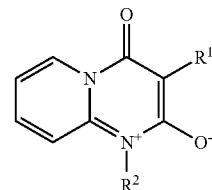
R$^1$
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R$^2$ is Y-57
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |

TABLE 1-continued
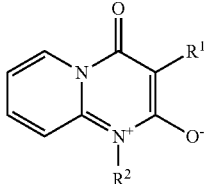
R¹
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68
X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
TABLE 1-continued
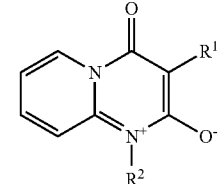
R¹
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128
R² is Y-58
X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29

TABLE 1-continued
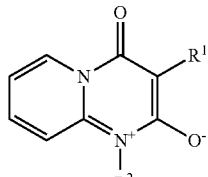
R¹
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68
X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
TABLE 1-continued
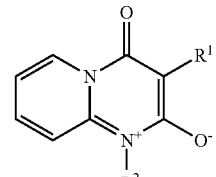
R¹
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128
R² is Y-59
X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42

TABLE 1-continued

| | |
|---|---|
| | R¹ |
| X-50 | X-118 |
| X-51 | X-119 |
| X-52 | X-120 |
| X-53 | X-121 |
| X-54 | X-122 |
| X-55 | X-123 |
| X-56 | X-124 |
| X-57 | X-125 |
| X-58 | X-126 |
| X-59 | X-127 |
| X-60 | X-128 |
| X-61 | R² is Y-60 |
| X-62 | |
| X-63 | X-1 |
| X-64 | X-2 |
| X-65 | X-3 |
| X-66 | X-4 |
| X-67 | X-5 |
| X-68 | X-6 |
| X-69 | X-7 |
| X-70 | X-8 |
| X-71 | X-9 |
| X-72 | X-10 |
| X-73 | X-11 |
| X-74 | X-12 |
| X-75 | X-13 |
| X-76 | X-14 |
| X-77 | X-15 |
| X-78 | X-16 |
| X-79 | X-17 |
| X-80 | X-18 |
| X-81 | X-19 |
| X-82 | X-20 |
| X-83 | X-21 |
| X-84 | X-22 |
| X-85 | X-23 |
| X-86 | X-24 |
| X-87 | X-25 |
| X-88 | X-26 |
| X-89 | X-27 |
| X-90 | X-28 |
| X-91 | X-29 |
| X-92 | X-30 |
| X-93 | X-31 |
| X-94 | X-32 |
| X-95 | X-33 |
| X-96 | X-34 |
| X-97 | X-35 |
| X-98 | X-36 |
| X-99 | X-37 |
| X-100 | X-38 |
| X-101 | X-39 |
| X-102 | X-40 |
| X-103 | X-41 |
| X-104 | X-42 |
| X-105 | X-50 |
| X-106 | X-51 |
| X-107 | X-52 |
| X-108 | X-53 |
| X-109 | X-54 |
| X-110 | X-55 |
| X-111 | X-56 |
| X-112 | X-57 |
| X-113 | X-58 |
| X-114 | X-59 |
| X-115 | X-60 |
| X-116 | |
| X-117 | |

TABLE 1-continued
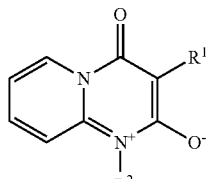
| R¹ |
|---|
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
TABLE 1-continued
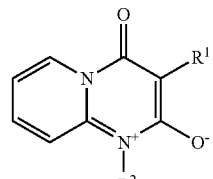
| R¹ |
|---|
| X-127 |
| X-128 |
R² is Y-61
| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |

TABLE 1-continued
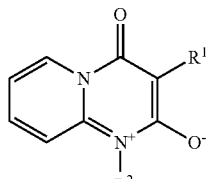
R[1]
| |
|---|
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
| R[2] is Y-62 |
| X-1 |
| X-2 |
| X-3 |
| X-4 |
| X-5 |
| X-6 |
| X-7 |
| X-8 |
| X-9 |
TABLE 1-continued
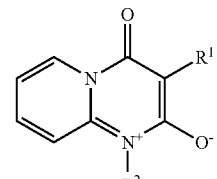
R[1]
| |
|---|
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |

TABLE 1-continued

[Structure: pyrido-pyrimidinone with O, R¹, N⁺-O⁻, R²]

R¹

| |
|---|
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
| R² is Y-63 |
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |

TABLE 1-continued

[Structure: pyrido-pyrimidinone with O, R¹, N⁺-O⁻, R²]

R¹

| |
|---|
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |

TABLE 1-continued
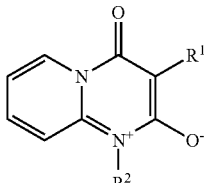
R¹
| | |
|---|---|
| X-98 | |
| X-99 | |
| X-100 | |
| X-101 | |
| X-102 | |
| X-103 | |
| X-104 | |
| X-105 | |
| X-106 | |
| X-107 | |
| X-108 | |
| X-109 | |
| X-110 | |
| X-111 | |
| X-112 | |
| X-113 | |
| X-114 | |
| X-115 | |
| X-116 | |
| X-117 | |
| X-118 | |
| X-119 | |
| X-120 | |
| X-121 | |
| X-122 | |
| X-123 | |
| X-124 | |
| X-125 | |
| X-126 | |
| X-127 | |
| X-128 | |
R² is Y-64
| | |
|---|---|
| X-1 | |
| X-2 | |
| X-3 | |
| X-4 | |
| X-5 | |
| X-6 | |
| X-7 | |
| X-8 | |
| X-9 | |
| X-10 | |
| X-11 | |
| X-12 | |
| X-13 | |
| X-14 | |
| X-15 | |
| X-16 | |
| X-17 | |
| X-18 | |
| X-19 | |
| X-20 | |
| X-21 | |
| X-22 | |
| X-23 | |
| X-24 | |
| X-25 | |
| X-26 | |
| X-27 | |
| X-28 | |
| X-29 | |
| X-30 | |
| X-31 | |
| X-32 | |
| X-33 | |
| X-34 | |
| X-35 | |
TABLE 1-continued
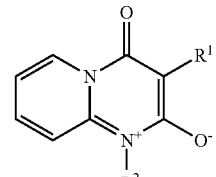
R¹
| | |
|---|---|
| X-36 | |
| X-37 | |
| X-38 | |
| X-39 | |
| X-40 | |
| X-41 | |
| X-42 | |
| X-50 | |
| X-51 | |
| X-52 | |
| X-53 | |
| X-54 | |
| X-55 | |
| X-56 | |
| X-57 | |
| X-58 | |
| X-59 | |
| X-60 | |
| X-61 | |
| X-62 | |
| X-63 | |
| X-64 | |
| X-65 | |
| X-66 | |
| X-67 | |
| X-68 | |
| X-69 | |
| X-70 | |
| X-71 | |
| X-72 | |
| X-73 | |
| X-74 | |
| X-75 | |
| X-76 | |
| X-77 | |
| X-78 | |
| X-79 | |
| X-80 | |
| X-81 | |
| X-82 | |
| X-83 | |
| X-84 | |
| X-85 | |
| X-86 | |
| X-87 | |
| X-88 | |
| X-89 | |
| X-90 | |
| X-91 | |
| X-92 | |
| X-93 | |
| X-94 | |
| X-95 | |
| X-96 | |
| X-97 | |
| X-98 | |
| X-99 | |
| X-100 | |
| X-101 | |
| X-102 | |
| X-103 | |
| X-104 | |
| X-105 | |
| X-106 | |
| X-107 | |
| X-108 | |
| X-109 | |
| X-110 | |

TABLE 1-continued

[Structure: pyrido-pyrimidine with O, R¹, N⁺, O⁻, R²]

| R¹ |
|---|
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |

R² is Y-65

| |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |

TABLE 1-continued

[Structure: pyrido-pyrimidine with O, R¹, N⁺, O⁻, R²]

| R¹ |
|---|
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |

TABLE 1-continued

[Structure: pyrido-pyrimidine with O, R¹, N⁺, O⁻, R²]

R¹

X-124
X-125
X-126
X-127
X-128

R² is Y-66

X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52
X-53
X-54
X-55
X-56
X-57
X-58
X-59
X-60
X-61
X-62
X-63
X-64
X-65
X-66
X-67
X-68

TABLE 1-continued

[Structure: pyrido-pyrimidine with O, R¹, N⁺, O⁻, R²]

R¹

X-69
X-70
X-71
X-72
X-73
X-74
X-75
X-76
X-77
X-78
X-79
X-80
X-81
X-82
X-83
X-84
X-85
X-86
X-87
X-88
X-89
X-90
X-91
X-92
X-93
X-94
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128

R² is Y-67

X-1
X-2
X-3
X-4
X-5
X-6

TABLE 1-continued
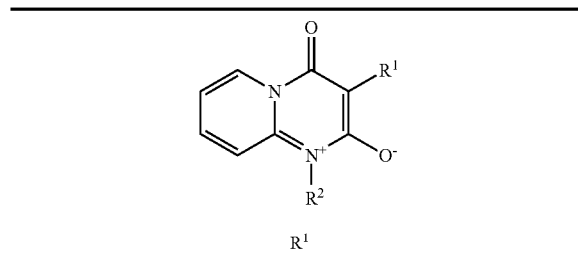
R$^1$
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
TABLE 1-continued
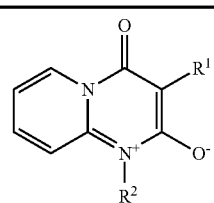
R$^1$
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |
R$^2$ is Y-68
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |

TABLE 1-continued
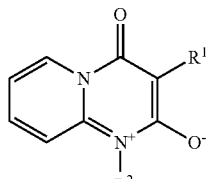
R¹
| | |
|---|---|
| X-20 | |
| X-21 | |
| X-22 | |
| X-23 | |
| X-24 | |
| X-25 | |
| X-26 | |
| X-27 | |
| X-28 | |
| X-29 | |
| X-30 | |
| X-31 | |
| X-32 | |
| X-33 | |
| X-34 | |
| X-35 | |
| X-36 | |
| X-37 | |
| X-38 | |
| X-39 | |
| X-40 | |
| X-41 | |
| X-42 | |
| X-50 | |
| X-51 | |
| X-52 | |
| X-53 | |
| X-54 | |
| X-55 | |
| X-56 | |
| X-57 | |
| X-58 | |
| X-59 | |
| X-60 | |
| X-61 | |
| X-62 | |
| X-63 | |
| X-64 | |
| X-65 | |
| X-66 | |
| X-67 | |
| X-68 | |
| X-69 | |
| X-70 | |
| X-71 | |
| X-72 | |
| X-73 | |
| X-74 | |
| X-75 | |
| X-76 | |
| X-77 | |
| X-78 | |
| X-79 | |
| X-80 | |
| X-81 | |
| X-82 | |
| X-83 | |
| X-84 | |
| X-85 | |
| X-86 | |
| X-87 | |
| X-88 | |
| X-89 | |
| X-90 | |
| X-91 | |
| X-92 | |
| X-93 | |
| X-94 | |
TABLE 1-continued
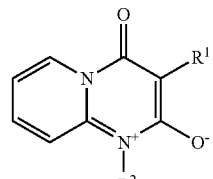
R¹
X-95
X-96
X-97
X-98
X-99
X-100
X-101
X-102
X-103
X-104
X-105
X-106
X-107
X-108
X-109
X-110
X-111
X-112
X-113
X-114
X-115
X-116
X-117
X-118
X-119
X-120
X-121
X-122
X-123
X-124
X-125
X-126
X-127
X-128
R² is Y-69
X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32

TABLE 1-continued
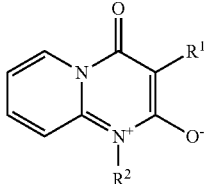
R¹
| | |
|---|---|
| X-33 | |
| X-34 | |
| X-35 | |
| X-36 | |
| X-37 | |
| X-38 | |
| X-39 | |
| X-40 | |
| X-41 | |
| X-42 | |
| X-50 | |
| X-51 | |
| X-52 | |
| X-53 | |
| X-54 | |
| X-55 | |
| X-56 | |
| X-57 | |
| X-58 | |
| X-59 | |
| X-60 | |
| X-61 | |
| X-62 | |
| X-63 | |
| X-64 | |
| X-65 | |
| X-66 | |
| X-67 | |
| X-68 | |
| X-69 | |
| X-70 | |
| X-71 | |
| X-72 | |
| X-73 | |
| X-74 | |
| X-75 | |
| X-76 | |
| X-77 | |
| X-78 | |
| X-79 | |
| X-80 | |
| X-81 | |
| X-82 | |
| X-83 | |
| X-84 | |
| X-85 | |
| X-86 | |
| X-87 | |
| X-88 | |
| X-89 | |
| X-90 | |
| X-91 | |
| X-92 | |
| X-93 | |
| X-94 | |
| X-95 | |
| X-96 | |
| X-97 | |
| X-98 | |
| X-99 | |
| X-100 | |
| X-101 | |
| X-102 | |
| X-103 | |
| X-104 | |
| X-105 | |
| X-106 | |
| X-107 | |
TABLE 1-continued
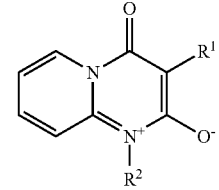
R¹
X-108
X-109
X-110
X-111
X-112
X-113
X-114
X-115
X-116
X-117
X-118
X-119
X-120
X-121
X-122
X-123
X-124
X-125
X-126
X-127
X-128
R² is Y-70
X-1
X-2
X-3
X-4
X-5
X-6
X-7
X-8
X-9
X-10
X-11
X-12
X-13
X-14
X-15
X-16
X-17
X-18
X-19
X-20
X-21
X-22
X-23
X-24
X-25
X-26
X-27
X-28
X-29
X-30
X-31
X-32
X-33
X-34
X-35
X-36
X-37
X-38
X-39
X-40
X-41
X-42
X-50
X-51
X-52

TABLE 1-continued
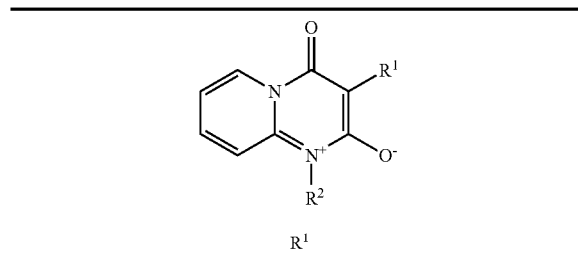
| R$^1$ |
|---|
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
TABLE 1-continued
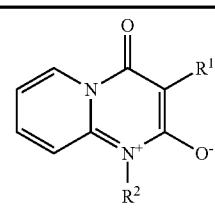
| R$^1$ |
|---|
| X-121 |
| X-122 |
| X-123 |
| X-124 |
| X-125 |
| X-126 |
| X-127 |
| X-128 |
| R$^2$ is Y-71 |
|---|
| X-1 |
| X-2 |
| X-3 |
| X-4 |
| X-5 |
| X-6 |
| X-7 |
| X-8 |
| X-9 |
| X-10 |
| X-11 |
| X-12 |
| X-13 |
| X-14 |
| X-15 |
| X-16 |
| X-17 |
| X-18 |
| X-19 |
| X-20 |
| X-21 |
| X-22 |
| X-23 |
| X-24 |
| X-25 |
| X-26 |
| X-27 |
| X-28 |
| X-29 |
| X-30 |
| X-31 |
| X-32 |
| X-33 |
| X-34 |
| X-35 |
| X-36 |
| X-37 |
| X-38 |
| X-39 |
| X-40 |
| X-41 |
| X-42 |
| X-50 |
| X-51 |
| X-52 |
| X-53 |
| X-54 |
| X-55 |
| X-56 |
| X-57 |
| X-58 |
| X-59 |
| X-60 |
| X-61 |
| X-62 |
| X-63 |
| X-64 |
| X-65 |

TABLE 1-continued

[Structure: pyrido-pyrimidine N-oxide with R¹ at position 3 and R² on N⁺]

| R¹ |
|---|
| X-66 |
| X-67 |
| X-68 |
| X-69 |
| X-70 |
| X-71 |
| X-72 |
| X-73 |
| X-74 |
| X-75 |
| X-76 |
| X-77 |
| X-78 |
| X-79 |
| X-80 |
| X-81 |
| X-82 |
| X-83 |
| X-84 |
| X-85 |
| X-86 |
| X-87 |
| X-88 |
| X-89 |
| X-90 |
| X-91 |
| X-92 |
| X-93 |
| X-94 |
| X-95 |
| X-96 |
| X-97 |
| X-98 |
| X-99 |
| X-100 |
| X-101 |
| X-102 |
| X-103 |
| X-104 |
| X-105 |
| X-106 |
| X-107 |
| X-108 |
| X-109 |
| X-110 |
| X-111 |
| X-112 |
| X-113 |
| X-114 |
| X-115 |
| X-116 |
| X-117 |
| X-118 |
| X-119 |
| X-120 |
| X-121 |
| X-122 |
| X-123 |
| X-124 |
| X-125 |
| X-126 |
| X-127 |
| X-128 |

TABLE 2

Table 2 is constructed the same as Table 1, except that the chemical structure under the Table 1 heading is replaced with the following structure:

[Structure: fluoro-substituted pyrido-pyrimidine N-oxide with R¹ and R²]

For example, the first compound in Table 2 is the structure shown immediately above wherein $R^1$ is X-1 and $R^2$ is Y-1 as defined for Table 1.

TABLE 3

Table 3 is constructed the same as Table 1, except that the chemical structure under the Table 1 heading is replaced with the following structure:

[Structure: thiazolo-pyrimidine N-oxide with R¹ and R²]

For example, the first compound in Table 3 is the structure shown immediately above wherein $R^1$ is X-1 and $R^2$ is Y-1 as defined for Table 1.

TABLE 4

Table 4 is constructed the same as Table 1, except that the chemical structure under the Table 1 heading is replaced with the following structure:

[Structure: dimethyl pyrimidine N-oxide with R¹ and R²]

For example, the first compound in Table 4 is the structure shown immediately above wherein $R^1$ is X-1 and $R^2$ is Y-1 as defined for Table 1.

TABLE 5

Table 5 is constructed the same as Table 1, except that the chemical structure under the Table 1 heading is replaced with the following structure:

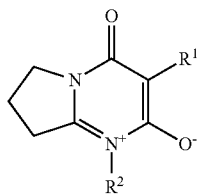

For example, the first compound in Table 5 is the structure shown immediately above wherein R¹ is X-1 and R² is Y-1 as defined for Table 1.

TABLE 6

Table 6 is constructed the same as Table 1, except that the chemical structure under the Table 1 heading is replaced with the following structure:

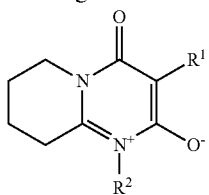

For example, the first compound in Table 6 is the structure shown immediately above wherein R¹ is X-1 and R² is Y-1 as defined for Table 1.

TABLE 7

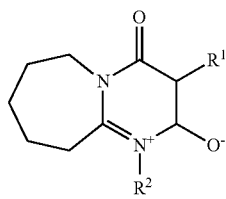

| R¹ | R¹ | R¹ | R¹ | R¹ | R¹ | R¹ | R¹ | R¹ | R¹ |
|---|---|---|---|---|---|---|---|---|---|
| R² is Y-3 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-19 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-20 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-22 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

TABLE 7-continued

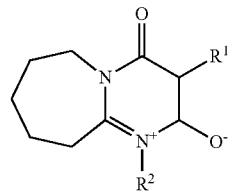

| R¹ | R¹ | R¹ | R¹ | R¹ | R¹ | R¹ | R¹ | R¹ | R¹ |
|---|---|---|---|---|---|---|---|---|---|
| R² is Y-30 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-31 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-33 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-34 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-36 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-37 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-38 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-39 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-40 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |
| R² is Y-45 ||||||||||
| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |

TABLE 7-continued

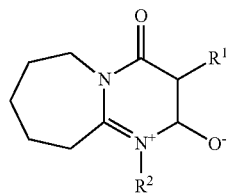

| R¹ | R¹ | R¹ | R¹ | R¹ | R¹ | R¹ | R¹ | R¹ | R¹ |
|---|---|---|---|---|---|---|---|---|---|
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-49

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-52

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-53

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-55

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-64

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-65

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-66

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-67

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

R² is Y-68

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

TABLE 7-continued

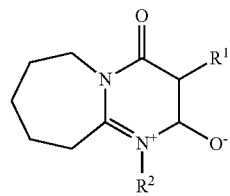

| R¹ | R¹ | R¹ | R¹ | R¹ | R¹ | R¹ | R¹ | R¹ | R¹ |
|---|---|---|---|---|---|---|---|---|---|

R² is Y-69

| X-15 | X-17 | X-25 | X-26 | X-27 | X-31 | X-35 | X-50 | X-51 | X-52 |
| X-53 | X-54 | X-55 | X-56 | X-57 | X-59 | X-60 | X-61 | X-63 | X-77 |
| X-78 | X-79 | X-80 | X-81 | X-82 | X-83 | X-84 | X-85 | X-86 | X-87 |
| X-88 | X-89 | X-90 | X-93 | X-94 | X-97 | X-100 | X-102 | X-103 | X-105 |
| X-106 | X-107 | X-108 | X-118 | X-120 | X-121 | X-122 | X-123 | X-124 | X-125 |

TABLE 8

Table 8 is constructed the same as Table 7, except that the chemical structure under the Table 7 heading is replaced with the following structure:

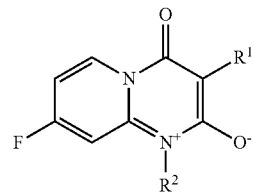

For example, the first compound in Table 8 is the structure shown immediately above wherein R¹ is X-15 and R² is Y-3 as defined for Table 7.

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids can be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which are branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention can also contain formulation auxiliaries and additives, known to those skilled in the art as formulation aids (some of which can be considered to also function as solid diluents, liquid diluents or surfactants). Such formulation auxiliaries and additives can control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48; *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all formulations are prepared in conventional ways. Compound numbers refer to compounds in Index Tables A-F. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

EXAMPLE A

High Strength Concentrate

| | |
|---|---|
| Compound 7 | 98.5% |
| silica aerogel | 0.5% |
| synthetic amorphous fine silica | 1.0% |

EXAMPLE B

Wettable Powder

| | |
|---|---|
| Compound 50 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

Granule

| | |
|---|---|
| Compound 138 | 10.0% |
| attapulgite granules (low volatile matter, 0.71/0.30 mm; U.S.S. No. 25-50 sieves) | 90.0% |

EXAMPLE D

Extruded Pellet

| | |
|---|---|
| Compound 157 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

Emulsifiable Concentrate

| | |
|---|---|
| Compound 7 | 10.0% |
| polyoxyethylene sorbitol hexoleate | 20.0% |
| $C_6$-$C_{10}$ fatty acid methyl ester | 70.0% |

EXAMPLE F

Microemulsion

| | |
|---|---|
| Compound 50 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

Seed Treatment

| | |
|---|---|
| Compound 138 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

EXAMPLE H

Fertilizer Stick

| | |
|---|---|
| Compound 157 | 2.50% |
| pyrrolidone-styrene copolymer | 4.80% |
| tristyrylphenyl 16-ethoxylate | 2.30% |
| talc | 0.80% |
| corn starch | 5.00% |
| Nitrophoska ® Permanent 15-9-15 slow-release fertilizer (BASF) | 36.00% |
| kaolin | 38.00% |
| water | 10.60% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera fugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocerus medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus* vestitus), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), June beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae. Also included are eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella fit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the invention also have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid),

*Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention may also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Note that some contemporary classification systems place Homoptera as a suborder within the order Hemiptera.

Of note is use of compounds of this invention for controlling potato leafhopper (*Empoasca fabae*). Of note is use of compounds of this invention for controlling corn planthopper (*Peregrinus maidis*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling diamondback moth (*Plutella xylostella*). Of note is use of compounds of this invention for controlling fall armyworm (*Spodoptera frugiperda*).

Of note is use of compounds of this invention for controlling southern green stink bug (*Nezara viridula*), western tarnished plant bug (*Lygus hesperus*), rice water weevil (*Lissorhoptrus oryzophilus*), rice brown planthopper (*Nilaparvata lugens*), rice green leafhopper (*Nephotettix virescens*) and striped rice borer (*Chilo suppressalis*).

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, at least one additional component selected from the group consisting of surfactants, solid diluents and liquid diluents, and at least one additional biologically active compound or agent. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, amidoflumet, amitraz, avermectin, azadirachtin, azinphos-methyl, bifenthrin, bifenazate, bistrifluoron, borate, 3-bromo-1-(3-chloro-2-pyridinyl)-N-[4-cyano-2-methyl-6-[(methylamino)carbonyl]phenyl]-1H-pyrazole-5-carboxamide (cyantraniliprole), buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino)carbonyl]phenyl]-1H-pyrazole-5-carboxamide (cyantraniliprole), buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole (see U.S. Pat. No. 6,747,047, PCT Publications WO 2003/015518 and WO 2004/067528) and flubendiamide (see U.S. Pat. No. 6,603,044); nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula 1 alone.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a compound of Formula 1 (e.g., "50:1 to 1:50" of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |
| (a) | ryanodine receptor ligands | 100:1 to 1:120 |

(a) 3-bromo-1-(3-chloro-2-pyridinyl)-N-[4-cyano-2-methyl-6-[(methylamino)carbonyl]phenyl]-1H-pyrazole-5-carboxamide (cyantraniliprole)

Of note is the composition of the present invention wherein the at least one additional biologically active compound or agent is selected from the Invertebrate Pest Control Agents listed in Table A above.

The weight ratios of a compound, including a compound of Formula 1, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Table B are embodiments of specific compositions comprising a compound of Formula 1 (compound numbers refer to compounds in Index Tables A-I) and an additional invertebrate pest control agent.

TABLE B

| Mixture No. | Comp. No. | and | Invertebrate Pest Control Agent |
|---|---|---|---|
| A-1 | 7 | and | Abamectin |
| A-2 | 7 | and | Acetamiprid |
| A-3 | 7 | and | Amitraz |
| A-4 | 7 | and | Avermectin |
| A-5 | 7 | and | Azadirachtin |
| A-6 | 7 | and | Beta-cyfluthrin |
| A-7 | 7 | and | Bifenthrin |
| A-8 | 7 | and | Buprofezin |
| A-9 | 7 | and | Cartap |
| A-10 | 7 | and | Chlorantraniliprole |
| A-11 | 7 | and | Chlorfenapyr |
| A-12 | 7 | and | Chlorpyrifos |
| A-13 | 7 | and | Clothianidin |
| A-14 | 7 | and | Cyfluthrin |
| A-15 | 7 | and | Cyhalothrin |
| A-16 | 7 | and | Cypermethrin |
| A-17 | 7 | and | Cyromazine |
| A-18 | 7 | and | Deltamethrin |
| A-19 | 7 | and | Dieldrin |
| A-20 | 7 | and | Dinotefuran |
| A-21 | 7 | and | Diofenolan |
| A-22 | 7 | and | Emamectin |
| A-23 | 7 | and | Endosulfan |
| A-24 | 7 | and | Esfenvalerate |
| A-25 | 7 | and | Ethiprole |
| A-26 | 7 | and | Fenothiocarb |
| A-27 | 7 | and | Fenoxycarb |
| A-28 | 7 | and | Fenvalerate |
| A-29 | 7 | and | Fipronil |
| A-30 | 7 | and | Flonicamid |
| A-31 | 7 | and | Flubendiamide |
| A-32 | 7 | and | Flufenoxuron |
| A-33 | 7 | and | Hexaflumuron |
| A-34 | 7 | and | Hydramethylnon |
| A-35 | 7 | and | Imidacloprid |
| A-36 | 7 | and | Indoxacarb |
| A-37 | 7 | and | Lambda-cyhalothrin |
| A-38 | 7 | and | Lufenuron |
| A-39 | 7 | and | Metaflumizone |
| A-40 | 7 | and | Methomyl |
| A-41 | 7 | and | Methoprene |
| A-42 | 7 | and | Methoxyfenozide |
| A-43 | 7 | and | Nitenpyram |
| A-44 | 7 | and | Nithiazine |
| A-45 | 7 | and | Novaluron |
| A-46 | 7 | and | Oxamyl |
| A-47 | 7 | and | Pymetrozine |
| A-48 | 7 | and | Pyrethrin |
| A-49 | 7 | and | Pyridaben |
| A-50 | 7 | and | Pyridalyl |
| A-51 | 7 | and | Pyriproxyfen |
| A-52 | 7 | and | Ryanodine |
| A-53 | 7 | and | Spinetoram |
| A-54 | 7 | and | Spinosad |
| A-55 | 7 | and | Spirodiclofen |
| A-56 | 7 | and | Spiromesifen |
| A-57 | 7 | and | Tebufenozide |
| A-58 | 7 | and | Thiacloprid |
| A-59 | 7 | and | Thiamethoxam |
| A-60 | 7 | and | Thiodicarb |
| A-61 | 7 | and | Thiosultap-sodium |
| A-62 | 7 | and | Tralomethrin |
| A-63 | 7 | and | Triazamate |
| A-64 | 7 | and | Triflumuron |
| A-65 | 7 | and | Bacillus thuringiensis |
| A-66 | 7 | and | Bacillus thuringiensis delta-endotoxin |
| A-67 | 7 | and | NPV (e.g., Gemstar) |
| A-68 | 7 | and | (a) |
| B-1 | 50 | and | Abamectin |
| B-2 | 50 | and | Acetamiprid |
| B-3 | 50 | and | Amitraz |
| B-4 | 50 | and | Avermectin |
| B-5 | 50 | and | Azadirachtin |
| B-6 | 50 | and | Beta-cyfluthrin |
| B-7 | 50 | and | Bifenthrin |
| B-8 | 50 | and | Buprofezin |
| B-9 | 50 | and | Cartap |
| B-10 | 50 | and | Chlorantraniliprole |
| B-11 | 50 | and | Chlorfenapyr |
| B-12 | 50 | and | Chlorpyrifos |
| B-13 | 50 | and | Clothianidin |
| B-14 | 50 | and | Cyfluthrin |
| B-15 | 50 | and | Cyhalothrin |
| B-16 | 50 | and | Cypermethrin |
| B-17 | 50 | and | Cyromazine |
| B-18 | 50 | and | Deltamethrin |
| B-19 | 50 | and | Dieldrin |
| B-20 | 50 | and | Dinotefuran |
| B-21 | 50 | and | Diofenolan |
| B-22 | 50 | and | Emamectin |
| B-23 | 50 | and | Endosulfan |
| B-24 | 50 | and | Esfenvalerate |
| B-25 | 50 | and | Ethiprole |
| B-26 | 50 | and | Fenothiocarb |
| B-27 | 50 | and | Fenoxycarb |
| B-28 | 50 | and | Fenvalerate |
| B-29 | 50 | and | Fipronil |
| B-30 | 50 | and | Flonicamid |
| B-31 | 50 | and | Flubendiamide |
| B-32 | 50 | and | Flufenoxuron |
| B-33 | 50 | and | Hexaflumuron |
| B-34 | 50 | and | Hydramethylnon |
| B-35 | 50 | and | Imidacloprid |
| B-36 | 50 | and | Indoxacarb |
| B-37 | 50 | and | Lambda-cyhalothrin |
| B-38 | 50 | and | Lufenuron |
| B-39 | 50 | and | Metaflumizone |
| B-40 | 50 | and | Methomyl |
| B-41 | 50 | and | Methoprene |
| B-42 | 50 | and | Methoxyfenozide |
| B-43 | 50 | and | Nitenpyram |
| B-44 | 50 | and | Nithiazine |
| B-45 | 50 | and | Novaluron |
| B-46 | 50 | and | Oxamyl |
| B-47 | 50 | and | Pymetrozine |
| B-48 | 50 | and | Pyrethrin |
| B-49 | 50 | and | Pyridaben |
| B-50 | 50 | and | Pyridalyl |
| B-51 | 50 | and | Pyriproxyfen |
| B-52 | 50 | and | Ryanodine |
| B-53 | 50 | and | Spinetoram |
| B-54 | 50 | and | Spinosad |
| B-55 | 50 | and | Spirodiclofen |
| B-56 | 50 | and | Spiromesifen |
| B-57 | 50 | and | Tebufenozide |
| B-58 | 50 | and | Thiacloprid |
| B-59 | 50 | and | Thiamethoxam |
| B-60 | 50 | and | Thiodicarb |
| B-61 | 50 | and | Thiosultap-sodium |
| B-62 | 50 | and | Tralomethrin |
| B-63 | 50 | and | Triazamate |
| B-64 | 50 | and | Triflumuron |
| B-65 | 50 | and | Bacillus thuringiensis |

TABLE B-continued

| Mixture No. | Comp. No. | and | Invertebrate Pest Control Agent |
|---|---|---|---|
| B-66 | 50 | and | *Bacillus thuringiensis* delta-endotoxin |
| B-67 | 50 | and | NPV (e.g., Gemstar) |
| B-68 | 50 | and | (a) |
| C-1 | 138 | and | Abamectin |
| C-2 | 138 | and | Acetamiprid |
| C-3 | 138 | and | Amitraz |
| C-4 | 138 | and | Avermectin |
| C-5 | 138 | and | Azadirachtin |
| C-6 | 138 | and | Beta-cyfluthrin |
| C-7 | 138 | and | Bifenthrin |
| C-8 | 138 | and | Buprofezin |
| C-9 | 138 | and | Cartap |
| C-10 | 138 | and | Chlorantraniliprole |
| C-11 | 138 | and | Chlorfenapyr |
| C-12 | 138 | and | Chlorpyrifos |
| C-13 | 138 | and | Clothianidin |
| C-14 | 138 | and | Cyfluthrin |
| C-15 | 138 | and | Cyhalothrin |
| C-16 | 138 | and | Cypermethrin |
| C-17 | 138 | and | Cyromazine |
| C-18 | 138 | and | Deltamethrin |
| C-19 | 138 | and | Dieldrin |
| C-20 | 138 | and | Dinotefuran |
| C-21 | 138 | and | Diofenolan |
| C-22 | 138 | and | Emamectin |
| C-23 | 138 | and | Endosulfan |
| C-24 | 138 | and | Esfenvalerate |
| C-25 | 138 | and | Ethiprole |
| C-26 | 138 | and | Fenothiocarb |
| C-27 | 138 | and | Fenoxycarb |
| C-28 | 138 | and | Fenvalerate |
| C-29 | 138 | and | Fipronil |
| C-30 | 138 | and | Flonicamid |
| C-31 | 138 | and | Flubendiamide |
| C-32 | 138 | and | Flufenoxuron |
| C-33 | 138 | and | Hexaflumuron |
| C-34 | 138 | and | Hydramethylnon |
| C-35 | 138 | and | Imidacloprid |
| C-36 | 138 | and | Indoxacarb |
| C-37 | 138 | and | Lambda-cyhalothrin |
| C-38 | 138 | and | Lufenuron |
| C-39 | 138 | and | Metaflumizone |
| C-40 | 138 | and | Methomyl |
| C-41 | 138 | and | Methoprene |
| C-42 | 138 | and | Methoxyfenozide |
| C-43 | 138 | and | Nitenpyram |
| C-44 | 138 | and | Nithiazine |
| C-45 | 138 | and | Novaluron |
| C-46 | 138 | and | Oxamyl |
| C-47 | 138 | and | Pymetrozine |
| C-48 | 138 | and | Pyrethrin |
| C-49 | 138 | and | Pyridaben |
| C-50 | 138 | and | Pyridalyl |
| C-51 | 138 | and | Pyriproxyfen |
| C-52 | 138 | and | Ryanodine |
| C-53 | 138 | and | Spinetoram |
| C-54 | 138 | and | Spinosad |
| C-55 | 138 | and | Spirodiclofen |
| C-56 | 138 | and | Spiromesifen |
| C-57 | 138 | and | Tebufenozide |
| C-58 | 138 | and | Thiacloprid |
| C-59 | 138 | and | Thiamethoxam |
| C-60 | 138 | and | Thiodicarb |
| C-61 | 138 | and | Thiosultap-sodium |
| C-62 | 138 | and | Tralomethrin |
| C-63 | 138 | and | Triazamate |
| C-64 | 138 | and | Triflumuron |
| C-65 | 138 | and | *Bacillus thuringiensis* |
| C-66 | 138 | and | *Bacillus thuringiensis* delta-endotoxin |
| C-67 | 138 | and | NPV (e.g., Gemstar) |
| C-68 | 138 | And | (a) |
| D-1 | 157 | and | Abamectin |
| D-2 | 157 | and | Acetamiprid |
| D-3 | 157 | and | Amitraz |
| D-4 | 157 | and | Avermectin |
| D-5 | 157 | and | Azadirachtin |
| D-6 | 157 | and | Beta-cyfluthrin |
| D-7 | 157 | and | Bifenthrin |
| D-8 | 157 | and | Buprofezin |
| D-9 | 157 | and | Cartap |
| D-10 | 157 | and | Chlorantraniliprole |
| D-11 | 157 | and | Chlorfenapyr |
| D-12 | 157 | and | Chlorpyrifos |
| D-13 | 157 | and | Clothianidin |
| D-14 | 157 | and | Cyfluthrin |
| D-15 | 157 | and | Cyhalothrin |
| D-16 | 157 | and | Cypermethrin |
| D-17 | 157 | and | Cyromazine |
| D-18 | 157 | and | Deltamethrin |
| D-19 | 157 | and | Dieldrin |
| D-20 | 157 | and | Dinotefuran |
| D-21 | 157 | and | Diofenolan |
| D-22 | 157 | and | Emamectin |
| D-23 | 157 | and | Endosulfan |
| D-24 | 157 | and | Esfenvalerate |
| D-25 | 157 | and | Ethiprole |
| D-26 | 157 | and | Fenothiocarb |
| D-27 | 157 | and | Fenoxycarb |
| D-28 | 157 | and | Fenvalerate |
| D-29 | 157 | and | Fipronil |
| D-30 | 157 | and | Flonicamid |
| D-31 | 157 | and | Flubendiamide |
| D-32 | 157 | and | Flufenoxuron |
| D-33 | 157 | and | Hexaflumuron |
| D-34 | 157 | and | Hydramethylnon |
| D-35 | 157 | and | Imidacloprid |
| D-36 | 157 | and | Indoxacarb |
| D-37 | 157 | and | Lambda-cyhalothrin |
| D-38 | 157 | and | Lufenuron |
| D-39 | 157 | and | Metaflumizone |
| D-40 | 157 | and | Methomyl |
| D-41 | 157 | and | Methoprene |
| D-42 | 157 | and | Methoxyfenozide |
| D-43 | 157 | and | Nitenpyram |
| D-44 | 157 | and | Nithiazine |
| D-45 | 157 | and | Novaluron |
| D-46 | 157 | and | Oxamyl |
| D-47 | 157 | and | Pymetrozine |
| D-48 | 157 | and | Pyrethrin |
| D-49 | 157 | and | Pyridaben |
| D-50 | 157 | and | Pyridalyl |
| D-51 | 157 | and | Pyriproxyfen |
| D-52 | 157 | and | Ryanodine |
| D-53 | 157 | and | Spinetoram |
| D-54 | 157 | and | Spinosad |
| D-55 | 157 | and | Spirodiclofen |
| D-56 | 157 | and | Spiromesifen |
| D-57 | 157 | and | Tebufenozide |
| D-58 | 157 | and | Thiacloprid |
| D-59 | 157 | and | Thiamethoxam |
| D-60 | 157 | and | Thiodicarb |
| D-61 | 157 | and | Thiosultap-sodium |
| D-62 | 157 | and | Tralomethrin |
| D-63 | 157 | and | Triazamate |
| D-64 | 157 | and | Triflumuron |
| D-65 | 157 | and | *Bacillus thuringiensis* |
| D-66 | 157 | and | *Bacillus thuringiensis* delta-endotoxin |
| D-67 | 157 | and | NPV (e.g., Gemstar) |
| D-68 | 157 | And | (a) |

(a) 3-bromo-1-(3-chloro-2-pyridinyl)-N-[4-cyano-2-methyl-6-[(methylamino)carbonyl]phenyl]-1H-pyrazole-5-carboxamide (cyantraniliprole)

The specific mixtures listed in Table B typically combine a compound of Formula 1 with the other invertebrate pest agent in the ratios specified in Table A.

Invertebrate pests are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting).

Compounds of this invention are also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1 and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Mongraph No. 57, and references listed therein.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as needed for application. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

Nonagronomic uses of the present compounds and compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compounds and compositions of the present invention are particularly suitable for combating external parasitic or disease transmitting pests. Compounds and compositions of the present invention are suitable for systemic and/or non-systemic control of infestation or infection by parasites on animals.

Compounds and compositions of the present invention are suitable for combating parasites that infest animal subjects including those in the wild, livestock and agricultural working animals such as cattle, sheep, goats, horses, pigs, donkeys, camels, bison, buffaloes, rabbits, hens, turkeys, ducks, geese and bees (e.g., raised for meat, milk, butter, eggs, fur, leather, feathers and/or wool). By combating parasites, fatalities and performance reduction (in terms of meat, milk, wool, skins, eggs, honey, etc.) are reduced, so that applying a composition comprising a compound of the present invention allows more economic and simple husbandry of animals.

Compounds and compositions of the present invention are especially suitable for combating parasites that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, bison, buffaloes, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the inventive compounds can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws, and parrots raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of invertebrate parasitic pests controlled by administering a parasiticidally effective amount of a compound of this invention to an animal to be protected include ectoparasites (arthropods, acarines, etc) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the Helminths, the group of worms described as nematodes causes widespread and at times serious infection in various species of animals. Nematodes that are contemplated to be treated by the compounds of this invention and by the inventive methods include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria*, and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the compounds of this invention and by the inventive methods include, without limitation, the following genera: *Alaria, Fasciola, Nanophyetus, Opisthorchis, Paragonimus* and *Schistosoma*.

Cestodes that are contemplated to be treated by the compounds of this invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongyloides, Trichinella, Capillaria, Trichuris*, and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other Helminth genera and species are known to the art, and are also contemplated to be treated by the compounds of the invention. These are enumerated in great detail in *Textbook of Veterinary Clinical Parasitology, Volume 1, Helminths*, E. J. L. Soulsby, F. A. Davis Co., Philadelphia, Pa.; *Helminths, Arthropods and Protozoa*, (6$^{th}$ Edition of Monnig's Veterinary Helminthology and Entomology), E. J. L. Soulsby, The Williams and Wilkins Co., Baltimore, Md.

It is also contemplated that the inventive compounds are effective against a number of ectoparasites of animals, e.g., arthropod ectoparasites of mammals and birds although it is also recognized that some arthropods can be endoparasites as well.

Thus, insect and acarine pests include, e.g., biting insects, such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp., and *Aedes* spp.

Mites include *Mesostigmata* spp. e.g., mesostigmatids such as the chicken mite, *Dermanyssus gallinae*; itch or scab mites such as *Sarcoptidae* spp. for example, *Sarcoptes scabiei*; mange mites such as *Psoroptidae* spp. including *Chorioptes bovis* and *Psoroptes ovis*; chiggers e.g., *Trombiculidae* spp. for example the North American chigger, *Trombicula alfreddugesi*.

Ticks include, e.g., soft-bodied ticks including *Argasidae* spp. for example *Argas* spp. and *Ornithodoros* spp.; hard-bodied ticks including *Ixodidae* spp., for example *Rhipicephalus sanguineus, Dermacentor variabilis, Dermacentor andersoni, Amblyomma americanum, Ixodes scapularis* and *Boophilus* spp.

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other arthropod pests and ectoparasites are known to the art, and are also contemplated to be treated by the compounds of the invention. These are enumerated in great detail in *Medical and Veterinary Entomology*, D. S. Kettle, John Wiley & Sons, New York and Toronto; *Control of Arthropod Pests of Livestock: A Review of Technology*, R. O. Drummand, J. E. George, and S. E. Kunz, CRC Press, Boca Raton, Fla.

The compounds and compositions of this invention may also be effective against a number of protozoa endoparasites of animals, such as those summarized by Table 1, as follows.

TABLE 1

Exemplary Parasitic Protozoa and Associated Human Diseases

| Phylum | Subphylum | Representative Genera | Human Disease or Disorder |
|---|---|---|---|
| Sarcomastigophora (with flagella, pseudopodia, or both) | Mastigophora (Flagella) | Leishmania | Visceral, cutaneous and mucocutaneous Infection |
| | | Trypansoma | Sleeping sickness |

TABLE 1-continued

Exemplary Parasitic Protozoa and Associated Human Diseases

| Phylum | Subphylum | Representative Genera | Human Disease or Disorder |
|---|---|---|---|
| | Sarcodina (pseudopodia) | Giardia | Chagas' disease |
| | | | Diarrhea |
| | | Trichomonas | Vaginitis |
| | | Entamoeba | Dysentery, liver Abscess |
| | | Dientamoeba | Colitis |
| | | Naegleria and Acanthamoeba | Central nervous system and corneal ulcers |
| | | Babesia | Babesiesis |
| Apicomplexa (apical complex) | | Plasmodium | Malaria |
| | | Isospora | Diarrhea |
| | | Sarcocystis | Diarrhea |
| | | Cryptosporidum | Diarrhea |
| | | Toxoplasma | Toxoplasmosis |
| | | Eimeria | Chicken coccidiosis |
| Microspora | | Enterocytozoon | Diarrhea |
| Ciliaphora (with cilia) | | Balantidium | Dysentery |
| Unclassified | | Pneumocystis | Pneumonia |

In particular, the compounds of this invention are effective against ectoparasites including fleas such as *Ctenocephalides felis* (cat flea) and *Ctenocephalides canis* (dog flea).

The compounds of this invention may also be effective against other ectoparasites including flies such as *Haematobia* (*Lyperosia*) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis* and *Gastrophilus naslis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites); and ticks such as *Ixodes* spp., *Boophilus* spp., *Rhipicephalus* spp., *Amblyomma* spp., *Dermacentor* spp., *Hyalomma* spp. and *Haemaphysalis* spp.

Biologically active compounds or agents useful in the compositions of the present invention include the organophosphate pesticides. This class of pesticides has very broad activity as insecticides and, in certain instances, anthelminitic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion and phosalone. It is also contemplated to include combinations of the inventive methods and compounds with carbamate type pesticides, including, e.g., carbaryl, carbofuran, aldicarb, molinate, methomyl, carbofuran, etc., as well as combinations with the organochlorine type pesticides. It is further contemplated to include combinations with biological pesticides, including repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *bacillus thuringensis*, chlorobenzilate, formamidines (e.g., amitraz), copper compounds (e.g., copper hydroxide and cupric oxychloride sulfate), cyfluthrin, cypermethrin, dicofol, endosulfan, esenfenvalerate, fenvalerate, lambda-cyhalothrin, methoxychlor and sulfur.

Of note are additional biologically active compounds or agents selected from art-known anthelmintics, such as, for example, avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole) and praziquantel.

Other biologically active compounds or agents useful in the compositions of the present invention can be selected from Insect Growth Regulators (IGRs) and Juvenile Hormone Analogues (JHAs) such as diflubenzuron, triflumuron, fluazuron, cyromazine, methoprene, etc., thereby providing both initial and sustained control of parasites (at all stages of insect development, including eggs) on the animal subject, as well as within the environment of the animal subject.

Of note are biologically active compounds or agents useful in the compositions of the present invention selected from the antiparasitic class of avermectin compounds. As stated above, the avermectin family of compounds is a series of very potent antiparasitic agents known to be useful against a broad spectrum of endoparasites and ectoparasites in mammals.

A notable compound for use within the scope of the present invention is ivermectin. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. Ivermectin is disclosed in U.S. Pat. No. 4,199,569.

Abamectin is an avermectin that is disclosed as Avermectin $B_{1a}/B_{1b}$ in U.S. Pat. No. 4,310,519. Abamectin contains at least 80% of avermectin $B_{1a}$ and not more than 20% of avermectin $B_{1b}$.

Another notable avermectin is Doramectin, also known as 25-cyclohexyl-avermectin $B_1$. The structure and preparation of Doramectin is disclosed in U.S. Pat. No. 5,089,480.

Another notable avermectin is Moxidectin. Moxidectin, also known as LL-F28249 alpha, is known from U.S. Pat. No. 4,916,154.

Another notable avermectin is Selamectin. Selamectin is 25-cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a Milbemycin producing strain of *Streptomyces*. The microorganism, the fermentation conditions and the isolation procedures are more fully described in U.S. Pat. No. 3,950,360 and U.S. Pat. No. 3,984,564.

Emamectin (4"-deoxy-4"-epi-methylaminoavermectin $B_1$), which can be prepared as described in U.S. Pat. No. 5,288,710 or U.S. Pat. No. 5,399,717, is a mixture of two homologues, 4"-deoxy-4"-epi-methylaminoavermectin $B_{1a}$ and 4"-deoxy-4"-epi-methylaminoavermectin $B_{1b}$. Preferably, a salt of Emamectin is used. Non-limiting examples of salts of Emamectin which can be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is Emamectin benzoate.

Eprinomectin is chemically known as 4"-epi-acetylamino-4"-deoxy-avermectin $B_1$. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The composition of the present invention optionally comprises combinations of one or more of the following antiparasite compounds: imidazo[1,2-b]pyridazine compounds as described by U.S. application Ser. No. 11/019,597, filed on Dec. 22, 2004; 1-(4-mono and di-halomethylsulphonylphenyl)-2-acylamino-3-fluoropropanol compounds, as described by U.S. application Ser. No. 11/018,156, filed on Dec. 21, 2004; trifluoromethanesulfonanilide oxime ether derivatives, as described by U.S. application Ser. No. 11/231,423, filed on Sep. 21, 2005; and n-[(phenyloxy)phenyl]-1,1,1-trifluoromethanesulfonamide and n-[(phenylsulfanyl)phenyl]-1,1,1-trifluoromethanesulfonamide derivatives, as described by U.S. Provisional Application Ser. No. 60/688,898, filed on Jun. 9, 2005.

The compositions of the present invention can also further comprise a flukicide. Suitable flukicides include, for example, triclabendazole, fenbendazole, albendazole, Clorsulon and oxibendazole. It will be appreciated that the above combinations can further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g., in a combined composition and/or in separate dosage forms. Art-known antibiotics suitable for this purpose include, for example, those listed herein below.

One useful antibiotic is Florfenicol, also known as D-(threo)-1-(4-methylsulfonylphenyl)-2-dichloroacetamido-3-fluoro-1-propanol. Another notable antibiotic compound is D-(threo)-1-(4-methylsulfonylphenyl)-2-difluoroacetamido-3-fluoro-1-propanol. Another useful antibiotic is Thiamphenicol. Processes for the manufacture of these antibiotic compounds, and intermediates useful in such processes, are described in U.S. Pat. No. 4,311,857; U.S. Pat. No. 4,582,918; U.S. Pat. No. 4,973,750; U.S. Pat. No. 4,876,352; U.S. Pat. No. 5,227,494; U.S. Pat. No. 4,743,700; U.S. Pat. No. 5,567,844; U.S. Pat. No. 5,105,009; U.S. Pat. No. 5,382,673; U.S. Pat. No. 5,352,832; and U.S. Pat. No. 5,663,361. Other florfenicol analogs and/or prodrugs have been disclosed and such analogs also can be used in the compositions and methods of the present invention (see e.g., U.S. Patent Application Publication No: 2004/0082553, and U.S. patent application Ser. No. 11/016,794).

Another useful antibiotic compound is Tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695.

Another useful antibiotic for use in the present invention is tulathromycin. Tulathromycin is also identified as (2R,3S,4R,5R,8R,10R,11R,12S,13S,14R) 13-[(2,6-dideoxy-3-C-methyl-3-O-methyl-4-C-[(propylamino)methyl]-alpha-L-ribo-hexopyranosyl]-oxy]-2-ethyl-3,4,10-trihydroxy-3,5,8,10,12,14-hexamethyl-11-[[3,4,6-trideoxy-3-(dimethyl-amino)-beta-D-xylo-hexopyranosyl]oxy]-1-oxa-6-azacyclopentadecan-15-one. Tulathromycin can be prepared in accordance with the procedures set forth in U.S. Patent Publication No. 2003/0064939 A1.

Further antibiotics for use in the present invention include the cephalosporins such as, for example, ceftiofur, cefquinome, etc. The concentration of the cephalosporin in the formulation of the present invention optionally varies between about 1 mg/mL to 500 mg/mL.

Another useful antibiotic includes the fluoroquinolones, such as, for example, enrofloxacin, danofloxacin, difloxacin, orbifloxacin and marbofloxacin. Enrofloxacin is typically administered in a concentration of about 100 mg/mL. Danofloxacin is typically administered at a concentration of about 180 mg/mL.

Other useful macrolide antibiotics include compounds from the class of ketolides, or, more specifically, the azalides. Such compounds are described in, for example, U.S. Pat. No. 6,514,945, U.S. Pat. No. 6,472,371, U.S. Pat. No. 6,270,768, U.S. Pat. No. 6,437,151, U.S. Pat. No. 6,271,255, U.S. Pat. No. 6,239,112, U.S. Pat. No. 5,958,888, U.S. Pat. No. 6,339,063 and U.S. Pat. No. 6,054,434.

Other useful antibiotics include the tetracyclines, particularly chlortetracycline and oxytetracycline. Other antibiotics may include β-lactams such as penicillins, e.g., penicillin, ampicillin, amoxicillin, or a combination of amoxicillin with clavulanic acid or other beta lactamase inhibitors.

Nonagronomic applications in the veterinary sector are by conventional means such as by enteral administration in the form of, for example, tablets, capsules, drinks, drenching preparations, granulates, pastes, boli, feed-through procedures, or suppositories; or by parenteral administration, such as by injection (including intramuscular, subcutaneous, intravenous, intraperitoneal) or implants; by nasal administration; by topical administration, for example, in the form of immersion or dipping, spraying, washing, coating with powder, or application to a small area of the animal, and through articles such as neck collars, ear tags, tail bands, limb bands or halters which comprise compounds or compositions of the present invention.

Any of the compounds of the present invention, or a suitable combination of such compounds, may be administered directly to the animal subject and/or indirectly by applying it to the local environment in which the animal dwells (such as bedding, enclosures, or the like). Direct administration includes contacting the skin, fur or feathers of a subject animal with the compounds, or by feeding or injecting the compounds into the animal.

The compounds of the present invention may be administered in a controlled release form, e.g., in a subcutaneous slow release formulation, or in the form of a controlled release device affixed to an animal such as a fleacollar. Collars for the controlled release of an insecticide agent for long term protection against flea infestation in a companion animal are art-known, and are described, for example, by U.S. Pat. No. 3,852,416, U.S. Pat. No. 4,224,901, U.S. Pat. No. 5,555,848 and U.S. Pat. No. 5,184,573.

Typically a parasiticidal composition according to the present invention comprises a mixture of a compound of Formula 1 with one or more pharmaceutically or veterinarily acceptable carriers comprising excipients and auxiliaries selected with regard to the intended route of administration (e.g., oral, topical or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a parasitically effective amount of a compound of the invention and at least one carrier.

For parenteral administration including intravenous, intramuscular and subcutaneous injection, a compound of the present invention can be formulated in suspension, solution or emulsion in oily or aqueous vehicles, and may contain adjuncts such as suspending, stabilizing and/or dispersing agents. The compounds of the present invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the present invention may also be formulated as a depot preparation. Such long acting formulations may be administered by implantation (for example, subcutaneously or intramuscularly) or by intramuscular or subcutaneous injection. The compounds of the present invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the present invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

Compounds of the present invention have been discovered to have favorable pharmacokinetic and pharmacodynamic properties providing systemic availability from oral administration and ingestion. Therefore after ingestion by the animal to be protected, parasiticidally effective concentrations of compounds of the invention in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, a compound of the present invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compounds of Formula 1 may also be formulated in rectal compositions such as suppositories or retention enemas, using, e.g., conventional suppository bases such as cocoa butter or other glycerides.

Formulations for topical administration are typically in the form of a powder, cream, suspension, spray, emulsion, foam, paste, aerosol, ointment, salve or gel. More typically a topical formulation is a water-soluble solution, which can be in the form of a concentrate that is diluted before use. Parasiticidal compositions suitable for topical administration typically comprise a compound of the present invention and one or more topically suitable carriers. In applications of a parasiticidal composition topically to the exterior of an animal as a line or spot (i.e. "spot-on" treatment), the active ingredient migrates over the surface of the animal to cover most or all of its external surface area. As a result, the treated animal is particularly protected from invertebrate pests that feed off the epidermis of the animal such as ticks, fleas and lice. Therefore formulations for topical localized administration often comprise at least one organic solvent to facilitate transport of the active ingredient over the skin and/or penetration into the epidermis of the animal. Carriers in such formulations include propylene glycol, paraffins, aromatics, esters such as isopropyl myristate, glycol ethers, alcohols such as ethanol, n-propanol, 2-octyl dodecanol or oleyl alcohol; solutions in esters of monocarboxylic acids, such as isopropyl myristate, isopropyl palmitate, lauric acid oxalic ester, oleic acid oleyl ester, oleic acid decyl ester, hexyl laurate, oleyl oleate, decyl oleate, caproic acid esters of saturated fatty alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or solutions of esters of aliphatic acids, e.g., glycols. It may be advantageous for a crystallization inhibitor or a dispersant known from the pharmaceutical or cosmetic industry also to be present.

A pour-on formulation may also be prepared for control of parasites in an animal of agricultural worth. The pour-on formulations of this invention can be in the form of a liquid, powder, emulsion, foam, paste, aerosol, ointment, salve or gel. Typically, the pour-on formulation is liquid. These pour-on formulations can be effectively applied to sheep, cattle, goats, other ruminants, camelids, pigs and horses. The pour-on formulation is typically applied by pouring in one or several lines or in a spot-on the dorsal midline (back) or shoulder of an animal. More typically, the formulation is applied by pouring it along the back of the animal, following the spine. The formulation can also be applied to the animal by other conventional methods, including wiping an impregnated material over at least a small area of the animal, or applying it using a commercially available applicator, by means of a syringe, by spraying or by using a spray race. The pour-on formulations include a carrier and can also include one or more additional ingredients. Examples of suitable additional ingredients are stabilizers such as antioxidants, spreading agents, preservatives, adhesion promoters, active solubilisers such as oleic acid, viscosity modifiers, UV blockers or absorbers, and colourants. Surface active agents, including anionic, cationic, non-ionic and ampholytic surface active agents, can also be included in these formulations.

The formulations of this invention typically include an antioxidant, such as BHT (butylated hydroxytoluene). The antioxidant is generally present in amounts of at 0.1-5% (wt/vol). Some of the formulations require a solubilizer, such as oleic acid, to dissolve the active agent, particularly if spinosad is used. Common spreading agents used in these pour-on formulations are: IPM, IPP, caprylic/capric acid esters of saturated $C_{12}$-$C_{18}$ fatty alcohols, oleic acid, oleyl ester, ethyl oleate, triglycerides, silicone oils and DPM. The pour-on formulations of this invention are prepared according to known techniques. Where the pour-on is a solution, the parasiticide/insecticide is mixed with the carrier or vehicle, using heat and stirring where required. Auxiliary or additional ingredients can be added to the mixture of active agent and carrier, or they can be mixed with the active agent prior to the addition of the carrier. If the pour-on is an emulsion or suspension, these formulations are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

For agronomic applications, the rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

In general for veterinary use, a compound of Formula 1 is administered in a parasiticidally effective amount to an animal to be protected from invertebrate parasite pests. A parasiticidally effective amount is the amount of active ingredient needed to achieve an observable effect diminishing the occurrence or activity of the target invertebrate parasite pest. One skilled in the art will appreciate that the parasitically effective dose can vary for the various compounds and compositions of the present invention, the desired parasitical effect and duration, the target invertebrate pest species, the animal to be protected, the mode of application and the like, and the amount needed to achieve a particular result can be determined through simple experimentation.

For oral administration to homeothermic animals, the daily dosage of a compound of the present invention typically ranges from about 0.01 mg/kg to about 100 mg/kg, more typically from about 0.5 mg/kg to about 100 mg/kg, of animal body weight. For topical (e.g., dermal) administration, dips and sprays typically contain from about 0.5 ppm to about 5000 ppm, more typically from about 1 ppm to about 3000 ppm, of a compound of the present invention.

The compounds of this invention prepared by the methods described herein are shown in Index Tables A-F. See Index Table G for $^1$H NMR data. For mass spectral data (AP$^+$ (M+1)), the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$). The alternate molecular ion peaks (e.g., M+2 or M+4) that occur with compounds containing multiple halogens are not reported. The variable "$R^a$" in Index Table C represents one or a combination of substituents as listed in Index Table C.

The following additional abbreviations are used in the Index Tables which follow: Cmpd means Compound, Me is methyl, Et is ethyl, i-Pr is isopropyl, n-Bu is normal-butyl, t-Bu is tertiary-butyl, Ph is phenyl, CHO is formyl, Ac is acetyl (i.e. C(O)CH$_3$) and SO$_2$Me is methyl sulfonyl.

Fragments A-1 through A-42 and B-1 through B-4 shown below are referred to in the Index Tables. The asterisk * denotes the attachment point of the fragment to the remainder of the molecule.

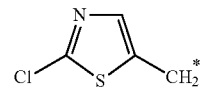

A-1

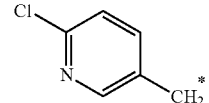

A-2

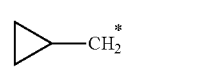

A-3

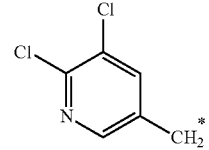

A-4

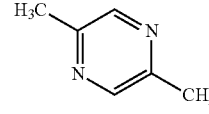

A-5

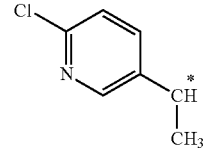

A-6

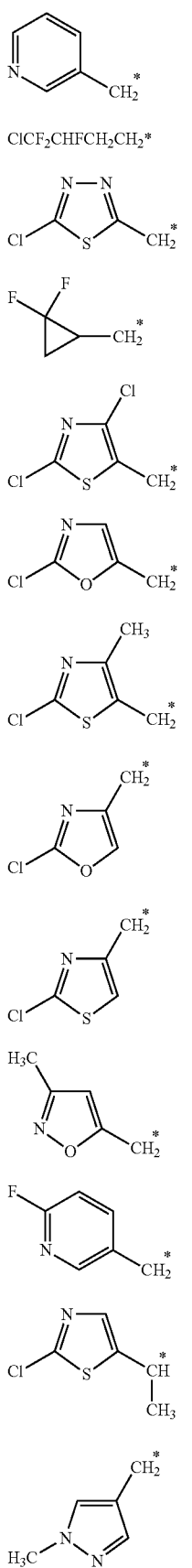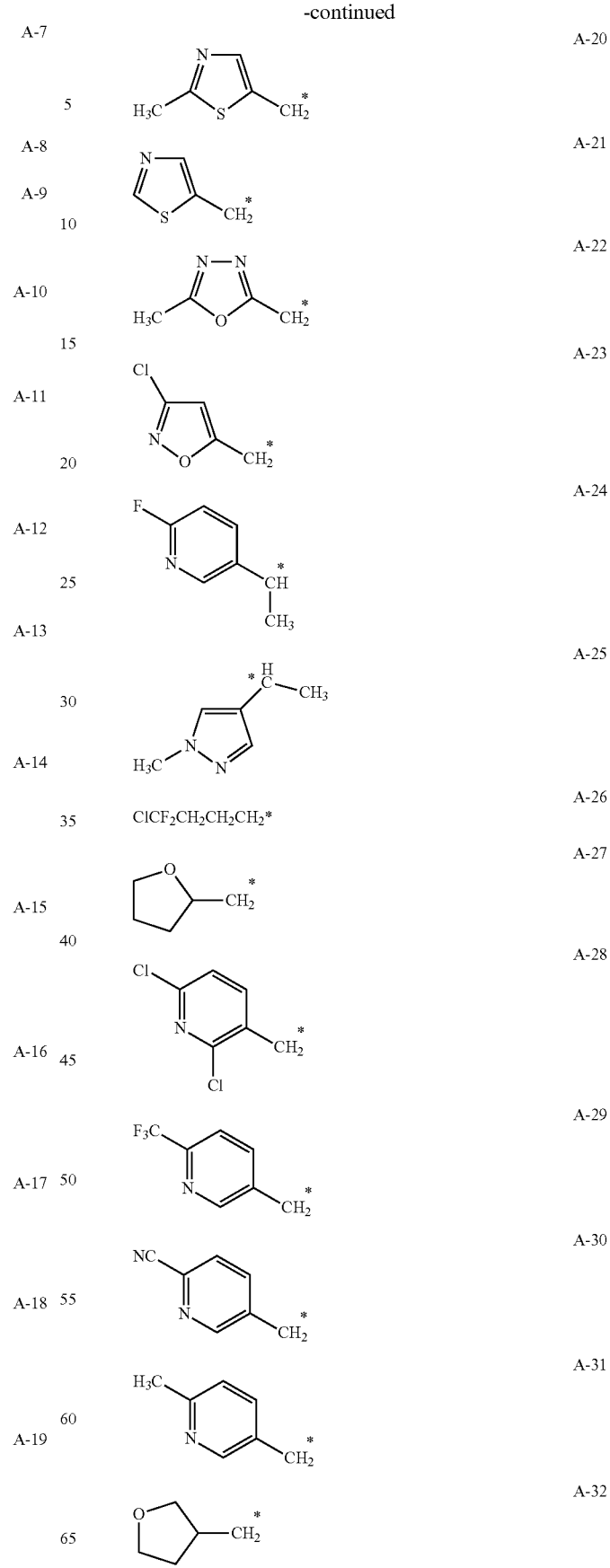

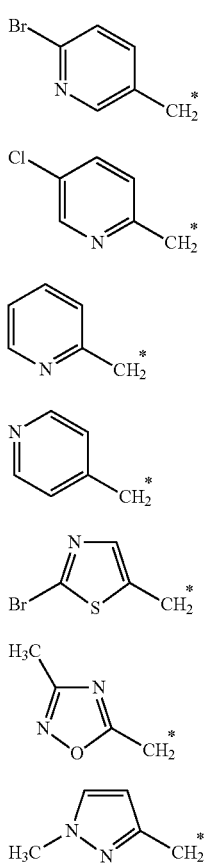
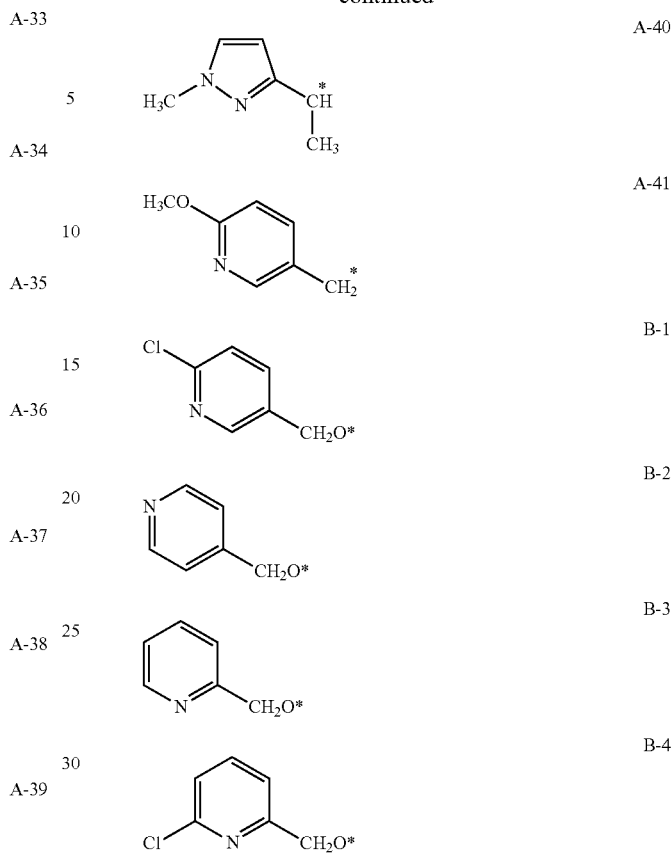
INDEX TABLE A
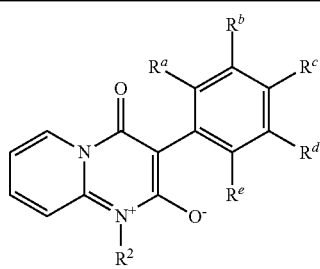
| Cmpd | $R^2$ | $R^a$ | $R^b$ | $R^c$ | $R^d$ | $R^e$ | m.p. (° C.) | AP+ (M + 1) |
|---|---|---|---|---|---|---|---|---|
| 1 | $CH_2CF_3$ | H | Br | H | H | H | 233-234 | |
| 2 | $CH_2CF_3$ | H | $OCH_3$ | H | H | H | 124-125 | |
| 3 | $CH_2CF_3$ | H | Cl | H | H | H | | * |
| 5 | $CH_2CF_3$ | H | H | F | H | H | 205-206 | |
| 6 | $CH_2CF_3$ | H | $CF_3$ | H | H | H | 178-179 | |
| 7 | $CH_2CF_3$ | H | H | H | H | H | | ** |
| 8 | $CH_2CH_2CH_3$ | H | $OCF_3$ | H | H | H | | * |
| 9 | $CH_2CF_3$ | Cl | Cl | H | H | H | | * |
| 10 | $CH_2CF_3$ | F | H | F | H | H | | * |
| 11 | $CH_2CF_3$ | F | H | H | H | H | 211-212 | |
| 12 | $CH_2CH_2CH_3$ | H | $CF_3$ | H | H | H | | * |
| 13 | $CH_2CF_3$ | H | $OCH_2CF_3$ | H | H | H | 162-163 | |
| 14 | $CH_2CF_3$ | F | H | H | $OCF_3$ | H | | * |
| 15 | $CH_2CF_3$ | H | Cl | H | Cl | H | | * |
| 16 | $CH_2CF_3$ | H | $CH_3$ | F | H | H | 239-240 | |
| 17 | $CH_2CF_3$ | $OCH_3$ | H | H | H | H | | * |
| 18 | A-3 | H | $OCF_3$ | H | H | H | | * |
| 19 | A-3 | H | H | F | H | H | 188-189 | |
| 20 | $CH_2CH_2CH_3$ | H | F | H | F | H | | * |

INDEX TABLE A-continued

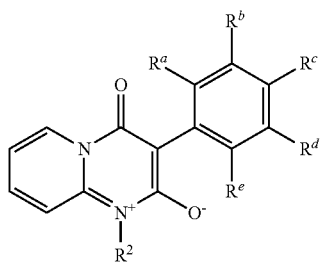

| Cmpd | R² | Rᵃ | Rᵇ | Rᶜ | Rᵈ | Rᵉ | m.p. (° C.) | AP+ (M + 1) |
|---|---|---|---|---|---|---|---|---|
| 21 | CH₂CF₃ | F | H | Cl | H | H | * | |
| 22 | A-8 | H | OCF₃ | H | H | H | * | |
| 23 | CH₂CF₃ | H | F | F | H | H | 118-119 | |
| 24 | CH₂CF₃ | H | Br | F | H | H | 213-214 | |
| 25 | CH₂CF₃ | OCH₃ | H | H | Cl | H | * | |
| 26 | CH₂CF₃ | H | H | Cl | H | H | 226-227 | |
| 27 | A-8 | H | H | F | H | H | * | |
| 28 | CH₂CH₂CH₃ | H | H | H | H | H | * | |
| 29 | A-3 | Cl | H | F | H | H | 191-192 | |
| 30 | A-8 | F | H | F | H | H | * | |
| 31 | A-3 | F | H | F | H | H | 204-205 | |
| 32 | CH₂CF₃ | H | F | H | F | H | * | |
| 33 | CH₂CF₂CF₃ | H | OCF₃ | H | H | H | * | |
| 34 | CH₂CF₂CF₃ | H | H | H | H | H | * | |
| 35 | CH₂CF₂CF₃ | H | H | F | H | H | * | |
| 36 | CH₂CF₂CF₃ | F | H | F | H | H | * | |
| 37 | CH₂CF=CF₂ | H | H | H | H | H | * | |
| 38 | CH₂CH₂CF₃ | H | H | H | H | H | * | |
| 39 | A-3 | H | H | H | H | H | * | |
| 40 | CH₂CF₃ | H | OCF₃ | H | H | H | 140-141 | |
| 41 | CH₂CH₂CH₃ | H | H | cyano | H | H | * | |
| 122 | CH₂CH=CH₂ | H | H | H | H | H | ** | |
| 42 | A-1 | H | H | F | H | H | * | |
| 43 | A-1 | H | H | H | H | H | 233-235 | |
| 44 | A-1 | F | H | F | H | H | * | |
| 45 | A-1 | H | OCF₃ | H | H | H | 123-125 | |
| 46 | A-1 | H | CF₃ | H | H | H | 152-153 | |
| 47 | A-1 | H | Cl | H | H | H | 235-237 | |
| 48 | A-1 | H | H | OCHF₂ | H | H | 182-183 | |
| 49 | A-1 | H | H | OCH₃ | H | H | 215-217 | |
| 50 | A-1 | F | H | H | H | H | * | |
| 51 | A-2 | H | Br | H | H | H | * | |
| 52 | A-2 | H | Cl | H | CF₃ | H | * | |
| 53 | A-2 | H | CF₃ | H | H | H | * | |
| 54 | A-2 | H | OCF₃ | H | H | H | * | |
| 55 | A-2 | H | Br | H | OCF₃ | H | * | |
| 56 | A-2 | H | Cl | H | H | H | * | |
| 57 | A-2 | H | H | F | H | H | * | |
| 58 | A-2 | F | H | H | OCF₃ | H | ** | |
| 59 | A-2 | H | H | H | H | H | ** | |
| 60 | A-2 | H | H | OCHF₂ | H | H | * | |
| 61 | A-2 | H | F | H | H | H | * | |
| 62 | A-2 | F | H | H | Br | H | * | |
| 63 | A-2 | F | H | F | H | H | * | |
| 64 | A-2 | Cl | H | F | H | H | * | |
| 65 | A-2 | H | H | F | H | H | 211-213 | |
| 66 | A-2 | F | H | H | CF₃ | H | * | |
| 67 | A-2 | Cl | H | H | OCF₃ | H | * | |
| 68 | A-2 | F | CF₃ | H | H | H | * | |
| 70 | A-2 | F | H | H | Cl | H | * | |
| 71 | A-2 | F | H | F | H | H | 226-228 | |
| 72 | A-2 | F | H | H | H | H | * | |
| 73 | A-2 | H | H | OCF₃ | H | H | * | |
| 74 | A-2 | H | CF₃ | F | H | H | * | |
| 75 | A-2 | H | H | OCH₃ | H | H | * | |
| 76 | A-2 | H | H | CF₃ | H | H | * | |
| 77 | A-2 | Cl | H | Cl | H | H | * | |
| 78 | A-2 | F | H | F | F | H | * | |
| 79 | A-2 | F | H | CF₃ | H | H | * | |
| 80 | A-2 | F | F | F | H | H | * | |
| 81 | A-2 | H | H | H | H | H | 241-243 | |
| 82 | A-2 | H | F | F | H | H | * | |
| 83 | A-2 | H | OCH₃ | H | H | H | * | |
| 84 | A-2 | H | H | CH₃ | H | H | * | |

INDEX TABLE A-continued

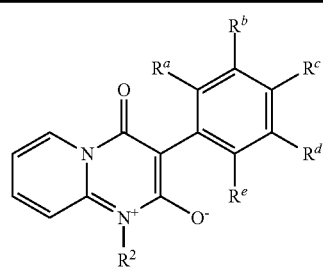

| Cmpd | R² | Rᵃ | Rᵇ | Rᶜ | Rᵈ | Rᵉ | m.p. (° C.) | AP+ (M + 1) |
|---|---|---|---|---|---|---|---|---|
| 85 | A-2 | F | H | Br | H | H | * | |
| 86 | A-2 | H | CH₂CH₂O | | H | H | * | |
| 87 | A-4 | H | H | F | H | H | * | |
| 88 | A-2 | F | H | H | F | H | * | |
| 89 | A-2 | F | F | H | H | H | * | |
| 90 | A-2 | CH₃ | H | cyano | H | H | * | |
| 91 | A-2 | CH₃ | H | Br | H | H | * | |
| 92 | A-2 | H | Br | F | H | H | * | |
| 93 | A-2 | H | Br | H | CF₃ | H | * | |
| 94 | A-2 | F | H | cyano | H | H | * | |
| 95 | A-2 | F | H | OCH₃ | H | H | * | |
| 96 | A-2 | CH₃ | H | F | H | H | * | |
| 97 | A-5 | H | OCF₃ | H | H | H | * | |
| 98 | A-2 | H | OCH₂O | | H | H | * | |
| 99 | A-2 | Br | H | F | H | H | * | |
| 100 | A-4 | H | H | H | H | H | * | |
| 101 | A-2 | H | OCH₃ | F | H | H | * | |
| 102 | A-2 | H | F | OCH₃ | H | H | * | |
| 103 | A-7 | H | Br | H | OCF₃ | H | * | |
| 104 | A-2 | H | H | Br | H | H | * | |
| 105 | A-2 | H | H | cyano | H | H | * | |
| 106 | A-2 | H | H | Cl | H | H | * | |
| 107 | A-2 | H | cyano | H | H | H | * | |
| 108 | A-2 | F | H | F | H | F | * | |
| 109 | A-6 | H | H | F | H | H | * | |
| 123 | A-1 | H | OCH₃ | H | H | H | 184-186 | |
| 124 | A-1 | H | Br | H | H | H | 224-226 | |
| 161 | CH₂CH₂CH₃ | H | Br | H | H | H | | 359 |
| 162 | CH₂CH₂CH₃ | F | F | H | H | H | | 317 |
| 163 | CH₂CH₂CH₃ | F | H | F | H | H | | 317 |
| 164 | CH₂CH₂CH₃ | H | H | i-Pr | H | H | | 323 |
| 165 | CH₂CH₂CH₃ | H | H | Ph | H | H | | 357 |
| 166 | A-1 | F | H | H | CF₃ | H | | 456 |
| 167 | A-2 | F | H | H | CF₃ | H | | 434 |
| 168 | A-1 | F | H | H | H | F | | 406 |
| 169 | A-1 | H | Cl | H | Cl | H | | 438 |
| 170 | A-9 | H | H | H | H | H | 208-210 | |
| 171 | A-3 | F | H | cyano | H | H | * | |
| 172 | A-10 | F | H | F | H | H | | 365 |
| 173 | A-1 | F | H | H | Cl | H | | 422 |
| 174 | A-11 | H | H | H | H | H | | 404 |
| 175 | A-11 | H | H | F | H | H | | 422 |
| 176 | A-11 | F | H | F | H | H | | 440 |
| 177 | A-11 | H | CF₃ | H | H | H | | 472 |
| 178 | A-12 | H | H | H | H | H | | 354 |
| 179 | A-1 | H | OCH₃ | H | Br | H | | 478 |
| 180 | A-1 | H | OCH₃ | H | H | F | | 418 |
| 181 | A-13 | H | H | H | H | H | | 384 |
| 182 | A-13 | H | H | F | H | H | | 402 |
| 183 | A-13 | F | H | F | H | H | | 420 |
| 184 | A-13 | H | CF₃ | H | H | H | | 452 |
| 185 | A-1 | H | OCH₃ | H | OCH₃ | H | | 430 |
| 186 | A-1 | H | CF₃ | H | CF₃ | H | | 506 |
| 187 | A-3 | H | CF₃ | H | CF₃ | H | | 429 |
| 188 | A-3 | H | CF₃ | H | Br | H | | 439 |
| 189 | CH₂CF₃ | H | CF₃ | H | Br | H | 189-190 | |
| 190 | A-14 | H | H | H | H | H | | 354 |
| 191 | A-14 | H | H | F | H | H | | 372 |
| 192 | A-1 | F | OCH₃ | H | H | H | | 418 |
| 193 | A-1 | H | OCF₃ | H | H | F | | 472 |
| 194 | A-15 | H | H | H | H | H | | 370 |
| 195 | A-15 | H | H | F | H | H | | 388 |
| 196 | A-16 | H | H | H | H | H | | 334 |
| 197 | A-16 | H | H | F | H | H | 175-177 | |

INDEX TABLE A-continued

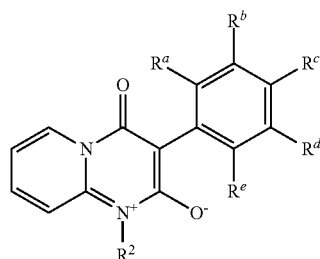

| Cmpd | $R^2$ | $R^a$ | $R^b$ | $R^c$ | $R^d$ | $R^e$ | m.p. (° C.) | AP+ (M + 1) |
|---|---|---|---|---|---|---|---|---|
| 198 | A-2 | H | OCH$_3$ | H | OCH$_3$ | H | | 424 |
| 199 | CH$_2$CF$_3$ | H | OCH$_3$ | H | OCH$_3$ | H | | 381 |
| 200 | A-1 | OCH$_3$ | H | H | H | H | | 400 |
| 201 | A-1 | OCH$_3$ | H | OCH$_3$ | H | H | | 430 |
| 202 | A-17 | H | OCH$_3$ | H | OCH$_3$ | H | | 408 |
| 203 | A-17 | H | CF$_3$ | H | H | H | | 416 |
| 204 | A-17 | F | H | F | F | H | 215-217 | |
| 205 | CH$_2$CF=CH$_2$ | H | H | F | H | H | | 315 |
| 206 | CH$_2$CF=CH$_2$ | H | OCF$_3$ | H | H | H | | 381 |
| 207 | A-17 | H | H | cyano | H | H | | 373 |
| 208 | A-17 | H | OCH$_3$ | H | H | H | | 378 |
| 209 | CH$_2$CF$_3$ | F | OCH$_3$ | H | H | H | * | |
| 210 | A-2 | F | OCH$_3$ | H | H | H | | 412 |
| 211 | A-18 | H | H | H | H | H | | 384 |
| 212 | A-18 | H | H | F | H | H | | 402 |
| 213 | A-19 | H | H | H | H | H | | 333 |
| 214 | A-19 | H | H | F | H | H | 210-211 | |
| 215 | A-1 | H | CF$_3$ | H | F | H | | 456 |
| 216 | CH(CH$_3$)CF$_3$ | H | H | F | H | H | | 353 |
| 217 | CH(CH$_3$)CF$_3$ | H | OCF$_3$ | H | H | H | | 419 |
| 218 | A-20 | H | H | H | H | H | | 350 |
| 219 | A-20 | H | H | F | H | H | | 368 |
| 220 | A-21 | H | H | H | H | H | | 336 |
| 221 | A-21 | H | H | F | H | H | | 354 |
| 222 | CH(CH$_3$)CF$_3$ | F | H | F | H | H | | 371 |
| 223 | CH$_2$CF$_3$ | F | H | cyano | H | H | | 364 |
| 224 | A-16 | F | H | H | H | H | | 352 |
| 225 | A-17 | F | H | H | H | H | | 366 |
| 226 | A-17 | H | OCF$_3$ | H | H | H | | 432 |
| 227 | CH$_2$CHFCF$_2$Cl | H | H | F | H | H | | 387 |
| 228 | CH$_2$CHFCF$_2$Cl | F | H | F | H | H | | 405 |
| 229 | A-18 | F | H | H | H | H | * | |
| 230 | A-19 | H | H | cyano | H | H | | 358 |
| 231 | A-19 | F | H | F | H | H | | 369 |
| 232 | A-19 | H | OCF$_3$ | H | H | H | | 417 |
| 233 | A-19 | F | H | H | H | H | | 431 |
| 234 | A-19 | OCH$_3$ | H | H | H | H | | 363 |
| 235 | A-2 | OCH$_3$ | H | H | Br | H | | 474 |
| 236 | A-2 | Cl | H | H | CF$_3$ | H | | 466 |
| 237 | CH(CH$_3$)CF$_3$ | F | H | H | H | H | | 353 |
| 238 | A-19 | F | H | H | CF$_3$ | H | | 419 |
| 239 | A-19 | F | H | cyano | H | H | | 376 |
| 240 | CH(CH$_3$)CF$_3$ | H | Br | H | H | H | | 353 |
| 241 | A-22 | H | H | H | H | H | | 335 |
| 242 | CH(CH$_3$)CF$_3$ | H | Br | H | CF$_3$ | H | | 481 |
| 243 | CH(CH$_3$)CF$_3$ | H | OCH$_3$ | H | H | H | | 365 |
| 244 | CH(CH$_3$)CF$_3$ | OCH$_3$ | H | H | H | H | | 365 |
| 245 | A-1 | H | SF$_5$ | H | H | Cl | | 530 |
| 246 | A-2 | OCH$_3$ | H | H | CF$_3$ | H | | 549 |
| 247 | A-2 | OCH$_3$ | H | H | Cl | H | | 428 |
| 248 | A-23 | H | OCF$_3$ | H | H | H | | 438 |
| 249 | A-17 | OCH$_3$ | H | H | H | H | | 378 |
| 250 | A-2 | CH$_3$ | H | CH$_3$ | H | CH$_3$ | | 406 |
| 251 | A-1 | CH$_3$ | H | CH$_3$ | H | CH$_3$ | | 412 |
| 252 | CH(CH$_3$)CF$_3$ | Cl | H | H | OCF$_3$ | H | | 453 |
| 253 | CH(CH$_3$)CF$_3$ | H | Br | H | OCF$_3$ | H | | 497 |
| 254 | A-2 | H | SF$_5$ | H | H | H | | 490 |
| 255 | CH$_2$CF$_3$ | H | SF$_5$ | H | H | H | | 447 |
| 256 | A-19 | H | Br | H | OCF$_3$ | H | | 495 |
| 257 | A-24 | F | H | H | H | H | | 380 |
| 258 | A-24 | OCH$_3$ | H | H | H | H | | 392 |
| 259 | A-24 | H | OCF$_3$ | H | H | H | | 446 |
| 260 | A-24 | F | H | F | H | H | | 398 |
| 261 | A-6 | H | Br | H | CF$_3$ | H | | 524 |

INDEX TABLE A-continued

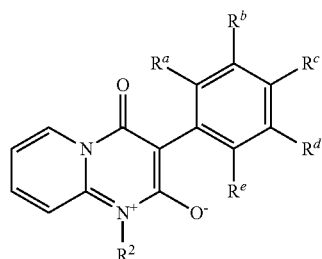

| Cmpd | $R^2$ | $R^a$ | $R^b$ | $R^c$ | $R^d$ | $R^e$ | m.p. (° C.) | AP+ (M + 1) |
|---|---|---|---|---|---|---|---|---|
| 262 | A-6 | $OCH_3$ | H | H | H | H | | 408 |
| 263 | A-1 | H | $SF_5$ | H | H | H | | 497 |
| 264 | A-17 | Cl | H | H | $OCF_3$ | H | | 466 |
| 265 | A-25 | H | H | H | H | H | 181-183 | |
| 266 | A-17 | F | $CF_3$ | H | H | H | | 434 |
| 267 | A-25 | H | $OCF_3$ | H | H | H | | 431 |
| 268 | A-17 | $OCF_3$ | H | H | H | H | | 432 |
| 269 | A-17 | $CF_3$ | H | H | H | H | | 416 |
| 270 | A-1 | $OCF_3$ | H | H | H | H | | 454 |
| 271 | A-1 | $CF_3$ | H | H | H | H | | 438 |
| 272 | A-6 | H | $OCF_3$ | H | H | H | | 462 |
| 273 | A-6 | F | H | H | H | H | | 396 |
| 274 | A-1 | I | H | H | H | H | | 496 |
| 275 | A-1 | H | I | H | H | H | | 496 |
| 276 | A-1 | H | Br | $OCH_3$ | H | H | | 478 |
| 277 | A-1 | $OCH_3$ | H | H | Br | H | | 478 |
| 278 | $CH_2CH_3$ | H | H | H | H | H | | 267 |
| 279 | $CH_2CH(CH_3)_2$ | H | H | H | H | H | | 295 |
| 280 | $CH_2CH_2CH_3$ | F | H | H | H | H | | 299 |
| 281 | $CH_2CH_2CH_3$ | H | H | F | H | H | | 299 |
| 282 | $CH_2CH_2CH_3$ | H | cyano | H | H | H | | 306 |
| 283 | $CH_2CH_2CH_3$ | cyano | H | H | H | H | | 306 |
| 284 | $CH_2CH_2CH_3$ | H | F | H | H | H | | 299 |
| 285 | $CH_2CH_2CH_3$ | $CH_3$ | H | H | H | H | | 295 |
| 286 | $CH_2CH_2CH_3$ | H | H | $CH_3$ | H | H | | 295 |
| 287 | $CH_2CH_2CH_3$ | H | $CF_3$ | H | $CF_3$ | H | | 417 |
| 288 | $CH_2CH_2CH_3$ | H | H | $CF_3$ | H | H | | 349 |
| 289 | $CH_2CH_2CH_3$ | H | $CH_3$ | H | H | H | | 295 |
| 290 | $CH_2CH_2CH_2CH_3$ | H | H | H | H | H | | 295 |
| 291 | $CH_2CH_2OCH_3$ | H | H | H | H | H | | 297 |
| 292 | $CH_2CH_2CH_3$ | $OCH_3$ | H | H | H | H | | 311 |
| 293 | $CH_2CH_2CH_3$ | H | H | $OCH_3$ | H | H | | 311 |
| 294 | $CH_2CH_2CH_3$ | H | H | Cl | H | H | | 315 |
| 295 | $CH_2CH_2CH_3$ | H | $OCH_3$ | H | H | H | | 311 |
| 296 | $CH_2CO_2Et$ | H | H | H | H | H | | 325 |
| 297 | $CH(CH_3)_2$ | H | H | H | H | H | | 281 |
| 298 | $CH_2CH_2CH_3$ | H | F | F | F | H | | 335 |
| 299 | $CH_2(CH_2)_3CH_3$ | H | H | H | H | H | | 309 |
| 300 | $CH_2CH_2CH_3$ | H | nitro | H | H | H | | 326 |
| 301 | $CH_2CH_2CH_3$ | H | Cl | H | H | H | | 315 |
| 302 | $CH_2CH_2CH_3$ | H | H | $OCF_3$ | H | H | | 365 |
| 303 | $CH_2CH_2CH_3$ | H | NHAc | H | H | H | | 338 |
| 304 | $CH_2CO_2CH_3$ | H | H | H | H | H | | 311 |
| 305 | $CH_2CH_2CH_3$ | H | CHO | H | H | H | | 309 |
| 306 | $CH_2CH_2CH_3$ | H | Ac | H | H | H | | 323 |
| 307 | $CH_2CH_2CH_3$ | H | $CO_2Et$ | H | H | H | | 353 |
| 308 | $CH_2CH_2CH_3$ | $CF_3$ | H | H | H | H | ** | 349 |
| 309 | $CH_2CH_2CH_3$ | F | H | H | F | H | | 317 |
| 310 | $CH_2CH_2CH_3$ | H | Cl | H | Cl | H | | 349 |
| 311 | $CH_2CF_3$ | H | H | $CF_3$ | H | H | | 389 |
| 312 | $CH_2CF_3$ | H | $CF_3$ | H | $CF_3$ | H | | 457 |
| 313 | $CH_2CF_3$ | H | F | H | F | H | | 357 |
| 314 | $CH_2CH_2CH_3$ | F | H | H | Br | H | | 377 |
| 315 | $CH_2CH_2CH_3$ | H | $OCH_3$ | H | Br | H | | 389 |
| 316 | $CH_2CH_2CH_3$ | H | $OCH_3$ | $OCH_3$ | H | H | | 341 |
| 317 | $CH_2CH_2CH_3$ | $OCH_3$ | H | H | F | H | | 329 |
| 318 | $CH_2CH_2CH_3$ | $OCH_3$ | H | H | Cl | H | | 345 |
| 319 | $CH_2CH_2CH_3$ | F | $CH_3$ | H | Cl | H | | 347 |
| 320 | $CH_2CF_3$ | H | $OCH_3$ | H | Br | H | | 429 |
| 321 | $CH_2CF_3$ | $CF_3$ | H | H | H | H | | 389 |
| 322 | $CH_2CH_2CH_3$ | $OCF_3$ | H | H | H | H | | 365 |
| 323 | $CH_2CF_3$ | $OCF_3$ | H | H | H | H | | 405 |
| 324 | $CH_2CF_3$ | H | H | $OCF_3$ | H | H | | 405 |
| 325 | $CH_2CF_3$ | H | H | cyano | H | H | | 346 |

INDEX TABLE A-continued

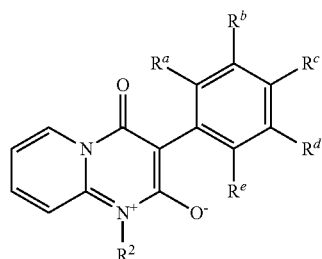

| Cmpd | R² | Rᵃ | Rᵇ | Rᶜ | Rᵈ | Rᵉ | m.p. (° C.) | AP+ (M + 1) |
|---|---|---|---|---|---|---|---|---|
| 326 | CH₂CH₂CH₃ | OCH₃ | OCH₃ | H | H | H | | 341 |
| 327 | A-8 | H | H | H | H | H | | 383 |
| 328 | CH₂CF₃ | H | OCH₃ | OCH₃ | H | H | | 381 |
| 329 | CH₂CF₃ | F | CH₃ | H | Cl | H | | 387 |
| 330 | CH₂CF₃ | F | F | H | H | H | | 357 |
| 331 | CH₂CH₂CH₃ | H | H | SCH₃ | H | H | | 327 |
| 332 | CH₂CH₂CH₃ | H | OCH₃ | Cl | H | F | | 363 |
| 333 | CH₂CH₂CH₃ | H | H | t-Bu | H | H | | 337 |
| 334 | CH₂CH₂CH₃ | NHCOt-Bu | H | H | CH₃ | H | | 394 |
| 335 | CH₂CH₂CH₃ | H | H | SO₂Me | H | H | | 359 |
| 336 | CH₂CF₃ | H | OCH₃ | Cl | H | F | | 403 |
| 337 | CH₂CH₂CH₃ | H | CF₃ | OCH₃ | H | H | | 379 |
| 338 | CH₂CF₃ | H | CF₃ | OCH₃ | H | H | | 419 |
| 339 | CH₂CH₂CH₃ | H | n-Bu | H | H | H | | 337 |
| 340 | CH₂CH₂CH₃ | F | H | CF₃ | H | H | | 367 |
| 341 | CH₂CH₂CH₃ | H | OCF₃ | H | H | F | | 383 |
| 342 | CH₂CH₂CH₃ | H | H | CO₂Et | H | H | | 353 |
| 343 | CH₂CH₂CH₃ | H | CH₃ | H | CH₃ | H | | 309 |
| 344 | CH₂CH₂CH₃ | OCH₃ | H | H | CF₃ | H | | 379 |
| 345 | CH₂CH₂CH₃ | OCH₂CH₃ | H | H | CF₃ | H | * | |
| 346 | CH₂CF₃ | OCH₂CH₃ | H | H | CF₃ | H | * | |
| 347 | CH₂CH₂CH₃ | F | CF₃ | H | H | H | | 367 |
| 348 | CH₂CH₂CH₃ | OCH₃ | Br | H | CH₃ | H | * | |
| 349 | CH₂CH₂CH₃ | CH₃ | H | H | CH₃ | H | * | |
| 350 | CH₂CF₃ | F | CF₃ | H | H | H | | 407 |
| 351 | A-8 | H | H | cyano | H | H | * | |
| 352 | CH₂CF₃ | F | H | H | F | H | * | |
| 353 | CH₂CF₃ | H | Cl | F | H | H | | 373 |
| 354 | CH₂CF₃ | H | H | n-Bu | H | H | | 377 |
| 355 | CH₂CF₃ | H | CF₃ | F | H | H | | 407 |
| 356 | CH₂CF₃ | H | F | cyano | H | H | | 338 |
| 357 | CH₂CF₃ | Cl | H | F | H | H | | 373 |
| 358 | CH₂CF₃ | OCH₃ | H | F | H | H | | 368 |
| 359 | CH₂CF₃ | OCH₃ | H | H | CF₃ | H | | 419 |
| 360 | CH₂CF₃ | H | F | H | H | H | | 339 |
| 361 | CH₂CF₃ | H | H | CH₃ | H | H | | 335 |
| 362 | CH₂CF₃ | H | H | OCH₃ | H | H | | 351 |
| 363 | CH₂CF₃ | H | CH₃ | H | H | H | | 335 |
| 364 | CH₂CF₃ | H | H | Br | H | H | | 399 |
| 365 | CH₂CH₂CF₃ | H | H | F | H | H | | 353 |
| 366 | CH₂CH₂CF=CF₂ | H | H | F | H | H | | 365 |
| 367 | CH₂CH₂CF=CF₂ | H | OCF₃ | H | H | H | | 431 |
| 368 | CH₂CH₂CF=CF₂ | F | H | F | H | H | | 383 |
| 369 | CH₂CF₃ | H | cyano | F | H | H | * | |
| 370 | CH₂CF₂CF₃ | H | CF₃ | H | H | H | | 439 |
| 371 | CH₂CH₂CF=CF₂ | H | CF₃ | H | H | H | | 415 |
| 372 | A-8 | H | CF₃ | H | H | H | | 451 |
| 373 | CH₂CH₂CF=CF₂ | Cl | H | Cl | H | H | | 415 |
| 374 | A-8 | Cl | H | Cl | H | H | | 451 |
| 375 | CH₂CF₂CF₃ | Cl | H | Cl | H | H | | 439 |
| 376 | CH₂CF₃ | CH₃ | H | H | H | H | | 335 |
| 377 | CH₂CF₃ | Br | H | H | H | H | | 399 |
| 378 | CH₂CF₃ | Cl | H | H | H | H | | 355 |
| 379 | CH₂CF₃ | H | n-Bu | I | H | H | | 503 |
| 380 | CH₂CF₃ | H | n-Bu | H | H | H | | 377 |
| 381 | CH₂CF₃ | Cl | H | Cl | H | Cl | | 423 |
| 382 | CH₂CH₂CF=CF₂ | Cl | H | Cl | H | Cl | | 449 |
| 383 | A-8 | Cl | H | Cl | H | Cl | | 485 |
| 384 | CH₂CF₃ | Cl | H | H | H | Cl | | 389 |
| 385 | CH₂CF₃ | CH₃ | H | CH₃ | H | H | | 349 |
| 386 | CH₂CF₃ | H | cyano | H | H | H | | 346 |
| 387 | CH₂CF₃ | n-Bu | H | H | H | H | | 377 |
| 388 | CH₂CF₂CF₃ | Cl | H | Cl | H | Cl | | 473 |
| 389 | A-26 | H | H | F | H | H | | 383 |

INDEX TABLE A-continued

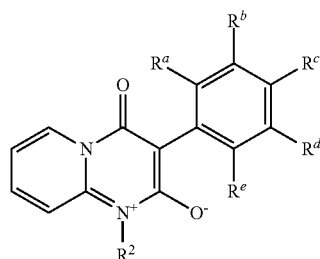

| Cmpd | $R^2$ | $R^a$ | $R^b$ | $R^c$ | $R^d$ | $R^e$ | m.p. (° C.) | AP+ (M + 1) |
|---|---|---|---|---|---|---|---|---|
| 390 | A-26 | F | H | F | H | H | | 401 |
| 391 | A-26 | H | $OCF_3$ | H | H | H | | 449 |
| 392 | $CH_2CF_3$ | F | F | F | H | H | | 375 |
| 393 | $CH_2CF_3$ | F | H | F | F | H | | 375 |
| 394 | $CH_2CF_3$ | F | H | F | H | F | | 375 |
| 395 | $CH_2CF_3$ | H | F | F | F | H | | 375 |
| 396 | $CH_2CF_3$ | $CF_3$ | H | F | H | H | | 407 |
| 397 | $CH_2CF_3$ | H | $OCF_3$ | H | H | Cl | | 439 |
| 398 | $CH_2CF_3$ | H | CHO | F | H | H | | 367 |
| 399 | $CH_2CF_3$ | cyano | H | H | H | H | | 346 |
| 400 | $CH_2CH_2CH_3$ | H | Br | F | H | H | | 377 |
| 401 | $CH_2CH_2CH_3$ | H | $CF_3$ | F | H | H | | 367 |
| 402 | $CH_2CO_2CH_3$ | H | H | F | H | H | | 329 |
| 403 | $CH_2CF_3$ | F | H | Br | H | H | | 417 |
| 404 | $CH_2CF_3$ | F | H | F | H | Br | | 435 |
| 405 | $CH_2CH_2CH_3$ | H | F | F | H | H | | 317 |
| 406 | $CH_2CH_2CH_3$ | H | Cl | F | H | H | | 333 |
| 407 | $CH_2CH_2CH_3$ | Cl | H | F | H | H | | 333 |
| 408 | $CH_2CH_2CH_3$ | F | H | F | H | H | | 317 |
| 409 | $CH_2CH_2CH_3$ | $OCH_3$ | H | F | H | H | | 329 |
| 410 | A-8 | H | cyano | F | H | H | | 426 |
| 411 | A-7 | H | $OCF_3$ | H | H | H | | 414 |
| 412 | A-7 | H | H | F | H | H | | 348 |
| 413 | A-7 | F | H | F | H | H | | 365 |
| 414 | A-7 | H | H | H | H | H | | 330 |
| 415 | A-2 | $CF_3$ | H | F | H | H | | 450 |
| 416 | A-34 | H | H | H | H | H | * | |
| 417 | A-2 | H | H | $SCH_3$ | H | H | | 410 |
| 418 | A-2 | H | Cl | H | Cl | H | * | |
| 419 | A-2 | Cl | H | F | H | H | | 398 |
| 420 | A-2 | $CH_3$ | H | H | H | H | | 378 |
| 421 | A-2 | $OCF_3$ | H | H | H | H | | 448 |
| 422 | A-2 | cyano | H | H | H | H | | 389 |
| 423 | A-2 | $OCH_3$ | H | H | H | H | | 394 |
| 424 | A-3 | H | $OCH_3$ | H | H | H | | 323 |
| 425 | A-2 | H | $SCH_3$ | H | H | H | * | |
| 426 | $CH_2CF_3$ | H | nitro | H | H | H | * | |
| 427 | A-2 | H | $Si(CH_3)_3$ | H | H | H | * | |
| 428 | A-27 | H | H | H | H | H | | 323 |
| 429 | A-27 | F | H | F | H | H | | 359 |
| 430 | A-2 | H | H | $Si(CH_3)_3$ | H | H | * | |
| 431 | $CH_2CF_3$ | H | $OCH_2O$ | | H | H | | 365 |
| 432 | $CH_2CF_3$ | H | OH | H | H | H | | 337 |
| 433 | $CH_2CF_3$ | $CH_3$ | H | F | H | H | * | |
| 434 | $CH_2CF_3$ | H | OAc | H | H | H | | 379 |
| 435 | $CH_2CF_3$ | H | $CH_2CH_2O$ | | H | H | | 363 |
| 436 | A-4 | H | $OCF_3$ | H | H | H | * | |
| 437 | A-4 | F | H | F | H | H | | 434 |
| 438 | $CH_2CF_3$ | H | $OCF_2O$ | | H | H | | 401 |
| 439 | A-27 | H | H | F | H | H | | 341 |
| 440 | A-2 | H | $CF_3$ | H | $CF_3$ | H | | 500 |
| 441 | A-2 | H | nitro | H | H | H | | 409 |
| 442 | A-2 | $OCH_3$ | H | $OCH_3$ | H | H | | 424 |
| 443 | A-4 | H | H | $OCH_3$ | H | H | * | |
| 444 | A-4 | F | H | H | H | H | | 416 |
| 445 | A-2 | H | $CF_3$ | $OCH_3$ | H | H | | 462 |
| 446 | A-2 | H | $OCF_2O$ | | H | H | | 444 |
| 447 | A-2 | H | OAc | H | H | H | | 422 |
| 448 | A-2 | F | F | $OCH_3$ | H | H | | 430 |
| 449 | A-5 | H | H | F | H | H | | 363 |
| 450 | A-5 | H | H | H | H | H | | 345 |
| 451 | A-28 | H | H | F | H | H | | 416 |
| 452 | A-29 | H | H | H | H | H | | 398 |
| 453 | A-28 | H | $OCF_3$ | H | H | H | * | |

INDEX TABLE A-continued

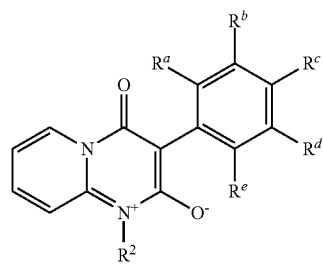

| Cmpd | R² | Rᵃ | Rᵇ | Rᶜ | Rᵈ | Rᵉ | m.p. (° C.) | AP+ (M + 1) |
|---|---|---|---|---|---|---|---|---|
| 454 | A-29 | H | H | F | H | H | | 416 |
| 455 | A-29 | F | H | F | H | H | | 434 |
| 456 | A-30 | H | H | H | H | H | | 355 |
| 457 | A-30 | H | H | F | H | H | | 373 |
| 458 | A-30 | F | H | F | H | H | | 391 |
| 459 | A-2 | H | OCH₂CF₃ | H | H | H | * | |
| 460 | A-6 | H | H | H | H | H | | 378 |
| 461 | A-2 | F | H | H | H | F | | 400 |
| 462 | A-17 | F | H | cyano | H | H | | 391 |
| 463 | A-31 | H | H | H | H | H | | 344 |
| 464 | A-31 | H | H | F | H | H | | 362 |
| 465 | A-31 | F | H | F | H | H | | 380 |
| 466 | A-32 | H | H | H | H | H | | 323 |
| 467 | A-32 | H | H | F | H | H | | 341 |
| 468 | A-32 | F | H | F | H | H | | 359 |
| 469 | A-1 | F | H | cyano | H | H | | 413 |
| 470 | A-33 | H | H | H | H | H | | 408 |
| 471 | A-33 | H | H | F | H | H | | 426 |
| 472 | A-33 | F | H | F | H | H | | 444 |
| 473 | A-1 | H | CF₃ | F | H | H | | 455 |
| 474 | A-1 | Cl | H | F | H | H | | 422 |
| 475 | A-1 | H | H | cyano | H | H | | 395 |
| 476 | A-2 | H | F | H | F | H | | 400 |
| 477 | A-1 | H | F | H | H | H | | 388 |
| 478 | A-1 | H | H | CF₃ | H | H | | 438 |
| 479 | A-1 | H | H | OCF₃ | H | H | | 454 |
| 480 | A-1 | H | H | CH₃ | H | H | | 384 |
| 481 | A-1 | cyano | H | H | H | H | | 395 |
| 482 | A-1 | H | F | F | H | H | | 406 |
| 483 | A-10 | H | H | F | H | H | * | |
| 484 | A-10 | H | OCF₃ | H | H | H | | 413 |
| 485 | A-10 | H | H | H | H | H | | 329 |
| 486 | A-1 | H | OCH₃ | F | H | H | * | |
| 487 | A-1 | Br | H | F | H | H | | 466 |
| 488 | A-1 | CH₃ | H | cyano | H | H | | 409 |
| 489 | A-1 | Cl | H | Cl | H | H | | 438 |
| 490 | A-1 | H | OCF₃ | H | H | Cl | | 488 |
| 491 | A-1 | H | OCF₃ | H | Br | H | 209-210 | |
| 492 | A-1 | F | F | F | H | H | 196-198 | 424 |
| 493 | A-1 | F | H | F | F | H | 195-197 | 424 |
| 494 | A-1 | H | OCH₂O | | H | H | >250 | 414 |
| 495 | A-1 | H | CH₂CH₂O | | H | H | 188-190 | 412 |
| 496 | A-1 | F | H | H | Br | H | | 466 |
| 497 | A-6 | F | H | F | H | H | | 414 |
| 498 | A-1 | H | CF₃ | H | Br | H | 188-190 | 516 |
| 499 | A-1 | H | F | H | F | H | | 406 |
| 500 | A-1 | H | F | OCH₃ | H | H | 205-207 | 418 |
| 501 | A-1 | F | H | F | H | F | * | |
| 502 | A-33 | H | OCF₃ | H | H | H | 153-155 | 504 |
| 503 | A-33 | H | OCH₃ | H | H | H | | 438 |
| 604 | A-35 | H | H | H | H | H | | 330 |
| 605 | A-36 | H | H | H | H | H | | 330 |
| 606 | A-35 | H | H | F | H | H | * | |
| 618 | A-1 | F | F | H | H | F | | 424 |
| 619 | A-1 | H | CF₃ | H | Cl | F | | 490 |
| 621 | A-2 | H | SF₅ | H | H | Cl | | 524 |
| 622 | A-1 | H | OCF₃ | H | Cl | H | | 488 |
| 623 | A-37 | F | H | H | H | H | | 432 |
| 624 | A-37 | H | H | F | H | H | | 432 |
| 625 | A-37 | H | OCF₃ | H | H | H | | 498 |
| 627 | A-37 | H | CF₃ | H | Br | H | | 560 |
| 629 | CH₂CO₂H | H | H | H | H | H | | 297 |
| 631 | A-38 | H | H | H | H | H | | 335 |
| 632 | A-2 | I | H | H | H | H | | 490 |

INDEX TABLE A-continued

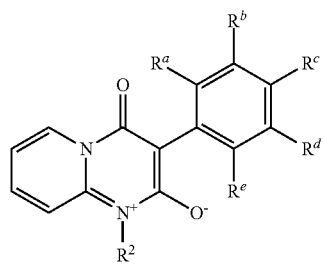

| Cmpd | R² | Rᵃ | Rᵇ | Rᶜ | Rᵈ | Rᵉ | m.p. (°C.) | AP+ (M + 1) |
|---|---|---|---|---|---|---|---|---|
| 634 | A-1 | H | CF₃ | H | Cl | H | | 472 |
| 642 | A-40 | F | H | F | H | H | 159-160 | |
| 648 | A-40 | OCH₃ | H | H | H | H | * | |
| 649 | CH₂CH₂CH(OMe)₂ | H | H | H | H | H | | 341 |
| 650 | CH₂CH(OMe)₂ | H | H | H | H | H | | 327 |
| 651 | A-2 | F | F | H | H | F | | 418 |
| 652 | A-2 | H | CF₃ | H | Cl | F | | 484 |
| 654 | A-1 | F | H | OCH₃ | H | H | | 418 |
| 663 | A-1 | F | Cl | H | H | F | | 440 |
| 664 | A-1 | OCH₃ | H | H | F | F | | 436 |
| 665 | A-2 | OCH₃ | H | H | F | F | | 430 |
| 666 | A-2 | F | Cl | H | H | F | | 434 |
| 673 | A-41 | H | H | H | H | H | | 360 |
| 674 | A-41 | F | H | H | H | H | | 378 |
| 675 | A-40 | F | H | H | H | H | | 365 |
| 676 | A-41 | H | H | F | H | H | | 378 |
| 677 | A-17 | H | H | F | H | H | | 372 |
| 678 | A-41 | F | H | F | H | H | | 396 |
| 679 | A-41 | H | OCF₃ | H | H | H | | 444 |
| 720 | CH₂CF₃ | H | H | SF₅ | H | H | | 447 |
| 721 | A-1 | H | H | SF₅ | H | H | | 496 |
| 722 | A-2 | H | H | SF₅ | H | H | | 490 |
| 737 | A-37 | H | Br | H | OCF₃ | H | | 576 |
| 740 | A-2 | OCH₃ | F | H | F | H | | 430 |
| 741 | A-2 | F | OCH₃ | H | H | F | | 430 |
| 742 | A-1 | OCH₃ | F | H | F | H | | 436 |
| 743 | A-1 | F | OCH₃ | H | H | F | | 436 |
| 744 | A-2 | F | H | H | OCH₃ | H | | 412 |
| 745 | CH₂CF₃ | F | H | H | OCH₃ | H | | 369 |
| 746 | A-17 | F | F | H | H | H | | 384 |

* See Index Table G for ¹H NMR data.
** See synthesis example for ¹H NMR data.

INDEX TABLE B

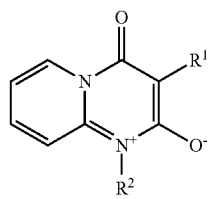

| Compound | R¹ | R² | m.p. (°C.) | AP+ (M + 1) |
|---|---|---|---|---|
| 110 | Br | CH₂CH₂CH₃ | * | |
| 111 | I | CH₂CF₃ | * | |
| 112 | I | CH₂CH₂CH₃ | * | |
| 113 | I | A-8 | * | |
| 114 | I | CH₂CF₂CF₃ | * | |
| 115 | CH(CH₃)₂ | CH₂CF₃ | * | |
| 116 | CH₂CH(CH₃)₂ | CH₂CF₃ | * | |
| 117 | CH₂CH₂CF=CF₂ | CH₂CF₃ | * | |
| 118 | I | A-2 | ** | |
| 125 | H | A-1 | ** | |
| 119 | 6-fluoro-3-pyridinyl | A-2 | * | |
| 120 | 6-chloro-3-pyridinyl | A-2 | * | |
| 121 | 3-chloro-4-pyridinyl | CH₂CF₃ | 248-249 | |
| 521 | 4-trifluoromethyl-2-pyridinyl | CH₂CF₃ | * | |

INDEX TABLE B-continued

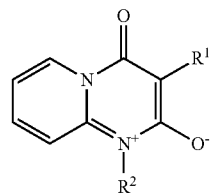

| Compound | R¹ | R² | m.p. (°C.) | AP+ (M + 1) |
|---|---|---|---|---|
| 522 | 4-trifluoromethyl-2-pyridinyl | A-17 | | 417 |
| 537 | 2-bromo-4-pyridinyl | A-2 | | 443 |
| 540 | 2-bromo-4-pyridinyl | A-1 | | 449 |
| 547 | 6-trifluoromethyl-2-pyridinyl | A-17 | * | |
| 550 | 2-cyano-4-pyridinyl | A-1 | | 396 |
| 552 | 2-pyridinyl | $CH_2CH_2CH_3$ | | 282 |
| 553 | 3-pyridinyl | $CH_2CH_2CH_3$ | | 282 |
| 554 | phenyl | $CH_2CO_2CH(CH_3)_2$ | | 339 |
| 555 | 2-naphthalenyl | $CH_2CH_2CH_3$ | | 331 |
| 556 | 1-naphthalenyl | $CH_2CH_2CH_3$ | | 331 |
| 561 | 4-pyridinyl | $CH_2CH_2CH_3$ | | 282 |
| 562 | 2-chloro-4-pyridinyl | $CH_2CH_2CH_3$ | | 316 |
| 564 | 4-fluoro-1-naphthalenyl | $CH_2CH_2CH_3$ | * | |
| 570 | 6-chloro-3-pyridinyl | $CH_2CF_3$ | | 356 |
| 571 | 6-fluoro-3-pyridinyl | $CH_2CF_3$ | | 340 |
| 573 | 4-fluoro-1-naphthalenyl | A-2 | | 432 |
| 574 | 6-methoxy-2-naphthalenyl | A-2 | | 444 |
| 575 | 6-methoxy-3-pyridinyl | A-2 | | 395 |
| 576 | 5-fluoro-2-pyridinyl | A-2 | | 383 |
| 577 | 5-trifluoromethyl-3-pyridinyl | A-2 | | 433 |
| 579 | 2-fluoro-3-pyridinyl | A-2 | | 383 |
| 584 | 3-fluoro-4-pyridinyl | A-2 | | 383 |
| 585 | 5-methoxy-2-pyridinyl | A-2 | | 395 |
| 586 | 3-fluoro-2-pyridinyl | A-2 | | 383 |
| 587 | 3-chloro-2-pyridinyl | A-2 | | 399 |
| 591 | 4-trifluoromethyl-2-pyridinyl | A-2 | | 433 |
| 593 | 6-trifluoromethyl-2-pyridinyl | A-2 | | 433 |
| 597 | 4-trifluoromethyl-2-pyridinyl | A-1 | 225-227 | 439 |
| 598 | 2-chloro-4-pyridinyl | A-1 | 242-243 | 405 |
| 600 | 6-trifluoromethyl-2-pyridinyl | A-1 | * | |
| 608 | I | A-1 | ** | |
| 609 | H | $CH_2CH_2CH_3$ | ** | |
| 610 | H | $CH_2CF_3$ | 214-215 | |
| 611 | H | A-2 | ** | |
| 612 | H | A-7 | * | |
| 628 | 2-bromo-4-pyridinyl | A-37 | | 493 |
| 636 | 2-methoxy-4-pyridinyl | A-1 | | 401 |
| 637 | $C(=NOCH_3)CF_3$ | $CH_2CF_3$ | ** | |
| 638 | $C(=NOCH_2CH_3)CF_3$ | $CH_2CF_3$ | * | |
| 653 | 2-trifluoromethyl-4-pyridinyl | A-1 | | 439 |
| 656 | $C(=NOCH_2CHMe_2)CF_3$ | $CH_2CF_3$ | * | |
| 657 | $C(=NOCMe_3)CF_3$ | $CH_2CF_3$ | * | |
| 658 | $C(=NOCH_2CMe_3)CF_3$ | $CH_2CF_3$ | * | |
| 659 | $C(=NOCH_2CO_2Et)CF_3$ | $CH_2CF_3$ | * | |
| 660 | C(O)NHphenyl | A-1 | | 413 |
| 661 | C(O)NH(3-methoxyphenyl) | A-1 | | 443 |
| 687 | C(O)OEt | $CH_2CH_2CH_3$ | | 277 |
| 688 | C(O)NH(4-fluorophenyl) | $CH_2CH_2CH_3$ | | 342 |
| 689 | C(O)NH(2-chlorophenyl) | $CH_2CH_2CH_3$ | | 358 |
| 690 | C(O)NH(3-chlorophenyl) | $CH_2CH_2CH_3$ | | 358 |
| 691 | C(O)NH(4-chlorophenyl) | $CH_2CH_2CH_3$ | | 358 |
| 692 | C(O)NHphenyl | $CH_2CH_2CH_3$ | | 324 |
| 693 | C(O)O(4-nitrophenyl) | $CH_2CH_2CH_3$ | | 370 |
| 694 | C(O)phenyl | $CH_2CH_2CH_3$ | | 309 |
| 695 | C(O)(2-fluorophenyl) | $CH_2CH_2CH_3$ | | 327 |
| 696 | C(O)(3-fluorophenyl) | $CH_2CH_2CH_3$ | | 327 |
| 697 | C(O)(4-fluorophenyl) | $CH_2CH_2CH_3$ | | 327 |
| 698 | C(O)(2-methylphenyl) | $CH_2CH_2CH_3$ | | 323 |
| 699 | C(O)(3-methylphenyl) | $CH_2CH_2CH_3$ | | 323 |
| 700 | C(O)OEt | A-1 | * | |
| 701 | C(O)phenyl | A-1 | * | |
| 702 | $C(O)CF_3$ | A-1 | 236-238 | |
| 703 | C(O)(4-fluorophenyl) | A-1 | 235-237 | |
| 704 | C(O)(3-fluorophenyl) | A-1 | 226-228 | |
| 706 | C(O)(2-fluorophenyl) | A-1 | 190-192 | |
| 707 | C(O)[3-(trifluoromethyl)phenyl] | A-1 | 225-226 | |
| 708 | C(O)(2-thienyl) | A-1 | 214-216 | |
| 709 | C(O)[4-(trifluoromethyl)phenyl] | A-1 | 242-243 | |

INDEX TABLE B-continued

| Compound | R¹ | R² | m.p. (° C.) | AP+ (M + 1) |
|---|---|---|---|---|
| 710 | C(O)CH$_3$ | A-1 | 183-185 | |
| 711 | C(O)CF$_3$ | CH$_2$CF$_3$ | 202-203 | |
| 712 | C(O)CF$_3$ | A-2 | 209-210 | |
| 713 | C(O)CF$_2$CF$_3$ | A-1 | 204-205 | |
| 714 | C(O)CF$_2$CF$_3$ | A-2 | 189-190 | |
| 715 | C(O)CF$_2$CF$_2$CF$_3$ | A-1 | 156-157 | |
| 716 | C(O)CF$_2$CF$_2$CF$_3$ | A-2 | 134-135 | |
| 729 | C(=NOC(CH$_3$)$_3$)H | CH$_2$CF$_3$ | * | |
| 730 | C(=NOCH$_2$CH$_3$)H | CH$_2$CF$_3$ | * | |
| 731 | C(=NOCH$_2$C(CH$_3$)$_3$)H | CH$_2$CF$_3$ | * | |
| 758 | C(=NOCH$_3$)H | CH$_2$CF$_3$ | * | |
| 759 | C(=NOCH$_2$Ph)H | CH$_2$CF$_3$ | * | |

\* See Index Table G for ¹H NMR data.
\*\* See synthesis example for ¹H NMR data.

INDEX TABLE C

| Compound | Rᵃ | R² | m.p. (° C.) | AP+ (M + 1) |
|---|---|---|---|---|
| 523 | 3-(3-pyridinyl) | A-2 | | 441 |
| 524 | 3-(6-chloro-3-pyridinyl) | A-2 | | 474 |
| 525 | 3-(6-fluoro-3-pyridinyl) | A-2 | | 459 |
| 527 | 3-(6-fluoro-3-pyridinyl), 6-fluoro | A-2 | | 477 |
| 528 | 4-(6-chloro-3-pyridinyl) | A-2 | | 475 |
| 529 | 3-(6-methoxy-3-pyridinyl) | A-2 | | 471 |
| 530 | 3-(6-chloro-3-pyridinyl) | A-1 | | 481 |
| 531 | 3-(6-fluoro-3-pyridinyl), 5-trifluoromethyl | A-2 | | 527 |
| 534 | 3-(6-chloro-3-pyridinyl) | CH(CH$_3$)CF$_3$ | | 446 |
| 536 | 3-(6-fluoro-3-pyridinyl), 4-fluoro | A-2 | | |
| 539 | 3-(6-chloro-3-pyridinyl), 6-methoxy | A-2 | | 505 |
| 541 | 3-(6-chloro-3-pyridinyl), 4-fluoro | A-1 | | 499 |
| 542 | 3-(6-fluoro-3-pyridinyl) | A-1 | | 465 |
| 543 | 3-(6-chloro-3-pyridinyl), 5-trifluoromethyl | A-1 | | 549 |
| 544 | 3-(6-fluoro-3-pyridinyl), 5-trifluoromethyl | A-1 | | 533 |
| 545 | 3-(6-fluoro-3-pyridinyl) | A-19 | | 428 |
| 546 | 3-(6-fluoro-3-pyridinyl) | A-6 | | 473 |
| 549 | 3-(6-fluoro-3-pyridinyl), 5-trifluoromethoxy | A-1 | | 549 |
| 551 | 2-(6-chloro-3-pyridinyl) | A-1 | | 481 |
| 557 | 3-phenyl | CH$_2$CH$_2$CH$_3$ | | 357 |
| 558 | 4-phenoxy | CH$_2$CH$_2$CH$_3$ | | 373 |
| 559 | 2-phenoxy | CH$_2$CH$_2$CH$_3$ | | 373 |
| 560 | 2-phenyl | CH$_2$CH$_2$CH$_3$ | | 357 |
| 563 | 3-phenoxy | CH$_2$CH$_2$CH$_3$ | | 373 |
| 565 | 3-benzyloxy | CH$_2$CH$_2$CH$_3$ | | 387 |
| 566 | 3-benzyloxy | CH$_2$CF$_3$ | 178-179 | 427 |
| 567 | 4-benzyloxy | CH$_2$CF$_3$ | 203-204 | 427 |
| 568 | 2-benzyloxy | CH$_2$CF$_3$ | 165-166 | 427 |
| 578 | 2-(B-1), 4-fluoro | CH$_2$CF$_3$ | | 480 |
| 580 | 3-(B-2) | CH$_2$CF$_3$ | 223-225 | 428 |
| 581 | 3-(B-1) | CH$_2$CF$_3$ | | 462 |

INDEX TABLE C-continued

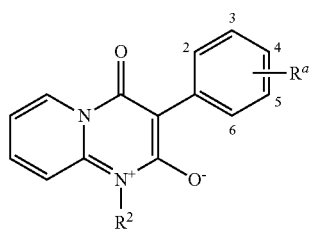

| Compound | $R^a$ | $R^2$ | m.p. (° C.) | AP+ (M + 1) |
|---|---|---|---|---|
| 582 | 3-(B-1) | A-2 | | 505 |
| 594 | 3-(B-3), 4-fluoro | A-2 | | 446 |
| 595 | 3-(B-3), 4-fluoro | $CH_2CF_3$ | | 446 |
| 596 | 3-(B-4) | $CH_2CF_3$ | 170-172 | 462 |
| 616 | 3-(6-bromo-3-pyridinyl) | A-1 | | 525 |
| 617 | 3-(6-trifluoromethyl-3-pyridinyl) | A-1 | | 515 |
| 626 | 3-(6-chloro-3-pyridinyl) | A-37 | | 525 |
| 635 | 3-(6-chloro-3-pyridinyl), 5-trifluoromethoxy | A-1 | | 565 |
| 655 | 3-(6-chloro-3-pyridinyl), 5-methoxy | A-1 | | 511 |
| 682 | 3-(6-trifluoromethyl-3-pyridinyl), 5-trifluoromethoxy | A-1 | | 599 |
| 684 | 3-(6-trifluoromethyl-3-pyridinyl), 5-trifluoromethyl | A-1 | | 583 |
| 685 | 3-(6-trifluoromethyl-3-pyridinyl), 4-methoxy | A-1 | | 545 |
| 717 | 3-(6-chloro-3-pyridinyl), 4-methoxy | A-1 | | 511 |
| 734 | 3-(6-trifluoromethyl-3-pyridinyl) | A-17 | | 493 |
| 735 | 3-(6-trifluoromethyl-3-pyridinyl) | A-2 | | 509 |
| 736 | 3-(6-trifluoromethyl-3-pyridinyl) | A-37 | | 559 |
| 738 | 3-(6-trifluoromethyl-3-pyridinyl), 6-fluoro | A-1 | | 533 |
| 739 | 3-(6-trifluoromethyl-3-pyridinyl), 6-fluoro | A-37 | | 577 |

INDEX TABLE D

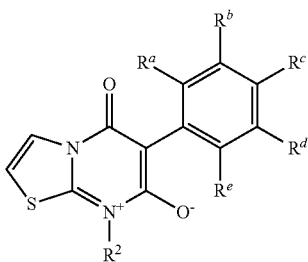

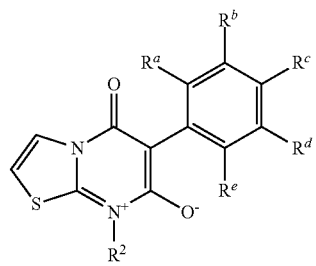

| Cmpd | $R^2$ | $R^a$ | $R^b$ | $R^c$ | $R^d$ | $R^e$ | m.p. (° C.) | AP+ (M + 1) |
|---|---|---|---|---|---|---|---|---|
| 126 | $CH_2CH_2CH_3$ | H | H | H | H | H | 161-168 | |
| 127 | $CH_2CH_2CH_3$ | F | H | H | H | Cl | 216-219 | |
| 128 | $CH_2CH_2CH_3$ | H | Cl | H | Cl | H | 180-183 | |
| 129 | $CH_2CH_2CH_3$ | Cl | Cl | H | H | H | 188-192 | |
| 130 | $CH_2CH_2CH_3$ | F | H | H | H | F | 207-210 | |
| 131 | $CH_2CH_2CH_3$ | $CH_3$ | H | H | H | H | 223-225 | |
| 132 | $CH_2CH_2CH_3$ | H | H | i-Pr | H | H | * | |
| 133 | $CH_2CF_3$ | F | H | F | H | H | * | |
| 134 | $CH_2CF_3$ | H | H | H | H | H | * | |
| 135 | $CH_2CF_3$ | H | $OCF_3$ | H | H | H | * | |
| 136 | A-2 | H | H | H | H | H | * | |
| 137 | A-2 | H | H | F | H | H | * | |
| 138 | A-2 | H | $OCF_3$ | H | H | H | ** | |
| 139 | A-1 | H | H | H | H | H | * | |
| 140 | A-1 | H | H | F | H | H | * | |
| 141 | A-1 | H | $OCF_3$ | H | H | H | * | |
| 142 | $CH_2CH_2CH_3$ | F | H | F | H | H | * | |
| 143 | $CH_2CH_2CH_3$ | H | H | Ph | H | H | | 363 |
| 144 | $CH_2CO_2CH_2CH_3$ | H | H | H | H | H | | 331 |
| 145 | A-1 | H | $OCF_3$ | H | Br | H | | 538 |
| 146 | A-1 | F | H | F | H | H | | 412 |
| 147 | A-1 | H | $OCH_3$ | H | H | H | * | |
| 148 | A-1 | F | H | H | Cl | H | | 428 |
| 149 | A-2 | H | $OCH_3$ | H | H | H | | 400 |
| 150 | A-2 | H | $OCH_3$ | H | $OCH_3$ | H | | 430 |
| 151 | A-2 | F | H | F | H | H | | 406 |
| 152 | A-2 | F | H | H | $CF_3$ | H | * | |
| 153 | A-2 | F | H | H | $CF_3$ | H | | 456 |
| 154 | A-2 | F | H | H | Cl | H | | 422 |
| 155 | A-2 | H | $OCF_3$ | H | Br | H | | 532 |
| 156 | A-1 | H | $OCH_3$ | H | $OCH_3$ | H | | 436 |
| 157 | A-2 | F | H | H | H | H | 216-218 | 388 |
| 158 | A-2 | $OCH_3$ | H | H | H | H | 99-100 | |
| 159 | A-1 | F | H | H | H | H | 192-194 | |
| 160 | A-1 | $OCH_3$ | H | H | H | H | * | |
| 630 | A-17 | H | H | H | H | H | 223-225 | |
| 633 | A-2 | I | H | H | H | H | | 496 |
| 639 | A-17 | H | $OCF_3$ | H | H | H | * | |
| 640 | A-39 | H | $OCF_3$ | H | H | H | 147-149 | |
| 641 | A-17 | F | H | F | H | H | 235-237 | |

INDEX TABLE D-continued

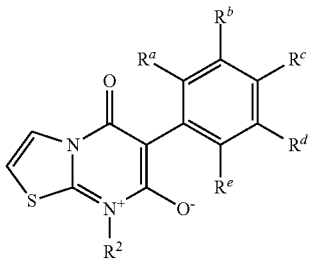

| Cmpd | R² | Rᵃ | Rᵇ | Rᶜ | Rᵈ | Rᵉ | m.p. (° C.) | AP+ (M + 1) |
|---|---|---|---|---|---|---|---|---|
| 643 | A-17 | F | H | H | H | H | 223-225 | |
| 644 | A-39 | F | H | H | H | H | 169-171 | |
| 645 | A-39 | H | H | H | H | H | 190-192 | |
| 646 | A-17 | OCH₃ | H | H | H | H | * | |
| 647 | A-39 | OCH₃ | H | H | H | H | * | |
| 747 | A-17 | H | OCH₃ | H | H | H | | 384 |

INDEX TABLE D-continued

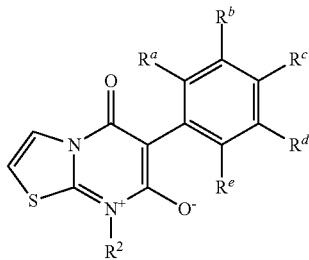

| Cmpd | R² | Rᵃ | Rᵇ | Rᶜ | Rᵈ | Rᵉ | m.p. (° C.) | AP+ (M + 1) |
|---|---|---|---|---|---|---|---|---|
| 748 | A-2 | F | F | H | H | H | | 406 |
| 749 | A-1 | F | F | H | H | H | | 412 |
| 750 | A-17 | F | F | H | H | H | | 390 |

\* See Index Table G for ¹H NMR data.
\*\* See synthesis example for ¹H NMR data.

INDEX TABLE E

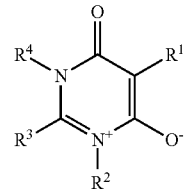

| Cmpd | R¹ | R² | R³  | R⁴  | m.p. (° C.) | AP+ (M + 1) |
|---|---|---|---|---|---|---|
| 504 | phenyl | A-2 | CH₃ | phenyl | | 404 |
| 505 | phenyl | A-2 | phenyl | CH₃ | | 404 |
| 506 | 4-fluorophenyl | A-2 | CH₃ | phenyl | | 422 |
| 507 | phenyl | CH₂CF₃ | phenyl | CH₃ | | 361 |
| 508 | 4-fluorophenyl | CH₂CF₃ | phenyl | CH₃ | | 379 |
| 509 | phenyl | CH₂CH₂CH₃ | CH₃ | CH₃ | | 259 |
| 510 | 4-fluorophenyl | CH₂CH₂CH₃ | CH₃ | CH₃ | | 276 |
| 511 | phenyl | A-2 | CH₃ | CH₃ | * | |
| 512 | phenyl | CH₂CF₃ | CH₃ | CH₃ | | 299 |
| 513 | 4-fluorophenyl | A-2 | CH₃ | CH₃ | | 360 |
| 514 | phenyl | A-1 | CH₃ | CH₃ | 222-224 | 388 |
| 515 | 3-(trifluoromethoxy)phenyl | CH₂CH₂CH₃ | CH₂CH₂CH₂CH₂ | | | 369 |
| 516 | 4-fluorophenyl | CH₂CH₂CH₃ | CH₂CH₂CH₂CH₂ | | | 303 |
| 517 | phenyl | A-2 | 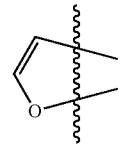 | | | 354 |
| 518 | 3-(trifluoromethoxy)phenyl | A-2 | 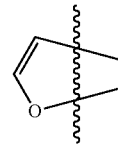 | | * | |
| 519 | phenyl | CH₂CH₂CH₃ | 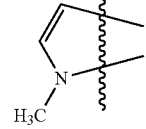 | | | 284 |

INDEX TABLE E-continued
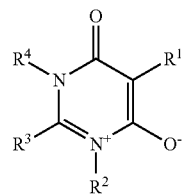
| Cmpd | R¹ | R² | R³  R⁴  | m.p. (° C.) | AP+ (M + 1) |
|---|---|---|---|---|---|
| 588 | 4-fluorophenyl | A-2 | 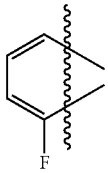 | | 400 |
| 589 | 3-(trifluoromethoxy)-phenyl | A-2 | 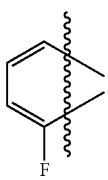 | | 466 |
| 590 | 2,4-difluorophenyl | A-2 | 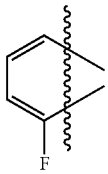 | | 418 |
| 592 | phenyl | A-2 | 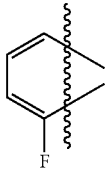 | | 382 |
| 667 | 2-fluorophenyl | A-1 | 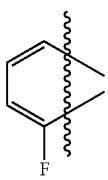 | | 406 |
| 668 | 2-fluorophenyl | A-2 | 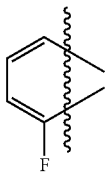 | | 400 |
| 669 | 2-methoxyphenyl | A-2 | 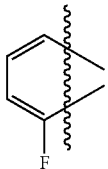 | | 412 |

INDEX TABLE E-continued
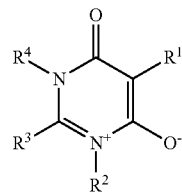
| Cmpd | R¹ | R² | R³ | R⁴ | m.p. (°C.) | AP+ (M + 1) |
|---|---|---|---|---|---|---|
| 670 | 2-methoxyphenyl | A-1 | 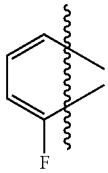 | | | 418 |
| 671 | 4-fluorophenyl | A-1 | 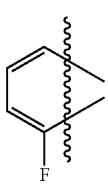 | | | 406 |
| 672 | 3-(trifluoromethoxy)-phenyl | A-1 | 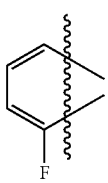 | | | 472 |
| 683 | 3-bromo-5-(trifluoromethoxy)phenyl | A-1 | 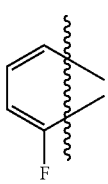 | | | 550 |
| 718 | 2-fluorophenyl | A-2 | $CH_3$ | $CH_3$ | 249-252 | 360 |
| 719 | 2-fluorophenyl | A-1 | $CH_3$ | $CH_3$ | 190-193 | 366 |
| 751 | 2-fluorophenyl | A-2 | 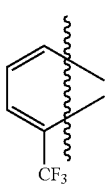 | | | 450 |
| 752 | 4-fluorophenyl | A-2 | 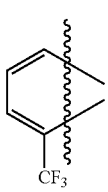 | | | 450 |

INDEX TABLE E-continued

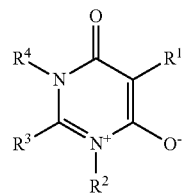

| Cmpd | R¹ | R² | R³ | R⁴ | m.p. (° C.) | AP+ (M + 1) |
|---|---|---|---|---|---|---|
| 753 | 3-(trifluoromethoxy)-phenyl | A-2 | 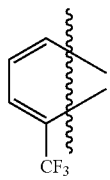 | | | 516 |
| 754 | 3-(trifluoromethoxy)-phenyl | A-1 | 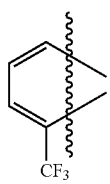 | | | 522 |
| 755 | 2-fluorophenyl | A-1 | 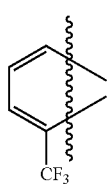 | | | 456 |
| 756 | 4-fluorophenyl | A-1 | 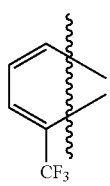 | | | 456 |

\* See Index Table G for ¹H NMR data.

\*\* When R³ and R⁴ are taken together with the contiguous linking nitrogen and carbon atoms to form a ring, the wavy line indicates that the ring is attached to the remainder of the molecule with the orientation shown below.

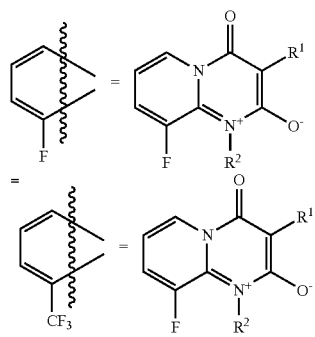

INDEX TABLE F

| Cmpd | Structure | m.p. (° C.) | AP+ (M + 1) |
|------|-----------|-------------|-------------|
| 520 | 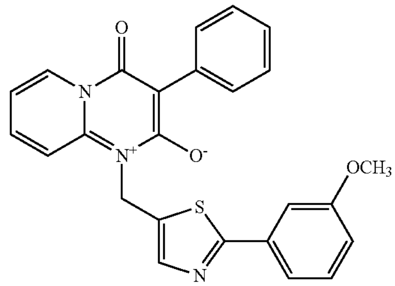 [SMILES: COc1cccc(-c2ncc(C[n+]3c([O-])c(-c4ccccc4)c(=O)n4ccccc43)s2)c1] | | 442 |
| 526 | 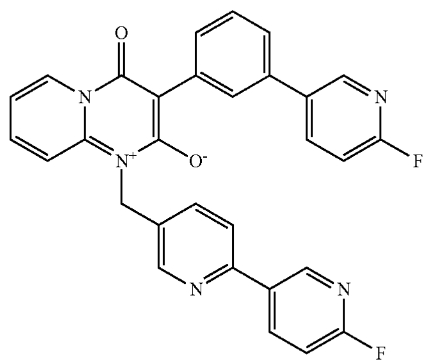 [SMILES: O=c1c(-c2cccc(-c3ccc(F)nc3)c2)c([O-])[n+](Cc2ccc(-c3ccc(F)nc3)nc2)c2ccccn12] | | 520 |
| 532 | 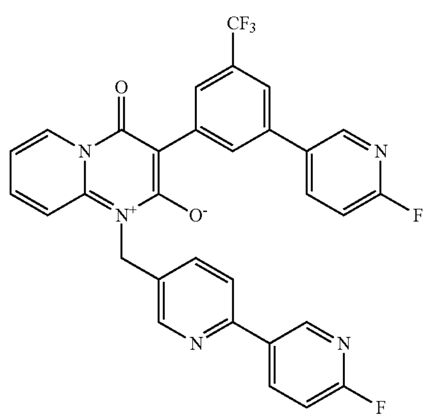 [SMILES: O=c1c(-c2cc(-c3ccc(F)nc3)cc(C(F)(F)F)c2)c([O-])[n+](Cc2ccc(-c3ccc(F)nc3)nc2)c2ccccn12] | | 588 |
| 533 | 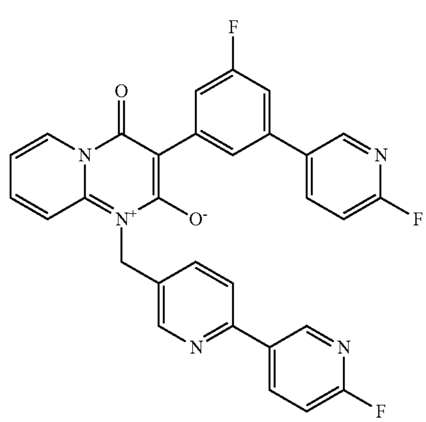 [SMILES: O=c1c(-c2cc(F)cc(-c3ccc(F)nc3)c2)c([O-])[n+](Cc2ccc(-c3ccc(F)nc3)nc2)c2ccccn12] | | 538 |

INDEX TABLE F-continued

| Cmpd | Structure | m.p. (° C.) | AP+ (M + 1) |
|------|-----------|-------------|-------------|
| 535 | 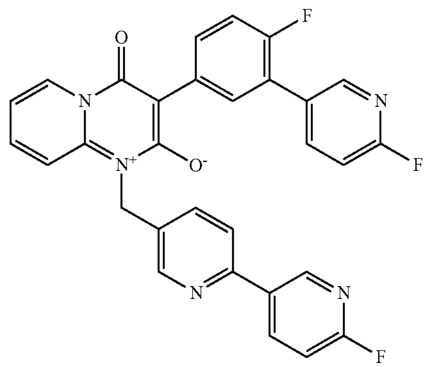 [SMILES: O=c1c(-c2ccc(F)c(-c3ccc(F)nc3)c2)c([O-])[n+](Cc2ccc(-c3ccc(F)nc3)nc2)c2ccccn12] | | 538 |
| 538 | 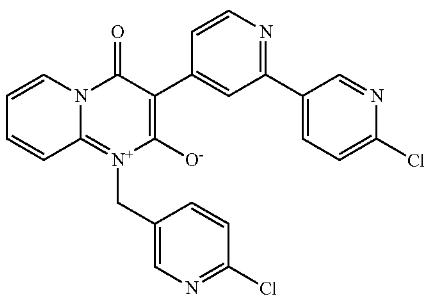 [SMILES: O=c1c(-c2ccnc(-c3ccc(Cl)nc3)c2)c([O-])[n+](Cc2ccc(Cl)nc2)c2ccccn12] | | 476 |
| 548 | 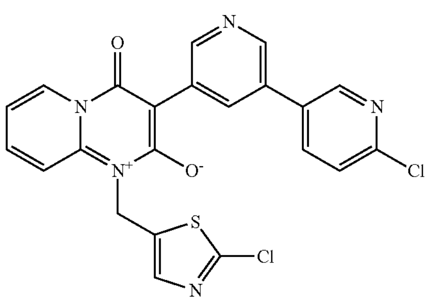 [SMILES: O=c1c(-c2cncc(-c3ccc(Cl)nc3)c2)c([O-])[n+](Cc2cnc(Cl)s2)c2ccccn12] | | 482 |
| 569 | 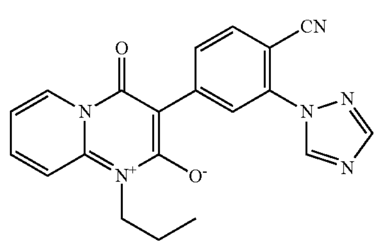 [SMILES: CCC[n+]1c([O-])c(-c2ccc(C#N)c(-n3cncn3)c2)c(=O)n2ccccc21] | | * |
| 572 | 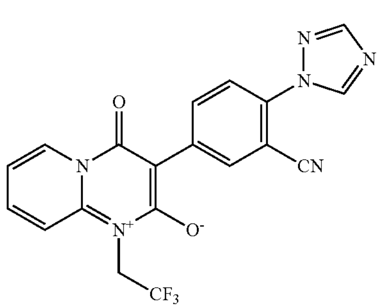 [SMILES: N#Cc1cc(-c2c([O-])[n+](CC(F)(F)F)c3ccccn3c2=O)ccc1-n1cncn1] | | 413 |

INDEX TABLE F-continued

| Cmpd | Structure | m.p. (° C.) | AP+ (M + 1) |
|------|-----------|-------------|-------------|
| 583  | 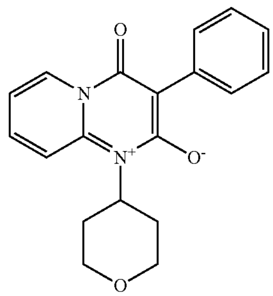 [SMILES: O=c1c(-c2ccccc2)c([O-])[n+](C2CCOCC2)c2ccccn12]          | *           |             |
| 599  | 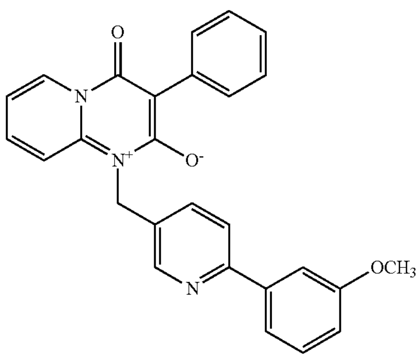 [SMILES: COc1cccc(-c2ccc(C[n+]3c([O-])c(-c4ccccc4)c(=O)n4ccccc43)cn2)c1]          | *           |             |
| 601  | 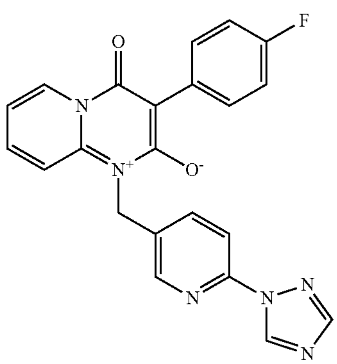 [SMILES: O=c1c(-c2ccc(F)cc2)c([O-])[n+](Cc2ccc(-n3cncn3)nc2)c2ccccn12]          | *           |             |
| 602  | 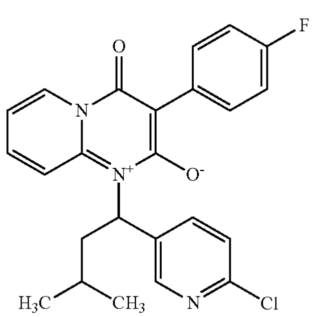 [SMILES: CC(C)CC(c1ccc(Cl)nc1)[n+]1c([O-])c(-c2ccc(F)cc2)c(=O)n2ccccc21]          |             | 438         |

INDEX TABLE F-continued
| Cmpd | Structure | m.p. (° C.) | AP+ (M + 1) |
|---|---|---|---|
| 603 | 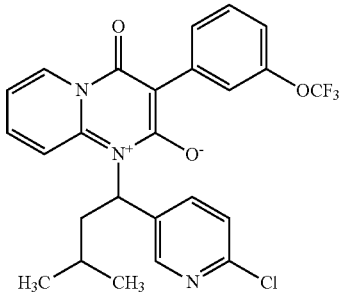 [SMILES: CC(C)CC(c1ccc(Cl)nc1)[n+]1c([O-])c(-c2cccc(OC(F)(F)F)c2)c(=O)n2ccccc21] | | 504 |
| 613 | 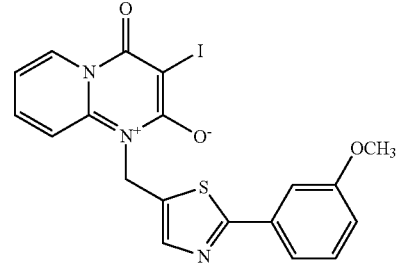 [SMILES: COc1cccc(-c2ncc(C[n+]3c([O-])c(I)c(=O)n4ccccc43)s2)c1] | | ** |
| 614 | 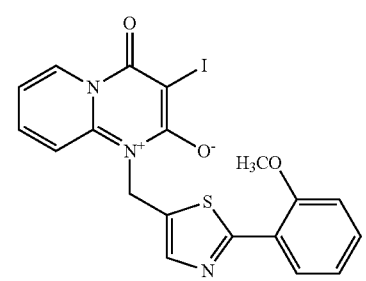 [SMILES: COc1ccccc1-c1ncc(C[n+]2c([O-])c(I)c(=O)n3ccccc32)s1] | | 492 |
| 615 | 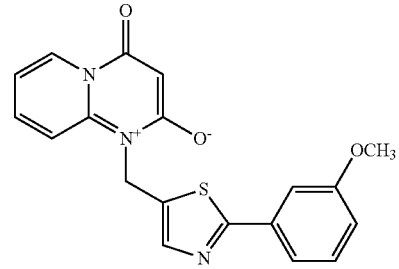 [SMILES: COc1cccc(-c2ncc(C[n+]3c([O-])cc(=O)n4ccccc43)s2)c1] | | 366 |
| 705 | 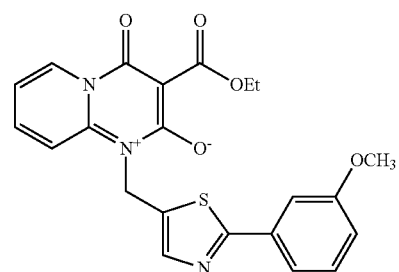 [SMILES: CCOC(=O)c1c([O-])[n+](Cc2cnc(-c3cccc(OC)c3)s2)c2ccccn2c1=O] | | 438 |

INDEX TABLE F-continued

| Cmpd | Structure | m.p. (° C.) | AP+ (M + 1) |
|---|---|---|---|
| 732 | 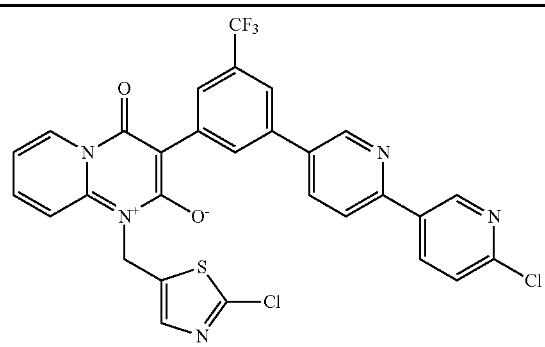 | | 626 |
| 733 | 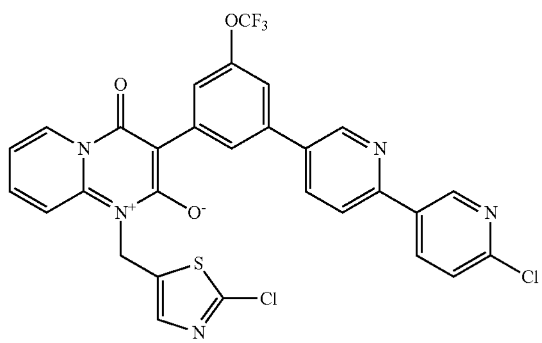 [SMILES: O=c1c(-c2cc(OC(F)(F)F)cc(-c3ccc(-c4ccc(Cl)nc4)nc3)c2)c([O-])[n+](Cc2cnc(Cl)s2)c2ccccn12] | | 642 |
| 757 | 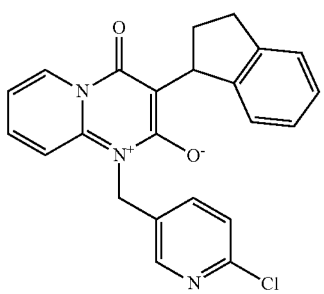 [SMILES: O=c1c(C2CCc3ccccc32)c([O-])[n+](Cc2ccc(Cl)nc2)c2ccccn12] | | 404 |

\* See Index Table G for ¹H NMR data.
\*\* See synthesis example for ¹H NMR data.

INDEX TABLE G

| Cmpd No. | ¹H NMR Data $^{a,\,b}$ |
|---|---|
| 3 | δ (acetone-d$_6$) 9.5 (m, 1H), 8.5 (m, 1H), 8.1 (m, 1H), 7.97 (s, 1H), 7.75 (dd, 1H), 7.69 (m, 1H), 7.31 (t, 1H), 7.15 (m, 1H), 5.35 (br s, 2H). |
| 8 | δ 9.51 (d, 1H), 8.09 (m, 1H), 7.85-7.69 (m, 2H), 7.45 (d, 1H), 7.38 (t, 1H), 7.32 (t, 1H), 7.07 (d, 1H), 4.29 (t, 2H), 1.87-1.75 (m, 2H), 1.08 (t, 3H). |
| 9 | δ 9.57 (d, 1H), 8.23 (t, 1H), 7.61 (d, 1H), 7.49 (t, 2H), 7.41 (d, 1H), 7.29 (d, 1H), 5.2 (br s, 2H). |
| 10 | δ 9.57 (d, 1H), 8.23 (t, 1H), 7.61 (d, 1H), 7.49 (m, 2H), 6.8-6.95 (m, 2H), 5.2 (br s, 2H). |
| 12 | δ 9.52 (dd, 1H), 8.15-8.07 (m, 2H), 8.03-7.98 (m, 1H), 7.47 (t, 3H), 7.34 (m, 1H), 4.30 (t, 2H), 1.91-1.74 (m, 2H), 1.09 (t, 3H). |
| 14 | δ 9.58 (d, 1H), 8.23 (t, 1H), 7.61 (d, 1H), 7.51 (t, 1H), 7.48 (d, 1H), 7.14 (m, 2H). |
| 15 | δ 9.60 (d, 1H), 8.23 (t, 1H), 7.75 (d, 2H), 7.59 (d, 1H), 7.51 (t, 2H), 7.24 (m, 2H). |
| 17 | δ (acetone-d$_6$) 9.45 (d, 1H), 8.45 (m, 1H), 8.1 (d, 1H), 7.63 (t, 1H), 7.3 (d, 1H), 7.22 (m, 1H), 7.95 (dd, 1H), 6.9 (t, 1H), 5.35 (br s, 2H), 3.73 (s, 3H). |
| 18 | δ 9.5 (m, 1H), 8.1 (m, 1H), 7.75 (m, 2H), 7.63 (dd, 1H), 7.4-7.3 (m, 2H), 7.05 (m, 1H), 4.30 (m, 2H), 1.2 (m, 1H), 0.62 (m, 4H). |
| 20 | δ 9.51 (dd, 1H), 8.12 (ddd, 2H), 7.51-7.42 (m, 3H), 7.38-7.31 (m, 1H), 6.72-6.60 (m, 1H), 4.29 (t, 2H), 1.93-1.68 (m, 2H), 1.09 (t, 3H). |
| 21 | δ 9.56 (d, 1H), 8.23 (t, 1H), 7.59 (d, 1H), 7.49 (m, 2H), 7.16 (t, 2H), 5.2 (br s, 2H). |
| 22 | δ 9.57 (d, 1H), 8.19 (t, 1H), 7.78 (dd, 1H), 7.67 (dd, 1H), 7.35-7.55 (m, 3H), 7.09 (d, 1H), 4.7-5.05 (m, 2H), 4.37 (m, 1H), 2.2-2.55 (m, 2H). |
| 25 | δ 9.57 (d, 1H), 8.23 (t, 1H), 7.58 (d, 1H), 7.46 (t, 2H), 7.38(s, 1H), 6.90 (d, 1H), 3.79 (s, 3H). |

INDEX TABLE G-continued

| Cmpd No. | $^1$H NMR Data $^{a,\ b}$ |
|---|---|
| 27 | δ 9.57 (d, 1H), 8.17 (t, 1H), 7.74 (m, 2H), 7.49 (d, 1H), 7.41 (t, 1H), 7.08 (t, 2H), 4.7-5.05 (m, 2H), 4.37 (m, 1H), 2.2-2.55 (m, 2H). |
| 28 | δ 9.53 (dd, 1H), 8.07 (ddd, 1H), 7.81-7.72 (m, 2H), 7.45 (d, 1H), 7.42-7.36 (m, 2H), 7.31 (m, 1H), 7.25-7.20 (m, 1H), 4.30 (d, 1H), 1.90-1.73 (m, 2H), 1.08 (t, 3H). |
| 30 | δ 9.54 (d, 1H), 8.21 (t, 1H), 7.51 (m, 2H), 7.42 (t, 1H), 6.9 (m, 2H), 4.7-5.05 (m, 2H), 4.37 (m, 1H), 2.2-2.55 (m, 2H). |
| 32 | δ 9.61 (d, 1H), 8.24 (t, 1H), 7.78 (dd, 1H), 7.67 (d, 1H), 7.50 (t, 1H), 7.44 (d, 2H), 6.69 (t, 1H). |
| 33 | δ 9.61 (d, 1H), 8.21 (t, 1H), 7.76 (d, 1H), 7.71 (s, 1H), 7.55 (dt, 1H), 7.49 (t, 1H), 7.39 (t, 1H), 7.10 (d, 1H). |
| 34 | δ 9.59 (d, 1H), 8.15 (t, 1H), 7.72 (d, 2H), 7.52 (d, 1H), 7.44 (t, 1H), 7.38 (t, 2H), 7.23 (t, 1H), 5.5 (br s, 2H). |
| 35 | δ 9.61 (d, 1H), 8.21 (t, 1H), 7.73 (m, 2H), 7.56 (d, 1H), 7.49 (t, 1H), 7.08 (t, 2H). |
| 36 | δ 9.59 (d, 1H), 8.23 (t, 1H), 7.58 (d, 1H), 7.50 (m, 2H), 7.50 (t, 1H), 6.85-6.95 (m, 2H). |
| 37 | δ 9.57 (d, 1H), 8.13 (t, 1H), 7.74 (d, 2H), 7.49 (d, 1H), 7.40 (m, 3H), 7.26 (m, 1H), 4.54 (t, 2H), 2.85 (m, 2H). |
| 38 | δ 9.58 (d, 1H), 8.16 (t, 1H), 7.74 (d, 2H), 7.49 (d, 1H), 7.40 (m, 3H), 7.25 (m, 1H), 4.58 (dd, 2H), 2.85 (m, 2H). |
| 39 | δ 9.49 (dd, 1H), 8.03 (ddd, 1H), 7.73 (d, 2H), 7.58 (d, 1H), 7.36 (t, 2H), 7.28 (m, 1H), 7.23-7.17 (m, 1H), 4.28 (d, 2H), 1.24-1.09 (m, 1H), 0.69-0.45 (m, 4H). |
| 41 | δ 9.51 (dd, 1H), 8.13 (ddd, 1H), 8.03-7.97 (m, 2H), 7.68-7.62 (m, 2H), 7.48 (d, 1H), 7.39-7.33 (m, 1H), 4.29 (t, 2H), 1.90-1.72 (m, 2H), 1.09 (t, 3H). |
| 42 | δ 9.55 (m, 1H), 8.15 (m, 1H), 7.75 (m, 2H), 7.67 (s, 1H), 7.6 (dd, 1H), 7.42 (m, 1H), 7.1 (m, 2H), 5.58 (br s, 2H). |
| 44 | δ 9.5 (m, 1H), 8.15 (m, 1H), 7.65 (s, 1H), 7.6 (dd, 1H), 7.5 (m, 1H), 7.4 (m, 1H), 6.9 (m, 2H), 5.55 (br s, 2H). |
| 50 | δ (acetone-d$_6$) 9.4 (m, 1H), 8.45 (m, 1H), 8.1 (dd, 1H), 7.95 (s, 1H), 7.6 (m, 1H), 7.55 (m, 1H), 7.3 (m, 1H), 7.1 (m, 2H), 5.74 (d, 2H). |
| 51 | δ 9.54 (d, 1H), 8.47 (s, 1H), 8.07 (dd, 1H), 7.99 (s, 1H), 7.76 (d, 1H), 7.68 (d, 1H), 7.25-7.45 (m, 5H), 5.58 (br s, 2H). |
| 52 | δ 9.55 (d, 1H), 8.48 (s, 1H), 8.10 (m, 3H), 7.67 (d, 1H), 7.48 (s, 1H), 7.42 (m, 2H), 7.36 (d, 1H), 5.59 (br s, 2H). |
| 53 | δ 9.56 (d, 1H), 8.48 (s, 1H), 8.14 (s, 1H), 8.09 (dd, 1H), 8.07 (d, 1H), 7.69 (dd, 1H), 7.51 (m, 2H), 7.40 (m, 2H), 5.6 (br s, 2H). |
| 54 | δ 9.56 (d, 1H), 8.47 (s, 1H), 8.08 (dd, 1H), 7.81 (d, 1H), 7.77 (s, 1H), 7.68 (dd, 1H), 7.3-7.45 (m, 4H), 7.12 (d, 1H), 5.59 (br s, 2H). |
| 55 | δ 9.52 (d, 1H), 8.47 (s, 1H), 8.10 (dd, 1H), 8.04 (s, 1H), 7.78 (s, 1H), 7.66 (dd, 1H), 7.3-7.45 (m, 4H), 5.57 (br s, 2H). |
| 56 | δ 9.55 (d, 1H), 8.48 (s, 1H), 8.08 (dd, 1H), 7.83 (d, 1H), 7.77 (dd, 1H), 7.3-7.45 (m, 4H), 7.24 (d, 1H), 5.59 (br s, 2H). |
| 57 | δ 9.56 (d, 1H), 8.48 (s, 1H), 8.05 (dd, 1H), 7.79 (d, 1H), 7.77 (dd, 1H), 7.3-7.45 (m, 4H), 7.24 (d, 1H), 5.59 (br s, 2H). |
| 59 | δ 9.56 (d, 1H), 8.48 (s, 1H), 8.05 (dd, 1H), 7.79 (d, 2H), 7.70 (dd, 1H), 7.2-7.45 (m, 6H), 5.59 (br s, 2H). |
| 60 | δ 9.56 (d, 1H), 8.48 (s, 1H), 8.05 (dd, 1H), 7.81 (d, 2H), 7.69 (dd, 1H), 7.3-7.45 (m, 3H), 7.17 (d, 2H), 6.52 (t, 1H), 5.59 (br s, 2H). |
| 61 | δ 9.56 (d, 1H), 8.48 (s, 1H), 8.08 (dd, 1H), 7.70 (dd, 1H), 7.63 (d, 1H), 7.58 (m, 1H), 7.3-7.45 (m, 4H), 6.95 (td, 1H), 5.58 (br s, 2H). |
| 62 | δ 9.51 (d, 1H), 8.48 (s, 1H), 8.10 (dd, 1H), 7.10 (m, 2H), 7.3-7.45 (m, 4H), 7.03 (dd, 1H), 5.58 (br s, 2H). |
| 63 | δ 9.51 (d, 1H), 8.48 (s, 1H), 8.08 (dd, 1H), 7.69 (ddd, 1H), 7.54 (q, 1H), 7.3-7.45 (m, 4H), 6.85-7.0 (m, 2H), 5.57 (br s, 2H). |
| 64 | δ 9.52 (d, 1H), 8.48 (s, 1H), 8.10 (dd, 1H), 7.70 (d, 1H), 7.48 (dd, 1H), 7.42 (m, 2H), 7.34 (d, 1H), 7.25 (d, 1H), 7.06 (td, 1H), 5.59 (br s, 2H). |
| 66 | δ 9.53 (d, 1H), 8.49 (s, 1H), 8.12 (dd, 1H), 7.90 (d, 1H), 7.69 (dd, 1H), 7.65 (m, 1H), 7.2-7.45 (m, 4H), 5.59 (br s, 2H). |
| 67 | δ 9.53 (d, 1H), 8.48 (s, 1H), 8.11 (dd, 1H), 7.79 (d, 1H), 7.70 (dd, 1H), 7.51 (d, 1H), 7.4 (m, 3H), 7.35 (d, 1H), 7.15 (d, 1H), 5.75 (br d, 1H), 5.4 (br d, 1H). |
| 68 | δ 9.53 (d, 1H), 8.48 (s, 1H), 8.11 (dd, 1H), 7.79 (t, 1H), 7.69 (dd, 1H), 7.25-7.45 (m, 4H), 5.58 (br s, 2H). |
| 70 | δ 9.52 (d, 1H), 8.49 (s, 1H), 8.10 (dd, 1H), 7.69 (dd, 1H), 7.56 (dd, 1H), 7.4 (m, 2H), 7.09 (t, 1H), 5.58 (br s, 2H). |
| 72 | δ 9.50 (d, 1H), 8.47 (s, 1H), 8.03 (dd, 1H), 7.69 (dd, 1H), 7.57 (td, 1H), 7.26-7.45 (m, 4H), 7.19 (t, 1H), 7.12 (dd, 1H), 5.56 (br s, 2H). |
| 73 | δ 9.56 (d, 1H), 8.48 (s, 1H), 8.08 (dd, 1H), 7.86 (d, 2H), 7.69 (dd, 1H), 7.3-7.45 (m, 3H), 7.26 (d, 1H), 5.59 (br s, 2H). |
| 74 | δ 9.54 (d, 1H), 8.47 (s, 1H), 8.0-8.15 (m, 3H), 7.67 (dd, 1H), 7.4 (m, 2H), 7.33 (d, 1H), 7.21 (dd, 1H), 5.59 (br s, 2H). |
| 75 | δ 9.56 (d, 1H), 8.48 (s, 1H), 8.03 (dd, 1H), 7.74 (d, 2H), 7.69 (dd, 1H), 7.3-7.4 (m, 3H), 6.97 (d, 2H), 5.59 (br s, 2H). |
| 76 | δ 9.56 (d, 1H), 8.48 (s, 1H), 8.10 (dd, 1H), 7.97 (d, 2H), 7.6-7.75 (m, 3H), 7.41 (m, 2H), 7.33 (d, 1H), 5.60 (br s, 2H). |
| 77 | δ 9.50 (d, 1H), 8.47 (s, 1H), 8.08 (dd, 1H), 7.68 (dd, 1H), 7.50 (d, 1H), 7.3-7.45 (m, 5H), 5.7 (br d, 1H), 5.4 (br d, 1H). |
| 78 | δ 9.52 (d, 1H), 8.48 (s, 1H), 8.11 (dd, 1H), 7.68 (dd, 2H), 7.35-7.45 (m, 3H), 7.34 (d, 1H), 6.95-7.05 (m, 1H), 5.57 (br s, 2H). |
| 79 | δ 9.52 (d, 1H), 8.48 (s, 1H), 8.12 (dd, 1H), 7.65-7.75 (m, 2H), 7.47 (d, 1H), 7.42 (t, 2H), 7.37 (d, 1H), 5.58 (br s, 2H). |

INDEX TABLE G-continued

| Cmpd No. | ¹H NMR Data [a, b] |
|---|---|
| 80 | δ 9.51 (d, 1H), 8.48 (s, 1H), 8.12 (dd, 1H), 7.69 (dd, 1H), 7.4-7.5 (m, 2H), 7.33 (d, 1H), 7.27 (m, 1H), 7.02 (dd, 1H), 5.58 (br s, 2H). |
| 82 | δ 9.55 (d, 1H), 8.48 (s, 1H), 8.09 (dd, 1H), 7.65-7.75 (m, 2H), 7.6 (m, 1H), 7.41 (m, 2H), 7.33 (d, 1H), 7.17 (q, 1H), 5.58 (br s, 2H). |
| 83 | δ 9.56 (d, 1H), 8.48 (s, 1H), 8.05 (dd, 1H), 7.70 (d, 1H), 7.28-7.40 (m, 6H), 6.84 (m, 1H), 5.59 (br s, 2H), 3.84 (s, 3H). |
| 84 | δ 9.56 (d, 1H), 8.48 (s, 1H), 8.03 (dd, 1H), 7.68 (m, 3H), 7.36 (m, 1H), 7.31 (d, 1H), 7.23 (d, 1H), 5.58 (br s, 2H), 2.37 (s, 3H). |
| 85 | δ 9.52 (d, 1H), 8.48 (s, 1H), 8.10 (dd, 1H), 7.68 (dd, 2H), 7.3-7.5 (m, 6H), 5.57 (br s, 2H). |
| 86 | δ (acetone-d₆) 9.45 (d, 1H), 8.55 (s, 1H), 8.25 (m, 1H), 7.9-7.8 (m, 2H), 7.75 (s, 1H), 7.6 (dd, 1H), 7.5 (m, 1H), 7.4 (d, 1H), 6.65 (d, 1H), 5.72 (br s, 2H), 4.53 (m, 2H), 3.2 (m, 2H). |
| 87 | δ 9.59 (d, 1H), 8.38 (s, 1H), 8.10 (dd, 1H), 7.8 (m, 3H), 7.42 (t, 1H), 7.36 (d, 1H), 7.11 (t, 2H), 5.59 (br s, 2H). |
| 88 | δ 9.53 (d, 1H), 8.49 (s, 1H), 8.10 (dd, 1H), 7.70 (d, 1H), 7.26-7.45 (m, 4H), 7.10 (td, 1H), 7.00 (m, 1H), 5.58 (br s, 2H). |
| 89 | δ 9.51 (d, 1H), 8.48 (s, 1H), 8.10 (dd, 1H), 7.70 (dd, 1H), 7.28-7.45 (m, 4H), 7.12 (m, 2H), 5.57 (br s, 2H). |
| 90 | δ 9.53 (d, 1H), 8.47 (s, 1H), 8.13 (dd, 1H), 7.68 (d, 1H), 7.60 (s, 1H), 7.53 (s, 2H), 7.43 (m, 2H), 7.35 (d, 1H) 5.60 (br d, 2H). |
| 91 | δ 9.52 (d, 1H), 8.46 (s, 1H), 8.06 (dd, 1H), 7.68 (d, 1H), 7.3-7.55 (m, 5H), 7.25 (d, 1H), 5.6 (br dd, 2H), 2.26 (s, 3H). |
| 92 | δ 9.54 (d, 1H), 8.48 (s, 1H), 8.1 (m, 2H), 7.75 (m, 1H), 7.68 (dd, 1H), 7.4 (m, 3H), 7.37 (d, 1H), 7.15 (t, 1H), 5.58 (br s, 2H). |
| 93 | δ 9.55 (d, 1H), 8.48 (s, 1H), 8.25 (s, 1H), 8.14 (s, 1H), 8.11 (dd, 1H), 7.66 (m, 2H), 7.4 (m, 2H), 7.34 (d, 1H), 5.59 (br s, 2H). |
| 94 | δ 9.53 (d, 1H), 8.48 (s, 1H), 8.14 (t, 1H), 7.75 (t, 1H), 7.68 (dd, 1H), 7.51 (d, 1H), 7.4 (m, 3H), 7.34 (d, 1H), 5.58 (br s, 2H). |
| 95 | δ 9.53 (d, 1H), 8.48 (s, 1H), 8.07 (t, 1H), 7.71 (d, 1H), 7.47 (t, 1H), 7.38 (m, 2H), 7.32 (d, 1H), 6.75 (m, 2H), 5.58 (br s, 2H). |
| 96 | δ 9.53 (d, 1H), 8.47 (s, 1H), 8.08 (dd, 1H), 7.69 (t, 1H), 7.3-7.45 (m, 4H), 6.9-7.05 (m, 2H), 5.6 (br dd, 2H), 2.28 (s, 3H). |
| 97 | δ 9.52 (d, 1H), 8.77 (s, 1H), 8.34 (t, 1H), 8.08 (dd, 1H), 7.98 (d, 1H), 7.78 (m, 2H), 7.4 (m, 2H), 7.10 (d, 1H), 5.67 (br s, 2H), 2.55 (s, 3H). |
| 98 | δ 9.55 (dd, 1H), 8.48 (d, 1H), 8.04 (ddd, 1H), 7.69 (dd, 1H), 7.40-7.34 (m, 2H), 7.32 (d, 1H), 7.29-7.26 (m, 2H), 6.88 (d, 1H), 5.95 (s, 2H), 5.58 (br s, 2H). |
| 99 | δ 9.52 (d, 1H), 8.48 (s, 1H), 8.10 (dd, 1H), 7.72 (dd, 1H), 7.3-7.5 (m, 5H), 7.11 (td, 1H), 5.8 (br d, 1H), 5.4 (br d, 1H). |
| 100 | δ 9.58 (d, 1H), 8.38 (s, 1H), 8.07 (dd, 1H), 7.8 (m, 3H), 7.3-7.45 (m, 4H), 7.26 (m, 1H), 5.57 (br s, 2H). |
| 101 | δ 9.56 (d, 1H), 8.48 (s, 1H), 8.07 (dd, 1H), 7.69 (d, 1H), 7.49 (d, 1H), 7.3-7.45 (m, 4H), 7.12 (dd, 1H), 5.59 (br s, 2H), 3.93 (s, 3H). |
| 102 | δ 9.55 (d, 1H), 8.48 (s, 1H), 8.05 (dd, 1H), 7.55-7.95 (m, 3H), 7.3-7.45 (m, 3H), 7.02 (dd, 1H), 5.58 (br s, 2H), 3.91 (s, 3H). |
| 103 | δ 9.53 (d, 1H), 8.69 (s, 1H), 8.60 (d, 1H), 8.07 (m, 2H), 7.80 (s, 1H), 7.66 (d, 1H), 7.4 (m, 2H), 7.25 (m, 2H), 5.63 (br s, 2H). |
| 104 | δ 9.55 (d, 1H), 8.47 (s, 1H), 8.07 (dd, 1H), 7.65-7.75 (m, 3H), 7.53 (d, 2H), 7.51 (d, 1H), 7.4 (m, 2H), 7.32 (d, 1H), 5.58 (br s, 2H). |
| 105 | δ 9.56 (d, 1H), 8.48 (s, 1H), 8.12 (dd, 1H), 8.02 (d, 2H), 7.67 (d, 2H), 7.4 (m, 3H), 7.34 (d, 1H), 5.59 (br s, 2H). |
| 106 | δ 9.55 (d, 1H), 8.48 (s, 1H), 8.07 (dd, 1H), 7.78 (d, 2H), 7.69 (dd, 1H), 7.4 (m, 4H), 7.32 (d, 1H), 5.59 (br s, 2H). |
| 107 | δ 9.53 (d, 1H), 8.48 (s, 1H), 8.20 (s, 1H), 8.11 (m, 2H), 7.68 (dd, 1H), 7.4-7.55 (m, 4H), 7.34 (d, 1H), 5.59 (br s, 2H). |
| 108 | δ 9.51 (d, 1H), 8.48 (s, 1H), 8.11 (dd, 1H), 7.68 (dd, 1H), 7.4 (m, 3H), 7.34 (d, 1H), 6.76 (dd, 2H), 5.58 (br s, 2H). |
| 109 | δ 9.57 (d, 1H), 8.46 (s, 1H), 7.88 (dd, 1H), 7.77 (m, 2H), 7.57 (dd, 1H), 7.3 (m, 3H), 7.1 (m, 3H), 5.35 (br m, 1H), 2.00 (s, 3H). |
| 110 | δ 9.46 (dd, 1H), 8.14 (ddd, 1H), 7.47 (d, 1H), 7.36 (m, 1H), 4.31 (t, 2H), 1.87-1.70 (m, 2H), 1.07 (t, 3H). |
| 111 | δ 9.54 (d, 1H), 8.26 (dd, 1H), 7.61 (d, 1H), 7.49 (t, 1H), 5.12 (br s, 2H). |
| 112 | δ 9.45 (d, 1H), 8.14 (dd, 1H), 7.49 (d, 1H), 7.33 (t, 1H), 4.32 (t, 2H), 1.78 (m, 2H), 1.07 (t, 3H). |
| 113 | δ 9.50 (d, 1H), 8.23 (dd, 1H), 7.52 (d, 1H), 7.41 (t, 1H), 4.96 (m, 1H), 4.77 (m, 1H), 4.40 (m, 1H), 2.40 (m, 1H), 2.25 (m, 1H). |
| 114 | δ (acetone-d₆) 9.42 (d, 1H), 8.53 (m, 1H), 8.09 (d, 1H), 7.69 (t, 1H), 5.42 (br s, 2H). |
| 115 | δ 8.12 (d, 1H), 7.45 (dd, 1H), 6.68 (dd, 1H), 6.48 (d, 1H), 4.6 (br s, 2H), 2.4 (m, 1H), 1.01 (d, 6H). |
| 116 | δ 8.12 (d, 1H), 7.45 (dd, 1H), 6.68 (dd, 1H), 6.49 (d, 1H), 4.6 (br s, 2H), 1.6 (m, 1H), 0.92 (d, 6H). |
| 117 | δ 9.51 (d, 1H), 8.18 (dd, 1H), 7.58 (d, 1H), 7.46 (t, 1H), 5.10 (br s, 2H), 2.91 (t, 2H), 2.60 (m, 2H). |
| 118 | δ 9.49 (d, 1H), 8.45 (s, 1H), 8.12 (dd, 1H), 7.65 (dd, 1H), 7.4 (m, 2H), 7.32 (d, 1H), 5.60 (br s, 2H). |
| 119 | δ 9.55 (d, 1H), 8.71 (s, 1H), 8.47 (s, 1H), 8.30 (dd, 1H), 8.11 (dd, 1H), 7.67 (dd, 1H), 7.42 (m, 2H), 7.33 (d, 1H), 5.60 (br s, 2H). |
| 120 | δ 9.56 (d, 1H), 8.92 (s, 1H), 8.47 (s, 1H), 8.21 (dd, 1H), 8.11 (dd, 1H), 7.3-7.45 (m, 4H), 5.59 (br s, 2H). |

INDEX TABLE G-continued

| Cmpd No. | $^1$H NMR Data $^{a,\,b}$ |
|---|---|
| 132 | δ 8.23 (d, 1H), 7.64 (d, 2H), 7.23 (d, 2H), 4.06 (dd, 2H), 2.89 (m, 1H), 1.89 (q, 2H), 1.25 (d, 6H), 1.06 (t, 3H). |
| 133 | δ 8.30 (d, 1H), 7.46 (m, 1H), 7.16 (d, 1H), 6.8-6.9 (m, 2H), 4.8 (br s, 2H). |
| 134 | δ 8.32 (d, 1H), 7.72 (d, 2H), 7.38 (dd, 2H), 7.23 (dd, 1H), 7.13 (d, 1H), 4.81 (q, 2H). |
| 135 | δ 8.32 (d, 1H), 7.73 (d, 1H), 7.69 (s, 1H), 7.37 (t, 1H), 7.15 (d, 1H), 7.08 (d, 1H), 4.81 (q, 2H). |
| 136 | δ 8.52 (d, 1H), 8.28 (d, 1H), 7.91 (dd, 1H), 7.72 (d, 2H), 7.35-7.4 (m, 3H), 7.25 (m, 1H, partially obscured by solvent peak), 7.03 (d, 1H), 5.31 (s, 2H). |
| 137 | δ (acetone-d$_6$) 8.61 (d, 1H), 8.20 (d, 1H), 7.98 (d, 1H), 7.89 (m, 2H), 7.55 (dd, 1H), 7.47 (m, 1H), 7.03 (dd, 2H), 5.46 (s, 2H). |
| 138 | δ 8.49 (d, 1H), 8.23 (d, 1H), 7.86 (dd, 1H), 7.75 (d, 1H), 7.70 (s, 1H), 7.37 (dd, 2H), 7.08 (d, 1H), 7.03 (d, 1H), 5.29 (s, 2H). |
| 139 | δ 8.29 (d, 1H), 7.67-7.72 (m, 3H), 7.25 (m, 1H, partially obscured by solvent peak), 7.09 (d, 1H), 5.34 (s, 2H). |
| 140 | δ 8.28 (d, 1H), 7.67-7.73 (m, 3H), 7.04-7.11 (m, 3H), 5.33 (s, 2H). |
| 141 | δ 8.25 (s, 1H), 7.65-7.75 (m, 3H), 7.38 (dd, 1H), 7.08 (d, 1H), 5.32 (d, 1H). |
| 142 | δ 8.01 (d, 1H), 7.39 (m, 1H), 6.95 (d, 1H), 6.92-6.88 (m, 2H), 4.31 (m, 2H), 1.70 (m, 2H), 0.92 (t, 3H). |
| 147 | δ 8.27 (d, 1H), 7.67 (s, 1H), 7.31 (m, 3H), 7.07 (d, 1H), 6.80 (m, 1H), 5.33 (s, 2H), 3.82 (s, 3H). |
| 152 | δ 8.27 (d, 1H), 7.82 (m, 1H), 7.69 (s, 1H), 7.56 (m, 1H), 7.23 (m, 1H), 7.14 (d, 1H), 5.35 (s, 2H). |
| 160 | δ (acetone-d$_6$) 8.17 (d, 1H), 7.88 (s, 1 H), 7.59 (d, 1H), 7.21-7.29 (m, 2H), 6.99 (d, 1H), 6.88 (t, 1H), 5.45 (d, 2H), 3.76 (s, 3H). |
| 171 | δ 9.49 (dd, 1H), 8.18 (t, 1H), 7.65-7.75 (m, 2H), 7.38-7.49 (m, 2H), 4.31 (d, 2H), 1.15-1.22 (m, 1H), 0.62 (m, 4H). |
| 209 | δ (acetone-d$_6$) 9.45 (d, 1H), 8.48 (t, 1 H), 8.13 (d, 1H), 7.63 (t, 1H), 6.98-7.08 (m, 3H), 5.38 (br d, 2H), 3.87 (s, 3H). |
| 229 | δ 9.58 (d, 1H), 8.02 (t, 1 H), 7.47-7.59 (m, 3H), 7.38 (t, 1H), 7.15-7.35 (m, 4H), 2.01 (d, 3H). |
| 345 | δ 9.47 (dd, 1H), 8.08 (d, 1H), 7.68 (m, 1H), 7.45-7.55 (m, 3H), 7.31 (t, 2H), 7.00 (d, 2H), 4.15-4.4 (m, 2H), 4.11 (q, 2H), 1.7-1.85 (m, 2H), 1.31 (t, 2H), 1.07 (t, 3H). |
| 346 | δ 9.55 (dd, 1H), 8.17 (t, 1H), 7.67 (d, 1H), 7.59 (d, 1H), 7.52 (dd, 1H), 7.45 (t, 1H), 6.99 (d, 1h), 5.3 (br s, 1H), 4.9 (br s, 1H), 4.10 (q, 2H), 1.31 (t, 3H). |
| 348 | δ 9.49 (dd, 1H), 8.11 (t, 1H), 7.48 (d, 1H), 7.34 (m, 2H), 7.13 (s, 1H), 4.32 (m, 2H), 3.71 (s, 3H), 2.29 (s, 3H), 1.7-1.85 (m, 2H), 1.06 (t, 3H). |
| 349 | δ 9.49 (d, 1H), 8.05 (t, 1H), 7.48 (d, 1H), 7.29 (t, 1H), 7.16 (m, 2H), 7.01 (d, 1H) 4.31 (m, 2H), 2.31 (s, 3H), 2.20 (s, 3H) 1.7-1.85 (m, 2H), 1.06 (t, 3H). |
| 351 | δ 9.55 (d, 1H), 8.23 (t, 1H), 7.98 (d, 2H), 7.66 (d, 2H), 7.52 (d, 1H), 7.44 (t, 1H), 4.85-5.05 (m, 1H), 4.75 (m, 1H), 4.40 (m, 1H), 2.2-2.6 (m, 2H). |
| 352 | δ 9.59 (dd, 1H), 8.25 (t, 1H), 7.59 (d, 1H), 7.50 (t, 1H), 7.23-7.28 (m, 1H), 7.07 (td, 1H), 7.04 (m, 1H), 5.10 (br s, 2H). |
| 369 | δ 9.60 (dd, 1H), 8.26 (t, 1H), 8.16 (d, 1H), 8.12 (m, 1H), 7.62 (d, 1H), 7.53 (t, 1H), 7.20 (t, 1H), 5.10 (br s, 2H). |
| 416 | δ 9.51 (d, 1H), 8.50 (s, 1H), 8.08 (d, 2H), 7.75 (d, 2H), 7.66 (dd, 2H), 7.3-7.45 (m, 3H), 7.2-7.25 (m, 1H), 5.69 (s, 2H). |
| 418 | δ 9.54 (dd, 1H), 8.47 (d, 1H), 8.10 (m, 1H), 7.79 (d, 1H), 7.67(dd, 1H), 7.33-7.43 (m, 2H), 7.2-7.3 (m, 3H), 5.58 (br s, 2H). |
| 425 | δ 9.56 (d, 1H), 8.48 (s, 1H), 8.06 (t, 1H), 7.74 (s, 1H), 7.66 (dd, 2H), 7.3-7.4 (m, 3H), 7.19 (d, 1H), 5.59 (br s, 1H), 2.51 (s, 3H). |
| 426 | δ 9.62 (dd, 1H), 8.75 (t, 1H), 8.26 (m, 1H), 8.20 (d, 1H), 7.63 (d, 1H), 7.53 (m, 2H), 5.3 (br s, 2H). |
| 427 | δ 9.57 (dd, 1H), 8.48 (s, 1H), 8.04 (m, 1H), 7.93 (s, 1H), 7.70 (dd, 2H), 7.42 (s, 2H), 7.35 (m, 3H), 5.60 (br s, 2H), 0.29 (s, 9H). |
| 430 | δ 9.56 (dd, 1H), 8.76 (s, 1H), 8.04 (m, 1H), 7.93 (d, 1H), 7.7-7.8 (m, 3H), 7.60 (m, 3H), 7.34 (m, mH), 5.65 (br s, 2H), 0.28 (s, 9H). |
| 433 | δ 9.58 (d, 1H), 8.22 (m, 1H), 7.61 (d, 1H), 7.48 (t, 1H), 7.30 (m, 1H), 6.98 (d, 1H), 6.93 (m, 1H), 5.2 (br s, 2H), 2.24 (s, 3H). |
| 436 | δ 9.58 (dd, 1H), 8.38 (s, 1H), 8.11 (t, 1H), 7.80 (m, 3H), 7.42 (m, 2H), 7.36 (d, 1H), 7.11 (d, 1H), 5.58 (br s, 2H). |
| 443 | δ 9.59 (dd, 1H), 8.38 (s, 1H), 8.07 (t, 1H), 7.82 (s, 1H), 7.74 (d, 2H), 7.40 (t, 1H), 7.37 (d, 1H), 6.98 (d, 2H), 5.58 (br s, 2H), 3.84 (s, 3H). |
| 453 | δ 9.58 (dd, 1H), 8.12 (m, 1H), 7.82 (d, 1H), 7.78 (s, 1H), 7.49 (d, 1H), 7.42 (m, 2H), 7.26 (m, 2H), 7.12 (d, 1H), 5.67 (br s, 2H). |
| 459 | δ 9.55 (d, 1H), 8.45 (d, 1H), 8.05 (t, 1H), 7.66 (dd, 1H), 7.52 (d, 1H), 7.42 (s, 1H), 7.31-7.39 (m, 4H), 6.85 (d, 1H), 5.59 (br s, 2H), 4.38 (q, 2H). |
| 483 | δ 9.57 (dd, 1H), 8.15 (m, 1H), 7.74 (m, 2H), 7.59 (d, 1H), 7.40 (t, 1H), 7.08(t, 2H), 5.0 (m, 1H), 4.0 (m, 1H), 2.07 (m, 1H), 1.5-1.65 (m, 4H). |
| 486 | δ (acetone-d$_6$) 9.43 (d, 1H), 8.41 (t, 1H), 8.18 (d, 1H), 7.96 (s, 1H), 7.75 (d, 1H), 7.59 (t, 1H), 7.50-7.56 (m, 1H), 7.05 (dd, 1H), 5.77 (s, 2H), 3.88 (s, 3H). |
| 501 | δ 9.51 (d, 1H), 8.21 (t, 1H), 7.67 (s, 1H), 7.62 (d, 1H), 7.42 (t, 1H), 6.75 (t, 2H), 5.59 (s, 2H). |
| 511 | δ (acetone-d$_6$) 7.87 (dd, 1H), 7.84-7.82 (m, 2H), 7.50 (d, 1H), 7.45 (d, 1H), 7.25-7.21 (m, 2H), 7.10-7.05 (m, 1H), 5.58 (s, 2H), 3.64 (s, 3H), 2.29 (s, 3H). |
| 518 | δ (acetone-d$_6$) 8.60 (d, 1H), 8.13 (s, 1 H), 8.04 (s, 1H), 8.00 (d, 1H), 7.92-7.97 (m, 2H), 7.43 (d, 1H), 7.38 (t, 1H), 7.03 (d, 1H), 5.42 (s, 2H). |
| 521 | δ (acetone-d$_6$) 9.50 (d, 1H), 8.85 (d, 1 H), 8.55 (t, 1H), 8.17 (d, 1H), 7.92 (s, 1H), 7.71 (t, 1H), 7.45 (d, 1H), 5.39 (br d, 2H). |
| 547 | δ (acetone-d$_6$) 9.41 (d, 1H), 8.35-8.43 (m, 2H), 7.98-8.05 (m, 2H), 7.88-7.92 (m, 2H), 7.63 (d, 1H), 7.59 (t, 1H), 7.05 (d, 1H), 5.74 (s, 2H). |

INDEX TABLE G-continued

| Cmpd No. | ¹H NMR Data [a, b] |
|---|---|
| 564 | δ 9.53 (dd, 1H), 8.14 (m, 1H), 7.73 (m, 2H), 7.4-7.6 (m, 4H), 7.36 (t, 2H), 7.20 (m, 1H), 5.58 (br s, 2H), 4.32 (m, 2H), 1.84 (m, 2H), 1.09 (t, 3H). |
| 569 | δ 9.48 (dd, 1H), 8.70 (s, 1H), 8.43 (d, 1H), 8.22 (d, 1H), 8.17 (m, 2H), 7.78 (d, 1H), 7.52 (d, 1h), 7.37 (t, 1H) 4.3 (t, 2H), 1.83 (m, 2H), 1.09 (t, 3H). |
| 583 | δ (acetone-$d_6$) 9.42 (dd, 1H), 8.35 (t, 1H), 8.15 (d, 1H), 7.82 (d, 2H), 7.52 (t, 1H), 7.25-7.31 (m, 2H), 7.13 (t, 1H), 5.34 (Br s, 1H), 4.05 (dd, 2H), 3.58 (td, 2H), 2.91 (qd, 2H), 1.80 (dd, 2H). |
| 599 | δ 9.57 (dd, 1H), 8.76 (d, 1H), 8.03 (m, 1H), 7.7-7.83 (m, 4H), 7.34-7.57 (m, 6H), 7.2-7.3 (m, 2H), 6.98 (dd, 1H), 5.65 (br s, 2H). |
| 600 | δ (acetone-$d_6$) 9.41 (d, 1H), 8.45 (t, 1H), 8.20 (d, 1H), 7.95-8.05 (m, 2H), 7.88 (d, 1H), 7.59-7.65 (m, 2H), 5.75 (br s, 2H). |
| 601 | δ 9.57 (dd, 1H), 9.14 (s, 1H), 8.52 (s, 1H), 8.05-8.10 (m, 2H), 7.91 (s, 26H), 7.78-7.82 (m, 2H), 7.38-7.43 (d, 2H), 7.11 (t, 2H), 5.67 (Br s, 2H). |
| 606 | δ 9.49 (d, 1H), 8.53 (d, 1H), 8.05 (s, 2H), 7.78 (m, 2H), 7.68 (t, 1H), 7.55 (d, 1H), 7.33 (m, 1H), 7.09 (t, 2H), 5.68 (br s, 2H). |
| 612 | δ 9.44 (dd, 1H), 8.65 (d, 1H), 8.57 (dd, 1H), 8.03 (m, 1H), 7.62 (dt, 1H), 7.27-7.37 (m, 3H), 5.55 (br s, 2H), 5.47 (s, 1H). |
| 638 | δ 9.49 (d, 0.5H), 9.47 (d, 0.5H), 8.23 (t, 1H), 7.61 (d, 1H), 7.50 (m, 1H), 5.00 (m, 2H), 4.35 (q, 1H), 4.32 (q, 1H), 1.35 (t, 1.5H), 1.28 (t, 1.5H) (1:1 mix of E and Z isomers). |
| 639 | δ (acetone-$d_6$) 8.45 (d, 1H), 8.19 (m, 1H), 8.10 (m, 1H), 8.00 (m, 2H), 7.53 (m, 1H), 7.38 (m, 1H), 7.10-7.00 (m, 2H), 5.45 (s, 2H). |
| 646 | δ (acetone-$d_6$) 8.45 (s, 1H), 8.10 (m, 2H), 7.50 (m, 1H), 7.30 (m, 1H), 7.20 (m, 1H), 7.15 (m, 1H), 6.95 (m, 1H), 6.90 (m, 1H), 5.50-5.30 (dd, 2H), 3.76 (s, 3H). |
| 647 | δ (acetone-$d_6$) 8.10 (m, 1H), 7.70 (s, 1H), 7.55 (s, 1H), 7.50 (d, 1H), 7.25 (m, 1H), 7.20 (m, 1H), 6.95 (m, 1H), 6.90 (m, 1H), 5.13 (m, 2H), 3.83 (s, 3H), 3.74 (s, 3H). |
| 648 | δ (acetone-$d_6$) 9.40 (m, 1H), 8.10 (m, 1H), 7.70 (m, 1H), 7.60 (dd, 1H), 7.45-7.35 (m, 3H), 7.20 (m, 1H), 7.05 (m, 1H), 6.95 (m, 1H), 6.90 (m, 1H), 3.83 (m, 3H), 3.75 (m, 3H), 1.90 (m, 3H). |
| 656 | δ 9.50 (m, 1H), 8.23 (t, 1H), 7.61 (d, 1H), 7.50 (m, 1H), 5.00 (m, 2H), 4.09 (d, 2H), 2.00 (m, 1H), 0.98 (d, 4H), 0.89 (d, 2H) (2:1 mix of E and Z isomers). |
| 657 | δ 9.50 (d, 1H), 8.23 (t, 1H), 7.61 (d, 1H), 7.50 (t, 1H), 5.00 (m, 2H), 1.38 (s, 9H) (single isomer). |
| 658 | δ 9.50 (m, 1H), 8.23 (t, 1H), 7.61 (d, 1H), 7.50 (m, 1H), 5.00 (m, 2H), 4.00 (s, 2H), 0.99 (s, 6H), 0.89 (s, 3H) (2:1 mix of E and Z isomers). |
| 659 | δ 9.50 (m, 1H), 8.23 (t, 1H), 7.61 (d, 1H), 7.50 (m, 1H), 5.00 (m, 2H), 4.82 (s, 0.66H), 4.76 (s, 1.34H), 4.22 (q, 0.66H), 4.20 (q, 1.34H), 1.29 (t, 1H), 1.27 (t, 2H) (2:1 mix of E and Z isomers). |
| 700 | δ 9.44 (d, 1H), 8.22 (t, 1H), 7.64 (s, 1H), 7.58 (d, 1H), 7.42 (t, 1H), 5.55 (br s, 2H), 4.42 (q, 2H), 1.04 (t, 3H). |
| 701 | δ 9.44 (d, 1H), 8.26 (t, 1H), 7.91 (d, 2H), 7.65 (s, 1H), 7.63 (d, 1H), 7.55 (t, 1H), 7.44 (m, 3H), 5.56 (br s, 2H). |
| 729 | δ 9.49 (d, 1H), 8.23 (s, 1H), 8.21 (t, 1H), 7.52 (d, 1H), 7.47 (t, 1H), 5.05 (br m, 2H), 1.38 (s, 9H). |
| 730 | δ 9.53 (d, 1H), 8.42 (s, 1H), 8.21 (t, 1H), 7.53 (d, 1H), 7.46 (t, 1H), 5.05 (br m, 2H), 4.22 (q, 2H), 1.32 (t, 3H). |
| 731 | δ 9.53 (d, 1H), 8.44 (s, 1H), 8.21 (t, 1H), 7.53 (d, 1H), 7.49 (t, 1H), 5.05 (br m, 2H), 3.93 (s, 2H), 0.98 (s, 9H). |
| 758 | δ 9.53 (d, 1H), 8.40 (s, 1H), 8.22 (t, 1H), 7.54 (d, 1H), 7.50 (t, 1H), 5.05 (br m, 2H), 3.91 (s, 3H). |
| 759 | δ 9.53 (d, 1H), 8.41 (s, 1H), 8.18 (t, 1H), 7.47 (m, 3H), 7.37 (m, 3H), 7.30 (t, 1H), 5.24 (s, 2H), 5.05 (br m, 2H). |

[a] ¹H NMR data are in ppm downfield from tetramethylsilane. CDCl₃ solution unless indicated otherwise; "acetone-$d_6$" is $CD_3C(=O)CD_3$. Couplings are designated by (s)—singlet, (d)—doublet, (t)—triplet, (m)—multiplet, (dd)—doublet of doublets, (ddd)—doublet of doublet of doublets, (dt)—doublet of triplets, (td)—triplet of doublets, (br)—broad.
[b] ¹H NMR spectra of compounds wherein $R^2$ is $CH_2CF_3$ often do not show peaks corresponding to the $CH_2CF_3$ protons.

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A-F for compound descriptions.

Biological Examples of the Invention

Test A

For evaluating control of diamondback moth (*Plutella xylostella*) the test unit consisted of a small open container with a 12-14-day-old radish plant inside. This was pre-infested with ~50 neonate larvae that were dispensed into the test unit via corn cob grits using a bazooka inoculator. The larvae moved onto the test plant after being dispensed into the test unit.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with ⅛ JJ custom body (Spraying Systems Co. Wheaton, Ill., USA) positioned 1.27 cm (0.5 inches) above the top of each test unit. Test compounds were sprayed at 250 ppm and replicated three times. After spraying of the formulated test compound, each test unit was allowed to dry for 1 h and then a black, screened cap was placed on top. The test units were held for 6 days in a growth chamber at 25° C. and 70% relative humidity. Plant feeding damage was then visually assessed based on foliage consumed.

Of the compounds of Formula 1 tested the following provided very good to excellent levels of control efficacy (40% or less feeding damage and/or 100% mortality): 1, 2, 3, 5, 6, 7, 8, 9, 10, 12, 13, 14, 15, 16, 17, 18, 19, 20, 22, 23, 24, 25, 26, 27, 28, 32, 33, 37, 39, 40, 42, 43, 44, 45, 46, 47, 48, 49, 50, 51, 52, 53, 54, 55, 56, 57, 58, 59, 60, 61, 62, 63, 64, 65, 66, 67, 68, 70, 72, 73, 74, 75, 76, 77, 78, 79, 80, 81, 82, 83, 84, 85, 86, 87, 88, 89, 90, 91, 92, 93, 95, 97, 98, 100, 101, 102, 103, 104, 106, 107, 108, 109, 120, 121, 122, 123, 128, 135, 136, 137, 138, 139, 140, 141, 145, 146, 147, 148, 149, 150, 152, 153, 154, 155, 156, 159, 161, 162, 164, 166, 167, 168, 169, 170, 173, 178, 179, 180, 185, 186, 187, 188, 189, 190, 192, 193, 196, 197, 198, 199, 200, 201, 202, 203, 205, 206, 207, 208, 209, 210, 211, 212, 215, 216, 217, 218, 219, 220, 221, 222, 226, 227, 229, 232, 235, 236, 237, 240, 242, 243, 245, 246, 247, 248, 252, 253, 254, 255, 256, 257, 259, 261, 262, 263, 264, 266, 267, 270, 271, 272, 273, 274, 275, 276, 277, 278, 279, 281, 282, 284, 286, 287, 288, 289, 290, 291, 293, 294, 295, 297, 298, 299, 300, 301, 302, 307, 310, 311, 312, 313, 314, 319, 321, 323, 324, 327, 330, 332, 339, 340, 341, 342, 343, 347, 350, 351, 352, 353, 355, 359, 361, 362, 363, 364, 366, 367, 370, 371, 372, 374, 377, 379, 380, 386, 389, 391, 400, 401, 405, 406, 412, 414, 418, 421, 422, 424, 426, 427, 431, 436, 438, 440, 441, 446, 459, 460, 461, 463, 469, 470, 471, 472, 473, 474, 475, 476, 477, 478, 479, 480, 481, 482, 483, 484, 485, 486, 487, 488, 489, 490, 491, 492, 493, 494, 495, 496, 498, 499, 500, 501, 502, 503, 511, 515, 524, 525, 527, 528, 529, 530, 531, 532, 534, 536, 537, 539, 540, 541, 542, 544, 545, 546, 548, 549, 550, 551, 557, 562, 563, 566, 567, 575, 581, 582, 589, 596, 597, 598, 600, 603, 608, 609, 613, 616, 617, 618, 619, 620, 621, 622, 623, 624, 625, 626, 627, 628, 630, 632, 634, 635, 636, 639, 640, 651, 652, 653, 654, 655, 663, 664, 666, 667, 670, 671, 672, 679, 682, 683, 684, 685, 701, 702, 713, 715, 717, 732, 733, 753, 754, 755 and 756.

Test B

For evaluating control of fall armyworm (*Spodoptera frugiperda*) the test unit consisted of a small open container with a 4-5-day-old maize (corn) plant inside. This was pre-infested (using a core sampler) with 10-15 1-day-old larvae on a piece of insect diet.

Test compounds were formulated and sprayed at 250 ppm as described for Test A. The applications were replicated three times. After spraying, the test units were maintained in a growth chamber at 25° C. and 70% relative humidity and then visually rated as described for Test A.

Of the compounds of Formula 1 tested the following provided very good to excellent levels of control efficacy (40% or less feeding damage and/or 100% mortality): 1, 3, 8, 15, 18, 22, 40, 42, 43, 44, 45, 46, 47, 48, 49, 50, 51, 53, 54, 55, 56, 58, 59, 60, 62, 65, 66, 68, 70, 73, 74, 75, 76, 79, 81, 83, 84, 92, 93, 95, 103, 123, 141, 145, 166, 168, 169, 173, 179, 180, 185, 186, 187, 188, 189, 192, 193, 196, 200, 215, 217, 226, 232, 240, 242, 245, 252, 253, 254, 255, 256, 261, 270, 272, 275, 276, 277, 310, 312, 372, 418, 427, 436, 440, 451, 461, 473, 475, 476, 477, 478, 479, 480, 481, 482, 484, 486, 489, 490, 491, 493, 495, 496, 498, 499, 500, 501, 502, 524, 525, 530, 531, 534, 540, 541, 542, 544, 549, 550, 574, 598, 609, 616, 617, 618, 619, 620, 622, 623, 624, 625, 626, 627, 628, 634, 635, 636, 652, 653, 654, 655, 663, 671, 672, 682, 683, 684, 685, 717, 733 and 754.

Test C

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The aphids moved onto the test plant as the leaf piece desiccated. After pre-infestation, the soil of the test unit was covered with a layer of sand.

Test compounds were formulated and sprayed at 250 ppm as described for Test A. The applications were replicated three times. After spraying of the formulated test compound, each test unit was allowed to dry for 1 h and then a black, screened cap was placed on top. The test units were held for 6 days in a growth chamber at 19-21° C. and 50-70% relative humidity. Each test unit was then visually assessed for insect mortality.

Of the compounds of Formula 1 tested, the following resulted in at least 80% mortality: 5, 10, 19, 29, 30, 31, 42, 43, 44, 49, 50, 53, 57, 59, 60, 63, 64, 65, 66, 68, 71, 72, 74, 75, 77, 78, 79, 80, 82, 83, 87, 94, 99, 100, 101, 102, 105, 108, 109, 111, 118, 119, 120, 123, 139, 140, 151, 153, 157, 166, 171, 172, 173, 178, 180, 185, 192, 193, 196, 197, 198, 200, 203, 207, 213, 214, 216, 218, 220, 224, 231, 232, 238, 256, 277, 357, 365, 373, 389, 390, 394, 396, 397, 404, 407, 411, 422, 437, 443, 444, 445, 463, 464, 469, 471, 472, 476, 477, 481, 482, 483, 486, 491, 492, 493, 495, 496, 498, 499, 500, 501, 503, 513, 530, 531, 536, 537, 540, 544, 549, 550, 575, 577, 590, 593, 597, 598, 600, 608, 617, 623, 626, 627, 628, 636, 651, 653, 654, 655, 660, 700, 714 and 717.

Test D

For evaluating control of cotton melon aphid (*Aphis gossypii*) through contact and/or systemic means, the test unit consisted of a small open container with a 6-7-day-old cotton plant inside. This was pre-infested with 30-40 insects on a piece of leaf according to the cut-leaf method described for Test C, and the soil of the test unit was covered with a layer of sand.

Test compounds were formulated and sprayed at 250 ppm as described for Test C. The applications were replicated three times. After spraying, the test units were maintained in a growth chamber and then visually rated as described for Test C.

Of the compounds of Formula 1 tested, the following resulted in at least 80% mortality: 5, 10, 30, 31, 49, 54, 66, 75, 87, 94, 95, 166, 167, 192, 193, 198, 204, 210, 213, 214, 220, 230, 231, 235, 238, 264, 277, 486, 490, 540, 544, 550, 617, 619, 623, 627, 636, 653 and 654.

Test E

For evaluating control of corn planthopper (Peregrinus maidis) through contact and/or systemic means, the test unit consisted of a small open container with a 3-4-day-old maize plant (spike) inside. White sand was added to the top of the soil prior to application. Test compounds were formulated and sprayed at 250 and 50 ppm and replicated three times as described for Test A. After spraying, the test units were allowed to dry for 1 h before they were post-infested with ~15-20 nymphs (18 to 21 day old) by sprinkling them onto the sand with a salt shaker. A black, screened cap was placed on the top of the cylinder. The test units were held for 6 days in a growth chamber at 22-24° C. and 50-70% relative humidity. Each test unit was then visually assessed for insect mortality.

Of the compounds of Formula 1 tested at 250 ppm, the following resulted in at least 80% mortality: 1, 2, 3, 5, 6, 7, 8, 9, 10, 11, 12, 13, 14, 15, 16, 17, 18, 19, 21, 22, 23, 24, 25, 26, 27, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 70, 71, 72, 73, 74, 75, 76, 77, 78, 79, 80, 81, 82, 83, 84, 85, 86, 87, 88, 89, 90, 91, 93, 94, 95, 96, 97, 98, 99, 100, 101, 103, 104, 105, 106, 107, 108, 109, 111, 114, 115, 116, 118, 119, 120, 121, 122, 123, 161, 162, 163, 237, 278, 279, 280, 281, 282, 283, 284, 285, 289, 290, 291, 292, 293, 294, 295, 296, 297, 298, 299, 301, 302, 304, 306, 308, 309, 314, 317, 318, 319, 320, 321, 322, 323, 324, 325, 327, 329, 330, 336, 340, 341, 343, 344, 345, 346, 347, 348, 349, 350, 351, 352, 353, 356, 357, 358, 359, 360, 361, 362, 363, 364, 365, 366, 368, 375, 376, 377, 378, 384, 386, 389, 390, 392, 393, 394, 396, 397, 399, 400, 402, 403, 404, 406, 407, 408, 409, 411, 412, 413, 414, 415, 416, 419, 420, 421, 422, 423, 424, 425, 426, 428, 431, 433, 435, 436, 437, 438, 441, 442, 443, 444, 445, 446, 447, 449, 450, 459, 460, 461, 462, 463, 464, 465, 466, 467, 468, 469, 470, 471, 472, 474, 475, 476, 477, 479, 481, 482, 483, 484, 485, 519, 556, 562, 564, 568, 570, 571, 573, 574, 575, 576, 577, 579, 582, 583, 584, 586, 587, 588, 590, 591, 592, 593, 594, 604, 606, 608, 611, 612, 613, 687 and 757.

Of the compounds of Formula 1 tested at 50 ppm the following provided very good to excellent levels of control efficacy (80% or more mortality): 1, 2, 3, 5, 6, 7, 8, 9, 10, 11, 12, 13, 14, 16, 17, 18, 19, 20, 21, 23, 24, 25, 26, 27, 28, 29, 30, 31, 32, 36, 38, 39, 40, 42, 43, 44, 45, 46, 47, 48, 49, 50, 51, 52, 53, 54, 55, 56, 57, 58, 59, 60, 61, 62, 63, 64, 65, 66, 67, 68, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 107, 108, 109, 111, 118, 119, 120, 121, 123, 124, 125, 134, 136, 137, 138, 139, 140, 141, 146, 147, 148, 149, 150, 151, 154, 156, 157, 161, 166, 167, 168, 171, 172, 173, 180, 185, 192, 193, 196, 197, 198, 199, 200, 201, 202, 203, 204, 207, 208, 209, 210, 212, 213, 214, 215, 216, 217, 218, 219, 220, 221, 222, 223, 224, 225, 226, 229, 230, 231, 232, 233, 234, 235, 236, 237, 238, 239, 240, 241, 243, 244, 245, 246, 247, 248, 249, 252, 254, 255, 256, 257, 259, 260, 262, 264, 266, 278, 280, 284, 289, 290, 291, 292, 293, 295, 297, 301, 304, 314, 318, 319, 320, 321, 323, 324, 325, 327, 330, 343, 344, 345, 346, 347, 348, 349, 350, 351, 352, 357, 359, 360, 361, 362, 363, 365, 376, 377, 378, 390, 392, 393, 394, 399, 400, 403, 404, 408, 411, 412, 413, 414, 419, 420, 421, 422, 423, 424, 425, 426, 431, 433, 435, 436, 437, 438, 441, 442, 443, 444, 446, 448, 449, 450, 456, 459, 460, 461, 462, 463, 464, 466, 468, 469, 470, 471, 472, 473, 474, 475, 476, 477, 481, 482, 483, 485, 486, 487, 488, 489, 490, 491, 492, 493, 495, 496, 497, 498, 499, 500, 501, 502, 503, 511, 513, 514, 522, 523, 524, 525, 527, 530, 531, 536, 537, 539, 540, 542, 544, 546, 547, 570, 571, 573, 574, 575, 576, 577, 579, 584, 586, 587, 588, 591, 592, 593, 597, 598, 599, 600, 604, 608, 613, 621, 622, 623, 625, 626, 630, 631, 632, 634, 636, 637, 639, 640, 641, 643, 645, 651, 652, 663, 664, 665, 666, 677, 700, 701, 702, 708, 713, 718, 751, 752, 756 and 757.

6 days in a growth chamber at 24° C. and 70% relative humidity. Each test unit was then visually assessed for insect mortality.

Of the compounds of Formula 1 tested at 250 ppm the following provided very good to excellent levels of control efficacy (80% or more mortality): 1, 2, 3, 5, 6, 7, 8, 9, 10, 11, 12, 13, 14, 16, 17, 18, 19, 21, 23, 24, 25, 26, 27, 28, 29, 30, 31, 36, 37, 38, 39, 40, 41, 42, 43, 44, 45, 46, 47, 48, 49, 50, 51, 52, 53, 54, 55, 56, 57, 57, 58, 59, 60, 61, 62, 63, 64, 65, 66, 67, 67, 68, 70, 71, 72, 73, 73, 74, 75, 76, 77, 78, 79, 80, 81, 82, 83, 84, 86, 87, 88, 89, 90, 91, 92, 93, 94, 95, 96, 97, 98, 99, 100, 101, 102, 104, 105, 106, 108, 109, 111, 113, 116, 117, 118, 120, 120, 122, 123, 163, 163, 237, 278, 279, 280, 281, 283, 285, 286, 288, 289, 291, 292, 295, 297, 302, 308, 311, 314, 315, 317, 318, 324, 325, 327, 328, 330, 340, 341, 343, 344, 345, 347, 349, 352, 357, 358, 359, 360, 361, 362, 363, 364, 365, 369, 375, 376, 377, 378, 381, 385, 389, 390, 392, 393, 394, 396, 397, 399, 400, 403, 404, 405, 406, 407, 408, 409, 410, 411, 415, 416, 417, 419, 422, 423, 424, 425, 426, 431, 433, 435, 437, 438, 443, 444, 445, 446, 449, 450, 459, 460, 461, 462, 463, 464, 465, 466, 467, 468, 469, 470, 471, 472, 473, 474, 475, 476, 477, 478, 479, 480, 481, 482, 483, 484, 485, 515, 568, 570, 571, 573, 574, 575, 581, 588, 591, 593, 604, 606, 608, 609 and 613.

Of the compounds of Formula 1 tested at 50 ppm the following provided very good to excellent levels of control efficacy (80% or more mortality): 1, 2, 3, 5, 6, 7, 9, 10, 11, 12, 13, 14, 16, 17, 19, 21, 23, 24, 25, 26, 27, 28, 29, 30, 31, 40, 41, 42, 43, 44, 45, 46, 47, 48, 49, 50, 51, 52, 53, 54, 55, 56, 57, 58, 59, 60, 61, 62, 63, 64, 65, 67, 68, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 104, 105, 106, 108, 109, 111, 118, 119, 120, 123, 124, 136, 137, 138, 139, 140, 141, 146, 147, 151, 153, 155, 156, 157, 160, 166, 167, 168, 171, 172, 173, 178, 180, 185, 186, 189, 192, 193, 194, 196, 197, 198, 199, 200, 201, 202, 203, 204, 207, 208, 209, 210, 211, 212, 213, 214, 215, 216, 217, 218, 219, 220, 222, 223, 224, 225, 226, 232, 233, 235, 236, 237, 238, 240, 243, 244, 245, 246, 247, 252, 254, 255, 256, 258, 259, 260, 261, 262, 264, 266, 273, 274, 277, 280, 318, 324, 327, 330, 340, 341, 357, 359, 361, 362, 363, 364, 369, 374, 377, 381, 389, 390, 392, 394, 396, 397, 399, 403, 404, 407, 408, 411, 416, 417, 423, 424, 431, 433, 435, 437, 449, 460, 461, 462, 463, 464, 466, 467, 469, 470, 471, 472, 473, 474, 475, 476, 477, 479, 480, 481, 482, 483, 486, 487, 488, 489, 490, 491, 492, 493, 494, 495, 496, 497, 498, 500, 501, 502, 503, 514, 515, 524, 525, 530, 531, 534, 536, 537, 539, 540, 541, 542, 544, 545, 551, 570, 575, 591, 597, 598, 600, 608, 609, 617, 618, 619, 620, 621, 622, 623, 624, 627, 634, 635, 641, 645, 651, 652, 653, 654, 663, 666, 671, 672, 682, 702, 711, 713, 715, 717, 753, 755 and 756.

Test F

For evaluating control of potato leafhopper (*Empoasca fabae*) through contact and/or systemic means, the test unit consisted of a small open container with a 5-6-day-old Soleil bean plant (primary leaves emerged) inside. White sand was added to the top of the soil and one of the primary leaves was excised prior to application.

Test compounds were formulated and sprayed at 250 and 50 ppm, and the tests were replicated three times as described for Test A. After spraying, the test units were allowed to dry for 1 h before they were post-infested with 5 potato leafhoppers (18-21-day-old adults). A black, screened cap was placed on the top of the cylinder. The test units were held for Test G For evaluating control of the Western Flower Thrip (*Frankliniellla occidentalis*) through contact and/or systemic means, the test unit consisted of a small open container with a 5-7-day-old Soleil bean plant inside.

Test compounds were formulated and sprayed at 250 ppm and replicated three times as described for Test A. After spraying, the test units were allowed to dry for 1 hour and then 22-27 adult thrips were added to the unit and then a black, screened cap was placed on top. The test units were held for 7 days at 25° C. and 45-55% relative humidity.

Of the compounds of Formula 1 tested the following provided very good to excellent levels of control efficacy (30% or less plant damage and/or 100% mortality): 158, 211, 212, 229, 235, 257, 258, 262, 273, 497, 528, 531, 544, 549, 579, 608, 617, 635 and 682.

Test H

For evaluating control of the cat flea (*Ctenocephalides felis*), a test compound was solubilized in propylene glycol/glycerol formal (60:40) and then diluted in bovine blood to a final test rate of 30 ppm. The treated blood was placed in a tube with the bottom of the tube covered with a membrane. Approximately 10 adult cat fleas were allowed to feed through the membrane on the treated blood. The adult fleas were evaluated for mortality 72 h later.

Of the compounds of Formula 1 tested, the following compounds resulted in 50% or greater mortality: 1, 2, 3, 5, 6, 8, 9, 10, 12, 14, 16, 17, 19, 21, 26, 29, 34, 36, 37, 38, 39, 41, 42, 43, 44, 45, 46, 47, 48, 49, 50, 52, 53, 54, 55, 56, 57, 58, 59, 61, 62, 65, 66, 71, 72, 75, 76, 78, 81, 82, 83, 88, 90, 92, 98, 100, 101, 103, 104, 105, 106, 107, 114, 118, 119, 120, 121, 123, 124, 125, 134, 135, 136, 137, 138, 149, 150, 153, 154, 155, 156, 157, 161, 166, 167, 169, 172, 179, 186, 188, 189, 190, 191, 192, 193, 196, 199, 203, 204, 206, 207, 208, 210, 211, 216, 217, 218, 219, 223, 224, 225, 230, 280, 281, 289, 290, 294, 295, 301, 312, 314, 318, 319, 323, 324, 327, 331, 343, 346, 348, 350, 360, 361, 362, 363, 364, 369, 371, 372, 373, 374, 378, 382, 383, 385, 389, 391, 393, 406, 411, 420, 421, 422, 423, 431, 435, 438, 440, 461, 466, 468, 469, 470, 471, 473, 475, 476, 477, 478, 479, 480, 491, 492, 493, 494, 495, 496, 497, 498, 500, 503, 511, 513, 521, 528, 589, 590, 592, 596, 597, 599, 604 and 606.

Test I

For evaluating control of the cat flea (*Ctenocephalides felis*), a test compound was solubilized in acetone:water (75:25) to a final test rate of 500 ppm. Then 20 μL of the 500 ppm solution was applied to filter paper in the bottom of a tube. The tube was allowed to dry for 3 hours. Then approximately 10 adult fleas were added to the tube and the tube was capped. The fleas were evaluated for mortality 48 hours later.

Of the compounds of Formula 1 tested, the following compounds resulted in 50% or greater mortality: 5, 6, 10, 12, 19, 21, 22, 23, 26, 27, 28, 38, 39, 40, 41, 42, 43, 44, 45, 47, 48, 50, 54, 56, 57, 59, 61, 62, 63, 65, 70, 71, 72, 75, 81, 82, 83, 102, 107, 108, 114, 115, 121, 124, 136, 138, 141, 151, 154, 161, 166, 173, 186, 193, 196, 197, 203, 204, 208, 211, 216, 218, 224, 229, 232, 281, 290, 291, 295, 301, 310, 321, 343, 350, 353, 357, 360, 361, 364, 408, 419, 424, 437, 446, 450, 461, 464, 466, 468, 470, 471, 474, 476, 483, 485, 487, 490, 491, 492, 493, 494, 496, 498, 501, 507, 520, 521, 576, 597 and 599.

Test J

For evaluating control of the cat flea (*Ctenocephalides felis*) following oral administration of the test compound to a mouse, a CD-1® mouse (about 30 g, male, obtained from Charles River Laboratories, Wilmington, Mass.) was orally dosed with a test compound in an amount of 10 mg/kg solubilized in propylene glycol/glycerol formal (60:40). Two hours after oral administration of the test compound, approximately 8 to 16 adult fleas were applied to each mouse. The fleas were then evaluated for mortality 48 hours after flea application to the mouse.

Of the compounds of Formula 1 tested, the following compounds resulted in 20% or greater mortality: 2, 10, 19, 41, 42, 43, 44, 45, 46, 47, 51, 56, 57, 59, 61, 63, 72, 75, 80, 81, 82, 83, 88, 92, 96, 101, 104, 105, 106, 107, 111, 119, 120, 121, 123, 124, 136, 137, 140, 148, 151, 154, 169, 186, 319, 461, 475, 476, 477, 493, 497, 498, 588 and 599.

What is claimed is:
1. A compound of Formula 1, wherein
X is O;
Y is O;
$R^1$ is phenyl or a 6-membered heteroaromatic ring, each optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_7$ dialkylaminocarbonyl, C(O)N—(CH$_2$Z$^2$CH$_2$—), $C_1$-$C_4$ alkoxy, $C_1$-$C_4$ haloalkoxy, $C_2$-$C_6$ alkoxyalkyl, S(O)$_n$R$^{12}$, S(O)$_2$R$^{13}$, $C_1$-$C_4$ alkylamino, $C_2$-$C_6$ dialkylamino, SF$_5$, Si(CH$_3$)$_3$, CHO, hydroxy, OC(O)R$^{19}$ and N(R$^{20}$)C(O)R$^{19}$;
$R^2$ is $C_2$-$C_6$ alkyl, $C_1$-$C_6$ haloalkyl or CR$^5$R$^6$CH$_2$OR$^{21}$; or
$R^2$ is $C_4$-$C_7$ cycloalkylalkyl optionally substituted with 1 to 4 substituents selected from the group consisting of halogen, $C_1$-$C_2$ alkyl, 1 cyclopropyl and 1CF$_3$;
$R^3$ and $R^4$ are taken together with the contiguous linking nitrogen and carbon atoms to form an optionally substituted ring R-2

Z is C(R$^{8a}$)=C(R$^{8b}$), provided that the C(R$^{8a}$)=C(R$^{8b}$) moiety is oriented so the carbon atom bonded to R$^{8b}$ is connected as R$^3$ in Formula 1;
each R$^5$ is independently H, F, Cl, cyano or $C_1$-$C_4$ alkyl;
each R$^6$ is independently H, F, Cl or CH$_3$;
R$^{8a}$ is H;
R$^{8b}$ is H or F;
each R$^{12}$ is independently $C_1$-$C_4$ alkyl or $C_1$-$C_4$ haloalkyl;
each R$^{13}$ is independently $C_1$-$C_4$ alkylamino, $C_2$-$C_6$ dialkylamino or —N—(CH$_2$Z$^2$CH$_2$—);
each R$^{19}$ is independently $C_1$-$C_4$ alkyl;
each R$^{20}$ is independently H or $C_1$-$C_4$ alkyl;
each R$^{21}$ is independently H or $C_1$-$C_4$ alkyl;
each n is independently 0, 1 or 2; and
each Z$^2$ is independently CH$_2$CH$_2$, CH$_2$CH$_2$CH$_2$ or CH$_2$OCH$_2$.

2. The compound of claim 1 wherein
R$^1$ is phenyl or pyridinyl, each optionally substituted with 1 to 3 substituents independently selected from the group consisting of halogen, cyano, nitro, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ alkylcarbonyl, C$_2$-C$_4$ haloalkylcarbonyl, C$_2$-C$_4$ alkoxycarbonyl, C$_2$-C$_4$ alkylaminocarbonyl, C$_3$-C$_7$ dialkylaminocarbonyl, C(O)N$-\!(\mathrm{CH}_2\mathrm{Z}^2\mathrm{CH}_2)\!-$, C$_1$-C$_4$ alkoxy, C$_1$-C$_4$ haloalkoxy, C$_2$-C$_6$ alkoxyalkyl, S(O)$_n$R$^{12}$, S(O)$_2$R$^{13}$, C$_1$-C$_4$ alkylamino, C$_2$-C$_6$ dialkylamino, SF$_5$, Si(CH$_3$)$_3$, CHO, hydroxy, OC(O)R$^{19}$ and N(R$^{20}$)C(O)R$^{19}$.

3. The compound of claim 2 wherein
each R$^5$ is independently H or C$_1$-C$_4$ alkyl.

4. The compound of claim 3 wherein
each R$^5$ is independently H or methyl.

5. The compound of claim 4 wherein
R$^6$ is H.

6. The compound of claim 1 that is selected from the group consisting of
3-(2,4-difluorophenyl)-2-hydroxy-4-oxo-1-(2,2,2-trifluoroethyl)-4H-pyrido[1,2-a]pyrimidinium inner salt;
3-(4-fluorophenyl)-2-hydroxy-4-oxo-1-(2,2,2-trifluoroethyl)-4H-pyrido[1,2-a]pyrimidinium inner salt; and
2-hydroxy-4-oxo-3-phenyl-1-(2,2,2-trifluoroethyl)-4H-pyrido[1,2-a]pyrimidinium inner salt.

7. A composition comprising a compound of claim 1 and at least one additional component selected from the group consisting of surfactants, solid diluents and liquid diluents, said composition optionally further comprising at least one additional biologically active compound or agent.

8. The composition of claim 7 wherein the at least one additional Biologically active compound or agent is selected from the group consisting of abamectin, acephate, acequinocyl, acetamiprid, acrinathrin, amidoflumet, amitraz, avermectin, azadirachtin, azinphos-methyl, bifenthrin, bifenazate, bistrifluoron, borate, 3-bromo-1-(3-chloro-2-pyridinyl)-N-[4-cyano-2-methyl-6-[(methylamino)carbonyl]phenyl]-1H-pyrazole-5-carboxamide (cyantraniliprole), buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin,zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

9. The composition of claim 8 wherein the at least one additional biologically active compound or agent is selected from the group consisting of abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino)carbonyl]phenyl]-1H-pyrazole-5-carboxamide (cyantraniliprole), buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

10. A composition for protecting an animal from an invertebrate parasitic pest comprising a parasiticidally effective amount of a compound of claim 1 and at least one carrier.

11. A method for controlling an invertebrate pest comprising contacting the invertebrate pest or its environment with a biologically effective amount of a compound of claim 1.

12. A treated seed comprising a compound of claim 1 in an amount of from 0.0001 to 1% by weight of the seed before treatment.

* * * * *